US011130815B2

(12) United States Patent
Sonoda et al.

(10) Patent No.: US 11,130,815 B2
(45) Date of Patent: Sep. 28, 2021

(54) FUSION PROTEINS CONTAINING A BDNF AND AN ANTI-HUMAN TRANSFERRIN RECEPTOR ANTIBODY

(71) Applicant: JCR Pharmaceuticals Co., Ltd., Hyogo (JP)

(72) Inventors: Hiroyuki Sonoda, Hyogo (JP); Kenichi Takahashi, Hyogo (JP)

(73) Assignee: JCR Pharmaceuticals Co., Ltd., Hyogo (JP)

( * ) Notice: Subject to any disclaimer, the term of this patent is extended or adjusted under 35 U.S.C. 154(b) by 0 days.

(21) Appl. No.: 15/739,199

(22) PCT Filed: Jun. 24, 2016

(86) PCT No.: PCT/JP2016/068739
§ 371 (c)(1),
(2) Date: Dec. 22, 2017

(87) PCT Pub. No.: WO2016/208696
PCT Pub. Date: Dec. 29, 2016

(65) Prior Publication Data
US 2018/0179291 A1     Jun. 28, 2018

(30) Foreign Application Priority Data

Jun. 24, 2015 (JP) .............. JP2015-144380

(51) Int. Cl.
*A61K 38/00*  (2006.01)
*A61K 38/18*  (2006.01)
*A61K 39/00*  (2006.01)
*A61K 38/16*  (2006.01)
*A61K 38/17*  (2006.01)
*A61K 39/395* (2006.01)
*C07K 14/00*  (2006.01)
*C07K 14/475* (2006.01)
*C07K 16/18*  (2006.01)
*C07K 16/00*  (2006.01)
*A61P 25/28*  (2006.01)
*C07K 16/28*  (2006.01)
(Continued)

(52) U.S. Cl.
CPC .......... *C07K 16/2881* (2013.01); *A61K 38/22* (2013.01); *A61K 39/395* (2013.01); *A61P 25/00* (2018.01); *C07K 14/475* (2013.01); *C07K 14/48* (2013.01); *C07K 16/28* (2013.01); *C07K 19/00* (2013.01); *C12N 5/10* (2013.01); *C12N 15/09* (2013.01); *A61K 2039/505* (2013.01); *C07K 2317/24* (2013.01); *C07K 2317/33* (2013.01); *C07K 2317/54* (2013.01); *C07K 2317/55* (2013.01); *C07K 2317/56* (2013.01); *C07K 2317/565* (2013.01); *C07K 2317/622* (2013.01); *C07K 2317/92* (2013.01); *C07K 2319/74* (2013.01)

(58) Field of Classification Search
CPC .......... A61K 2039/505; A61K 2300/00; A61K 38/00; A61K 47/64; A61K 47/6849; A61K 47/68; A61K 38/40; A61K 47/62; A61K 47/642; A61K 47/65; A61K 47/6889; A61K 47/644; A61K 38/1709; A61K 38/177; A61K 39/00; A61K 39/39533; A61K 39/44; A61K 47/6801; A61K 47/6851; A61K 9/0085; A61K 38/185; A61K 39/395; A61K 47/42; A61K 47/6811; A61K 47/6879; A61K 51/1093; C07K 16/468; C07K 2319/00; C07K 16/28; C07K 16/2803; C07K 16/2896; C07K 16/00; C07K 16/46; C07K 16/18; C07K 16/2863; C07K 16/467; C07K 2317/622; C07K 2317/24; C07K 2317/55; C07K 2317/31; C07K 2317/94; C07K 2317/56; C07K 2317/22; C07K 2317/565; C07K 2317/569; C07K 2317/92; C07K 2317/64; C07K 2317/76; C07K 2317/21; C07K 2317/34; C07K 2317/33; C07K 2317/51; C07K 2317/70; C07K 2317/77; C07K 2317/54; C07K 2319/30; C07K 2319/33; C07K 2319/55; C07K 2319/70; C07K 2319/32; C07K 2319/74; C07K 14/475; C07K 14/48; C07K 14/70575; C07K 19/00; G01N 33/566; C12N 15/09; Y02A 50/586; Y02A 50/41
See application file for complete search history.

(56) References Cited

U.S. PATENT DOCUMENTS 5,154,924 A  10/1992  Friden
5,442,043 A   8/1995  Fukuta et al.
(Continued)

FOREIGN PATENT DOCUMENTS

CA  2607771 A1  5/2009
CA  3034589 A1  3/2018
(Continued)

OTHER PUBLICATIONS

Bowie et al. Science, 1990, 247:1306-1310.*
(Continued)

*Primary Examiner* — Chang-Yu Wang
(74) *Attorney, Agent, or Firm* — Morgan, Lewis & Bockius LLP

(57) ABSTRACT

Disclosed is a fusion protein containing a brain-derived neurotrophic factor (BDNF). The fusion protein is a fusion protein of BDNF and a specific range of human anti-transferrin receptor antibody, which makes BDNF administered into the blood able to pass through the blood-brain barrier.

22 Claims, 8 Drawing Sheets
Specification includes a Sequence Listing.

(51) Int. Cl.

| | |
|---|---|
| C12N 5/10 | (2006.01) |
| A61K 38/22 | (2006.01) |
| C07K 14/48 | (2006.01) |
| C12N 15/09 | (2006.01) |
| C07K 19/00 | (2006.01) |
| A61P 25/00 | (2006.01) |

(56) References Cited

U.S. PATENT DOCUMENTS

| | | | |
|---|---|---|---|
| 5,527,527 | A | 6/1996 | Friden |
| 5,977,307 | A | 11/1999 | Friden et al. |
| 6,472,147 | B1 | 10/2002 | Janda et al. |
| 7,560,431 | B2 | 7/2009 | Zankel et al. |
| 8,663,598 | B2 | 3/2014 | Yang et al. |
| 2004/0101904 | A1 | 5/2004 | Pardridge et al. |
| 2010/0077498 | A1 | 3/2010 | Pardridge et al. |
| 2010/0266613 | A1 | 10/2010 | Harding et al. |
| 2011/0110935 | A1 | 5/2011 | Pardridge et al. |
| 2012/0171120 | A1 | 7/2012 | Dennis et al. |
| 2012/0231023 | A1 | 9/2012 | Zurawski et al. |
| 2013/0171061 | A1 | 7/2013 | Yang et al. |
| 2014/0114054 | A1 | 4/2014 | Kurosawa et al. |
| 2015/0110791 | A1 | 4/2015 | Zhang et al. |
| 2016/0369001 | A1 | 12/2016 | Sonoda et al. |
| 2017/0044259 | A1 | 2/2017 | Tipton et al. |
| 2017/0252458 | A1 | 9/2017 | Albone et al. |
| 2017/0355756 | A1 | 12/2017 | Julien et al. |
| 2018/0171012 | A1 | 6/2018 | Sonoda et al. |
| 2018/0179291 | A1 | 6/2018 | Sonoda et al. |
| 2019/0338043 | A1 | 11/2019 | Sonoda et al. |

FOREIGN PATENT DOCUMENTS

| | | |
|---|---|---|
| CN | 101245107 A | 8/2008 |
| CN | 103502273 A | 1/2014 |
| EP | 3563863 A1 | 11/2019 |
| EP | 3679945 A1 | 7/2020 |
| JP | H05-500944 A | 2/1993 |
| JP | H06-228199 A | 8/1994 |
| JP | 2006-511516 A | 4/2006 |
| JP | 2007-504166 A | 3/2007 |
| JP | 2009-515819 A | 4/2009 |
| JP | 2009-525963 A | 7/2009 |
| JP | 2011-144178 A | 7/2011 |
| JP | 2012-062312 A | 3/2012 |
| JP | 2014-514313 A | 6/2014 |
| JP | 2018-033454 A | 3/2018 |
| WO | 91/003259 A1 | 3/1991 |
| WO | 93/10819 A1 | 6/1993 |
| WO | 95/02421 A1 | 1/1995 |
| WO | 02/031510 A1 | 4/2002 |
| WO | 02/034771 A2 | 5/2002 |
| WO | 03/083069 A2 | 10/2003 |
| WO | 2004/050016 A2 | 6/2004 |
| WO | 2005/021064 A2 | 3/2005 |
| WO | 2007/044323 A2 | 4/2007 |
| WO | 2007/084737 A2 | 7/2007 |
| WO | 2008/068048 A2 | 6/2008 |
| WO | 2010/037395 A2 | 4/2010 |
| WO | 2012/075037 A1 | 6/2012 |
| WO | 2012/143379 A1 | 10/2012 |
| WO | 2013/177062 A2 | 11/2013 |
| WO | 2014/105810 A1 | 7/2014 |
| WO | 2014/189973 A2 | 11/2014 |
| WO | 2014/190305 A2 | 11/2014 |
| WO | 2014/194282 A2 | 12/2014 |
| WO | 2015/098989 A1 | 12/2014 |
| WO | 2015/009961 A1 | 1/2015 |
| WO | 2015/014884 A1 | 2/2015 |
| WO | 2015/101588 A1 | 7/2015 |
| WO | 2016/208695 A1 | 12/2016 |
| WO | 2016/208696 A1 | 12/2016 |
| WO | 2017/011580 A2 | 1/2017 |
| WO | 2019/049967 A1 | 3/2019 |

OTHER PUBLICATIONS

Pawson et al. 2003, Science 300:445-452.*
Burgess et al. J of Cell Bio. 1990, 111:2129-2138.*
Alaoui-Ismaili et al., Cytokine Growth Factor Rev. 2009; 20:501-507.*
Guo et al., PNAS 2004; 101:9205-9210.*
Rudikoff et al, Proc Natl Acad Sci USA, 1982; 79:1979-.*
Holm et al. (2007) 44, 1075-1084.*
MacCallum et al., J. Mol. Biol. (1996) 262, 732-745.*
Pascalis et al., The Journal of Immunology (2002) 169, 3076-3084.*
Casset et al. (2003) BBRC 307, 198-205.*
Vajdos et al. (2002) 320, 415-428.*
Chen et al. J. Mol. Bio. (1999) 293, 865-881.*
Wu et al. J. Mol. Biol. (1999) 294, 151-162.*
Pardridge et al., Chapter Eleven, Reengineering Biopharmaceuticals for Targeted Delivery Across the Blood Brain Barrier, Methods in Enzymology, vol. 503, 2012, pp. 269-292.*
Torres et al. Trends in Immunology, 2007; 29: 91-97.*
Pardridge. Exp. Opi. Durg Deliv. 2015; 12: 207-222. DOI:10.1517/17425247.2014.952627.*
Yan et al. China Biotechnol. 2006; 26:1-5.*
Chao, "Neurotrophins and Their Receptors: A Convergence Point for Many Signalling Pathways," Nature Reviews: Neuroscience, 4: 299-309 (2003).
Tabakman et al., "Interactions between the cells of the immune and nervous system: neurotrophins as neuroprotection mediators in CNS injury," Progress in Brain Research, 146: 387-401 (2004).
Bollen et al., "7,8-Dihydroxyflavone improves memory consolidation processes in rats and mice," Behavioural Brain Research, 257: 8-12 (2013).
Altar et al., "Efficacy of Brain-Derived Neurotrophic Factor and Neurotrophin-3 on Neurochemical and Behavioral Deficits Associated with Partial Nigrostriatal Dopamine Lesions," Journal of Neurochemistry, 63: 1021-1032 (1994).
Zuccato et al., "Role of brain-derived neurotrophic factor in Huntington's disease," Progress in Neurobiology, 81: 294-330 (2007).
Wu, "Neuroprotection in Experimental Stroke with Targeted Neurotrophins," NeuroRx, 2: 120-128 (2005).
Katz, "Brain-Derived Neurotrophic Factor and Rett Syndrome," Handbook of Experimental Pharmacology, 220: 481-495 (2014).
Castrén, "Neurotrophins and Psychiatric Disorders," Handbook of Experimental Pharmacology, 220: 461-479 (2014).
Xie et al., "Transport of nerve growth factor encapsulated into liposomes across the blood-brain barrier: In vitro and in vivo studies," Journal of Controlled Release, 105: 106-119 (2005).
Ou et al., "High-Dose Enzyme Replacement Therapy in Murine Hurler Syndrome," Molecular Genetics and Metabolism (author manuscript), 111: 116-122 (2014).
Boado et al., "Genetic Engineering, Expression, and Activity of a Fusion Protein of a Human Neurotrophin and a Molecular Trojan Horse for Delivery Across the Human Blood-Brain Barrier," Biotechnology and Bioengineering, 97: 1376-1386 (2007).
Wu et al., "Neuroprotection with noninvasive neurotrophin delivery to the brain," Proceedings of the National Academy of Sciences, 96: 254-259 (1999).
Li et al., "Gentically engineered brain drug delivery vectors: cloning, expression and in vivo application of an anti-transferrin receptor single chain antibody-streptavidin fusion gene and protein," Protein Engineering, 12: 787-796 (1999).
Bien-Ly et al., "Transferrin receptor (TfR) trafficking determines brain uptake of TfR antibody affinity variants," Journal of Experimental Medicine, 211: 233-244 (2014).
Sade et al., "A Human Blood-Brain Barrier Transcytosis Assay Reveals Antibody Transcytosis Influenced by pH-Dependent Receptor Binding," PLOS One, 9: e96340 (2014).
Friden et al., "Characterization, Receptor Mapping and Blood-Brain Barrier Transcytosis of Antibodies to the Human Transferrin Receptor," Journal of Pharmacology and Experimental Therapeutics, 278: 1491-1498 (1996).
Pardridge, "Blood-brain barrier drug delivery of IgG fusion proteins with a transferrin receptor monoclonal antibody," Expert Opinion Drug Drug Delivery, 12: 207-222 (2015).

(56) References Cited

OTHER PUBLICATIONS

International Search Report issued in corresponding International Patent Application No. PCT/JP2016/068739 dated Sep. 6, 2016.
International Preliminary Report on Patentability and Written Opinion issued in corresponding International Patent Application No. PCT/JP2016/068739 dated Jan. 4, 2018.
Extended European Search Report issued in counterpart European Patent Application No. 16814465.7 dated May 8, 2019.
Gosk et al, "Targeting Anti-Transferrin Receptor Antibody (OX26) and OX26-Conjugated Liposomes to Brain Capillary Endothelial Cells Using in Situ Perfusion," Journal of Cerebral Blood Flow & Metabolism, 24: 1193-1196 (2004).
Li et al., "The role of the transferrin-transferrin-receptor system in drug delivery and targeting," Trends in Pharmacological Sciences, 23: 206-209 (2002).
Extended European Search Report issued in European Patent Application No. 17889016.6 dated Jul. 15, 2020.
Hiroyuki Sonoda et al., application of U.S. Appl. No. 16/473,816, filed Sep. 12, 2019.
Kussie, "A Single Engineered Amino Acid Substitution Changes Antibody Fine Specificity," Journal of Immunology, 152: 146-152 (1994).
Chen et al., "Enhancement and destruction of antibody function by somatic mutation: unequal occurrence is controlled V gene combinatorial associations," EMBO Journal, 14: 2784-2794 (1995).
Zhou et al., "Delivery of a Peptide Radiopharmaceutical to Brain with an IgG-Avidin Fusion Protein," Bioconjugate Chemistry, 22: 1611-1618 (2011).
Qing et al., "The in vitro antitumor effect and in vivo tumor-specificity distribution of human-mouse chimeric antibody against transferrin receptor", Cancer Immunology Immunotherapy, 55: 1111-1121 (2006).
Tucker et al., "Drug delivery to the brain via the blood-brain barrier: a review of the literature and some recent patent disclosures," Therapeutic Delivery, 2: 311-327 (2011).
Extended European Search Report issued in counterpart European Patent Application No. 16814464.0 dated Mar. 25, 2019.
Niewoehner et al., "Increased Brain Penetration and Potency of a Therapeutic Antibody Using a Monovalent Molecular Shuttle," Neuron 81: 49-60 (2014).
Formica et al., "5-Fluorouracil can cross brain-blood barrier and cause encephalopathy: should we expect the same from capecitabine? A case report on capecitabine-induced central neurotoxicity progressing to coma," Cancer Chemotherapy and Pharmacology, 58: 276-278 (2006).
International Search Report issued in corresponding International Patent Application No. PCT/JP2016/068738 dated Sep. 6, 2016.

International Preliminary Report on Patentability and Written Opinion issued in corresponding International Patent Application No. PCT/JP2016/068738 dated Dec. 26, 2017.
Office Action issued in counterpart Singapore Patent Application No. 11201710734U dated Jan. 3, 2019.
Holmes et al., "Structural Consequences of Humanizing an Antibody," Journal of Immunology, 2192-2201 (1997).
Partial Supplemental European Search Report issued in counterpart European Patent Application No. 16814464.0 dated Dec. 17, 2018.
Zhou et al., "Brain-Penetrating IgG Iduronate 2-Sulfatase Fusion Protein for the Mouse," Drug Metabolism and Disposition, 40: 329-335 (2012) (see English abstract).
International Preliminary Report on Patentability and Written Opinion issued in corresponding International Patent Application No. PCT/JP2017/046762 dated Jul. 11, 2019.
International Search Report issued in corresponding International Patent Application No. PCT/JP2017/046762 dated Mar. 27, 2018.
International Preliminary Report on Patentability and Written Opinion issued in corresponding International Patent Application No. PCT/JP2017/046735 dated Jul. 11, 2019.
International Search Report issued in corresponding International Patent Application No. PCT/JP2017/046735 dated Apr. 3, 2018.
Zhou et al., "Monoclonal Antibody-Glial-Derived Neurotrophic Factor Fusion Protein Penetrates the Blood-Brain Barrier in the Mouse," Drug Metabolism and Disposition, 38: 566-572 (2010).
Boado et al., "Engineering and Expression of a Chimeric Transferrin Receptor Monoclonal Antibody for Blood-Brain Barrier Delivery in the Mouse," Biotechnology and Bioengineering, 102: 1251-1258 (2009).
Walus et al., "Enhanced Uptake of rsCD4 across the Rodent and Primate Blood-Brain Barrier after Conjugation to Anti-Transferrin Receptor Antibodies," Journal of Pharmacology and Experimental Therapeutics, 277: 1067-1075 (1996).
Helguera et al., "An Antibody Recognizing the Apical Domain of Human Transferrin Receptor 1 Efficiently Inhibits the Entry of All New World Hemorrhagic Fever Arenaviruses," Journal of Virology, 86: 4024-4028 (2012).
"Overview of the Immune System," Immunology: A Short Course, 7th ed., Richard Coico and Geoffrey Sunshine, 61-62 (2015).
Altshuler et al., "Generation of Recombinant Antibodies and Means for Increasing Their Affinity," Biochemistry (Moscow), 75 (13): 1584-1605 (2010). (Original Russian text: Uspekhi Biologicheskoi Khimii, 50: 203-258 (2010)).
Brown, et al., "Tolerance to Single, but Not Multiple, Amino Acid Replacements in Antibody VH CDR2," Journal of Immunology, 3286-3291 (1996).
Office Action issued in related Eurasian Patent Application No. 201991577 dated Feb. 26, 2021.

* cited by examiner

*Fig.*6

FUSION PROTEINS CONTAINING A BDNF AND AN ANTI-HUMAN TRANSFERRIN RECEPTOR ANTIBODY

SEQUENCE LISTING SUBMISSION VIA EFS-WEB

A computer readable text file, entitled "SequenceListing.txt," created on or about Dec. 21, 2017 with a file size of about 232 kb contains the sequence listing for this application and is hereby incorporated by reference in its entirety.

TECHNICAL FIELD

The present invention relates to BDNF, which can pass through the blood-brain barrier, and more specifically to a fusion protein of an anti-human transferrin receptor antibody and BDNF, a method for production thereof, as well as a method of use thereof.

BACKGROUND ART

Unlike the capillaries in other tissues such as muscles, the capillaries that supply the blood to most of the brain tissues except some areas including the circumventricular organs (pineal gland, pituitary body, area postrema, etc.) differ in that the endothelial cells forming their endothelium are mutually connected by tight intercellular junctions. Passive transfer of substances from the capillaries to the brain is thereby restricted, and although there are some exceptions, substances are unlikely to move into the brain from the blood except such compounds as are lipid-soluble or of low-molecular-weight (not greater than 200 to 500 Dalton) and electrically neutral around the physiological pH. This system, which restricts exchange of substances between the blood and the tissue fluid of the brain through the endothelium of capillaries in the brain, is called the blood-brain barrier or BBB. The blood-brain barrier not only restricts exchange of substances between the blood and the brain but also between the tissue fluid of the central nervous system, including the brain and the spinal chord, and the blood.

Owing to the blood-brain barrier, most of the cells of the central nervous system escape the effects such as fluctuation of concentrations of substances like hormones and lymphokines in the blood, and their biochemical homeostasis is thus maintained.

The blood-brain barrier, however, imposes a problem when it comes to develop pharmaceutical agents. For example, it has been known that a brain-derived neurotrophic factor (BDNF) is one of the neurotrophin family, and that the dimer thereof specifically binds to a high-affinity BDNF receptor (TrkB; also referred to as Tyrosine receptor kinase B, Tropomyosin receptor kinase B, or Tropomyosin-related Kinase B) on the surface of a target cell, and plays an important role in differentiation of cells, function maintenance, synaptogenesis, and regeneration and damage repair when damaged, etc. in the central and peripheral nervous systems (Non-patent Documents 1 and 2). Thus, it is anticipated that BDNF will be developed as a therapeutic agent for various diseases including neurodegenerative diseases such as Alzheimer's disease, Parkinson's disease and Huntington's disease, spinal degenerative diseases such as amyotrophic lateral sclerosis, and further, diabetic neuropathy, cerebral ischemic disease, developmental disorder, schizophrenia, depression and Rett syndrome (Non-patent Documents 3-8). However, in general, since high molecular weight proteins hardly pass through the blood-brain barrier, it has been significantly difficult to use BDNF itself as a therapeutic agent for central nervous system diseases or as a disease-therapeutic agent acting on the central nervous system by peripheral administration.

Development of various methods has been attempted to make those macromolecular substances as proteins or the like, which need to be brought into function in the central nervous system, pass through the blood-brain barrier. In the case of nerve growth factor, for example, while attempts have been made for a method to cause the factor to pass through the blood-brain barrier by allowing liposomes encapsulating the factor to fuse with the cell membrane of endothelial cells in brain capillaries, they have not been reached practical application (Non Patent Literature 9). In the case of α-L-iduronidase, an attempt has been made to enhance the passive transfer of the enzyme through the blood-brain barrier by raising its blood concentration through an increased single dose of the enzyme, and it thus has been demonstrated, using a Hurler syndrome animal model, that the abnormality in the central nervous system (CNS) is ameliorated by that method (Non Patent Literature 10).

Furthermore, circumventing the blood-brain barrier, an attempt has also been made to administer a macromolecular substance directly into the medullary cavity or into the brain. For example, reports have been made about a method in which human α-L-iduronidase was intrathecally administered to a patient with a Hurler syndrome (mucopolysaccharidosis type I) (Patent Literature 1), a method in which human acid sphingomyelinase was administered into the brain ventricles of a patient with Niemann-Pick disease (Patent Literature 2), and a method in which iduronate 2-sulfatase (I2S) was administered into the brain ventricles of Hunter syndrome model animals (Patent Literature 3). While it seems possible by one of such methods to definitely let a pharmaceutical agent act in the central nervous system, they have a problem as being highly invasive.

There have been reported various methods to let a macromolecular substance get into the brain through the blood-brain barrier, in which the macromolecular substance is modified to give it an affinity to membrane proteins existing on the endothelial cells of the brain capillaries. Examples of those membrane proteins which exists on the endothelial cells of the brain capillaries include receptors for compounds such as insulin, transferrin, insulin-like growth factor (IGF-I, IGF-II), LDL, and leptin.

For example, a technique has been reported in which nerve growth factor (NGF) was synthesized in the form of a fusion protein with insulin, and this fusion protein was allowed to pass through the blood-brain barrier via its binding to the insulin receptor (Patent Literatures 4-6). Further, a technique has been reported in which nerve growth factor (NGF) was synthesized in the form of a fusion protein with anti-insulin receptor antibody, and this fusion protein was allowed to pass through the blood-brain barrier via its binding to the insulin receptor (Patent Literatures 4 and 7).

A technique has been reported in which brain-derived neurotrophic factor (BDNF) was synthesized in the form of a fusion protein with anti-insulin receptor antibody, and this fusion protein was allowed to pass through the blood-brain barrier via its binding to the insulin receptor (Non-patent Document 11). A technique has been reported in which nerve growth factor (NGF) was synthesized in the form of a fusion protein with transferrin, and this fusion protein was allowed to pass through the blood-brain barrier via its binding to the transferrin receptor (TfR) (Patent Literature 8). Further, a technique has been reported in which nerve growth factor (NGF) was synthesized in the form of a fusion protein with anti-transferrin receptor antibody (anti-TfR antibody), and this fusion protein is allowed to pass through the blood-brain barrier via its binding to TfR (Patent Literatures 4 and 9). Moreover, a technique has been reported in which polyethylene glycol (PEG)-added brain-derived neurotrophic factor (BDNF) was synthesized in the form of a conjugate chemically bound to a mouse anti-rat transferrin receptor antibody (anti-TfR antibody) via a streptavidin-biotin linker, and this conjugate was allowed to pass through the blood-brain barrier via its binding to TfR in rats (Non-patent Document 12).

Looking further into the techniques that utilize an anti-TfR antibody, there has been reported that in the field of the technique to make a pharmaceutical agent pass through the blood-brain barrier by binding it to such an anti-TfR antibody, in the case of streptavidin, a single-chain antibody could be used (Non-patent Document 13). Further, it has been reported that anti-hTfR antibodies exhibiting relatively high dissociation constants with human TfR (hTfR) (low-affinity anti-hTfR antibody) could be favorably used in the technique to make pharmaceutical agents pass through the blood-brain barrier (Patent Literatures 10 and 11, and Non Patent Literature 14). Still further, it has also been reported that an anti-TfR antibodies whose affinity to hTfR varies depending on pH could be employed as a carrier for making pharmaceutical agents pass through the blood-brain barrier (Patent Literature 12, and Non Patent Literature 15).

CITATION LIST

Patent Literature

Patent Literature 1: JP2007-504166 A1
Patent Literature 2: JP2009-525963 A1
Patent Literature 3: JP2012-62312 A1
Patent Literature 4: U.S. Pat. No. 5,154,924 B1
Patent Literature 5: JP2011-144178 A1
Patent Literature 6: US2004/0101904 A1
Patent Literature 7: JP2006-511516 A1
Patent Literature 8: JPH06-228199 A1
Patent Literature 9: U.S. Pat. No. 5,977,307 B1
Patent Literature 10: WO 2012/075037
Patent Literature 11: WO 2013/177062
Patent Literature 12: WO 2012/143379

Non Patent Literature

Non Patent Literature 1: Moses V. Chao. Nature Reviews Neuroscience. 4. 299-309 (2003)
Non Patent Literature 2: Tabakman R. Progress in Brain Research. 146. 387-401 (2004)
Non Patent Literature 3: Bollen E. Behavioural Brain Research. 257C. 8-12 (2013)
Non Patent Literature 4: Altar C. Anthony. Journal of Neurochemistry. 63. 1021-32 (1994)
Non Patent Literature 5: Zuccato C. Progress in Neurobiology. 81. 294-330 (2007)
Non Patent Literature 6: Dafang Wu. The Journal of the American Society for Experimental Neurotherapeutics. 2. 120-8 (2005)
Non Patent Literature 7: David M. Katz. The Handbook of Experimental Pharmacology. 220. 481-95 (2014)
Non Patent Literature 8: E. Castren. The Handbook of Experimental Pharmacology. 220. 461-79 (2014)
Non Patent Literature 9: Xie Y. J Control Release. 105. 106-19 (2005)
Non Patent Literature 10: Ou L. Mol Genet Metab. 111. 116-22 (2014)
Non Patent Literature 11: Ruben J. B. Biotechnology Bioengineering, 97. 1376-1386 (2007)
Non Patent Literature 12: Dafang W. Proc. Natl. Acad. Sci. USA, 96. 254-259 (1999)
Non Patent Literature 13: Li J Y. Protein Engineering. 12. 787-96 (1999)
Non Patent Literature 14: Bien-Ly N. J Exp Med. 211. 233-44 (2014)
Non Patent Literature 15: Sada H. PLoS ONE. 9. E96340 (2014)

SUMMARY OF INVENTION

Problems to be Solved by the Invention

Against the above background, it is an objective of the present invention to provide: a fusion protein of an anti-TfR antibody and BDNF, which makes BDNF administered into the blood able to pass through the blood-brain barrier, so that it can act in the brain; a method for production thereof; a method of use thereof; and a preventive and/or therapeutic method for a certain range of diseases by administering the fusion protein.

Means for Solving the Problems

As a result of intense studies aimed at the above objective, the present inventors have found that anti-human transferrin receptor antibodies (anti-hTfR antibodies) that recognize the extracellular region of hTfR which are to be obtained by the method for antibody production described in detail in the specification, efficiently passes through the blood-brain barrier when administered into the blood, and further that a fusion protein of the antibody and BDNF also passes through the blood-brain barrier, and thereby, the present inventors have completed the present invention thereupon. Thus the present invention provides what follows:

1. A fusion protein of a brain-derived neurotrophic factor (BDNF) and an anti-human transferrin receptor antibody, wherein the amino acid sequence of the light chain variable region of the antibody is selected from the group consisting of (1) to (14) below:

(1) an amino acid sequence comprising the amino acid sequence set forth as SEQ ID NO:6 or SEQ ID NO:7 in CDR1, the amino acid sequence set forth as SEQ ID NO:8 or SEQ ID NO:9 or the amino acid sequence Trp-Thr-Ser in CDR2, and the amino acid sequence set forth as SEQ ID NO:10 in CDR3;

(2) an amino acid sequence comprising the amino acid sequence set forth as SEQ ID NO:11 or SEQ ID NO: 12 in CDR1, the amino acid sequence set forth as SEQ ID NO: 13 or SEQ ID NO: 14 or the amino acid sequence Tyr-Ala-Ser in CDR2, and the amino acid sequence set forth as SEQ ID NO: 15 in CDR3;

(3) an amino acid sequence comprising the amino acid sequence set forth as SEQ ID NO: 16 or SEQ ID NO: 17 in CDR1, the amino acid sequence set forth as SEQ ID NO: 18 or SEQ ID NO: 19 or the amino acid sequence Lys-Val-Ser in CDR2, and the amino acid sequence set forth as SEQ ID NO:20 in CDR3;

(4) an amino acid sequence comprising the amino acid sequence set forth as SEQ ID NO:21 or SEQ ID NO:22 in CDR1, the amino acid sequence set forth as SEQ ID NO:23 or SEQ ID NO:24 or the amino acid sequence Asp-Thr-Ser in CDR2, and the amino acid sequence set forth as SEQ ID NO:25 in CDR3;

(5) an amino acid sequence comprising the amino acid sequence set forth as SEQ ID NO:26 or SEQ ID NO:27 in CDR1, the amino acid sequence set forth as SEQ ID NO:28 or SEQ ID NO:29 or the amino acid sequence Asp-Thr-Ser in CDR2, and the amino acid sequence set forth as SEQ ID NO:30 in CDR3;

(6) an amino acid sequence comprising the amino acid sequence set forth as SEQ ID NO:31 or SEQ ID NO:32 in CDR1, the amino acid sequence set forth as SEQ ID NO:33 or SEQ ID NO:34 or the amino acid sequence Ala-Ala-Ser in CDR2, and the amino acid sequence set forth as SEQ ID NO:35 in CDR3;

(7) an amino acid sequence comprising the amino acid sequence set forth as SEQ ID NO:36 or SEQ ID NO:37 in CDR1, the amino acid sequence set forth as SEQ ID NO:38 or SEQ ID NO:39 or the amino acid sequence Gln-Thr-Ser in CDR2, and the amino acid sequence set forth as SEQ ID NO:40 in CDR3;

(8) an amino acid sequence comprising the amino acid sequence set forth as SEQ ID NO:41 or SEQ ID NO:42 in CDR1, the amino acid sequence set forth as SEQ ID NO:43 or SEQ ID NO:44 or the amino acid sequence Gly-Thr-Ser in CDR2, and the amino acid sequence set forth as SEQ ID NO:45 in CDR3;

(9) an amino acid sequence comprising the amino acid sequence set forth as SEQ ID NO:46 or SEQ ID NO:47 in CDR1, the amino acid sequence set forth as SEQ ID NO:48 or SEQ ID NO:49 or the amino acid sequence Phe-Thr-Ser in CDR2, and the amino acid sequence set forth as SEQ ID NO:50 in CDR3;

(10) an amino acid sequence comprising the amino acid sequence set forth as SEQ ID NO:51 or SEQ ID NO:52 in CDR1, the amino acid sequence set forth as SEQ ID NO:53 or SEQ ID NO:54 or the amino acid sequence Ala-Ala-Ser in CDR2, and the amino acid sequence set forth as SEQ ID NO:55 in CDR3;

(11) an amino acid sequence comprising the amino acid sequence set forth as SEQ ID NO:56 or SEQ ID NO:57 in CDR1, the amino acid sequence set forth as SEQ ID NO:58 or SEQ ID NO:59 or the amino acid sequence Tyr-Ala-Ser in CDR2, and the amino acid sequence set forth as SEQ ID NO:60 in CDR3;

(12) an amino acid sequence comprising the amino acid sequence set forth as SEQ ID NO:61 or SEQ ID NO:62 in CDR1, the amino acid sequence set forth as SEQ ID NO:63 or SEQ ID NO:64 or the amino acid sequence Trp-Ser-Ser in CDR2, and the amino acid sequence set forth as SEQ ID NO:65 in CDR3;

(13) an amino acid sequence comprising the amino acid sequence set forth as SEQ ID NO:66 or SEQ ID NO:67 in CDR1, the amino acid sequence set forth as SEQ ID NO:68 or SEQ ID NO:69 or the amino acid sequence Tyr-Ala-Ser in CDR2, and the amino acid sequence set forth as SEQ ID NO:70 in CDR3; and

(14) an amino acid sequence comprising the amino acid sequence set forth as SEQ ID NO:71 or SEQ ID NO:72 in CDR1, the amino acid sequence set forth as SEQ ID NO:73 or SEQ ID NO:74 or the amino acid sequence Asp-Thr-Ser in CDR2, and the amino acid sequence set forth as SEQ ID NO:75 in CDR3.

2. The fusion protein of BDNF and an anti-human transferrin receptor antibody according to the above 1, wherein the amino acid sequence of the light chain variable region of the antibody is selected from the group consisting of (1) to (14) below:

(1) an amino acid sequence comprising the amino acid sequence set forth as SEQ ID NO:6 in CDR1, the amino acid sequence set forth as SEQ ID NO:8 in CDR2, and the amino acid sequence set forth as SEQ ID NO: 10 in CDR3;

(2) an amino acid sequence comprising the amino acid sequence set forth as SEQ ID NO:11 in CDR1, the amino acid sequence set forth as SEQ ID NO: 13 in CDR2, and the amino acid sequence set forth as SEQ ID NO: 15 in CDR3;

(3) an amino acid sequence comprising the amino acid sequence set forth as SEQ ID NO: 16 in CDR1, the amino acid sequence set forth as SEQ ID NO:18 in CDR2, and the amino acid sequence set forth as SEQ ID NO:20 in CDR3;

(4) an amino acid sequence comprising the amino acid sequence set forth as SEQ ID NO:21 in CDR1, the amino acid sequence set forth as SEQ ID NO:23 in CDR2, and the amino acid sequence set forth as SEQ ID NO:25 in CDR3;

(5) an amino acid sequence comprising the amino acid sequence set forth as SEQ ID NO:26 in CDR1, the amino acid sequence set forth as SEQ ID NO:28 in CDR2, and the amino acid sequence set forth as SEQ ID NO:30 in CDR3;

(6) an amino acid sequence comprising the amino acid sequence set forth as SEQ ID NO:31 in CDR1, the amino acid sequence set forth as SEQ ID NO:33 in CDR2, and the amino acid sequence set forth as SEQ ID NO:35 in CDR3;

(7) an amino acid sequence comprising the amino acid sequence set forth as SEQ ID NO:36 in CDR1, the amino acid sequence set forth as SEQ ID NO:38 in CDR2, and the amino acid sequence set forth as SEQ ID NO:40 in CDR3;

(8) an amino acid sequence comprising the amino acid sequence set forth as SEQ ID NO:41 in CDR1, the amino acid sequence set forth as SEQ ID NO:43 in CDR2, and the amino acid sequence set forth as SEQ ID NO:45 in CDR3;

(9) an amino acid sequence comprising the amino acid sequence set forth as SEQ ID NO:46 in CDR1, the amino acid sequence set forth as SEQ ID NO:48 in CDR2, and the amino acid sequence set forth as SEQ ID NO:50 in CDR3;

(10) an amino acid sequence comprising the amino acid sequence set forth as SEQ ID NO:51 in CDR1, the amino acid sequence set forth as SEQ ID NO:53 in CDR2, and the amino acid sequence set forth as SEQ ID NO:55 in CDR3;

(11) an amino acid sequence comprising the amino acid sequence set forth as SEQ ID NO:56 in CDR1, the amino acid sequence set forth as SEQ ID NO:58 in CDR2, and the amino acid sequence set forth as SEQ ID NO:60 in CDR3;

(12) an amino acid sequence comprising the amino acid sequence set forth as SEQ ID NO:61 in CDR1, the amino acid sequence set forth as SEQ ID NO:63 in CDR2, and the amino acid sequence set forth as SEQ ID NO:65 in CDR3;

(13) an amino acid sequence comprising the amino acid sequence set forth as SEQ ID NO:66 in CDR1, the amino acid sequence set forth as SEQ ID NO:68 in CDR2, and the amino acid sequence set forth as SEQ ID NO:70 in CDR3; and

(14) an amino acid sequence comprising the amino acid sequence set forth as SEQ ID NO:71 in CDR1, the amino acid sequence set forth as SEQ ID NO:73 in CDR2, and the amino acid sequence set forth as SEQ ID NO:75 in CDR3.

3. A fusion protein of BDNF and an anti-human transferrin receptor antibody, wherein the amino acid sequences of CDR1, CDR2 and CDR3 in the light chain of the antibody have a homology not lower than 80% to the amino acid sequences of CDR1, CDR2 and CDR3, respectively, in the light chain according to the above 1 or 2.

4. A fusion protein of BDNF and an anti-human transferrin receptor antibody, wherein the amino acid sequences of CDR1, CDR2 and CDR3 in the light chain of the antibody have a homology not lower than 90% to the amino acid sequences of CDR1, CDR2 and CDR3, respectively, in the light chain according to the above 1 or 2.

5. A fusion protein of BDNF and an anti-human transferrin receptor antibody, wherein 1 to 5 amino acids are substituted, deleted or added relative to the amino acid sequence that forms at least one of the CDRs in the light chain according to the above 1 or 2.

6. A fusion protein of BDNF and an anti-human transferrin receptor antibody, wherein 1 to 3 amino acids are substituted, deleted or added relative to the amino acid sequence that forms at least one of the CDRs in the light chain according to the above 1 or 2.

7. A fusion protein of BDNF and an anti-human transferrin receptor antibody, wherein the amino acid sequence of the heavy chain variable region of the antibody is selected from the group consisting of (1) to (14) below:

(1) an amino acid sequence comprising the amino acid sequence set forth as SEQ ID NO:76 or SEQ ID NO:77 in CDR1, the amino acid sequence set forth as SEQ ID NO:78 or SEQ ID NO:79 in CDR2, and the amino acid sequence set forth as SEQ ID NO:80 or SEQ ID NO:81 in CDR3;

(2) an amino acid sequence comprising the amino acid sequence set forth as SEQ ID NO:82 or SEQ ID NO:83 in CDR1, the amino acid sequence set forth as SEQ ID NO:84 or SEQ ID NO:85 in CDR2, and the amino acid sequence set forth as SEQ ID NO:86 or SEQ ID NO:87 in CDR3;

(3) an amino acid sequence comprising the amino acid sequence set forth as SEQ ID NO:88 or SEQ ID NO:89 in CDR1, the amino acid sequence set forth as SEQ ID NO:90 or SEQ ID NO:91 in CDR2, and the amino acid sequence set forth as SEQ ID NO:92 or SEQ ID NO:93 in CDR3;

(4) an amino acid sequence comprising the amino acid sequence set forth as SEQ ID NO:94 or SEQ ID NO:95 in CDR1, the amino acid sequence set forth as SEQ ID NO:96 or SEQ ID NO:97 in CDR2, and the amino acid sequence set forth as SEQ ID NO:98 or SEQ ID NO:99 in CDR3;

(5) an amino acid sequence comprising the amino acid sequence set forth as SEQ ID NO:100 or SEQ ID NO:101 in CDR1, the amino acid sequence set forth as SEQ ID NO:102 or SEQ ID NO:103 in CDR2, and the amino acid sequence set forth as SEQ ID NO:104 or SEQ ID NO: 105 in CDR3;

(6) an amino acid sequence comprising the amino acid sequence set forth as SEQ ID NO:106 or SEQ ID NO: 107 in CDR1, the amino acid sequence set forth as SEQ ID NO:108 or SEQ ID NO:266 in CDR2, and the amino acid sequence set forth as SEQ ID NO: 109 or SEQ ID NO: 110 in CDR3;

(7) an amino acid sequence comprising the amino acid sequence set forth as SEQ ID NO:111 or SEQ ID NO:112 in CDR1, the amino acid sequence set forth as SEQ ID NO:113 or SEQ ID NO:114 in CDR2, and the amino acid sequence set forth as SEQ ID NO:115 or SEQ ID NO:116 in CDR3;

(8) an amino acid sequence comprising the amino acid sequence set forth as SEQ ID NO:117 or SEQ ID NO:118 in CDR1, the amino acid sequence set forth as SEQ ID NO:119 or SEQ ID NO:267 in CDR2, and the amino acid sequence set forth as SEQ ID NO: 120 or SEQ ID NO: 121 in CDR3;

(9) an amino acid sequence comprising the amino acid sequence set forth as SEQ ID NO: 122 or SEQ ID NO: 123 in CDR1, the amino acid sequence set forth as SEQ ID NO:124 or SEQ ID NO:125 in CDR2, and the amino acid sequence set forth as SEQ ID NO: 126 or SEQ ID NO: 127 in CDR3;

(10) an amino acid sequence comprising the amino acid sequence set forth as SEQ ID NO: 128 or SEQ ID NO: 129 or CDR1, the amino acid sequence set forth as SEQ ID NO: 130 or SEQ ID NO: 131 in CDR2, and the amino acid sequence set forth as SEQ ID NO: 132 or SEQ ID NO: 133 in CDR3;

(11) an amino acid sequence comprising the amino acid sequence set forth as SEQ ID NO: 134 or SEQ ID NO: 135 in CDR1, the amino acid sequence set forth as SEQ ID NO: 136 or SEQ ID NO: 137 in CDR2, and the amino acid sequence set forth as SEQ ID NO:138 or SEQ ID NO: 139 in CDR3;

(12) an amino acid sequence comprising the amino acid sequence set forth as SEQ ID NO: 140 or SEQ ID NO: 141 in CDR1, the amino acid sequence set forth as SEQ ID NO: 142 or SEQ ID NO: 143 in CDR2, and the amino acid sequence set forth as SEQ ID NO: 144 or SEQ ID NO: 145 in CDR3;

(13) an amino acid sequence comprising the amino acid sequence set forth as SEQ ID NO: 146 or SEQ ID NO: 147 in CDR1, the amino acid sequence set forth as SEQ ID NO: 148 or SEQ ID NO: 149 in CDR2, and the amino acid sequence set forth as SEQ ID NO:150 or SEQ ID NO:151 in CDR3; and

(14) an amino acid sequence comprising the amino acid sequence set forth as SEQ ID NO: 152 or SEQ ID NO: 153 in CDR1, the amino acid sequence set forth as SEQ ID NO: 154 or SEQ ID NO: 155 in CDR2, and the amino acid sequence set forth as SEQ ID NO:156 or SEQ ID NO:157 in CDR3.

8. The fusion protein of BDNF and an anti-human transferrin receptor antibody according to the above 7, wherein the amino acid sequence of the heavy chain variable region of the antibody is selected from the group consisting of (1) to (14) below:

(1) an amino acid sequence comprising the amino acid sequence set forth as SEQ ID NO:76 in CDR1, the amino acid sequence set forth as SEQ ID NO:78 in CDR2, and the amino acid sequence set forth as SEQ ID NO:80 in CDR3;

(2) an amino acid sequence comprising the amino acid sequence set forth as SEQ ID NO:82 in CDR1, the amino acid sequence set forth as SEQ ID NO:84 in CDR2, and the amino acid sequence set forth as SEQ ID NO:86 in CDR3;

(3) an amino acid sequence comprising the amino acid sequence set forth as SEQ ID NO:88 in CDR1, the amino acid sequence set forth as SEQ ID NO:90 in CDR2, and the amino acid sequence set forth as SEQ ID NO:92 in CDR3;

(4) an amino acid sequence comprising the amino acid sequence set forth as SEQ ID NO:94 in CDR1, the amino acid sequence set forth as SEQ ID NO:96 in CDR2, and the amino acid sequence set forth as SEQ ID NO:98 in CDR3;

(5) an amino acid sequence comprising the amino acid sequence set forth as SEQ ID NO: 100 in CDR1, the amino acid sequence set forth as SEQ ID NO: 102 in CDR2, and the amino acid sequence set forth as SEQ ID NO: 104 in CDR3;

(6) an amino acid sequence comprising the amino acid sequence set forth as SEQ ID NO: 106 in CDR1, the amino acid sequence set forth as SEQ ID NO: 108 in CDR2, and the amino acid sequence set forth as SEQ ID NO: 109 in CDR3;

(7) an amino acid sequence comprising the amino acid sequence set forth as SEQ ID NO: 111 in CDR1, the amino acid sequence set forth as SEQ ID NO:113 in CDR2, and the amino acid sequence set forth as SEQ ID NO: 115 as CDR3;

(8) an amino acid sequence comprising the amino acid sequence set forth as SEQ ID NO: 117 in CDR1, the amino acid sequence set forth as SEQ ID NO: 119 in CDR2, and the amino acid sequence set forth as SEQ ID NO: 120 in CDR3;

(9) an amino acid sequence comprising the amino acid sequence set forth as SEQ ID NO: 122 in CDR1, the amino acid sequence set forth as SEQ ID NO: 124 in CDR2, and the amino acid sequence set forth as SEQ ID NO: 126 in CDR3;

(10) an amino acid sequence comprising the amino acid sequence set forth as SEQ ID NO:128 in CDR1, the amino acid sequence set forth as SEQ ID NO: 130 in CDR2, and the amino acid sequence set forth as SEQ ID NO: 132 in CDR3;

(11) an amino acid sequence comprising the amino acid sequence set forth as SEQ ID NO:134 in CDR1, the amino acid sequence set forth as SEQ ID NO:136 in CDR2, and the amino acid sequence set forth as SEQ ID NO: 138 in CDR3;

(12) an amino acid sequence comprising the amino acid sequence set forth as SEQ ID NO:140 in CDR1, the amino acid sequence set forth as SEQ ID NO: 142 in CDR2, and the amino acid sequence set forth as SEQ ID NO: 144 in CDR3;

(13) an amino acid sequence comprising the amino acid sequence set forth as SEQ ID NO:146 in CDR1, the amino acid sequence set forth as SEQ ID NO: 148 in CDR2, and the amino acid sequence set forth as SEQ ID NO: 150 in CDR3; and

(14) an amino acid sequence comprising the amino acid sequence set forth as SEQ ID NO:152 in CDR1, the amino acid sequence set forth as SEQ ID NO: 154 in CDR2, and the amino acid sequence set forth as SEQ ID NO: 156 in CDR3.

9. A fusion protein of BDNF and an anti-human transferrin receptor antibody, wherein the amino acid sequences of CDR1, CDR2 and CDR3 in the heavy chain of the antibody have a homology not lower than 80% to the amino acid sequences of CDR1, CDR2 and CDR3, respectively, in the heavy chain according to the above 7 or 8.

10. A fusion protein of BDNF and an anti-human transferrin receptor antibody, wherein the amino acid sequences of CDR1, CDR2 and CDR3 in the heavy chain of the antibody have a homology not lower than 90% to the amino acid sequences of CDR1, CDR2 and CDR3, respectively, in the heavy chain according to the above 7 or 8.

11. A fusion protein of BDNF and an anti-human transferrin receptor antibody, wherein 1 to 5 amino acids are substituted, deleted or added relative to the amino acid sequence that forms at least one of the CDRs in the heavy chain according to the above 7 or 8.

12. A fusion protein of BDNF and an anti-human transferrin receptor antibody, wherein 1 to 3 amino acids are substituted, deleted or added relative to the amino acid sequence that forms at least one of the CDRs in the heavy chain according to the above 7 or 8.

13. A fusion protein of BDNF and an anti-human transferrin receptor antibody, wherein the light chain variable region and the heavy chain variable region of the antibody are selected from the group consisting of (1) to (14) below:

(1) the light chain variable region comprising the amino acid sequence set forth as SEQ ID NO:6 or SEQ ID NO:7 as CDR1, the amino acid sequence set forth as SEQ ID NO:8 or SEQ ID NO:9 or the amino acid sequence Trp-Thr-Ser as CDR2, and the amino acid sequence set forth as SEQ ID NO:10 as CDR3; and the heavy chain variable region comprising the amino acid sequence set forth as SEQ ID NO:76 or SEQ ID NO:77 as CDR1, the amino acid sequence set forth as SEQ ID NO:78 or SEQ ID NO:79 as CDR2, and the amino acid sequence set forth as SEQ ID NO:80 or SEQ ID NO:81 as CDR3;

(2) the light chain variable region comprising the amino acid sequence set forth as SEQ ID NO:11 or SEQ ID NO:12 as CDR1, the amino acid sequence set forth as SEQ ID NO: 13 or SEQ ID NO: 14 or the amino acid sequence Tyr-Ala-Ser as CDR2, and the amino acid sequence set forth as SEQ ID NO:15 as CDR3; and the heavy chain variable region comprising the amino acid sequence set forth as SEQ ID NO:82 or SEQ ID NO:83 as CDR1, the amino acid sequence set forth as SEQ ID NO:84 or SEQ ID NO:85 as CDR2, and the amino acid sequence set forth as SEQ ID NO:86 or SEQ ID NO:87 as CDR3;

(3) the light chain variable region comprising the amino acid sequence set forth as SEQ ID NO: 16 or SEQ ID NO:17 as CDR1, the amino acid sequence set forth as SEQ ID NO: 18 or SEQ ID NO: 19 or the amino acid sequence Lys-Val-Ser as CDR2, and the amino acid sequence set forth as SEQ ID NO:20 as CDR3; and the heavy chain variable region comprising the amino acid sequence set forth as SEQ ID NO:88 or SEQ ID NO:89 as CDR1, the amino acid sequence set forth as SEQ ID NO:90 or SEQ ID NO:91 as CDR2, and the amino acid sequence set forth as SEQ ID NO:92 or SEQ ID NO:93 as CDR3;

(4) the light chain variable region comprising the amino acid sequence set forth as SEQ ID NO:21 or SEQ ID NO:22 as CDR1, the amino acid sequence set forth as SEQ ID NO:23 or SEQ ID NO:24 or the amino acid sequence Asp-Thr-Ser as CDR2, and the amino acid sequence set forth as SEQ ID NO:25 as CDR3; and the heavy chain variable region comprising the amino acid sequence set forth as SEQ ID NO:94 or SEQ ID NO:95 as CDR1, the amino acid sequence set forth as SEQ ID NO:96 or SEQ ID NO:97 as CDR2, and the amino acid sequence set forth as SEQ ID NO:98 or SEQ ID NO:99 as CDR3;

(5) the light chain variable region comprising the amino acid sequence set forth as SEQ ID NO:26 or SEQ ID NO:27 as CDR1, the amino acid sequence set forth as SEQ ID NO:28 or SEQ ID NO:29 or the amino acid sequence Asp-Thr-Ser as CDR2, and the amino acid sequence set forth as SEQ ID NO:30 as CDR3; and the heavy chain variable region comprising the amino acid sequence set forth as SEQ ID NO: 100 or SEQ ID NO: 101 as CDR1, the amino acid sequence set forth as SEQ ID NO: 102 or SEQ ID NO: 103 as CDR2, and the amino acid sequence set forth as SEQ ID NO: 104 or SEQ ID NO: 105 as CDR3;

(6) the light chain variable region comprising the amino acid sequence set forth as SEQ ID NO:31 or SEQ ID NO:32 as CDR1, the amino acid sequence set forth as SEQ ID NO:33 or SEQ ID NO:34 or the amino acid sequence Ala-Ala-Ser as CDR2, and the amino acid sequence set forth as SEQ ID NO:35 as CDR3; and the heavy chain variable region comprising the amino acid sequence set forth as SEQ ID NO: 106 or SEQ ID NO: 107 as CDR1, the amino acid sequence set forth as SEQ ID NO: 108 or SEQ ID NO:266, as CDR2, and the amino acid sequence set forth as SEQ ID NO: 109 or SEQ ID NO: 110 as CDR3;

(7) the light chain variable region comprising the amino acid sequence set forth as SEQ ID NO:36 or SEQ ID NO:37 as CDR1, the amino acid sequence set forth as SEQ ID NO:38 or SEQ ID NO:39 or the amino acid sequence Gln-Thr-Ser as CDR2, and the amino acid sequence set forth as SEQ ID NO:40 as CDR3; and the heavy chain variable region comprising the amino acid sequence set forth as SEQ ID NO:111 or SEQ ID NO:112 as CDR1, the amino acid sequence set forth as SEQ ID NO:113 or SEQ ID NO:114 as CDR2, and the amino acid sequence set forth as SEQ ID NO:115 or SEQ ID NO:116 as CDR3;

(8) the light chain variable region comprising the amino acid sequence set forth as SEQ ID NO:41 or SEQ ID NO:42 as CDR1, the amino acid sequence set forth as SEQ ID NO:43 or SEQ ID NO:44 or the amino acid sequence Gly-Thr-Ser as CDR2, and the amino acid sequence set forth as SEQ ID NO:45 as CDR3; and the heavy chain variable region comprising the amino acid sequence set forth as SEQ ID NO:117 or SEQ ID NO:118 as CDR1, the amino acid sequence set forth as SEQ ID NO:119 or SEQ ID NO:267 as CDR2, and the amino acid sequence set forth as SEQ ID NO: 120 or SEQ ID NO: 121 as CDR3;

(9) the light chain variable region comprising the amino acid sequence set forth as SEQ ID NO:46 or SEQ ID NO:47 as CDR1, the amino acid sequence set forth as SEQ ID NO:48 or SEQ ID NO:49 or the amino acid sequence Phe-Thr-Ser as CDR2, and the amino acid sequence set forth as SEQ ID NO:50 as CDR3; and the heavy chain variable region comprising the amino acid sequence set forth as SEQ ID NO: 122 or SEQ ID NO: 123 as CDR1, the amino acid sequence set forth as SEQ ID NO:124 or SEQ ID NO: 125 as CDR2, and the amino acid sequence set forth as SEQ ID NO: 126 or SEQ ID NO: 127 as CDR3;

(10) the light chain variable region comprising the amino acid sequence set forth as SEQ ID NO:51 or SEQ ID NO:52 as CDR1, the amino acid sequence set forth as SEQ ID NO:53 or SEQ ID NO:54 or the amino acid sequence Ala-Ala-Ser as CDR2, and the amino acid sequence set forth as SEQ ID NO:55 as CDR3; and the heavy chain variable region comprising the amino acid sequence set forth as SEQ ID NO: 128 or SEQ ID NO: 129 as CDR1, the amino acid sequence set forth as SEQ ID NO: 130 or SEQ ID NO: 131 as CDR2, and the amino acid sequence set forth as SEQ ID NO: 132 or SEQ ID NO: 133 as CDR 3;

(11) the light chain variable region comprising the amino acid sequence set forth as SEQ ID NO:56 or SEQ ID NO:57 as CDR1, the amino acid sequence set forth as SEQ ID NO:58 or SEQ ID NO:59 or the amino acid sequence Tyr-Ala-Ser as CDR2, and the amino acid sequence set forth as SEQ ID NO:60 as CDR3; and the heavy chain variable region comprising the amino acid sequence set forth as SEQ ID NO: 134 or SEQ ID NO: 135 as CDR1, the amino acid sequence set forth as SEQ ID NO: 136 or SEQ ID NO: 137 as CDR2, and the amino acid sequence set forth as SEQ ID NO: 138 or SEQ ID NO: 139 as CDR3;

(12) the light chain variable region comprising the amino acid sequence set forth as SEQ ID NO:61 or SEQ ID NO:62 as CDR1, the amino acid sequence set forth as SEQ ID NO:63 or SEQ ID NO:64 or the amino acid sequence Trp-Ser-Ser as CDR2, and the amino acid sequence set forth as SEQ ID NO:65 as CDR3; and the heavy chain variable region comprising the amino acid sequence set forth as SEQ ID NO: 140 or SEQ ID NO: 141 as CDR1, the amino acid sequence set forth as SEQ ID NO: 142 or SEQ ID NO: 143 as CDR2, and the amino acid sequence set forth as SEQ ID NO: 144 or SEQ ID NO: 145 as CDR3;

(13) the light chain variable region comprising the amino acid sequence set forth as SEQ ID NO:66 or SEQ ID NO:67 as CDR1, the amino acid sequence set forth as SEQ ID NO:68 or SEQ ID NO:69 or the amino acid sequence Tyr-Ala-Ser as CDR2, and the amino acid sequence set forth as SEQ ID NO:70 as CDR3; and the heavy chain variable region comprising the amino acid sequence set forth as SEQ ID NO: 146 or SEQ ID NO: 147 as CDR1, the amino acid sequence set forth as SEQ ID NO: 148 or SEQ ID NO: 149 as CDR2, and the amino acid sequence set forth as SEQ ID NO:150 or SEQ ID NO:151 as CDR3; and

(14) the light chain variable region comprising the amino acid sequence set forth as SEQ ID NO:71 or SEQ ID NO:72 as CDR1, the amino acid sequence set forth as SEQ ID NO:73 or SEQ ID NO:74 or the amino acid sequence Asp-Thr-Ser as CDR2, and the amino acid sequence set forth as SEQ ID NO:75 as CDR3; and the heavy chain variable region comprising the amino acid sequence set forth as SEQ ID NO: 152 or SEQ ID NO: 153 as CDR1, the amino acid sequence set forth as SEQ ID NO:154 or SEQ ID NO: 155 as CDR2, and the amino acid sequence set forth as SEQ ID NO: 156 or SEQ ID NO: 157 as CDR3.

14. The fusion protein of BDNF and an anti-human transferrin receptor antibody according to the above 13, wherein the light chain variable region and the heavy chain variable region of the antibody are selected from the group consisting of (1) to (14) below:

(1) the light chain variable region comprising the amino acid sequence set forth as SEQ ID NO:6 as CDR1, the amino acid sequence set forth as SEQ ID NO:8 as CDR2, and the amino acid sequence set forth as SEQ ID NO: 10 as CDR3; and the heavy chain variable region comprising the amino acid sequence set forth as SEQ ID NO:76 as CDR1, the amino acid sequence set forth as SEQ ID NO:78 as CDR2, and the amino acid sequence set forth as SEQ ID NO:80 as CDR3;

(2) the light chain variable region comprising the amino acid sequence set forth as SEQ ID NO: 11 as CDR1, the amino acid sequence set forth as SEQ ID NO: 13 as CDR2, and the amino acid sequence set forth as SEQ ID NO: 15 as CDR3; and the heavy chain variable region comprising the amino acid sequence set forth as SEQ ID NO:82 as CDR1, the amino acid sequence set forth as SEQ ID NO:84 as CDR2, and the amino acid sequence set forth as SEQ ID NO:86 as CDR3;

(3) the light chain variable region comprising the amino acid sequence set forth as SEQ ID NO: 16 as CDR1, the amino acid sequence set forth SEQ ID NO:18 as CDR2, and the amino acid sequence set forth as SEQ ID NO:20 as CDR3; and the heavy chain variable region comprising the amino acid sequence set forth as SEQ ID NO:88 as CDR1, the amino acid sequence set forth as SEQ ID NO:90 as CDR2, and the amino acid sequence set forth as SEQ ID NO:92 as CDR3;

(4) the light chain variable region comprising the amino acid sequence set forth as SEQ ID NO:21 as CDR1, the amino acid sequence set forth as SEQ ID NO:23 as CDR2, and the amino acid sequence set forth as SEQ ID NO:25 as CDR3; and the heavy chain variable region comprising the amino acid sequence set forth as SEQ ID NO:94 as CDR1, the amino acid sequence set forth as SEQ ID NO:96 as CDR2, and the amino acid sequence set forth as SEQ ID NO:98 as CDR3;

(5) the light chain variable region comprising the amino acid sequence set forth as SEQ ID NO:26 as CDR1, the amino acid sequence set forth as SEQ ID NO:28 as CDR2, and the amino acid sequence set forth as SEQ ID NO:30 as CDR3; and the heavy chain variable region comprising the amino acid sequence set forth as SEQ ID NO:100 as CDR1, the amino acid sequence set forth as SEQ ID NO: 102 as CDR2, and the amino acid sequence set forth as SEQ ID NO: 104 as CDR3;

(6) the light chain variable region comprising the amino acid sequence set forth as SEQ ID NO:31 as CDR1, the amino acid sequence set forth as SEQ ID NO:33 as CDR2, and the amino acid sequence set forth as SEQ ID NO:35 as CDR3; and the heavy chain variable region comprising the amino acid sequence set forth as SEQ ID NO:106 as CDR1, the amino acid sequence set forth as SEQ ID NO: 108 as CDR2, and the amino acid sequence set forth as SEQ ID NO: 109 as CDR3;

(7) the light chain variable region comprising the amino acid sequence set forth as SEQ ID NO:36 as CDR1, the amino acid sequence set forth as SEQ ID NO:38 as CDR2, and the amino acid sequence set forth as SEQ ID NO:40 as CDR3; and the heavy chain variable region comprising the amino acid sequence set forth as SEQ ID NO:111 as CDR1, the amino acid sequence set forth as SEQ ID NO: 113 as CDR2, and the amino acid sequence set forth as SEQ ID NO: 115 as CDR3;

(8) the light chain variable region comprising the amino acid sequence set forth as SEQ ID NO:41 as CDR1, the amino acid sequence set forth as SEQ ID NO:43 as CDR2, and the amino acid sequence set forth as SEQ ID NO:45 as CDR3; and the heavy chain variable region comprising the amino acid sequence set forth as SEQ ID NO:117 as CDR1, the amino acid sequence set forth as SEQ ID NO: 119 as CDR2, and the amino acid sequence set forth as SEQ ID NO: 120 as CDR 3;

(9) the light chain variable region comprising the amino acid sequence set forth as SEQ ID NO:46 as CDR1, the amino acid sequence set forth as SEQ ID NO:48 as CDR2, and the amino acid sequence set forth as SEQ ID NO:50 as CDR3; and the heavy chain variable region comprising the amino acid sequence set forth as SEQ ID NO:122 as CDR1, the amino acid sequence set forth as SEQ ID NO: 124 as CDR2, and the amino acid sequence set forth as SEQ ID NO: 126 as CDR3;

(10) the light chain variable region comprising the amino acid sequence set forth as SEQ ID NO:51 as CDR1, the amino acid sequence set forth as SEQ ID NO:53 as CDR2, and the amino acid sequence set forth as SEQ ID NO:55 as CDR3; and the heavy chain variable region comprising the amino acid sequence set forth as SEQ ID NO:128 as CDR1, the amino acid sequence set forth as SEQ ID NO: 130 as CDR2, and the amino acid sequence set forth as SEQ ID NO: 132 as CDR3;

(11) the light chain variable region comprising the amino acid sequence set forth as SEQ ID NO:56 as CDR1, the amino acid sequence set forth as SEQ ID NO:58 as CDR2, and the amino acid sequence set forth as SEQ ID NO:60 as CDR3; and the heavy chain variable region comprising the amino acid sequence set forth as SEQ ID NO:134 as CDR1, the amino acid sequence set forth as SEQ ID NO: 136 as CDR2, and the amino acid sequence set forth as SEQ ID NO: 138 as CDR3;

(12) the light chain variable region comprising the amino acid sequence set forth as SEQ ID NO:61 as CDR1, the amino acid sequence set forth as SEQ ID NO:63 as CDR2, and the amino acid sequence set forth as SEQ ID NO:65 as CDR3; and the heavy chain variable region comprising the amino acid sequence set forth as SEQ ID NO:140 as CDR1, the amino acid sequence set forth as SEQ ID NO: 142 as CDR2, and the amino acid sequence set forth as SEQ ID NO: 144 as CDR3;

(13) the light chain variable region comprising the amino acid sequence set forth as SEQ ID NO:66 as CDR1, the amino acid sequence set forth as SEQ ID NO:68 as CDR2, and the amino acid sequence set forth as SEQ ID NO:70 as CDR3; and the heavy chain variable region comprising the amino acid sequence set forth as SEQ ID NO:146 as CDR1, the amino acid sequence set forth as SEQ ID NO: 148 as CDR2, and the amino acid sequence set forth as SEQ ID NO: 150 as CDR3; and

(14) the light chain variable region comprising the amino acid sequence set forth as SEQ ID NO:71 as CDR1, the amino acid sequence set forth as SEQ ID NO:73 as CDR2, and the amino acid sequence set forth as SEQ ID NO:75 as CDR3; and the heavy chain variable region comprising the amino acid sequence set forth as SEQ ID NO:152 as CDR1, the amino acid sequence set forth as SEQ ID NO: 154 as CDR2, and the amino acid sequence set forth as SEQ ID NO: 156 as CDR3.

15. A fusion protein of BDNF and an anti-human transferrin receptor antibody, wherein the amino acid sequence of each of CDR1, CDR2 and CDR3 in the light chain and the heavy chain of the antibody has a homology not lower than 80% to the amino acid sequence of the CDR1, CDR2 and CDR3, of one of the combinations of the light chain and the heavy chain according to the above 13 or 14.

16. A fusion protein of BDNF and an anti-human transferrin receptor antibody, wherein the amino acid sequence of each of CDR1, CDR2 and CDR3 in the light chain and the heavy chain of the antibody has a homology not lower than 90% to the amino acid sequence of the CDR1, CDR2 and CDR3, of one of the combinations of the light chain and the heavy chain according to the above 13 or 14.

17. A fusion protein of BDNF and an anti-human transferrin receptor antibody, wherein 1 to 5 amino acids are substituted, deleted or added relative to the amino acid sequence that forms at least one CDR in each of the light chain and the heavy chain of one of the combinations of the light chain and the heavy chain according to the above 13 or 14.

18. A fusion protein of BDNF and an anti-human transferrin receptor antibody, wherein 1 to 3 amino acids are substituted, deleted or added relative to the amino acid sequence that forms at least one CDR in each of the light chain and the heavy chain of one of the combinations of the light chain and the heavy chain according to the above 13 or 14.

19. A fusion protein of BDNF and an anti-human transferrin receptor antibody, wherein the light chain variable region of the antibody comprises an amino acid sequence selected from the group consisting of the amino acid sequences set forth as SEQ ID NO: 158, SEQ ID NO:159, SEQ ID NO:160, SEQ ID NO:161, SEQ ID NO:162, and SEQ ID NO:163; and wherein the heavy chain variable region of the antibody comprises an amino acid sequence selected from the group consisting of the amino acid sequences set forth as SEQ ID NO: 166, SEQ ID NO: 167, SEQ ID NO:168, SEQ ID NO: 169, SEQ ID NO:170, and SEQ ID NO:171.

20. A fusion protein of BDNF and an anti-human transferrin receptor antibody, wherein the light chain variable region of the antibody comprises an amino acid sequence selected from the group consisting of the amino acid sequences set forth as SEQ ID NO: 174, SEQ ID NO:175, SEQ ID NO:176, SEQ ID NO:177, SEQ ID NO:178, and SEQ ID NO: 179; and wherein the heavy chain variable region of the antibody comprises an amino acid sequence selected from the group consisting of the amino acid sequences set forth as SEQ ID NO: 182, SEQ ID NO:183, SEQ ID NO:184, SEQ ID NO:185, SEQ ID NO:186, and SEQ ID NO: 187.

21. A fusion protein of BDNF and an anti-human transferrin receptor antibody, wherein the light chain variable region of the antibody comprises an amino acid sequence selected from the group consisting of the amino acid sequences set forth as SEQ ID NO: 190, SEQ ID NO: 191, SEQ ID NO:192, SEQ ID NO: 193, SEQ ID NO: 194, and SEQ ID NO:195; and wherein the heavy chain variable region of the antibody comprises an amino acid sequence selected from the group consisting of the amino acid sequences set forth as SEQ ID NO:204, SEQ ID NO:205, SEQ ID NO:206, SEQ ID NO:207, SEQ ID NO:208, and SEQ ID NO:209.

22. A fusion protein of BDNF and an anti-human transferrin receptor antibody, selected from the group consisting of (1a) to (3d) below:

(1a) an antibody, wherein the light chain variable region thereof comprises the amino acid sequence set forth as SEQ ID NO:163; and wherein the heavy chain variable region thereof comprises the amino acid sequence set forth as SEQ ID NO: 171, (2a) an antibody, wherein the light chain variable region thereof comprises the amino acid sequence set forth as SEQ ID NO:179; and wherein the heavy chain variable region thereof comprises the amino acid sequence set forth as SEQ ID NO: 187, (3a) an antibody, wherein the light chain variable region thereof comprises the amino acid sequence set forth as SEQ ID NO:191; and wherein the heavy chain variable region thereof comprises the amino acid sequence set forth as SEQ ID NO:205, (3b) an antibody, wherein the light chain variable region thereof comprises the amino acid sequence set forth as SEQ ID NO:193; and wherein the heavy chain variable region thereof comprises the amino acid sequence set forth as SEQ ID NO:205, (3c) an antibody, wherein the light chain variable region thereof comprises the amino acid sequence set forth as SEQ ID NO:194; and wherein the heavy chain variable region thereof comprises the amino acid sequence set forth as SEQ ID NO:205, and (3d) an antibody, wherein the light chain variable region thereof comprises the amino acid sequence set forth as SEQ ID NO:195; and wherein the heavy chain variable region thereof comprises the amino acid sequence set forth as SEQ ID NO:205.

23. A fusion protein of BDNF and an anti-human transferrin receptor antibody, selected from the group consisting of (1b) to (3l) below:

(1b) an antibody, wherein the light chain thereof comprises the amino acid sequence set forth as SEQ ID NO:164; and wherein the heavy chain thereof comprises the amino acid sequence set forth as SEQ ID NO: 172, (2b) an antibody, wherein the light chain thereof comprises the amino acid sequence set forth as SEQ ID NO:180; and wherein the heavy chain thereof comprises the amino acid sequence set forth as SEQ ID NO: 188, (3e) an antibody, wherein the light chain thereof comprises the amino acid sequence set forth as SEQ ID NO:196; and wherein the heavy chain thereof comprises the amino acid sequence set forth as SEQ ID NO:210, (3f) an antibody, wherein the light chain thereof comprises the amino acid sequence set forth as SEQ ID NO:198; and wherein the heavy chain thereof comprises the amino acid sequence set forth as SEQ ID NO:210, (3g) an antibody, wherein the light chain thereof comprises the amino acid sequence set forth as SEQ ID NO:200; and wherein the heavy chain thereof comprises the amino acid sequence set forth as SEQ ID NO:210, (3h) an antibody, wherein the light chain thereof comprises the amino acid sequence set forth as SEQ ID NO:202; and wherein the heavy chain thereof comprises the amino acid sequence set forth as SEQ ID NO:210, (3i) an antibody, wherein the light chain thereof comprises the amino acid sequence set forth as SEQ ID NO:196; and wherein the heavy chain thereof comprises the amino acid sequence set forth as SEQ ID NO:212, (3j) an antibody, wherein the light chain thereof comprises the amino acid sequence set forth as SEQ ID NO:198; and wherein the heavy chain thereof comprises the amino acid sequence set forth as SEQ ID NO:212, (3k) an antibody, wherein the light chain thereof comprises the amino acid sequence set forth as SEQ ID NO:200; and wherein the heavy chain thereof comprises the amino acid sequence set forth as SEQ ID NO:212, and (3l) an antibody, wherein the light chain thereof comprises the amino acid sequence set forth as SEQ ID NO:202; and wherein the heavy chain thereof comprises the amino acid sequence set forth as SEQ ID NO:212.

24. A fusion protein of BDNF and an anti-human transferrin receptor antibody, wherein the amino acid sequence of the light chain variable region and the amino acid sequence of the heavy chain variable region of the antibody have a homology not lower than 80% to the amino acid sequence of the light chain variable region and the amino acid sequence of the heavy chain variable region of the fusion proteins according to any one of the above 19 to 23.

25. A fusion protein of BDNF and an anti-human transferrin receptor antibody, wherein the amino acid sequence of the light chain variable region and the amino acid sequence of the heavy chain variable region of the antibody have a homology not lower than 90% to the amino acid sequence of the light chain variable region and the amino acid sequence of the heavy chain variable region of the fusion proteins according to any one of the above 19 to 23.

26. A fusion protein of BDNF and an anti-human transferrin receptor antibody, wherein 1 to 10 amino acids are substituted, deleted or added relative to the amino acid sequence that forms the light chain variable region of the fusion protein according to any one of the above 19 to 23.

27. A fusion protein of BDNF and an anti-human transferrin receptor antibody, wherein 1 to 3 amino acids are substituted, deleted or added relative to the amino acid sequence that forms the light chain variable region of the fusion protein according to any one of the above 19 to 23.

28. A fusion protein of BDNF and an anti-human transferrin receptor antibody, wherein 1 to 10 amino acids are substituted, deleted or added relative to the amino acid sequence that forms the heavy chain variable region of the fusion protein according to any one of the above 19 to 23.

29. A fusion protein of BDNF and an anti-human transferrin receptor antibody, wherein 1 to 3 amino acids are substituted, deleted or added relative to the amino acid sequence that forms the heavy chain variable region of the fusion protein according to any one of the above 19 to 23.

30. A fusion protein of BDNF and an anti-human transferrin receptor antibody, wherein 1 to 10 amino acids are substituted, deleted or added relative to the respective amino acid sequence that forms the light chain variable region and the heavy chain variable region of the fusion protein according to any one of the above 19 to 23.

31. A fusion protein of BDNF and an anti-human transferrin receptor antibody, wherein 1 to 3 amino acids are substituted, deleted or added relative to the respective amino acid sequence that forms the light chain variable region and the heavy chain variable region of the fusion protein according to any one of the above 19 to 23.

32. The fusion protein according to any one of the above 1 to 31, wherein the BDNF is linked to the light chain of the antibody on the C-terminal side thereof or the N-terminal side thereof.

33. The fusion protein according to the above 32, wherein the BDNF is linked, directly or via a linker, to the light chain of the antibody on the C-terminal side thereof or the N-terminal side thereof.

34. The fusion protein according to the above 33, wherein the linker is a peptide consisting of 1 to 50 amino acid residues.

35. The fusion protein, wherein the linker is a peptide comprising an amino acid sequence selected from the group consisting of glycine, serine, the amino acid sequence (Gly-Ser), the amino acid sequence (Gly-Gly-Ser), SEQ ID NO:3, SEQ ID NO:4, SEQ ID NO:5, and the amino acid sequence consisting of 1 to 10 thereof that are consecutively linked.

36. The fusion protein according to any one of the above 1 to 31, wherein the BDNF is linked to the heavy chain of the antibody on the C-terminal side thereof or the N-terminal side thereof.

37. The fusion protein according to the above 36, wherein the BDNF is linked, directly or via a linker, to the heavy chain of the antibody on the C-terminal side thereof or the N-terminal side thereof.

38. The fusion protein according to the above 37, wherein the linker is a peptide consisting of 1 to 50 amino acid residues.

39. The fusion protein according to the above 37, wherein the linker is a peptide comprising an amino acid sequence selected from the group consisting of the amino acid sequence (Gly-Ser), the amino acid sequence (Gly-Gly-Ser), SEQ ID NO:3, SEQ ID NO:4, and SEQ ID NO:5.

40. The fusion protein according to any one of the above 1 to 39, wherein the BDNF is human BDNF.

41. The fusion protein according to the above 40, wherein the human BDNF comprises the amino acid sequence set forth as SEQ ID NO:247 or an amino acid sequence substantially identical thereto, or has an equivalent function to the protein set forth as SEQ ID NO:247.

42. The fusion protein according to any one of the above 1 to 41, having an affinity to both the extracellular region of human transferrin receptor and the extracellular region of monkey transferrin receptor.

43. The fusion protein according to the above 42, wherein the dissociation constant of the anti-transferrin receptor antibody with the extracellular region of human transferrin receptor is not greater than $1 \times 10^{-8}$ M, and the dissociation constant of the anti-transferrin receptor antibody with the extracellular region of monkey transferrin receptor is not greater than $5 \times 10^{-8}$ M.

44. The fusion protein according to the above 40, wherein the fusion protein is selected from the group consisting of (1) to (4) below:

(1) the fusion protein, wherein the light chain of the humanized anti-hTfR antibody has the amino acid sequence set forth as SEQ ID NO:164, and wherein the heavy chain of the humanized anti-hTfR antibody is linked, on the C-terminal side thereof and via a linker sequence Gly-Ser, to the human BDNF, and the whole linked heavy chain has the amino acid sequence set for as SEQ ID NO:248;

(2) the fusion protein, wherein the light chain of the humanized anti-hTfR antibody has the amino acid sequence set forth as SEQ ID NO:180, and wherein the heavy chain of the humanized anti-hTfR antibody is linked, on the C-terminal side thereof and via a linker sequence Gly-Ser, to the human BDNF, and the whole linked heavy chain has the amino acid sequence set forth as SEQ ID NO:250;

(3) the fusion protein, wherein the light chain of the humanized anti-hTfR antibody has the amino acid sequence set forth as SEQ ID NO:196, and wherein the heavy chain of the humanized anti-hTfR antibody is linked, on the C-terminal side thereof and via a linker sequence Gly-Ser, to the human BDNF, and the whole linked heavy chain has the amino acid sequence set forth as SEQ ID NO:252; and (4) the fusion protein, wherein the light chain of the humanized anti-hTfR antibody has the amino acid sequence set forth as SEQ ID NO:196, and wherein the heavy chain of the humanized anti-hTfR antibody is linked, on the C-terminal side thereof and via a linker sequence consisting of 27 amino acids that is composed of the amino acid sequence Gly-Ser followed by consecutively linked five copies of the amino acid sequence Gly-Gly-Gly-Gly-Ser (SEQ ID NO:3), to the human BDNF, and the whole linked heavy chain has the amino acid sequence set forth as SEQ ID NO:254.

45. The fusion protein according to any one of the above 1 to 43, wherein the anti-human transferrin receptor antibody is an antigen-binding fragment.

46. The fusion protein according to the above 45, wherein the antigen-binding fragment is linked, on the N-terminal side thereof, and directly or via a linker, to the human BDNF.

47. The fusion protein according to the above 45 or 46, wherein the antigen-binding fragment is a single-chain antibody.

48. The fusion protein according to the above 47, wherein the light chain variable region of the anti-human transferrin receptor antibody is linked to the heavy chain variable region thereof and via a linker sequence binding a light chain to a heavy chain.

49. The fusion protein according to the above 48, wherein the light chain variable region of the anti-human transferrin receptor antibody is linked, on the C-terminal side thereof and via a linker sequence binding a light chain to a heavy chain, to the heavy chain variable region of the anti-human transferrin receptor antibody.

50. The fusion protein according to the above 48, wherein the heavy chain variable region of the anti-human transferrin receptor antibody is linked, on the C-terminal side thereof and via a linker sequence binding a light chain to a heavy chain, to the light chain variable region of the anti-human transferrin receptor antibody.

51. The fusion protein according to the above 48 to 50, wherein the linker sequence binding a light chain to a heavy chain consists of 2 to 50 amino acid residues.

52. The fusion protein according to the above 51, wherein the linker sequence binding a light chain to a heavy chain comprises an amino acid sequence selected from the group consisting of the amino acid sequence (Gly-Ser), the amino acid sequence (Gly-Gly-Ser), the amino acid sequence (Gly-Gly-Gly), SEQ ID NO:3, SEQ ID NO:4, SEQ ID NO:5, and the amino acid sequence consisting of 2 to 10 thereof that are consecutively linked.

53. The fusion protein according to the above 47 to 52, wherein the single-chain antibody is a single-chain antibody comprising a heavy chain variable region having the amino acid sequence set forth as SEQ ID NO:205 and a light chain variable region having the amino acid sequence set forth as SEQ ID NO: 191.

54. The fusion protein according to the above 53, wherein the single-chain antibody is a single-chain antibody consisting of the amino acid sequence set forth as SEQ ID NO:257, and wherein human BDNF is linked to the N-terminal side thereof directly or via a linker.

55. The fusion protein according to the above 54, wherein the single-chain antibody is a single-chain antibody consisting of the amino acid sequence set forth as SEQ ID NO:257, human pro-BDNF is linked to the N-terminal side thereof via a linker, and the fusion protein comprises the amino acid sequence set forth as SEQ ID NO:259.

56. The fusion protein according to the above 54, wherein the single-chain antibody is a single-chain antibody consisting of the amino acid sequence set forth as SEQ ID NO:257, human BDNF is linked to the N-terminal side thereof via a linker, and the fusion protein comprises the amino acid sequence set forth as SEQ ID NO:260.

57. The fusion protein according to the above 45 or 46, wherein the antigen-binding fragment is any one of Fab, F(ab')$_2$, or F(ab').

58. The fusion protein according to the above 57, wherein human BDNF is linked, directly or via a linker, to the heavy chain of any one of Fab, F(ab')$_2$, and F(ab'), on the N-terminal side thereof.

59. The fusion protein according to the above 58, wherein the light chain consists of the amino acid sequence set forth as SEQ ID NO: 196, the heavy chain is a Fab heavy chain consisting of the amino acid sequence set forth as SEQ ID NO:261, and the human BDNF is linked, directly or via a linker, to the heavy chain on the N-terminal side thereof.

60. The fusion protein according to the above 59, wherein the light chain consists of the amino acid sequence set forth as SEQ ID NO:196, and a portion consisting of the Fab heavy chain and human pro-BDNF linked, directly or via a linker, to the N-terminal side thereof, consists of the amino acid sequence set forth as SEQ ID NO:263.

61. The fusion protein according to the above 59, wherein the light chain consists of the amino acid sequence set forth as SEQ ID NO: 196, and a portion consisting of the Fab heavy chain and human BDNF linked, directly or via a linker, to the N-terminal side thereof, consists of the amino acid sequence set forth as SEQ ID NO:264.

62. A DNA fragment encoding the fusion protein according to any one of the above 1 to 61.

63. An expression vector comprising the DNA fragment according to the above 62 that is incorporated therein.

64. A mammalian cell transformed with the expression vector according to the above 63.

65. A pharmaceutical agent for preventing and/or treating disease or disorder benefiting from the exposure to BDNF, wherein the pharmaceutical agent comprises, as an active ingredient, the fusion protein according to any one of the above 1 to 61.

66. The pharmaceutical agent according to the above 65, wherein the disease or disorder is a nervous system disease or disorder.

67. The pharmaceutical agent according to the above 66, wherein the nervous system disease or disorder is neurodegenerative disease, depression, schizophrenia, epilepsy, autism, Rett syndrome, West syndrome, neonatal convulsion, behavior problems associated with dementia, anxiety, pain, Hirschsprung disease, or REM sleep behavior disorder.

68. The pharmaceutical agent according to the above 67, wherein the neurodegenerative disease is cerebral neurodegenerative disease, spinal degenerative disease, retinal degenerative disease, or peripheral neurodegenerative disease.

69. The pharmaceutical agent according to the above 68, wherein the cerebral neurodegenerative disease is neurodegenerative disease of cranial nervous system, cerebral ischemic disease, traumatic brain injury, leukoencephalopathy, or multiple sclerosis.

70. The pharmaceutical agent according to the above 69, wherein the neurodegenerative disease of cranial nervous system is Alzheimer's disease, Parkinson's disease, Huntington's disease, dementia with Lewy bodies, Pick's disease, multiple system atrophy, progressive ascending paralysis, or Down's syndrome.

71. Use of the fusion protein according to any one of the above 1 to 61, for preventing and/or treating disease or disorder benefiting from the exposure to BDNF.

72. Use of the fusion protein according to any one of the above 1 to 61, for the manufacture of a medicament for preventing and/or treating disease or disorder benefiting from the exposure to BDNF.

73. A method for preventing and/or treating disease or disorder benefiting from the exposure to BDNF, comprising administering a pharmaceutical composition containing a therapeutically effective amount of the fusion protein according to any one of the above 1 to 61 into the blood of a patient having the disease or disorder.

Effects of the Invention

By the present invention, a brain-derived neurotrophic factor (BDNF), which cannot pass through the blood-brain barrier, was synthesized in the form of a fusion protein with a specific anti-hTfR antibody, so as to make BDNF able to pass through the blood-brain barrier. Accordingly, BDNF is administered into the blood in such a fusion protein form by intravenous injection or the like, so as to make BDNF able to act on the central nervous system.

EMBODIMENTS FOR CARRYING OUT THE INVENTION

Figure 1:
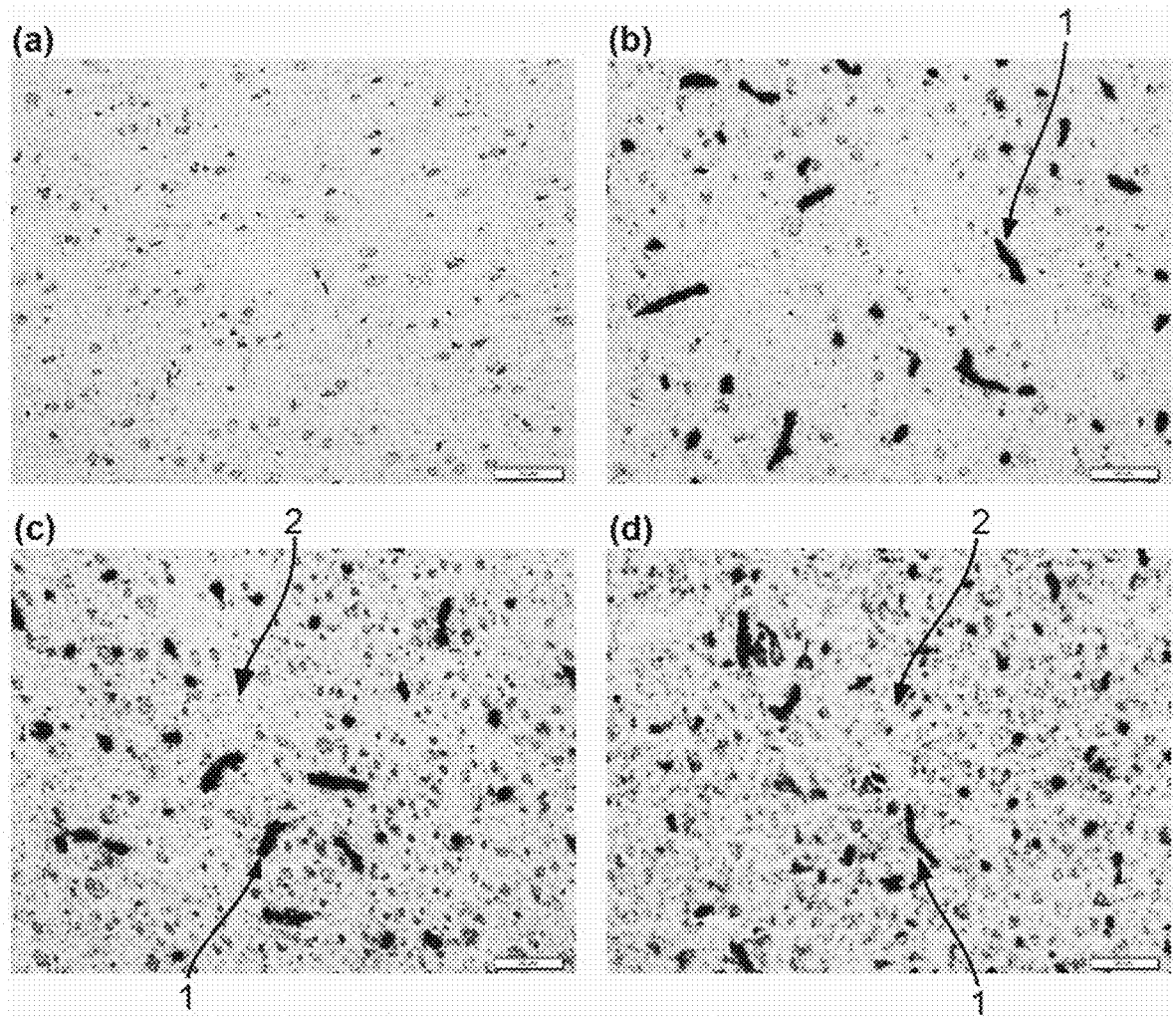
FIG. 1 Substitute photographs for drawings showing the result of the immunohistochemical staining of the anti-hTfR antibody in the cerebral cortex of a cynomolgus monkey after a single intravenous administration of the anti-hTfR antibody. Staining photographs of the cerebral cortex: (a) anti-hTfR antibody non-administered, (b) anti-hTfR antibody No. 1 administered, (c) anti-hTfR antibody No. 2 administered, (d) anti-hTfR antibody No. 3 administered. The bar at the bottom right in each photograph is a 50-µm gauge.

In the present invention, the term "antibody" refers mainly to any one of a human antibody, mouse antibody, humanized antibody, as well as a chimeric antibody between human antibody and non-human mammalian antibody, and a chimeric antibody between mouse antibody and non-mouse mammalian antibody, but the meaning of the term is not limited to them insofar as a substance of interest has a property to specifically bind to a certain antigen, and there is no specific limitation as to the animal species of the antibody, either. However, a humanized antibody is preferable.

In the present invention, the term "human antibody" refers to an antibody whose entire protein is encoded by a gene originating from human. The term "human antibody", however, also includes an antibody encoded by a gene obtained by introducing a mutation into an original human gene for a purpose of enhancing expression efficiency of the gene, for example, without modifying the original amino acid sequence. The term "human antibody" also includes an antibody which is produced by combining two or more genes encoding human antibodies and replacing a certain part of a human antibody with a part of another human antibody. A human antibody includes three complementarity determining regions (CDRs) in the light chain of the immunoglobulin and three complementarity determining regions (CDRs) in the heavy chain of the immunoglobulin. The three CDRs in the light chain of the immunoglobulin are called, from the N-terminal side, CDR1, CDR2 and CDR3, respectively. The three CDRs in the heavy chain of the immunoglobulin are also called, from the N-terminal side, CDR1, CDR2 and CDR3, respectively. The term "human antibody" also includes a human antibody produced by replacing a CDR of a human antibody with a CDR of another human antibody to modify such properties as the antigen specificity and the affinity of the original human antibodies, etc.

In the present invention, the term "human antibody" also includes an antibody which is produced through modification of the gene of the original human antibody by introducing a mutation, such as substitution, deletion, addition, to the amino acid sequence of the original antibody. When replacing one or more amino acids of the amino acid sequence of the original antibody with other amino acids, the number of amino acid replaced may preferably be 1 to 20, more preferably 1 to 5, and still more preferably 1 to 3. When deleting one or more amino acids of the amino acid sequence of the original antibody, the number of amino acids deleted may preferably be 1 to 20, more preferably 1 to 5, and still more preferably 1 to 3. An antibody produced by a combined mutation of these substitution and deletion of amino acids is also a "human antibody". In some cases, one or more amino acids, preferably 1 to 20, more preferably 1 to 5, and still more preferably 1 to 3 amino acids may be added inside the amino acid sequence of the original antibody or on its N- or C-terminus. An antibody produced by a combined mutation of addition, substitution, and deletion of amino acids is also a "human antibody". The amino acid sequence of such a mutated antibody has a homology of preferably not lower than 80%, more preferably not lower than 90%, still more preferably not lower than 95%, and even more preferably not lower than 98%, to the amino acid sequence of the original antibody. Thus, in the present invention, the term "gene originating from human" includes not only the unmutated gene originating from human but also a gene produced by modifying it.

In the present invention, the term "mouse antibody" refers to an antibody whose entire protein is encoded by a gene originating from a mouse. However, the term "mouse antibody" also includes an antibody that is encoded by a gene produced by introducing a mutation into the original mouse gene without causing a change in its amino acid sequence but in order, for example, to improve the expression efficiency of the gene. Further, the term "mouse antibody" also includes an antibody produced through combining two or more genes encoding mouse antibodies by replacing a part of a mouse antibody with a part of another mouse antibody.

A mouse antibody has three complementarity determining regions (CDRs) in the light chain of the immunoglobulin and three complementarity determining regions (CDRs) in the heavy chain of the immunoglobulin. The three CDRs in the light chain of the immunoglobulin are called, from the N-terminal side, CDR1, CDR2 and CDR3, respectively. The three CDRs in the heavy chain of the immunoglobulin are also called, from the N-terminal side, CDR1, CDR2 and CDR3, respectively. The term "mouse antibody" also includes an antibody produced by replacing a CDR of a mouse antibody with a CDR of another mouse antibody to modify the specificity and affinity of the original mouse antibodies.

In the present invention, the term "mouse antibody" also includes an antibody which is produced through modification of the gene of the original mouse antibody by introducing a mutation, such as substitution, deletion, addition, to the amino acid sequence of the original antibody. When replacing one or more amino acids of the amino acid sequence of the original antibody with other amino acids, the number of amino acid replaced may preferably be 1 to 20, more preferably 1 to 5, and still more preferably 1 to 3. When deleting one or more amino acids of the amino acid sequence of the original antibody, the number of amino acids deleted may preferably be 1 to 20, more preferably 1 to 5, and still more preferably 1 to 3. An antibody produced by a combined mutation of these substitution and deletion of amino acids is also included in the term "mouse antibody". When adding one or more amino acids, they may be added inside the amino acid sequence of the original antibody or on its N to or C to terminal side, preferably 1 to 20, more preferably 1 to 5, and still more preferably 1 to 3, in number. An antibody produced by a combined mutation of addition, substitution, and deletion of amino acids is also included in the term "mouse antibody". The amino acid sequence of such a mutated antibody has a homology of preferably not lower than 80%, more preferably not lower than 90%, still more preferably not lower than 95%, and even more preferably not lower than 98%, to the amino acid sequence of the original antibody. Thus, in the present invention, the term "gene originating from mouse" includes not only the unmutated gene originating from mouse but also a gene produced by modifying it.

In the present invention, the term "humanized antibody" refers to an antibody in which part of the amino acid sequence of its variable region (e.g., especially the whole or part of its CDRs) originates from a non-human mammal while the rest originates from human. An example of humanized antibody is an antibody produced by replacing the three complementarity determining regions (CDRs) of the light chain of the immunoglobulin and the three complementarity determining regions (CDRs) of the heavy chain of the immunoglobulin constituting a human antibody, with CDRs from a non-human mammal. As far as it originates from a non-human mammal, there is no particular limitation as to the biological species from which those CDRs originate that are grafted into a proper position of the human antibody, though preferred are mouse, rat, rabbit, horse or non-human primate, more preferred are mouse and rat, and still more preferred is mouse.

In the present invention, the term "chimeric antibody" refers to an antibody produced by connecting fragments of two or more different antibodies originating from two or more different species.

A chimeric antibody between a human antibody and a non-human mammalian antibody is an antibody provided by replacing part of a human antibody with part of a non-human mammalian antibody. As explained below, an antibody is made of an Fc region, a Fab region and a hinge region. A specific example of such chimeric antibodies is a chimeric antibody whose Fc region originates from a human antibody while its Fab region originates from a non-human mammalian antibody. The hinge region either originates from a human antibody or from a non-human mammalian antibody. On the contrary, the term chimeric antibody also includes one whose Fc region originates from a non-human mammalian antibody while its Fab region originates from a human antibody. In such a case also, the hinge region either originates from a human antibody or from a non-human mammalian antibody.

An antibody can be viewed as composed of a variable region and a constant region. Additional examples of chimeric antibodies include an antibody in which the heavy chain constant region ($C_H$) and the light chain constant region ($C_l$) both originate from a human antibody while the heavy chain variable region ($V_H$) and the light chain variable region ($V_L$) both originate from an antibody of a non-human mammal, and conversely, an antibody in which the heavy chain constant region ($C_H$) and the light chain constant region ($C_l$) both originate from an antibody of a non-human mammal, while the heavy chain variable region ($V_H$) and the light chain variable region ($V_L$) both originate from a human antibody. In these, there is no particular limitation as to the biological species of the non-human mammal, as far as it is a non-human mammal, though preferred are mouse, rat, rabbit, horse or non-human primate, and mouse, for example.

A chimeric antibody between a mouse antibody and a non-mouse mammalian antibody is an antibody provided by replacing part of a mouse antibody with part of a non-mouse mammalian antibody. Specific examples of such chimeric antibodies include a chimeric antibody whose Fc region originates from a mouse antibody while its Fab region originates from a non-mouse mammalian antibody, and conversely, a chimeric antibody whose Fc region originates from a non-mouse mammal while its Fab region originates from a mouse antibody. In these, the biological species of the non-mouse mammal is preferably human.

A chimeric antibody between a human antibody and a mouse antibody is designated in particular "human/mouse chimeric antibody". Examples of human/mouse chimeric antibodies include a chimeric antibody in which the Fc region originates from a human antibody while the Fab region originates from a mouse antibody, and conversely, a chimeric antibody whose Fc region originates from mouse antibody, while its Fab region originates from a human antibody. A hinge region either originate from a human antibody or a mouse antibody. Additional specific examples of human/mouse chimeric antibodies include those whose heavy chain constant region ($C_H$) and light chain constant region ($C_l$) originate from a human antibody while its heavy chain variable region ($V_H$) and light chain variable region ($V_L$) originate from a mouse antibody, and conversely, those whose heavy chain constant region ($C_H$) and light chain constant region ($C_l$) originate from a mouse antibody while its heavy chain variable region ($V_H$) and light chain variable region ($V_L$) originate from a human antibody.

Originally, an antibody is of the basic structure having four polypeptide chains in total consisting of two immunoglobulin light chains and two immunoglobulin heavy chains. However, in the present invention the term "antibody" refers, besides an antibody having this basic structure, also to:

(1) one consisting of two polypeptide chains: a single immunoglobulin light chain and a single immunoglobulin heavy chain, and also, as explained later, (2) a single-chain antibody consisting of an immunoglobulin light chain which is linked, on the C-terminal side thereof, to a linker sequence which in turn is linked, on the C-terminal side thereof, to an immunoglobulin heavy chain, (3) single-chain antibodies consisting of an immunoglobulin heavy chain which is linked, on the C-terminal side thereof, to a linker sequence which in turn is linked, on the C-terminal side thereof, to an immunoglobulin light chain, and (4) one consisting of a Fab region, i.e., a structure left behind by removal of the Fc region from an antibody having the basic structure, as the original meaning, and one consisting of the Fab region and the whole or part of the hinge region (including Fab, F(ab'), and F(ab')$_2$) also are included in the term "antibody" in the present invention.

The term "Fab" refers to a molecule consisting of a light chain comprising the variable region and the $C_L$ region (light chain constant region) and a heavy chain comprising the variable region and the $C_H1$ region (portion 1 of heavy chain constant region) which are combined by a disulfide bond between their respective cysteine residues. While the heavy chain in a Fab can include part of the hinge region in addition to the variable region and the $C_H1$ region (portion 1 of heavy chain constant region), the hinge region in such a case lacks the cysteine residue that otherwise is present in the hinge region and would serve to link two heavy chains of an antibody together. In Fab, the light chain and the heavy chain are connected by a disulfide bond formed between the cysteine residue present in the light chain constant region ($C_L$ region) and the cysteine residue located in the heavy chain $C_H1$ region or the hinge region. As it lacks the cysteine residue in the hinge region which serves to bind two heavy chains of an antibody, Fab consists of a single light chain and a single heavy chain. In F(ab'), the heavy chain includes, in addition to a variable region and a $C_H1$ region, the whole or part of a hinge region containing a cysteine residue that could bind two heavy chains. F(ab')$_2$ is a molecule consisting of two F(ab')s bound together through a disulfide bond formed between the cysteine residues present in their respective hinge regions. Further, a polymer such as a dimer and a trimer, which consists of two or more antibodies connected with each other, directly or via a linker, is also included in the term "antibody". Moreover, in addition to the aforementioned, any molecule that includes part of an immunoglobulin molecule and has a property to specifically bind to the antigen is also included in the term "antibody" in the present invention. Thus, in the present invention, the term "immunoglobulin light chain" includes a molecule that is derived from an original immunoglobulin light chain and having the amino acid sequence of the whole or part of its variable region. Likewise, the term "immunoglobulin heavy chain" includes a molecule that is derived from an original immunoglobulin heavy chain and having the amino acid sequence of the whole or part of its variable region. Therefore, insofar as having the whole or part of the amino acid sequence of the variable region, a molecule is included in the term "immunoglobulin heavy chain", even if it lacks its Fc region, for example.

In the above, the term "Fc" or "Fc region" refers to a region comprising a fragment consisting of $C_H2$ region (portion 2 of the heavy chain constant region), and $C_H3$ region (portion 3 of the heavy chain constant region) in the antibody molecule. Fc or an Fc region may comprise a part of a hinge region, in addition to a $C_H^2$ region and a $C_H^3$ region.

Furthermore, in the present invention, the term "antibody" also includes:

(5) scFab, scF(ab'), and scF(ab')2, which are single-chain antibodies produced by binding the light chain to the heavy chain that form, respectively, the Fab, F(ab') and F(ab')$_2$ mentioned in (4) above, via a linker sequence. Such scFab, scF(ab') and scF(ab')2 may be a molecule in which either the light chain is linked, on the C-terminal side thereof, to a linker sequence, which in turn is linked, on the C-terminal side thereof, to the heavy chain, or the heavy chain is linked, on the C-terminal side thereof, to a linker sequence, which in turn is linked, on the C-terminal side thereof, to the light chain. Furthermore, a scFv, which is a single-chain antibody provided by binding the light chain variable region to the heavy chain variable region, via a linker sequence between them, is also included in the term "antibody" in the present invention. Such scFv may be a molecule in which either the light chain variable region is linked, on the C-terminal side thereof, to a linker sequence, which in turn is linked, on the C-terminal side thereof, to the heavy chain variable region, or the heavy chain variable region is linked, on the C-terminal side thereof, to a linker sequence, which in turn is linked, on the C-terminal side thereof, to the light chain variable region.

Furthermore, in addition to a full-length antibody and those described in (1) to (3) above, the term "antibody" in the present specification includes, any form of antigen-binding fragment which lacks part of the full-length antibody (antibody fragment), a concept which includes (4) and (5) above.

The term "antigen-binding fragment" refers to an antibody fragment that retains at least part of the specific binding activity to its antigen. In addition to those described above in (4) and (5), examples of binding fragments include variable region (Fv); a single-chain antibody (scFv) produced by linking the heavy chain variable region ($V_H$) and the light chain variable region ($V_L$), via a proper linker between them; a diabody, which is a dimer of a polypeptide that comprises a heavy chain variable region ($V_H$) and a light chain variable region ($V_L$); a minibody, which is a dimer of a molecule in which the heavy chain (H chain) of a scFv is linked to part of the constant region ($C_H3$), and other low-molecular-antibodies. However, as far as it has an antigen-binding ability, the term is not limited to these molecules. Such binding fragments include not only those produced by treating a full-length molecule of an antibody protein with a proper enzyme but also those produced by proper host cells using a genetically engineered antibody gene.

In the present invention, the term "single-chain antibody" refers to a protein in which an amino acid sequence comprising the whole or part of an immunoglobulin light chain variable region linked, on the C-terminal side thereof, to a linker sequence, which in turn is linked, on the C-terminal side thereof, to the amino acid sequence of the whole or part of an immunoglobulin heavy chain variable region, and having an ability to specifically bind a certain antigen. For example, those described in (2), (3) and (5) are included in "single-chain antibody". Further, a protein in which an amino acid sequence comprising the whole or part of an immunoglobulin heavy chain variable region is linked, on the C-terminal side thereof, to a linker sequence, which in turn is further linked, on the C-terminal side thereof, to the amino acid sequence of the whole or part of an immunoglobulin light chain variable region, and which has an ability to specifically bind to a certain antigen, is also included in the term "single-chain antibody" in the present invention. In a single-chain antibody in which an immunoglobulin heavy chain is linked, on the C-terminal side thereof and via a linker sequence, to an immunoglobulin light chain, the immunoglobulin heavy chain generally lacks the Fc region. An immunoglobulin light chain variable region has three complementarity determining regions (CDRs) which participate in determining the antigen specificity of an antibody. Likewise, an immunoglobulin heavy chain variable region also has three CDRs. Those CDRs are the primary regions that determine the antigen specificity of an antibody. Therefore, a single-chain antibody preferably contains all the three CDRs of the immunoglobulin heavy chain and all the three CDRs of the immunoglobulin light chain. However, it is also possible to provide a single-chain antibody in which one or more of those CDRs are deleted, insofar as the antigen-specific affinity of the antibody is retained.

In a single-chain antibody, the linker sequence placed between the light chain and the heavy chain of the immunoglobulin is preferably a peptide chain consisting of preferably 2 to 50, more preferably 8 to 50, still more preferably 10 to 30, even preferably 12 to 18, or 15 to 25, for example 15 or 25 amino acid residues. While there is no particular limitation as to the specific amino acid sequence of such a linker sequence insofar as the anti-hTfR antibody comprising the both chains linked thereby retains the affinity to hTfR, it is preferably made of glycine only, or of glycine and serine. For example, there are the amino acid sequence Gly-Ser, the amino acid sequence Gly-Gly-Ser, the amino acid sequence Gly-Gly-Gly, the amino acid sequence Gly-Gly-Gly-Ser (SEQ ID NO:3), the amino acid sequence Gly-Gly-Gly-Gly-Gly-Ser (SEQ ID NO:4), the amino acid sequence Ser-Gly-Gly-Gly-Gly-Gly (SEQ ID NO:5), or a sequence which includes a sequence corresponding to 2 to 10 or 2 to 5 of any of those amino acid sequences consecutively linked. For example, in linking the amino acid sequence of the entire immunoglobulin heavy chain variable region on the C-terminal side thereof and via a linker sequence, to immunoglobulin light chain variable region, a preferable linker sequence comprises a linker sequence consisting of a total of 15 amino acids corresponding to three of the amino acid sequence Gly-Gly-Gly-Gly-Ser (SEQ ID NO:3) consecutively linked.

In the present invention, the term "human transferrin receptor" or "hTfR" refers to a membrane protein having the amino acid sequence set forth as SEQ ID NO:1. The anti-hTfR antibody to be fused with BDNF is, in one of the embodiments of the present invention, that which specifically binds to the region from the cysteine residue at the position 89th from the N-terminus to the phenylalanine at the C-terminus in the amino acid sequence set forth as SEQ ID NO:1 (i.e., the extracellular region of the hTfR), though it is not limited to this embodiment. Further, in the present invention, the term "monkey transferrin receptor" or "monkey TfR" refers in particular to the membrane protein having the amino acid sequence set forth as SEQ ID NO:2, originating from cynomolgus monkey (*Macaca fascicularis*). The anti-hTfR antibody of the present invention is, in one of its embodiments, that which binds also to the region from the cysteine residue at the position 89th from the N-terminus to the phenylalanine at the C-terminus in the amino acid sequence set forth as SEQ ID NO:2 (i.e., the extracellular region of the monkey TfR), though it is not limited to this embodiment.

For preparation of an antibody to hTfR, there is known a general method according to which a recombinant human transferrin receptor (rhTfR) is produced using cells which have an introduced expression vector having an incorporated hTfR gene, and then animals such as mice are immunized with this rhTfR. By collecting those cells which produce antibodies to hTfR from the immunized animals and fusing them with myeloma cells, hybridoma cells can be obtained having an ability to produce the anti-hTfR antibody.

Further, cells producing an antibody to hTfR can also be obtained by collecting immunocompetent cells from an animal such as mouse, and immunizing them with rhTfR by in vitro immunization. In conducting in vitro immunization, there is no particular limitation as to the animal species from which the immunocompetent cells are derived, though preferred are mouse, rat, rabbit, guinea pig, dog, cat, horse, and primates including human, and more preferred are mouse, rat and human, and still more preferably mouse and human. As mouse immunocompetent cells, spleen cells prepared from mouse spleen may be used, for example. As human immunocompetent cells, such cells can be used as prepared from human peripheral blood, bone marrow, spleen, and the like. By immunizing human immunocompetent cells according to in vitro immunization, a human antibody to hTfR can be obtained.

After immunizing the immunocompetent cells according to in vitro immunization, the cells can be fused with myeloma cells to prepare hybridoma cells having an ability to produce the antibody. Further, it is also possible to extract mRNAs from the immunized cells, synthesize cDNA, perform PCR reaction using the cDNA as a template to amplify a DNA fragment containing the gene encoding the light chain and the heavy chain of the immunoglobulin, and artificially reconstruct the antibody gene using them.

The hybridoma cells freshly obtained above also include such cells that produce antibodies that recognize other proteins than hTfR. Furthermore, not all the hybridoma cells producing an anti-hTfR antibody necessarily produce an anti-hTfR antibody that exhibits high affinities to hTfR.

Likewise, artificially reconstructed antibody genes include such genes as encode antibodies recognizing other proteins than hTfR as antigens. Moreover, not all the genes encoding anti-hTfR antibodies necessarily have desired properties such as encoding an anti-hTfR antibody exhibiting high affinity to hTfR.

Therefore, a selection step is necessary to select hybridoma cells producing an antibody having desired properties (such as high affinity to hTfR) from the hybridoma cells freshly obtained above. Further, in the case where antibody genes are artificially reconstructed, a selection step is necessary to select from the antibody genes a gene encoding an antibody having desired properties (such as high affinities to hTfR). For selecting hybridoma cells that produce antibodies exhibiting high affinities to hTfR (high affinity antibodies), or for selecting genes encoding high affinity antibodies, following methods explained in detail below are effective. Besides, antibodies exhibiting high affinity to hTfR are those whose dissociation constant ($K_D$) with hTfR as measured by the method described in Example 7 is preferably not greater than $1 \times 10^{-8}$ M, more preferably not greater than $1 \times 10^{-9}$ M, still more preferably not greater than $1 \times 10^{-10}$ M, and even more preferably not greater than $1 \times 10^{-11}$ M. For example, those having a dissociation constant of $1 \times 10^{-13}$ M to $1 \times 10^{-9}$ M, or $1 \times 10^{-13}$ M to $1 \times 10^{-10}$ M are preferable.

For example, for selecting hybridoma cells which produce high affinity antibodies to anti-hTfR antibody, a method is employed in which recombinant hTfR is added to a plate and held by it, then the culture supernatant of the hybridoma cells is added, and after removing antibody unbound to the recombinant hTfR from the plate, the amount of the antibody held by the plate is measured. According to this method, the higher the affinity to hTfR of the antibody contained in the culture supernatant of the hybridoma cells added to the plate is, the greater the amount of antibody held by the plate becomes. Therefore, by measuring the amount of the antibody held by the plate, it is possible to select those hybridoma cells corresponding to the plates where the antibody is held in the greater amount as cell lines producing an anti-hTfR antibody having the relatively higher affinity to hTfR. It is also possible to isolate the gene encoding the high-affinity antibody by extracting mRNAs from each cell line selected in this manner, synthesizing cDNAs, and amplifying a DNA fragment containing the gene encoding the anti-hTfR antibody by PCR using the cDNA as a template.

In order to select the gene encoding the high-affinity anti-hTfR antibody from the above artificially reconstructed antibody genes, the artificially reconstructed antibody genes are once incorporated into an expression vector, and the expression vector then is introduced into host cells. Although there is no particular limitation as to the cells to be employed as host cells, even whether they are prokaryotic or eukaryotic, insofar as they can express the antibody gene after introduction of an expression vector having the incorporated artificially reconstructed antibody gene, preferred are cells originating mammals such as human, mouse, Chinese hamster, and the like, and particularly preferred are CHO cells originating from Chinese hamster ovary cells, or NS/0 cells originating from mouse myeloma. Further, there is no particular limitation as to an expression vector to be employed for incorporation of the antibody encoding gene and expression of it, and any expression vector may be used as far as it can express the gene when introduced into mammalian cells. The gene incorporated into an expression vector is located downstream of a DNA sequence that can regulate the frequency of transcription of a gene in mammalian cells (gene expression regulatory site). Examples of gene expression regulatory sites that may be employed in the present invention include cytomegalovirus-derived promoter, SV40 early promoter, human elongation factor-1α (EF-1α) promoter, human ubiquitin C promoter.

Mammalian cells having such an introduced expression vector come to express the artificially reconstructed antibody incorporated in the expression vector. In order to select those cells that produce a high-affinity antibody to anti-hTfR antibody from the above obtained cells expressing the artificially reconstructed antibody, a method is employed in which the recombinant hTfR is added to a plate and held by it, then the recombinant hTfR is contacted by the culture supernatant of the cells, and after the removal of antibody unbound to the recombinant hTfR from the plate, the amount of the antibody held by the plate is measured. According to this method, the higher the affinity to hTfR of the antibody contained in the cells culture supernatant is, the greater the amount of antibody held by the plate becomes. Therefore, by measuring the amount of the antibody held by the plate, one can select those cells corresponding to the plate where the antibody is held in the greater amount, as a cell line producing an anti-hTfR antibody having relatively the high-affinity anti-hTfR antibody, and eventually can select a gene encoding an anti-hTfR antibody having a high-affinity anti-hTfR antibody to hTfR. Using cell line selected in this manner, one can perform PCR to amplify a DNA fragment containing the gene encoding the anti-hTfR antibody to isolate the gene encoding the high-affinity antibody.

Selection of the gene encoding a high affinity anti-hTfR antibody from the above artificially reconstructed antibody genes can also be carried out by incorporating the artificially reconstructed antibody genes into an expression vector, introducing the expression vector into E. coli cells, culturing the E. coli cells, and selecting the E. coli cells having the desired gene, in the same manner as in the above selection of hybridoma cells, using the culture supernatant of the E. coli cells or an antibody-containing solution prepared by lysing the E. coli cells. E. coli cells thus selected express the gene encoding an anti-hTfR antibody having a relatively high affinity to hTfR. From this cell line, the gene encoding the anti-hTfR antibody having a relatively the high-affinity anti-hTfR antibody to hTfR can be selected. In order to allow the antibody to be secreted into the E. coli culture supernatant, the antibody gene may be incorporated into the expression vector so that a secretion signal sequence is attached on the N-terminal side of the gene.

Another method for selection of the gene encoding a high-affinity anti-hTfR antibody is a method in which the antibody encoded by the above artificially reconstructed antibody gene is expressed and retained on phage particles. For this, the antibody gene is reconstructed as a gene encoding a single-chain antibody. A method for retaining the antibody on the surface of phage particles is disclosed in international publications WO1997/09436 and WO1995/11317, and the like, and thus well known. In order to select phages retaining the high-affinity antibody to anti-hTfR antibody from the phages retaining the antibodies encoded by the artificially reconstructed antibody genes, a method is employed in which a recombinant hTfR is added to a plate and held by it, contacted by the phages, and after removal of the phages unbound to the recombinant hTfR from the plate, the amount of the phages held by the plate is measured. According to this method, the higher the affinity to hTfR of the antibody retained on the phage particles is, the greater the amount of the phage held by the plate becomes. Therefore, by measuring the amount of the phage held by the plate, one can select the phage particles corresponding to the plate where the phages' were held in the greater amount, as the phage particles producing anti-hTfR antibody having a relatively high-affinity anti-hTfR antibody to hTfR, and eventually can select the gene encoding the high-affinity anti-hTfR antibody to hTfR. Using the phage particles thus selected, PCR can be performed to amplify a DNA fragment containing the gene encoding the anti-hTfR antibody and isolate the gene encoding the high-affinity antibody.

Applying publicly known binding assays such as direct and indirect sandwich assay using enzyme-linked immunosorbent assay (EIA, ELISA), flow cytometry, surface plasmon resonance method (hereinafter referred to as "SPR method"), BioLayer Interferometry (hereinafter referred to as "BLI method"), or immunoprecipitation assay, hybridoma cells producing antibodies having high affinity to hTfR can be selected. Thereafter, cDNA is prepared from the high-affinity antibody-producing cells, and using it as a template, a DNA fragment containing the gene encoding the whole or part of the anti-hTfR antibody light chain, the anti-hTfR antibody heavy chain, or a single-chain antibody which is an anti-hTfR antibody, can be amplified and isolated by a PCR method or the like. In the same manner, it is also possible to perform PCR or the like to amplify and isolate a DNA fragment containing the gene encoding the whole or part of the light chain variable region of the anti-hTfR antibody, or a DNA fragment containing the gene encoding the whole or part of the heavy chain variable region of the anti-hTfR antibody.

A high-affinity anti-hTfR antibody can be obtained by incorporating the whole or part of the gene encoding the light chain and the heavy chain of this high-affinity anti-hTfR antibody into an expression vector, transforming host cells such as mammalian cells with this expression vector, and culturing the obtained transformant cells. Using the nucleotide sequence of the isolated gene encoding the anti-hTfR antibody, it is also possible to translate the amino acid sequence of the anti-hTfR antibody, and artificially synthesize a DNA fragment encoding the same amino acid sequence. In artificially synthesizing a DNA fragment, the expression level of the anti-hTfR antibody in the host cells can also be enhanced by proper selection of the codons.

In order to introduce a mutation such as substitution, deletion, addition and the like into the amino acid sequence of the original anti-hTfR antibody, a mutation may be introduced as desired into the gene encoding the anti-hTfR antibody contained in the isolated DNA fragment. Though the gene encoding the mutated anti-hTfR antibody has a homology preferably not lower than 80%, more preferably not lower than 90%, to the original gene, there is no particular limitation as to the level of homology. By introducing a mutation into the amino acid sequence so as to modify the number or the type of sugar chains bound to the anti-hTfR antibody, it is also possible to enhance the stability of the anti-hTfR antibody in the body.

When introducing a mutation into the gene encoding the whole or part of the light chain variable region of the anti-hTfR antibody, the gene thus mutated has a homology that is preferably not lower than 80%, more preferably not lower than 90%, to the original gene, though there is no particular limitation as to the level of homology. When replacing one or more amino acids of the amino acid sequence of the light chain variable region with other amino acids, the number of amino acids to be replaced is preferably 1 to 10, more preferably 1 to 5, still more preferably 1 to 3, and even more preferably 1 to 2. When deleting one or more amino acids of the amino acid sequence of the light chain variable region, the number of amino acid to be deleted is preferably 1 to 10, more preferably 1 to 5, still more preferably 1 to 3, even more preferably 1 or 2. A combined mutation of these substitution and deletion of amino acids can also be carried out. When adding one or more amino acids to the light chain variable region, they may be added inside, or on the N-terminus or C-terminus of, the amino acid sequence of the light chain variable region, and the number of amino acids added is preferably 1 to 10, more preferably 1 to 5, still more preferably 1 to 3, and even more preferably 1 or 2. A combined mutation of these addition, substitution, and deletion of amino acids can also be carried out. The amino acid sequence of the light chain variable region thus mutated has a homology that is preferably not lower than 80%, more preferably not lower than 90%, still more preferably not lower than 95% to the amino acid sequence of the original light chain variable region. In particular, when replacing one or more amino acids of the amino acid sequence of CDR with other amino acids, the number of amino acid replaced may preferably be 1 to 5, more preferably 1 to 3, still more preferably 1 to 2, and even more preferably 1. When deleting one or more amino acid of the amino acid sequence of CDR, the number of amino acids to be deleted is preferably 1 to 5, more preferably 1 to 3, still more preferably 1 or 2, and still more preferably 1. A combined mutation of these substitution and deletion of the amino acid can also be carried out. When adding one or more amino acids, they may be added inside, or on the N to or C to terminus of, the amino acid sequence, and preferably 1 to 5, more preferably 1 to 3, still more preferably 1 to 2, and even more preferably 1, in number. A combined mutation of these addition, substitution, and deletion of amino acids can also be carried out. The amino acid sequence of respective mutated CDR has a homology that is preferably not lower than 80%, more preferably not lower than 90%, and still more preferably not lower than 95% to the amino acid sequence of the original CDR.

When introducing mutation into the gene encoding the whole or part of the heavy chain variable region of the anti-hTfR antibody, the gene thus mutated has a homology that is preferably not lower than 80%, more preferably not lower than 90%, to the original gene, though there is no particular limitation as to the level of homology. When replacing one or more amino acids of the amino acid sequence of the heavy chain variable region with other amino acids, the number of amino acids to be replaced is preferably 1 to 10, more preferably 1 to 5, still more preferably 1 to 3, and even more preferably 1 to 2. When deleting one or more amino acids of the amino acid sequence of the heavy chain variable region, the number of amino acids to be deleted is preferably 1 to 10, more preferably 1 to 5, still more preferably 1 to 3, even more preferably 1 or 2. A combined mutation of these substitution and deletion of amino acids can also be carried out. When adding one or more amino acid to the heavy chain variable region, they may be added inside, or on the N-terminus or C-terminus of, the amino acid sequence of the heavy chain variable region, and the number of amino acids added is preferably 1 to 10, more preferably 1 to 5, still more preferably 1 to 3, and even more preferably 1 or 2. A combined mutation of these addition, substitution, and deletion of amino acids can also be carried out. The amino acid sequence of the heavy chain variable region thus mutated has a homology that is preferably not lower than 80%, more preferably not lower than 90%, still more preferably not lower than 95% to the amino acid sequence of the original heavy chain variable region. In particular, when replacing one or more amino acids of the amino acid sequence of CDR with other amino acids, the number of amino acid to be replaced is preferably 1 to 5, more preferably 1 to 3, still more preferably 1 to 2, and even more preferably 1. When deleting one or more amino acid of the amino acid sequence of CDR, the number of amino acids to be deleted is preferably 1 to 5, more preferably 1 to 3, still more preferably 1 or 2, and still more preferably 1. A combined mutation of these substitution and deletion of the amino acid can also be carried out. When adding one or more amino acids, they may be added inside, or on the N- or C-terminus of, the amino acid sequence, and preferably 1 to 5, more preferably 1 to 3, still more preferably 1 to 2, and even more preferably 1, in number. A combined mutation of these addition, substitution, and deletion of amino acids can also be carried out. The amino acid sequence of respective mutated CDR has a homology that is preferably not lower than 80%, more preferably not lower than 90%, and still more preferably not lower than 95% to the amino acid sequence of the original CDR.

A mutation may be introduced into both the variable regions of the light chain and the heavy chain of the anti-hTfR antibody, by combining the above mutation into the light chain variable region of the anti-hTfR antibody and the above mutation into the heavy chain variable region of the anti-hTfR antibody.

Examples of the above mentioned substitution of one or more amino acids in the amino acid sequence of the light chain and the heavy chain of the anti-hTfR antibody include substitution between acidic amino acids, i.e., aspartic acid and glutamic acid, substitution between amide-type amino acids, i.e., asparagine and glutamine, substitution between basic amino acids, i.e., lysine and arginine, substitution between branched amino acids, i.e., valine, leucine and isoleucine, substitution between aliphatic amino acids, i.e., glycine and alanine, substitution between hydroxyamino acids, i.e., serine and threonine, and substitution between aromatic amino acids, i.e., phenylalanine and tyrosine.

Besides, in the case where a mutation is introduced into the anti-hTfR antibody by adding one or more amino acids to the C-terminus or the N-terminus, if the anti-hTfR antibody and BDNF are fused via the added amino acids, the added amino acids constitute part of a linker. A detailed explanation will be given later on a linker sequence that is placed between the anti-hTfR antibody and BDNF in the fusion protein of the anti-hTfR antibody and the BDNF.

The anti-hTfR antibody obtained by culturing the cells selected by the above methods and the like to produce an anti-hTfR antibody that has a relatively high-affinity to hTfR, and the anti-hTfR antibody obtained by expression of the gene encoding a high-affinity anti-hTfR antibody, may be modified by introducing a mutation into their amino acid sequences, such as substitution, deletion, addition to give them desired properties. Introduction of a mutation into the amino acid sequence of the anti-hTfR antibody may be performed by introducing a mutation into the gene corresponding to the amino acid sequence.

The affinity of an anti-hTfR antibody to hTfR can be adjusted as desired by introduction of a mutation, such as substitution, deletion, and addition, into the amino acid sequence of a variable region of the antibody. For example, if an antibody has such a high affinity to its antigen that leads to too low a dissociation constant in an aqueous solution, there is a possibility that the antibody could, after administered to the body, fail to dissociate from the antigen, thereby leading to a functional disadvantage. In such a case, a most preferable antibody suitable to a given purpose can be obtained by introducing a mutation into the variable region of the antibody so as to adjust its dissociation constant stepwise to 2 to 5 times, 5 to 10 times, 10 to 100 times, and so on, that of the original antibody. Conversely, the dissociation constant can be adjusted stepwise to 1/2 to 1/5 times, 1/5 to 1/10 times, 1/10 to 1/100 times, and so on, that of the original antibody, by introducing a mutation.

Introduction of a mutation such as substitution, deletion and addition to the amino acid sequence of the anti-hTfR antibody can be performed, for example, either by introducing a mutation into certain positions of the nucleotide sequence of the gene or by random introduction of a mutation, by PCR or the like using the gene encoding the anti-hTfR antibody as a template.

Introduction of a mutation into the amino acid sequence of the anti-hTfR antibody for adjusting the affinity of the antibody to hTfR can be carried out by, for example, incorporating a gene encoding the anti-hTfR antibody as a single-chain antibody into a phagemid, preparing with this phagemid a phage with expressed single-chain antibody on the surface of its capsid, letting the phage multiply while introducing a mutation into the gene encoding the single-chain antibody by application of a mutagen or the like, and selecting, from the multiplied phage, a phage expressing a single-chain antibody having a desired dissociation constant either by the method described above or by purification using an antigen column under a certain condition.

The antibodies produced from the above described hybridoma cells are those whose dissociation constant ($K_D$) with hTfR, which is measured by the method described in Example 7, is preferably not greater than $1 \times 10^{-8}$ M, more preferably not greater than $1 \times 10^{-9}$ M, still more preferably not greater than $1 \times 10^{-10}$ M, and even more preferably not greater than $1 \times 10^{-1}$ M. For example, those having a dissociation constant of $1 \times 10^{-13}$ M to $1 \times 10^{-9}$ M, or $1 \times 10^{-13}$ M to $1 \times 10^{-10}$ M are preferable. The same also applies if the antibodies are single-chain antibodies. Once an antibody is obtained, it can be modified as desired by, e.g., introducing a mutation into the gene encoding the antibody to give it a desired property.

Antibody having affinity both to human and monkey TfRs can be obtained by selection of antibodies having affinity to monkey TfR from the anti-hTfR antibodies. Selection of antibodies having affinity to monkey TfR can be carried out by, for example, ELISA using a recombinant monkey TfR which is prepared utilizing recombinant DNA technologies. In such an ELISA, a recombinant monkey TfR is added to a plate and held by it, and contacted by the anti-hTfR antibody, and, after removal of antibody unbound to the recombinant monkey TfR from the plate, the amount of the antibody held by the plate is measured. The higher the affinity of it to the recombinant monkey TfR is, the greater the amount of the antibody held by the plate becomes. Consequently, the antibody corresponding to the plate which held the greater amount of antibody can be selected as the antibody having affinity to monkey TfR. Here, the term "monkey" is preferably classified as simians except human, more preferably as Cercopithecidae, still more preferably as macaques, and for example cynomolgus monkey or Rhesus monkey, among which cynomolgus monkey is convenient for use in examination.

An antibody having affinity both to human and monkey hTfRs offers an advantage that it allows pharmacokinetic observation of the fusion protein of the antibody and BDNF administered to the body using a monkey. For example, if a medical drug of the fusion protein of the anti-hTfR antibody and BDNF of the present invention is being developed, the progress of its development can be remarkably accelerated, for its pharmacokinetic study can be performed using a monkey.

An antibody having a relatively high-affinity to hTfR and having affinity both to human and monkey TfRs, simultaneously, exhibits a dissociation constant ($K_D$) with monkey TfR, as measured by the method described in Example 7, that is preferably not greater than $5 \times 10^{-8}$ M, more preferably not greater than $2 \times 10^{-8}$ M, and still more preferably not greater than $1 \times 10^{-8}$ M. For example, one which exhibits a dissociation constant of $1 \times 10^{-13}$ M to $2 \times 10^{-8}$ M, or $1 \times 10^{-13}$ M to $2 \times 10^{-8}$ M is preferred. The same also applies if the antibody is a single-chain antibody.

If an antibody having a relatively high-affinity to hTfR and obtained by the above method in which those cells producing a high affinity antibody were selected, is an antibody of a non-human animal, it may be converted to a humanized antibody. A humanized antibody is an antibody produced by using the amino acid sequence of part of the variable region (e.g., in particular, the whole or part of the CDRs) of a non-human animal antibody, and replacing a proper region of a human antibody with the aforementioned amino acid sequence (implant of the sequence into a human antibody), while maintaining the specificity to the antigen. Examples of humanized antibodies include an antibody produced by replacing the three complementarity determining regions (CDRs) in the immunoglobulin light chain and the three complementarity determining regions (CDRs) in the immunoglobulin heavy chain, both constituting a human antibody, with CDRs of a non-human mammal. Though there is no particular limitation as to the biological species from which the CDRs to be incorporated into the human antibody are derived so long as it is a non-human mammal, it preferably is a mouse, rat, rabbit, horse, and non-human primate, more preferably a mouse and rat, and still more preferably a mouse.

Methods for preparation of humanized antibody are well known in the art and the most common is a method in which the amino acid sequence of the complementarity determining regions (CDRs) in the variable region of a human antibody is replaced with the CDRs of an antibody of non-human mammal, as devised by Winter et al. (Verhoeyen M. Science. 239, 1534-1536 (1988)). It is also well known that in some cases, corresponding part of an acceptor human antibody needs to be replaced not only with the CDRs of the non-human mammalian antibody but also amino acid sequences occurring in regions outside the CDRs that play a role either in maintaining the structure of the CDRs or in binding to the antigen, in order to reproduce the activity that the donor antibody originally possesses (Queen C. Proc. Natl. Acad. Sci. USA. 86. 10029-10033 (1989)). Here, the regions outside the CDRs are called framework (FR) regions.

Preparation of humanized antibody involves processes of implanting the CDRs (and their neighboring FRs, as the case may be) of non-human mammalian antibody in place of the CDRs (and their neighboring FRs, as the case may be) in the variable region of a human antibody. In such processes, the starting framework region of the variable region of a human antibody can be obtained from a public DNA database and the like which includes germ line antibody genes. For example, germ line DNA sequences, as well as amino acid sequences, of human heavy chain and light chain variable regions can be selected from "VBase" human germline database (available in the Internet, at www.mrc-cpe.cam.ac.uk/vbase). Besides, they can be selected from DNA sequences and amino acid sequences described in published literatures, such as "Kabat E A. Sequences of Proteins of Immunological Interest, 5th Ed., U.S. Department of Health and Human Services, NIH Publication No. 91-3242 (1991)"; "Tomlinson I M. J. Mol. Biol. 227. 776-98 (1992)"; and "Cox J P L. Eur. J Immunol. 24:827-836 (1994)".

As aforementioned, in a humanized antibody, the regions of a non-human mammal antibody to be implanted into the variable regions of the original human antibody generally include CDRs themselves, or CDRs and their neighboring part of FRs. However, such FRs implanted together with CDRs also play a role either in maintaining the structure of the CDRs or in binding to the antigen, thus having a substantial function in determining the complementarity of an antibody, and the term "CDR" in the present invention, therefore, refers to such regions that are, or could be, taken from a non-human mammal antibody and grafted into a humanized antibody, in preparing a humanized antibody. Thus, a region generally considered to be in a FR region is included in a CDR in the present invention as far as it takes part either in maintaining the structure of the CDR or in binding to the antigen, and is thus considered to have a substantial function in determining the complementarity of the antigen.

The anti-hTfR antibody in the present invention, when administered to the body, e.g., by intravenous injection, efficiently binds to hTfR existing on the endothelial cells of the capillaries in the brain. Further, the antibody bound to the hTfR is taken into the brain across the blood-brain barrier by such mechanisms as endocytosis, and transcytosis. Therefore, by binding BDNF to the anti-hTfR antibody of the present invention, BDNF can be efficiently delivered into the brain across the blood-brain barrier. Further, the anti-hTfR antibody of the present invention can, after passing through the blood-brain barrier, can reach the cerebral parenchyma, and neuron-like cells in the hippocampus; Purkinje cells and the like of the cerebellum or at least one of them. And it is also expected that it reaches to the neuron-like cells in the striatum of the cerebrum; and the neuron-like cells in the substantia nigra of the mesencephalon. Therefore, it is possible to make BDNF reach the tissues or cells, by binding it to the anti-hTfR antibody of the present invention.

The use of a fusion protein of an anti-hTfR antibody and BDNF can be an effective means to make the BDNF transfer from the blood into the brain and function there, wherein the BDNF generally cannot pass through the blood-brain barrier when intravenously administered and therefore cannot exhibit its function in the brain. In particular, the fusion protein of an anti-hTfR antibody and BDNF of the present invention can, after passing through the blood-brain barrier, reach the cerebral parenchyma, and neuron-like cells in the hippocampus; Purkinje cells and the like of the cerebellum or at least one of them. And it is also expected that it reaches to the neuron-like cells in the striatum of the cerebrum; as well as to the neuron-like cells in the substantia nigra of the mesencephalon. Therefore, it is possible to make BDNF function or augment their function, in those tissues or cells in the brain by administering BDNF in a combined form with the anti-hTfR antibody molecule, parenterally, e.g., intravenously.

In the present specification, BDNF is a conventional protein, which was discovered by Barde et al. in 1982 and was cloned by Jones et al. in 1990 (EMBO J, (1982) 1: 549-553, Proc. Natl. Acad. Sci. USA (1990) 87: 8060-8064), and as an example, the amino acid sequence of human mature BDNF set forth as SEQ ID NO:247 is shown. The BDNF in the present invention may also be BDNF derived from proteins comprising an amino acid sequence substantially identical to the aforementioned amino acid sequence, or from other warm-blooded animals (e.g., a guinea pig, a rat, a mouse, a chicken, a rabbit, a dog, a pig, a sheep, a bovine, a monkey, etc.).

Moreover, in the present specification, BDNF includes not only a "protein" or a "(poly)peptide" having a specific amino acid sequence (SEQ ID NO:247) showing human mature BDNF, but also a homologue thereof (a homolog or a splice variant), a mutant thereof, a derivative thereof, an amino acid modified form thereof, etc., as long as they have an equivalent function to the "protein" or the "(poly)peptide.

Here, "equivalent function" means that such a derivative or the like has qualitatively the same properties, for example, from a physiological or pharmacological viewpoint. Quantitative factors, such as the degree of the function (e.g., approximately 0.1 to approximately 10 times, and preferably 0.5 to 2 times) or the molecular weight of the protein, may be different. Furthermore, a protein having functions possessed by natural BDNF, such as, for example, (1) binding affinity to a BDNF receptor (TrkB), (2) activity of phosphorylating the BDNF receptor, (3) action to promote the growth of neurons, (4) action to maintain the survival of neurons, (5) neurite outgrowth action to neurons, or consisting of (6) a protein which can be recognized by an antibody specifically recognizing a protein consisting of the amino acid sequence set forth as SEQ ID NO:247, is considered to be a "protein having an equivalent function to" BDNF.

The aforementioned functions of BDNF can be examined using various conventional evaluation methods as described later in (2) "Function of BDNF", or the methods described in Examples 18-22 in the present specification.

Herein, examples of the homolog include proteins of other biological species such as a mouse or a rat, which correspond to a human protein. These proteins have been reported by Maisonpierre et al. (Genomics (1991) 10: 558-568), and can also be deductively identified from the amino acid sequences of the proteins described in UniProt (P21237-1, P23363-1, P25429-1, Q7YRB4-1, P14082-1, Q5IS78-1, and Q95106-1), etc. The mutant includes a naturally occurring allele mutant, a naturally not occurring mutant, and a mutant having an amino acid sequence modified by artificial deletion, substitution, addition or insertion. Examples of the above described mutant include mutants having a homology of at least 70%, preferably 80%, more preferably 90%, still more preferably 95%, even more preferably 97%, particularly preferably 98%, and most preferably 99%, to a protein or a (poly)peptide having no mutation. Examples of the amino acid modified form include a naturally occurring amino acid modified form and a non-naturally occurring amino acid modified form. A specific example of the amino acid modified form is a phosphorylated body of amino acid.

Furthermore, in the present specification, "BDNF" may be a precursor of the above described BDNF (a prepro form), which is capable of exhibiting an equivalent function to BDNF, or a pro form, which is obtained by cleaving a signal sequence from the precursor. Thus, BDNF includes not only a "protein" or a "(poly)peptide" having a specific amino acid sequence (UniProt ID No.P23560-1) showing a human BDNF precursor, but also includes a homologue thereof (a homolog or a splice variant), a mutant thereof, a derivative thereof, a pro form, an amino acid modified form, etc., as long as they have an equivalent function to the "protein" or the "(poly)peptide." An example of the pro form of the human BDNF (pro-BDNF) can be the amino acid sequence set forth as SEQ ID NO:256.

Herein, "equivalent function to the BDNF precursor" means the function possessed by the BDNF precursor, for example, that a pro form of BDNF (pro-BDNF) or mature BDNF can be generated. The equivalent function to the pro form of BDNF means the function possessed by the pro form of BDNF, for example, binding affinity to a p75 receptor.

Herein, examples of the splice variant of the human BDNF precursor include the amino acid sequences of the proteins described in UniProt (P23560-2, P23560-3, P23560-4, and P23560-5). In addition, genes encoding these human BDNF precursor proteins are also conventional, and examples thereof include the nucleotide sequences of the genes described in http://www.ncbi.nlm.nih.gov (NM_001143805.1, NM_001143806.1, NM_001143807.1, NM_001143808.1, NM_001143809.1, NM_001143810.1, NM_001143811.1, NM_001143812.1, NM_001143813.1, NM_001143814.1, NM_001143816.1, NM_001709.4, NM_170731.4, NM_170732.4, NM_170733.3, NM_170734.3, and NM_170735.5).

Examples of the homolog of the BDNF precursor and the splice variant thereof include proteins of other biological species corresponding to human proteins, such as a mouse and a rat, and the splice variants thereof. These can be deductively identified from the nucleotide sequences of the genes described in http://www.ncbi.nlm.nih.gov (the nucleotide sequences of mouse BDNF genes, such as NM_001048139.1, NM_001048141.1, NM_001048142.1, NM_001285416.1, NM_001285417.1, NM_001285418.1, NM_001285419.1, NM_001285420.1, NM_001285421.1, NM_001285422.1 and NM_007540.4, and the nucleotide sequences of rat BDNF genes, such as NM_001270630.1, NM_001270631.1, NM_001270632.1, NM_001270633.1, NM_001270634.1, NM_001270635.1, NM_001270636.1, NM_001270637.1, NM_001270638.1 and NM_012513.4) and the like.

Moreover, the mutant of the BDNF precursor includes a naturally occurring allele mutant, a naturally not occurring mutant, and a mutant having an amino acid sequence modified by artificial deletion, substitution, addition or insertion. Examples of the above described mutant include mutants having a homology of at least 70%, preferably 80%, more preferably 90%, still more preferably 95%, even more preferably 97%, particularly preferably 98%, and most preferably 99%, to a protein or a (poly)peptide having no mutation. Examples of the amino acid modified form include a naturally occurring amino acid modified form and a naturally not occurring amino acid modified form. A specific example of the amino acid modified form is a phosphorylated body of amino acid.

Examples of the amino acid sequence set forth as SEQ ID NO:247 or an amino acid sequence substantially identical thereto include the following (A) to (E):

(A) the amino acid sequence set forth as SEQ ID NO:247, (B) an amino acid sequence comprising a deletion, addition, insertion or substitution of one or more amino acids in the amino acid sequence set forth as SEQ ID NO:247, and having an equivalent function to the protein consisting of the amino acid sequence set forth as SEQ ID NO:247 or being able to be recognized by an antibody specifically recognizing the protein consisting of the amino acid sequence set forth as SEQ ID NO:247, (C) an amino acid sequence having a homology at least not lower than 80% to the amino acid sequence set forth as SEQ ID NO:247, and having an equivalent function to the protein consisting of the amino acid sequence set forth as SEQ ID NO:247 or being able to be recognized by an antibody specifically recognizing the protein consisting of the amino acid sequence set forth as SEQ ID NO:247, (D) an amino acid sequence encoded by DNA having the nucleotide sequence set forth as SEQ ID NO:246, and (E) an amino acid sequence being encoded by DNA hybridizing under stringent conditions with DNA having complementarity to DNA having the nucleotide sequence set forth as SEQ ID NO:246, and having an equivalent function to the protein consisting of the amino acid sequence set forth as SEQ ID NO:247 or being able to be recognized by an antibody specifically recognizing the protein consisting of the amino acid sequence set forth as SEQ ID NO:247.

Specific examples of the amino acid sequence include the amino acid sequence of an ortholog of a human protein consisting of the amino acid sequence set forth as SEQ ID NO:247 found in other mammals, and the amino acid sequence of the splice variant, allele mutant or polymorphic variant of the human protein consisting of the amino acid sequence set forth as SEQ ID NO:247 or the ortholog thereof.

Herein, "homology" means the percentage (%) of amino acid residues identical to or similar to all amino acid residues overlapped in an optimal alignment when two amino acid sequences are aligned using a mathematical algorithm which is conventional in the art (wherein, in the present algorithm, introduction of a gap into one of or both of the sequences can be preferably considered to obtain an optimal alignment). The term "similar amino acids" means amino acids similar to each other in terms of physicochemical properties, and examples thereof include amino acids classified in the same group, such as aromatic amino acids (Phe, Trp, and Tyr), aliphatic amino acids (Ala, Leu, Ile, and Val), polar amino acids (Gln and Asn), basic amino acids (Lys, Arg, and His), acidic amino acids (Glu and Asp), amino acids having a hydroxyl group (Ser and Thr), and amino acids having a small side chain (Gly, Ala, Ser, Thr, and Met). It is predicted that substitution with such similar amino acids does not provide a change in the phenotype of protein (namely, it is conservative amino acid substitution). Specific examples of such conservative amino acid substitution are publicly known in the present technical field, and are described in various publications (see, for example, Bowie et al., Science, 247: 1306-1310 (1990)).

The homology of amino acid sequences in the present specification can be calculated using the homology calculation algorithm NCBI BLAST (National Center for Biotechnology Information Basic Local Alignment Search Tool) under the following conditions (expected value=10; gap acceptable; matrix=BLOSUM62; filtering=OFF). Examples of other algorithms used to determine the homology of amino acid sequences include the algorithm described in Karlin et al., Proc. Natl. Acad. Sci. USA, 90: 5873-5877 (1993) [the algorithm is incorporated in NBLAST and XBLAST program (version 2.0) (Altschul et al., Nucleic Acids Res., 25: 3389-3402 (1997))], the algorithm described in Needleman et al., J. Mol. Biol., 48: 444-453 (1970) [the algorithm is incorporated in GAP program in GCG software package], the algorithm described in Myers and Miller, CABIOS, 4: 11-17 (1988) [the algorithm is incorporated in ALIGN program (version 2.0) as a part of CGC sequence alignment software package], and the algorithm described in Pearson et al., Proc. Natl. Acad. Sci. USA, 85: 2444-2448 (1988) [the algorithm is incorporated in FASTA program in GCG software package], and these algorithms can also be preferably used.

The stringent conditions applied in the above (E) are, for example, the conditions described in Current Protocols in Molecular Biology, John Wiley & Sons, 6.3.1 to 6.3.6, 1999, such as hybridization in 6×SSC (sodium chloride/sodium citrate)/45° C., and the subsequent washing operation one or more times in 0.2×SSC/0.1% SDS/50° C. to 65° C. A person skilled in the art can select hybridization conditions providing stringency equivalent thereto, as appropriate.

More preferably, the "amino acid sequence substantially identical to the amino acid sequence set forth as SEQ ID NO:247" can be an amino acid sequence having an identity not lower than approximately 70%, preferably not lower than approximately 80%, more preferably not lower than approximately 90%, still more preferably not lower than approximately 95%, even more preferably not lower than approximately 97%, particularly preferably not lower than approximately 98%, and most preferably not lower than approximately 99%, to the amino acid sequence set forth as SEQ ID NO:247.

Examples of the protein in the present invention, BDNF, include so-called muteins, such as proteins comprising the following amino acid sequences (i) to (v):

(i) an amino acid sequence comprising a deletion of 1 to 30, preferably 1 to 20, more preferably 1 to 10, or still more preferably 1 to several (6, 5, 4, 3 or 2) amino acids, in the amino acid sequence set forth as SEQ ID NO:247, (ii) an amino acid sequence comprising an addition of 1 to 30, preferably 1 to 20, more preferably 1 to 10, or still more preferably 1 to several (6, 5, 4, 3 or 2) amino acids, in the amino acid sequence set forth as SEQ ID NO:247, (iii) an amino acid sequence comprising an insertion of 1 to 30, preferably 1 to 20, more preferably 1 to 10, or still more preferably 1 to several (6, 5, 4, 3 or 2) amino acids, in the amino acid sequence set forth as SEQ ID NO:247, (iv) an amino acid sequence comprising a substitution of 1 to 30, preferably 1 to 20, more preferably 1 to 10, or still more preferably 1 to several (6, 5, 4, 3 or 2) amino acids with other amino acids, in the amino acid sequence set forth as SEQ ID NO:247, and (v) an amino acid sequence comprising a combination of these amino acid sequences.

As described above, when an amino acid sequence is subjected to an insertion, deletion, addition or substitution of amino acids, the position of the insertion, deletion, addition or substitution of amino acids is not particularly limited, as long as the thus modified protein has an equivalent function to the protein consisting of the amino acid sequence set forth as SEQ ID NO:247, or can be recognized by an antibody specifically recognizing the protein consisting of the amino acid sequence set forth as SEQ ID NO:247. In addition to mature BDNF consisting of the amino acid sequence set forth as SEQ ID NO:247, for example, Met-BDNF, to the N-terminus of which methionine has been added, and the like can also be used as BDNF in the fusion protein of the present invention, as long as it has an equivalent function to the protein consisting of the amino acid sequence set forth as SEQ ID NO:247.

Herein, the means for artificially carrying out a deletion, addition, insertion or substitution of amino acids is, for example, a means for performing commonly used site-specific mutagenesis on DNA encoding the amino acid sequence set forth as SEQ ID NO:247 and then allowing this DNA to express according to a conventional method. Herein, examples of the site-specific mutagenesis include a method of utilizing amber mutation (Gapped Duplex Method, Nucleic Acids Res., 12, 9441-9456 (1984)), and a method according to PCR using primers for mutagenesis.

Preferred examples of BDNF include a human protein consisting of the amino acid sequence set forth as SEQ ID NO:247, an allele mutant thereof, and a polymorphic variant thereof.

"Gene encoding BDNF" means a gene having a nucleotide sequence encoding the amino acid sequence set forth as SEQ ID NO:247 or amino acid sequences substantially identical thereto, which are as described in the above (A) to (E). Specific examples of the gene encoding BDNF include genes having the following nucleotide sequences (F) to (J):

(F) a nucleotide sequence encoding the amino acid sequence set forth as SEQ ID NO:247, (G) a nucleotide sequence encoding an amino acid sequence comprising a deletion, addition, insertion or substitution of one or more amino acids in the amino acid sequence set forth as SEQ ID NO:247, and having an equivalent function to the protein consisting of the amino acid sequence set forth as SEQ ID NO:247 or being able to be recognized by an antibody specifically recognizing the protein consisting of the amino acid sequence set forth as SEQ ID NO:247, (H) a nucleotide sequence encoding an amino acid sequence having a homology at least not lower than 80% to the amino acid sequence set forth as SEQ ID NO:247, and having an equivalent function to the protein consisting of the amino acid sequence set forth as SEQ ID NO:247 or being able to be recognized by an antibody specifically recognizing the protein consisting of the amino acid sequence set forth as SEQ ID NO:247, (I) a nucleotide sequence encoding an amino acid sequence encoded by DNA having the nucleotide sequence set forth as SEQ ID NO:246, and (J) a nucleotide sequence encoding an amino acid sequence being encoded by DNA hybridizing under stringent conditions with DNA having complementarity to DNA having the nucleotide sequence set forth as SEQ ID NO:246, and having an equivalent function to the protein consisting of the amino acid sequence set forth as SEQ ID NO:247 or being able to be recognized by an antibody specifically recognizing the protein consisting of the amino acid sequence set forth as SEQ ID NO:247.

Besides, herein, the gene may be either DNA such as cDNA or genomic DNA, or RNA such as mRNA, and also, the gene has a concept comprising both a single-stranded nucleic acid sequence and a double-stranded nucleic acid sequence. Moreover, in the present specification, nucleic acid sequences set forth as SEQ ID NO: 165, SEQ ID NO:173, SEQ ID NO:181, SEQ ID NO:189, SEQ ID NO: 197, SEQ ID NO:199, SEQ ID NO:201, SEQ ID NO:203, SEQ ID NO:211, SEQ ID NO:213, SEQ ID NO:246, SEQ ID NO:249, SEQ ID NO:251, SEQ ID NO:253, etc. are DNA sequences for convenience sake. However, when the nucleic acid sequence indicates an RNA sequence such as mRNA, thymine (T) is understood to be uracil (U).

Moreover, BDNF used in the present invention may also be a derivative and the like modified with a molecule and the like having action to stabilize proteins, such as polyethylene glycol (PEG), (Drug Delivery System (1998); 13: 173-178).

An example of the fusion protein of an anti-hTfR antibody and human BDNF in the present invention is a fusion protein of the type in which a "heavy chain" constituting the anti-hTfR antibody is fused, on the C-terminus thereof and via a linker sequence Gly-Ser, with human BDNF. Examples of such a fusion protein include (1) a fusion protein, in which the light chain of the humanized anti-hTfR antibody has the amino acid sequence set forth as SEQ ID NO: 164, and the heavy chain of the humanized anti-hTfR antibody is linked, on the C-terminal side thereof and via a linker sequence Gly-Ser, to human BDNF, and the whole linked heavy chain has the amino acid sequence set forth as SEQ ID NO:248;

(2) a fusion protein, in which the light chain of the humanized anti-hTfR antibody has the amino acid sequence set forth as SEQ ID NO: 180, and the heavy chain of the humanized anti-hTfR antibody is linked, on the C-terminal side thereof and via a linker sequence Gly-Ser, to human BDNF, and the whole linked heavy chain has the amino acid sequence set forth as SEQ ID NO:250;

(3) a fusion protein, in which the light chain of the humanized anti-hTfR antibody has the amino acid sequence set forth as SEQ ID NO: 196, and the heavy chain of the humanized anti-hTfR antibody is linked, on the C-terminal side thereof and via a linker sequence Gly-Ser, to human BDNF, and the whole linked heavy chain has the amino acid sequence set forth as SEQ ID NO:252; and (4) a fusion protein, in which the light chain of the humanized anti-hTfR antibody has the amino acid sequence set forth as SEQ ID NO: 196, and the heavy chain of the humanized anti-hTfR antibody is linked, on the C-terminal side thereof and via a linker sequence consisting of 27 amino acids that is composed of the linker sequence Gly-Ser followed by consecutively linked five copies of the amino acid sequence Gly-Gly-Gly-Gly-Ser (SEQ ID NO:3), to human BDNF, and the whole linked heavy chain has the amino acid sequence set forth as SEQ ID NO:254.

The fusion proteins described in the above (1) to (4) are:

(1) a fusion protein comprising the light chain of a humanized anti-hTfR antibody having the amino acid sequence set forth as SEQ ID NO: 164, and the heavy chain of a humanized anti-hTfR antibody having the amino acid sequence set forth as SEQ ID NO: 172 linked, on the C-terminal side thereof and via a linker sequence Gly-Ser, to human BDNF set forth as SEQ ID NO:247;

(2) a fusion protein comprising the light chain of a humanized anti-hTfR antibody having the amino acid sequence set forth as SEQ ID NO: 180, and the heavy chain of a humanized anti-hTfR antibody having the amino acid sequence set forth as SEQ ID NO:188 linked, on the C-terminal side thereof and via a linker sequence Gly-Ser, to human BDNF set forth as SEQ ID NO:247;

(3) a fusion protein comprising the light chain of a humanized anti-hTfR antibody having the amino acid sequence set forth as SEQ ID NO: 196, and the heavy chain of a humanized anti-hTfR antibody having the amino acid sequence set forth as SEQ ID NO:210 linked, on the C-terminal side thereof and via a linker sequence Gly-Ser, to human BDNF set forth as SEQ ID NO:247; and (4) a fusion protein comprising the light chain of a humanized anti-hTfR antibody having the amino acid sequence set forth as SEQ ID NO: 196, and the heavy chain of a humanized anti-hTfR antibody having the amino acid sequence set forth as SEQ ID NO:210 linked, on the C-terminal side thereof and via a linker sequence consisting of 27 amino acids that is composed of the amino acid sequence Gly-Ser followed by consecutively linked five copies of the amino acid sequence Gly-Gly-Gly-Gly-Ser (SEQ ID NO:3), to human BDNF set forth as SEQ ID NO:247.

Such a fusion protein can be produced by, for example, transforming host cells such as mammalian cells with an expression vector having an incorporated DNA fragment containing a nucleotide sequence (SEQ ID NO:251) encoding the amino acid sequence set forth as SEQ ID NO:250, and an expression vector having an incorporated DNA fragment containing a nucleotide sequence (SEQ ID NO:181) encoding the anti-hTfR antibody light chain having the amino acid sequence set forth as SEQ ID NO: 180, and then culturing the host cells.

A further example of specific embodiments of the fusion protein of a humanized anti-hTfR antibody and human BDNF in the present invention is one produced by fusing the anti-hTfR antibody heavy chain, on the C-terminal side thereof and via a linker sequence consisting of 27 amino acids that is composed of the amino acid sequence Gly-Ser followed by consecutively linked five copies of the amino acid sequence Gly-Gly-Gly-Gly-Ser (SEQ ID NO:3), with human BDNF. An example of such a fusion protein includes a peptide having a light chain consisting of the amino acid sequence set forth as SEQ ID NO:196 and a heavy chain linked, on the C-terminal side thereof and via the aforementioned linker, to human BDNF, wherein the peptide consists of the amino acid sequence set forth as SEQ ID NO:254.

Such a fusion protein can be produced by, for example, transforming host cells such as mammalian cells with an expression vector having an incorporated DNA fragment containing a nucleotide sequence (SEQ ID NO:255) encoding the amino acid sequence set forth as SEQ ID NO:254, and an expression vector having an incorporated DNA fragment containing a nucleotide sequence (SEQ ID NO:197) encoding the anti-hTfR antibody light chain having the amino acid sequence set forth as SEQ ID NO: 196, and then culturing the host cells.

It is to be noted that the protein having the amino acid sequence set forth as SEQ ID NO:254 is a protein, in which the an anti-hTfR antibody heavy chain set forth as SEQ ID NO:210 is linked, on the C-terminal side thereof and via a linker sequence consisting of 27 amino acids that is composed of the amino acid sequence Gly-Ser followed by consecutively linked five copies of the amino acid sequence Gly-Gly-Gly-Gly-Ser (SEQ ID NO:3), to human BDNF. Herein, as an anti-hTfR antibody heavy chain, one set forth as SEQ ID NO: 188 may be used instead of one set forth as SEQ ID NO:210, and in such a case, as an anti-hTfR antibody light chain, one set forth as SEQ ID NO: 196 is preferably used. Further, herein, as an anti-hTfR antibody heavy chain, one set forth as SEQ ID NO: 172 may be used instead of one set forth as SEQ ID NO:210, and in such a case, as an anti-hTfR antibody light chain, one set forth as SEQ ID NO: 164 is preferably used.

A preferred embodiment of the anti-hTfR antibody, which is linked to human BDNF, is an antigen-binding fragment of the antibody. Specific examples thereof include a single-chain antibody, Fab, F(ab'), and F(ab')$_2$.

In the case where the anti-hTfR antibody is a single-chain antibody, an example of specific embodiments of the fusion protein of the humanized anti-hTfR antibody and human BDNF in the present invention includes a fusion protein, in which human BDNF is linked, on the C-terminal side thereof and via a first linker sequence consisting of 27 amino acids composed of the amino acid sequence Gly-Ser followed by consecutively linked five copies of the amino acid sequence Gly-Gly-Gly-Gly-Ser (SEQ ID NO:3), to the single-chain antibody. An example of this fusion protein can be one consisting of the amino acid sequence set forth as SEQ ID NO:259 or 260. As a single-chain antibody employed here, an antibody, in which the anti-hTfR antibody heavy chain variable region having the amino acid sequence set forth as SEQ ID NO:205 is linked, on the C-terminus thereof and via a second linker sequence consisting of 15 amino acids consisting of consecutively linked three copies of the amino acid sequence Gly-Gly-Gly-Gly-Ser (SEQ ID NO:3), to the anti-hTfR antibody light chain variable region having the amino acid sequence set forth as SEQ ID NO:191. Accordingly, in the case where the anti-hTfR antibody is a single-chain antibody, an example of specific embodiments of the fusion protein of the humanized anti-hTfR antibody and human BDNF in the present invention can be a fusion protein, in which a single-chain antibody comprising a heavy chain variable region having the amino acid sequence set forth as SEQ ID NO:205 and a light chain variable region having the amino acid sequence set forth as SEQ ID NO: 191 is linked, on the N-terminal side thereof, and directly or via a linker, to human BDNF.

Where the anti-hTfR antibody is a single-chain antibody, such a fusion protein can be produced by, for example, transforming host cells such as mammalian cells with an expression vector having an incorporated DNA fragment containing a nucleotide sequence (SEQ ID NO:258) encoding the amino acid sequence set forth as SEQ ID NO:259, and then culturing the host cells.

Besides, in the present invention, when a peptide chain includes a plurality of linker sequences, each of those linker sequences is referred to as, from the N-terminal side, the first linker sequence, the second linker sequence, and so on, for convenience.

In the case where the anti-hTfR antibody is Fab, an example of specific embodiments of the fusion protein between a humanized anti-hTfR antibody and BDNF of the present invention is a fusion protein which is composed of BDNF that is fused, on the C-terminal side thereof and via a linker sequence consisting of 27 amino acids composed of the amino acid sequence Gly-Ser followed by consecutively linked five copies of the amino acid sequence Gly-Gly-Gly-Gly-Ser (SEQ ID NO:3), to a region having the anti-hTfR antibody heavy chain variable region and the $C_H1$ region. Though part of the hinge region may be included in addition to the $C_H1$ region here, the hinge region includes no cysteine residue which would form a disulfide bond between heavy chains. Fusion proteins set forth as SEQ ID NOS:263 and 264 are preferred examples thereof. In SEQ ID NOS:263 and 264, the amino acid sequence of an anti-hTfR antibody heavy chain consists of an amino acid sequence (SEQ ID NO:261) corresponding to a portion at the positions 1st to 226th from the N-terminus of the amino acid sequence of the heavy chain of the humanized anti-hTfR antibody set forth as SEQ ID NO:210. It is to be noted that a portion at the positions 1st to 118th from the N-terminus of SEQ ID NO:210 corresponds to SEQ ID NO:205 (amino acid sequence 2 of the heavy chain variable region of the humanized anti-hTfR antibody No. 3), a portion at the positions 119th to 216th corresponds to a $C_H1$ region, and a portion at the positions 217th to 226th corresponds to a hinge portion. In the case where the anti-hTfR antibody is Fab, an example of specific embodiments of the fusion protein of the humanized anti-hTfR antibody and human BDNF in the present invention can preferably be a fusion protein, in which the heavy chain of any one of Fab, F(ab')$_2$ and F(ab') of the humanized anti-hTfR antibody is linked, on the N-terminal side thereof, and directly or via a linker, to human BDNF.

In the case where the anti-hTfR antibody is Fab, an example of specific embodiments of the fusion protein of the humanized anti-hTfR antibody and human BDNF in the present invention can be a fusion protein, in which the light chain thereof consists of the amino acid sequence set forth as SEQ ID NO: 196, the heavy chain thereof is a Fab heavy chain consisting of the amino acid sequence set forth as SEQ ID NO:261, and human BDNF is linked to the N-terminal side of the heavy chain directly or via a linker. Further specific examples of such a fusion protein include: a fusion protein, in which the light chain thereof consists of the amino acid sequence set forth as SEQ ID NO: 196, and a portion consisting of a Fab heavy chain and human pro-BDNF binding to the N-terminal side thereof directly or via a linker consists of the amino acid sequence set forth as SEQ ID NO:263; and a fusion protein, in which the light chain thereof consists of the amino acid sequence set forth as SEQ ID NO: 196, and a portion consisting of a Fab heavy chain and human pro-BDNF binding to the N-terminal side thereof directly or via a linker consists of the amino acid sequence set forth as SEQ ID NO:264.

Such a fusion protein comprising an anti-hTfR antibody that is Fab can be produced by, for example, transforming host cells such as mammalian cells with an expression vector having an incorporated DNA fragment containing a nucleotide sequence (SEQ ID NO:262) encoding the amino acid sequence set forth as SEQ ID NO:263, and an expression vector having an incorporated DNA fragment containing a nucleotide sequence (SEQ ID NO: 197) encoding the anti-hTfR antibody light chain having the amino acid sequence set forth as SEQ ID NO: 196, and then culturing the host cells.

Such a fusion protein comprising an anti-hTfR antibody that is Fab can also be produced by, for example, transforming host cells such as mammalian cells with an expression vector having an incorporated DNA fragment containing a nucleotide sequence (SEQ ID NO:265) encoding the amino acid sequence set forth as SEQ ID NO:264, and an expression vector having an incorporated DNA fragment containing a nucleotide sequence (SEQ ID NO: 197) encoding the anti-hTfR antibody light chain having the amino acid sequence set forth as SEQ ID NO: 196, and then culturing the host cells.

In the case where a mutation is introduced to human BDNF (hBDNF) so as to add an amino acid to the C-terminus or N-terminus thereof, when such an added amino acid is positioned between hBDNF and an anti-hTfR antibody upon fusion of the hBDNF with the anti-hTfR antibody, the added amino acid constitutes a part of a linker.

For binding an anti-hTfR antibody to BDNF, a method is available to bind them together via a non-peptide linker or a peptide linker. As non-peptide linkers, there can be used polyethylene glycol, polypropylene glycol, copolymer of ethylene glycol and propylene glycol, polyoxyethylated polyol, polyvinyl alcohol, polysaccharides, dextran, polyvinyl ether, biodegradable polymer, polymerized lipid, chitins, and hyaluronic acid, or derivatives thereof, or combinations thereof. A peptide linker is a peptide chain consisting of 1 to 50 amino acids linked by peptide bonds or a derivative thereof, whose N-terminus and C-terminus are to be covalently bonded either to an anti-hTfR antibody or BDNF, respectively, to bind the anti-hTfR antibody to BDNF.

In particular, a conjugate which is formed by binding the anti-hTfR antibody of the present invention to BDNF via PEG as a non-peptide linker, is designated "anti-hTfR antibody-PEG-BDNF". An anti-hTfR antibody-PEG-BDNF can be prepared by first binding the anti-hTfR antibody to PEG to form anti-hTfR antibody-PEQ and then binding the anti-hTfR antibody-PEG to BDNF. Alternatively, an anti-hTfR antibody-PEG-BDNF can be prepared by first binding BDNF to PEG to form "BDNF-PEG", and then binding the "BDNF-PEG" to the anti-hTfR antibody. In order to bind PEG to the anti-hTfR antibody and BDNF, a PEG is employed which is modified with such functional groups as carbonate, carbonylimidazole, active ester of carboxylic acid, azlactone, cyclic imide thione, isocyanate, isothiocyanate, imidate, aldehyde or the like. Such a functional group introduced to PEG reacts mainly with amino groups in the anti-hTfR antibody and BDNF to covalently bind PEG to the hTfR antibody and BDNF. Though there is no particular limitation as to the molecular weight and the configuration of PEG employed here, its mean molecular weight (MW) is as follows: preferably MW=500 to 60000, more preferably MW=500 to 20000. For example, such PEG whose mean molecular weight is about 300, about 500, about 1000, about 2000, about 4000, about 10000, about 20000, and the like. PEG is preferably used as a non-peptide linker.

For example, "anti-hTfR antibody-PEG" can be prepared by mixing the anti-hTfR antibody with an aldehyde group-modified PEG (ALD-PEG-ALD) so that the molar ratio of the modified PEG to the antibody is 11, 12.5, 15, 110, 120 and the like, and then adding to the mixture a reducing agent such as NaCNBH$_3$ to let a reaction take place. Then, by reacting "anti-hTfR antibody-PEG" with BDNF in the presence of a reducing agent such as NaCNBH$_3$, "anti-hTfR antibody-PEG-BDNF" is obtained. On the contrary, it is also possible to obtain "anti-hTfR antibody-PEG-BDNF" by first binding BDNF to ALD-PEG-ALD to prepare "BDNF-PEG", and then binding the "BDNF-PEG" to the anti-hTfR antibody.

Since a dimer of BDNF binds to a high-affinity BDNF receptor on the surface of a target cell, the BDNF is considered to act in the form of a dimer. However, BDNF binding to an anti-hTfR antibody may be either a single molecule or two molecules. For example, a fusion protein formed by binding a single molecule of BDNF to an anti-hTfR antibody may be allowed to react with BDNF to obtain a dimer. Alternatively, two molecules of BDNF may bind to an anti-hTfR antibody to obtain a fusion protein. Moreover, such binding can be achieved by incorporating DNA encoding an anti-hTfR antibody and BDNF into an expression vector, as described below. Otherwise, an anti-hTfR antibody and BDNF have been produced, separately, and they may be then chemically bound to each other to produce such binding. Specifically, an anti-hTfR antibody and BDNF can be integrated by linking the heavy chain or light chain of the anti-hTfR antibody, on the C-terminal side or N-terminal side thereof, and via a linker sequence or directly, to BDNF on the N-terminal side or C-terminal side thereof, by peptide bonds. An example of the preferred embodiments of the fusion protein of BDNF and an anti-hTfR antibody is a fusion protein, in which the heavy chain or light chain of the anti-hTfR antibody is linked, on the N-terminal side thereof, and via a linker sequence or directly, to BDNF on the C-terminus thereof.

As mentioned above, examples of the preferred embodiments of the anti-hTfR antibody, to which human BDNF is linked, include antigen-binding fragments of the antibody, specifically, a single-chain antibody, Fab, F(ab'), and F(ab')$_2$. Accordingly, examples of the preferred embodiments of the fusion protein of BDNF and an anti-hTfR antibody include the following fusion proteins:

(1) a fusion protein of BDNF and an anti-hTfR antibody, wherein the anti-hTfR antibody is an antigen-binding fragment, and human BDNF is linked, directly or via a linker, to the antigen-binding fragment on the N-terminal side thereof, (2) a fusion protein of BDNF and an anti-hTfR antibody, wherein the anti-hTfR antibody is a single-chain antibody, and human BDNF is linked, directly or via a linker, to the single-chain antibody on the N-terminal side thereof, (3) a fusion protein of BDNF and an anti-hTfR antibody, wherein the anti-hTfR antibody is any one of Fab, F(ab')$_2$, and F(ab'), and human BDNF is linked, directly or via a linker, to the heavy chain or light chain of the Fab, F(ab')$_2$, or F(ab'), on the N-terminal side thereof.

Herein, in the case of the above (3), human BDNF can be particularly preferably linked to the heavy chain of one of Fab, F(ab')$_2$, or F(ab') of the anti-hTfR antibody, on the N-terminal side thereof. Accordingly, a more specific example of the fusion protein includes the following fusion protein:

(4) a fusion protein of BDNF and an anti-hTfR antibody, wherein the anti-hTfR antibody is any one of Fab, F(ab')$_2$, or F(ab'), and human BDNF is linked, directly or via a linker, to the heavy chain of the Fab, F(ab')$_2$, or F(ab'), on the N-terminal side thereof.

In a fusion protein of the type in which BDNF is linked to the "light chain" constituting an anti-hTfR antibody, on the C-terminal side thereof, the anti-human transferrin receptor antibody comprises an amino acid sequence comprising the whole or part of a light chain variable region, and an amino acid sequence comprising the whole or part of a heavy chain variable region, and BDNF is linked to the light chain on the C-terminal side thereof. Herein, the light chain of the anti-hTfR antibody may be directly linked to BDNF, or may also be linked thereto via a linker.

In a fusion protein of the type in which BDNF is linked to the "heavy chain" constituting an anti-hTfR antibody, on the C-terminal side thereof, the anti-human transferrin receptor antibody comprises an amino acid sequence comprising the whole or part of a light chain variable region, and an amino acid sequence comprising the whole or part of a heavy chain variable region, and BDNF is linked to the heavy chain on the C-terminal side thereof. Herein, the heavy chain of the anti-hTfR antibody may be directly linked to BDNF, or may also be linked thereto via a linker.

In a fusion protein of the type in which BDNF is linked to the "light chain" constituting an anti-hTfR antibody, on the N-terminal side thereof, the anti-human transferrin receptor antibody comprises an amino acid sequence comprising the whole or part of a light chain variable region, and an amino acid sequence comprising the whole or part of a heavy chain variable region, and BDNF is linked to the light chain on the N-terminal side thereof. Herein, the light chain of the anti-hTfR antibody may be directly linked to BDNF, or may also be linked thereto via a linker.

In a fusion protein of the type in which BDNF is linked to the "heavy chain" constituting an anti-hTfR antibody, on the N-terminal side thereof, the anti-human transferrin receptor antibody comprises an amino acid sequence comprising the whole or part of a light chain variable region, and an amino acid sequence comprising the whole or part of a heavy chain variable region, and BDNF is linked to the heavy chain on the N-terminal side thereof. Herein, the heavy chain of the anti-hTfR antibody may be directly linked to BDNF, or may also be linked thereto via a linker.

Such a fusion protein of an anti-hTfR antibody and BDNF can be obtained by incorporating into a mammalian expression vector a DNA fragment in which a cDNA encoding the BDNF (SEQ ID NO:246) is placed in-frame directly, or via a DNA fragment encoding a linker sequence, on the 3'-end side or 5'-end side of a cDNA encoding the heavy chain or light chain of the anti-hTfR antibody, and then culturing mammalian cells into which the above expression vector has been introduced. In the case where the DNA fragment encoding BDNF is linked to the heavy chain, a mammalian expression vector into which a cDNA fragment encoding the light chain constituting anti-hTfR antibody has been incorporated is also introduced together into the same host cells, whereas in the case where the DNA fragment encoding BDNF is linked to the light chain, a mammalian expression vector into which a cDNA fragment encoding the anti-hTfR antibody heavy chain has been incorporated is also introduced together into the same host cells.

Herein, both a mammalian expression vector into which a cDNA fragment encoding a fusion protein formed by linking BDNF, directly or via a linker sequence, to the heavy chain (or light chain) of the anti-hTfR antibody on the C-terminus thereof has been incorporated, and a mammalian expression vector into which a cDNA fragment encoding the light chain (or heavy chain) of the anti-hTfR antibody has been incorporated, are introduced together into the same host mammalian cells, so as to produce a fusion protein consisting of a fusion protein in which BDNF is linked to the heavy chain (or light chain) of the anti-hTfR antibody on the C-terminal side thereof, and the heavy chain (or light chain) of the anti-hTfR antibody.

Likewise, both a mammalian expression vector into which a cDNA fragment encoding a fusion protein formed by linking BDNF, directly or via a linker sequence, to the heavy chain (or light chain) of the anti-hTfR antibody on the N-terminus thereof has been incorporated, and a mammalian expression vector into which a cDNA fragment encoding the light chain (or heavy chain) of the anti-hTfR antibody has been incorporated, are introduced into the same host mammalian cells, so as to also produce a fusion protein consisting of a fusion protein in which BDNF is linked to the heavy chain (or light chain) of the anti-hTfR antibody on the N-terminal side thereof, and the light chain (or heavy chain) of the anti-hTfR antibody.

In the case where the anti-hTfR antibody is a single-chain antibody, the fusion protein formed by binding the anti-hTfR antibody to BDNF can be obtained by incorporating, into an expression vector for eukaryotic cells such as mammalian cells and yeasts, or for prokaryotic cells such as *E. coli.*, a DNA fragment which is formed by linking the cDNA encoding the single-chain anti-hTfR antibody, directly or via a DNA fragment encoding a linker sequence, to the cDNA encoding BDNF, on the 5'-end or on the 3'-end thereof, and then allowing the fusion protein to be expressed in those corresponding cells into which the expression vector has been introduced.

In the case where the anti-hTfR antibody is Fab, the fusion protein formed by binding the anti-hTfR antibody to BDNF can be obtained by introducing, into the same host cells, both an expression vector (eukaryotic cells such as mammalian cells and yeasts, or prokaryotic cells such as *E. coli.*), into which a DNA fragment formed by linking the cDNA fragment encoding either the heavy chain or light chain of the Fab, directly or via a DNA fragment encoding a linker sequence, to the cDNA encoding BDNF, on the 5'-end or on the 3'-end thereof, has been incorporated, and an expression vector into which a cDNA fragment encoding the other heavy chain or light chain of the Fab has been incorporated, and then allowing the fusion protein to be expressed in those cells.

When a linker sequence is positioned between an anti-hTfR antibody and BDNF, the linker sequence is preferably composed of 1 to 50 amino acids. Herein, the number of amino acids may be adjusted, as desired, like 1 to 17, 1 to 10, 10 to 40, 20 to 34, 23 to 31, 25 to 29, 27, and so on. The amino acid sequence of such a linker sequence is not limited, as long as the anti-hTfR antibody linked via the linker retains affinity to hTfR and the linked BDNF exhibits its physiological activity under physiological conditions. The amino acid sequence of the linker sequence is preferably composed of glycine and serine. Examples of the amino acid sequence of the linker sequence include an amino acid sequence consisting of either a glycine or serine amino acid, the amino acid sequence Gly-Ser, the amino acid sequence Gly-Gly-Ser, the amino acid sequence Gly-Gly-Gly-Gly-Ser (SEQ ID NO:3), the amino acid sequence Gly-Gly-Gly-Gly-Gly-Ser (SEQ ID NO:4), the amino acid sequence Ser-Gly-Gly-Gly-Gly-Gly (SEQ ID NO:5), the sequence consisting of not greater than 50 amino acids, which are formed by linking 1 to 10, or 2 to 5 of these amino acid sequences to one another, and the sequence comprising a sequence of 2 to 17, 2 to 10, 10 to 40, 20 to 34, 23 to 31, 25 to 29, or 27 amino acids. For example, a linker comprising 27 amino acids that is composed of the amino acid sequence Gly-Ser followed by consecutively linked five copies of the amino acid sequence Gly-Gly-Gly-Gly-Ser (SEQ ID NO:3) can be preferably used as a linker sequence.

In a fusion protein of an anti-hTfR antibody and BDNF, in the case where the anti-hTfR antibody is a single-chain antibody, an amino acid sequence comprising the whole or part of an immunoglobulin light chain variable region and an amino acid sequence comprising the whole or part of an immunoglobulin heavy chain variable region are linked to each other, in general, via a linker sequence. At this time, as long as the affinity of the anti-hTfR antibody to hTfR is retained, the linker sequence may be linked to the amino acid sequence comprising the whole or part of an immunoglobulin light chain variable region on the C-terminal side thereof, and the amino acid sequence comprising the whole or part of an immunoglobulin heavy chain variable region may be further linked to the C-terminal side thereof. Alternatively, the linker sequence may be linked to the amino acid sequence comprising the whole or part of an immunoglobulin heavy chain variable region on the C-terminal side thereof, and the amino acid sequence comprising the whole or part of an immunoglobulin light chain variable region may be further linked to the C-terminal side thereof.

The linker sequence positioned between the light chain and the heavy chain of immunoglobulin is composed of preferably 2 to 50, more preferably 8 to 50, still more preferably 10 to 30, even more preferably 12 to 18 or 15 to 25, and for example, 15 or 25 amino acids. The amino acid sequence of such a linker sequence is not limited, as long as the anti-hTfR antibody formed by linking both chains via the linker retains affinity to hTfR, and BDNF linked to the antibody can exhibit its physiological activity under physiological conditions. The amino acid sequence of the linker sequence is preferably composed of only glycine, or of glycine and serine. Examples of the amino acid sequence of the linker sequence include the amino acid sequence Gly-Ser, the amino acid sequence Gly-Gly-Ser, the amino acid sequence Gly-Gly-Gly, the amino acid sequence Gly-Gly-Gly-Gly-Ser (SEQ ID NO:3), the amino acid sequence Gly-Gly-Gly-Gly-Gly-Ser (SEQ ID NO:4), the amino acid sequence Ser-Gly-Gly-Gly-Gly-Gly (SEQ ID NO:5), and the sequence consisting of 2 to 10, or 2 to 5 of these amino acid sequences that are consecutively linked. For example, in the case where an amino acid sequence consisting of the entire variable region of an immunoglobulin heavy chain is linked, on the C-terminal side thereof and via a linker sequence, to an immunoglobulin light chain variable region, a linker consisting of 15 amino acids consisting of consecutively linked three copies of the amino acid sequence Gly-Gly-Gly-Gly-Ser (SEQ ID NO:3) set forth as SEQ ID NO:3 is linked, is preferable as a linker sequence.

An example of the specific embodiments of the fusion protein of an anti-hTfR antibody and BDNF can be a fusion protein having the amino acid sequence set forth as SEQ ID NO:252, which is formed by fusing the anti-hTfR antibody heavy chain, on the C-terminus thereof and via the amino acid sequence Gly-Ser used as a linker sequence, with human BDNF. By using host cells transformed by introduction therein both an expression vector into which a DNA fragment having the nucleotide sequence set forth as SEQ ID NO:253 encoding the aforementioned fusion protein has been incorporated, and an expression vector into which a DNA fragment having the nucleotide sequence set forth as SEQ ID NO: 197 encoding the anti-hTfR antibody light chain having the amino acid sequence set forth as SEQ ID NO: 196, a fusion protein of an anti-hTfR antibody and human BDNF can be produced.

If an anti-hTfR antibody originates from a non-human animal, its administration to human could entail a substantial risk of causing an antigen-antibody reaction, thereby provoking adverse side-effects. By converting them to humanized antibodies, the antigenicity of non-human animal antibodies can be reduced and therefore the provocation of side-effects due to antigen-antibody interaction can be suppressed when administered to a human. Further, it has been reported that according to experiments using monkeys, humanized antibodies are more stable than mouse antibodies in the blood, and it is expected that their therapeutic effect can therefore become longer-lasting accordingly. Provocation of side-effects due to an antigen-antibody interaction can be suppressed also by employing a human antibody as the anti-hTfR antibody.

A detailed explanation will be given below regarding the case where the anti-hTfR antibody is a humanized antibody or human antibody. In human antibody light chain, there are λ and κ chains. The light chain constituting the human antibody may either be λ and κ chain. And in human heavy chain, there are γ, μ, α, σ, and ε chains, which correspond to IgG, IgM, IgA, IgD and IgE, respectively. Though the heavy chain constituting the anti-hTfR antibody may be any of γ, μ, α, σ, and ε chains, preferred is a γ chain. Further, in γ chain of human heavy chain, there are γ1, γ2, γ3 and γ4 chains, which correspond to IgG1, IgG2, IgG3 and IgG4, respectively. Where the heavy chain constituting the anti-hTfR antibody is a γ chain, though the γ chain may be any of γ1, γ2, γ3 and γ4 chains, preferred is a γ1 or γ4 chain. In the case where the anti-hTfR antibody is a humanized antibody or human antibody and IgG, the human antibody light chain may either be λ chain or κ chain, and though the human antibody heavy chain may either be γ1, γ2, γ3 and γ4 chains, preferred is a γ1 or γ4 chain. For example, a preferable embodiment of anti-hTfR antibody includes an anti-hTfR antibody whose light chain is a λ chain and heavy chain is a γ1 chain.

In the case where the anti-hTfR antibody is a humanized antibody or a human antibody, the anti-hTfR antibody and BDNF can be bound to each other by linking the heavy chain or light chain of the anti-hTfR antibody, on the N-terminus (or the C-terminus) thereof, and via a linker sequence or directly, to the BDNF on the C-terminus (or the N-terminus) thereof, respectively, by peptide bonds. When linking BDNF to the anti-hTfR antibody heavy chain on the N-terminal side (or to the C-terminal side) thereof, the C-terminus (or the N-terminus), respectively, of BDNF is linked to the N-terminus (or the C-terminus) of the γ, μ, α, σ or ε chain of anti-hTfR antibody, via a linker sequence or directly, by peptide bonds. When linking BDNF to the anti-hTfR antibody light chain on the N-terminal side (or the C-terminal side) thereof, the C-terminus (or the N-terminus), respectively, of BDNF in linked to the N-terminus (or the C-terminus) of the λ chain and κ chain of anti-hTfR antibody, via a linker sequence or directly, by peptide bonds. However, in the case where the anti-hTfR antibody consists of the Fab region lacking an Fc region, or of the Fab region and the whole or part of the hinge region (Fab, F(ab') and F(ab')$_2$), the BDNF may be linked, on the C-terminus or the N-terminus thereof, and via a linker sequence or directly, to the heavy chain or light chain that constitutes the Fab, F(ab')$_2$ and F(ab'), on the N-terminus (or the C-terminus) thereof, respectively, by peptide bonds.

In a fusion protein of the type in which the BDNF is linked to the "light chain" of the anti-hTfR antibody, which is a humanized antibody or a human antibody, on the C-terminal side of thereof, the anti-human transferrin receptor antibody comprises an amino acid sequence comprising the whole or part of the light chain variable region and an amino acid sequence comprising the whole or part of the heavy chain variable region, and BDNF is linked to this light chain on the C-terminal side thereof. The anti-hTfR antibody light chain and the BDNF here may be linked together, directly or via a linker.

In a fusion protein of the type in which the BDNF is linked to the "heavy chain" of the anti-hTfR antibody, which is a humanized antibody or a human antibody, on the C-terminal side of thereof, the anti-human transferrin receptor antibody comprises an amino acid sequence comprising the whole or part of the light chain variable region and an amino acid sequence comprising the whole or part of the heavy chain variable region, and BDNF is linked to this heavy chain on the C-terminal side thereof. The anti-hTfR antibody heavy chain and the BDNF here may be linked directly or via a linker.

In a fusion protein produced by linking the BDNF to the "light chain" of the anti-hTfR antibody, which is a humanized antibody or a human antibody, on the N-terminal side of thereof, the anti-human transferrin receptor antibody comprises an amino acid sequence comprising the whole or part of the light chain variable region and an amino acid sequence comprising the whole or part of the heavy chain variable region, and BDNF is linked to this light chain on the N-terminal side thereof. The anti-hTfR antibody light chain and the BDNF here may be linked directly or via a linker.

In a fusion protein produced by linking the BDNF to the "heavy chain" of the anti-hTfR antibody, which is a humanized antibody or human antibody, on the N-terminal side thereof, the anti-human transferrin receptor antibody comprises an amino acid sequence comprising the whole or part of the light chain variable region and an amino acid sequence comprising the whole or part of the heavy chain variable region, and BDNF is linked to this heavy chain on the N-terminal side thereof. The anti-hTfR antibody heavy chain and the BDNF here may be linked together, directly or via a linker.

When placing a linker sequence between the anti-hTfR antibody and BDNF, the linker sequence is composed of preferably 1 to 50, more preferably 10 to 40, still more preferably 20 to 34, and for example, 27 amino acids. The number of the amino acids constituting such a linker sequence may be adjusted, as desired, like 1 to 17, 1 to 10, 10 to 40, 20 to 34, 23 to 31, 25 to 29, 27, and so on. The amino acid sequence of such a linker sequence is not limited, as long as the anti-hTfR antibody linked via the linker retains affinity to hTfR and the linked BDNF can exhibit its physiological activity under physiological conditions. The amino acid sequence of the linker sequence is preferably composed of glycine and serine. Examples of the amino acid sequence of the linker sequence include an amino acid sequence consisting of either a glycine or a serine amino acid, the amino acid sequence Gly-Ser, the amino acid sequence Gly-Gly-Ser, the amino acid sequence Gly-Gly-Gly-Gly-Ser (SEQ ID NO:3), the amino acid sequence Gly-Gly-Gly-Gly-Gly-Ser (SEQ ID NO:4), the amino acid sequence Ser-Gly-Gly-Gly-Gly-Gly (SEQ ID NO:5), the sequence consisting not greater than 50 amino acids, which are formed by linking 1 to 10, or 2 to 5 of these amino acid sequences to one another, and the sequence comprising a sequence consisting of 2 to 17, 2 to 10, 10 to 40, 20 to 34, 23 to 31, 25 to 29, or 27 amino acids. For example, a linker comprising 27 amino acids that is composed of the amino acid sequence Gly-Ser followed by consecutively linked five copies of the amino acid sequence Gly-Gly-Gly-Gly-Ser (SEQ ID NO:3) can be preferably used as a linker sequence.

The specific affinity of the anti-hTfR antibody to hTfR resides mainly in the amino acid sequences of CDRs of the heavy chain and light chain of the anti-hTfR antibody. There is no particular limitation as to the amino acid sequences of those CDRs insofar as the anti-hTfR antibody has a specific affinity to hTfR. However, the anti-hTfR antibody of the present invention is one whose dissociation constant ($K_D$) with hTfR as measured by the method described in Example 7 is preferably not greater than $1 \times 10^{-8}$ M, more preferably not greater than $1 \times 10^{-9}$ M, still more preferably not greater than $1 \times 10^{-10}$ M, and even more preferably not greater than $1 \times 10^{-11}$ M. For example, one having a dissociation constant of $1 \times 10^{-13}$ M to $1 \times 10^{-9}$ M, or $1 \times 10^{-13}$ M to $1 \times 10^{-10}$ M is preferable. Further, where the anti-hTfR antibody of the present invention has affinity also to monkey TfR, the dissociation constant of the anti-hTfR antibody with monkey TfR, as measured by the method described in Example 7, is preferably not greater than $5 \times 10^8$ M, more preferably not greater than $2 \times 10^{-8}$ M, and still more preferably not greater than $1 \times 10^{-8}$ M. For example, one which exhibits a dissociation constant of $1 \times 10^{-13}$ M to $2 \times 10^{-8}$ M is preferred. The same also applies if the antibody is a single-chain antibody.

Examples of preferable embodiments of the antibody having affinity to hTfR, which is to be fused with BDNF, include those whose light chain CDRs have amino acid sequences according to one of (1) to (14) below:

(1) the amino acid sequence set forth as SEQ ID NO:6 or SEQ ID NO:7 as CDR1; the amino acid sequence set forth as SEQ ID NO:8 or SEQ ID NO:9 or the amino acid sequence Trp-Thr-Ser as CDR2; and the amino acid sequence set forth as SEQ ID NO: 10 as CDR3;

(2) the amino acid sequence set forth as SEQ ID NO:11 or SEQ ID NO:12 as CDR1; the amino acid sequence set forth as SEQ ID NO: 13 or SEQ ID NO: 14 or the amino acid sequence Tyr-Ala-Ser as CDR2; and the amino acid sequence set forth as SEQ ID NO:15 as CDR3;

(3) the amino acid sequence set forth as SEQ ID NO: 16 or SEQ ID NO:17 as CDR1; the amino acid sequence set forth as SEQ ID NO: 18 or SEQ ID NO:19 or the amino acid sequence Lys-Val-Ser as CDR2; and the amino acid sequence set forth as SEQ ID NO:20 as CDR3;

(4) the amino acid sequence set forth as SEQ ID NO:21 or SEQ ID NO:22 as CDR1; the amino acid sequence set forth as SEQ ID NO:23 or SEQ ID NO:24 or the amino acid sequence Asp-Thr-Ser as CDR2; and the amino acid sequence set forth as SEQ ID NO:25 as CDR3;

(5) the amino acid sequence set forth as SEQ ID NO:26 or SEQ ID NO:27 as CDR1; the amino acid sequence set forth as SEQ ID NO:28 or SEQ ID NO:29 or the amino acid sequence Asp-Thr-Ser as CDR2; and the amino acid sequence set forth as SEQ ID NO:30 as CDR3;

(6) the amino acid sequence set forth as SEQ ID NO:31 or SEQ ID NO:32 as CDR1; the amino acid sequence set forth as SEQ ID NO:33 or SEQ ID NO:34 or the amino acid sequence Ala-Ala-Ser as CDR2; and the amino acid sequence set forth as SEQ ID NO:35 as CDR3;

(7) the amino acid sequence set forth as SEQ ID NO:36 or SEQ ID NO:37 as CDR1; the amino acid sequence set forth as SEQ ID NO:38 or SEQ ID NO:39 or the amino acid sequence Gln-Thr-Ser as CDR2; and the amino acid sequence set forth as SEQ ID NO:40 as CDR3;

(8) the amino acid sequence set forth as SEQ ID NO:41 or SEQ ID NO:42 as CDR1; the amino acid sequence set forth as SEQ ID NO:43 or SEQ ID NO:44 or the amino acid sequence Gly-Thr-Ser as CDR2; and the amino acid sequence set forth as SEQ ID NO:45 as CDR3;

(9) the amino acid sequence set forth as SEQ ID NO:46 or SEQ ID NO:47 as CDR1; the amino acid sequence set forth as SEQ ID NO:48 or SEQ ID NO:49 or the amino acid sequence Phe-Thr-Ser as CDR2; and the amino acid sequence set forth as SEQ ID NO:50 as CDR3;

(10) the amino acid sequence set forth as SEQ ID NO:51 or SEQ ID NO:52 as CDR1; the amino acid sequence set forth as SEQ ID NO:53 or SEQ ID NO:54 or the amino acid sequence Ala-Ala-Ser as CDR2; and the amino acid sequence set forth as SEQ ID NO:55 as CDR3;

(11) the amino acid sequence set forth as SEQ ID NO:56 or SEQ ID NO:57 as CDR1; the amino acid sequence set forth as SEQ ID NO:58 or SEQ ID NO:59 or the amino acid sequence Tyr-Ala-Ser as CDR2; and the amino acid sequence set forth as SEQ ID NO:60 as CDR3;

(12) the amino acid sequence set forth as SEQ ID NO:61 or SEQ ID NO:62 as CDR1; the amino acid sequence set forth as SEQ ID NO:63 or SEQ ID NO:64 or the amino acid sequence Trp-Ser-Ser as CDR2; and the amino acid sequence set forth as SEQ ID NO:65 as CDR3;

(13) the amino acid sequence set forth as SEQ ID NO:66 or SEQ ID NO:67 as CDR1; the amino acid sequence set forth as SEQ ID NO:68 or SEQ ID NO:69 or the amino acid sequence Tyr-Ala-Ser as CDR2; and the amino acid sequence set forth as SEQ ID NO:70 as CDR3; and

(14) the amino acid sequence set forth as SEQ ID NO:71 or SEQ ID NO:72 as CDR1; the amino acid sequence set forth as SEQ ID NO:73 or SEQ ID NO:74 or the amino acid sequence Asp-Thr-Ser as CDR2; and the amino acid sequence set forth as SEQ ID NO:75 as CDR3.

Examples of more specific embodiments of the antibody having affinity to hTfR, which is to be fused with BDNF, include those whose light chain CDRs have amino acid sequences according to one of (1) to (14) below:

(1) an amino acid sequence comprising the amino acid sequence set forth as SEQ ID NO:6 as CDR1; SEQ ID NO:8 as CDR2; and SEQ ID NO: 10 as CDR3;

(2) an amino acid sequence comprising the amino acid sequence set forth as SEQ ID NO:11 as CDR1; SEQ ID NO:13 as CDR2; and SEQ ID NO: 15 as CDR3;

(3) an amino acid sequence comprising the amino acid sequence set forth as SEQ ID NO:16 as CDR1; SEQ ID NO:18 as CDR2; and SEQ ID NO:20 as CDR3;

(4) an amino acid sequence comprising the amino acid sequence set forth as SEQ ID NO:21 as CDR1; SEQ ID NO:23 as CDR2; and SEQ ID NO:25 as CDR3;

(5) an amino acid sequence comprising the amino acid sequence set forth as SEQ ID NO:26 as CDR1; SEQ ID NO:28 as CDR2; and SEQ ID NO:30 as CDR3;

(6) an amino acid sequence comprising the amino acid sequence set forth as SEQ ID NO:31 as CDR1; SEQ ID NO:33 as CDR2; and SEQ ID NO:35 as CDR3;

(7) an amino acid sequence comprising the amino acid sequence set forth as SEQ ID NO:36 as CDR1; SEQ ID NO:38 as CDR2; and SEQ ID NO:40 as CDR3;

(8) an amino acid sequence comprising the amino acid sequence set forth as SEQ ID NO:41 as CDR1; SEQ ID NO:43 as CDR2; and SEQ ID NO:45 as CDR3;

(9) an amino acid sequence comprising the amino acid sequence set forth as SEQ ID NO:46 as CDR1; SEQ ID NO:48 as CDR2; and SEQ ID NO:50 as CDR3;

(10) an amino acid sequence comprising the amino acid sequence set forth as SEQ ID NO:51 as CDR1; SEQ ID NO:53 as CDR2; and SEQ ID NO:55 as CDR3;

(11) an amino acid sequence comprising the amino acid sequence set forth as SEQ ID NO:56 as CDR1; SEQ ID NO:58 as CDR2; and SEQ ID NO:60 as CDR3;

(12) an amino acid sequence comprising the amino acid sequence set forth as SEQ ID NO:61 as CDR1; SEQ ID NO:63 as CDR2; and SEQ ID NO:65 as CDR3;

(13) an amino acid sequence comprising the amino acid sequence set forth as SEQ ID NO:66 as CDR1; SEQ ID NO:68 as CDR2; and SEQ ID NO:70 as CDR3; and

(14) an amino acid sequence comprising the amino acid sequence set forth as SEQ ID NO:71 as CDR1; SEQ ID NO:73 as CDR2; and SEQ ID NO:75 as CDR3.

Examples of preferable embodiments of the antibody having affinity to hTfR, which is to be fused with BDNF, include those whose heavy chain CDRs have amino acid sequences according to one of (1) to (14) below:

(1) an amino acid sequence comprising the amino acid sequence set forth as SEQ ID NO:76 or SEQ ID NO:77 as CDR1; the amino acid sequence set forth as SEQ ID NO:78 or SEQ ID NO:79 as CDR2; and the amino acid sequence set forth as SEQ ID NO:80 or SEQ ID NO:81 as CDR3;

(2) an amino acid sequence comprising the amino acid sequence set forth as SEQ ID NO:82 or SEQ ID NO:83 as CDR1; the amino acid sequence set forth as SEQ ID NO:84 or SEQ ID NO:85 as CDR2; and the amino acid sequence set forth as SEQ ID NO:86 or SEQ ID NO:87 as CDR3;

(3) an amino acid sequence comprising the amino acid sequence set forth as SEQ ID NO:88 or SEQ ID NO:89 as CDR1; the amino acid sequence set forth as SEQ ID NO:90 or SEQ ID NO:91 as CDR2; and the amino acid sequence set forth as SEQ ID NO:92 or SEQ ID NO:93 as CDR3;

(4) an amino acid sequence comprising the amino acid sequence set forth as SEQ ID NO:94 or SEQ ID NO:95 as CDR1; the amino acid sequence set forth as SEQ ID NO:96 or SEQ ID NO:97 as CDR2; and the amino acid sequence set forth as SEQ ID NO:98 or SEQ ID NO:99 as CDR3;

(5) an amino acid sequence comprising the amino acid sequence set forth as SEQ ID NO:100 or SEQ ID NO: 101 as CDR1; the amino acid sequence set forth as SEQ ID NO:102 or SEQ ID NO:103 as CDR2; and the amino acid sequence set forth as SEQ ID NO: 104 or SEQ ID NO: 105 as CDR3;

(6) an amino acid sequence comprising the amino acid sequence set forth as SEQ ID NO:106 or SEQ ID NO: 107 as CDR1; the amino acid sequence set forth as SEQ ID NO: 108 or the amino acid sequence set forth as SEQ ID NO:266 as CDR2; and the amino acid sequence set forth as SEQ ID NO: 109 or SEQ ID NO: 110 as CDR3;

(7) an amino acid sequence comprising the amino acid sequence set forth as SEQ ID NO:111 or SEQ ID NO:112 as CDR1; the amino acid sequence set forth as SEQ ID NO:113 or SEQ ID NO:114 as CDR2; and the amino acid sequence set forth as SEQ ID NO:115 or SEQ ID NO:116 as CDR3;

(8) an amino acid sequence comprising the amino acid sequence set forth as SEQ ID NO:117 or SEQ ID NO:118 as CDR1; the amino acid sequence set forth as SEQ ID NO: 119 or the amino acid sequence set forth as SEQ ID NO:267 as CDR2; and the amino acid sequence set forth as SEQ ID NO: 120 or SEQ ID NO: 121 as CDR3;

(9) an amino acid sequence comprising the amino acid sequence set forth as SEQ ID NO:122 or SEQ ID NO: 123 as CDR1; the amino acid sequence set forth as SEQ ID NO:124 or SEQ ID NO:125 as CDR2; and the amino acid sequence set forth as SEQ ID NO: 126 or SEQ ID NO: 127 as CDR3;

(10) an amino acid sequence comprising the amino acid sequence set forth as SEQ ID NO: 128 or SEQ ID NO: 129 as CDR1; the amino acid sequence set forth as SEQ ID NO: 130 or SEQ ID NO: 131 as CDR2; and the amino acid sequence set forth as SEQ ID NO: 132 or SEQ ID NO: 133 as CDR3;

(11) an amino acid sequence comprising the amino acid sequence set forth as SEQ ID NO: 134 or SEQ ID NO: 135 as CDR1; the amino acid sequence set forth as SEQ ID NO: 136 or SEQ ID NO: 137 as CDR2; and the amino acid sequence set forth as SEQ ID NO: 138 or SEQ ID NO: 139 as CDR3;

(12) an amino acid sequence comprising the amino acid sequence set forth as SEQ ID NO: 140 or SEQ ID NO: 141 as CDR1; the amino acid sequence set forth as SEQ ID NO: 142 or SEQ ID NO: 143 as CDR2; and the amino acid sequence set forth as SEQ ID NO: 144 or SEQ ID NO: 145 as CDR3;

(13) an amino acid sequence comprising the amino acid sequence set forth as SEQ ID NO: 146 or SEQ ID NO: 147 as CDR1; the amino acid sequence set forth as SEQ ID NO: 148 or SEQ ID NO: 149 as CDR2; and the amino acid sequence set forth as SEQ ID NO:150 or SEQ ID NO:151 as CDR3; and

(14) an amino acid sequence comprising the amino acid sequence set forth as SEQ ID NO:152 or SEQ ID NO:153 as CDR1; the amino acid sequence set forth as SEQ ID NO: 154 or SEQ ID NO: 155 as CDR2; and the amino acid sequence set forth as SEQ ID NO:156 or SEQ ID NO: 157 as CDR3.

Examples of more specific embodiments of the antibody having affinity to hTfR, which is to be fused with BDNF, include those whose heavy chain CDRs have amino acid sequences according to one of (1) to (14) below:

(1) an amino acid sequence comprising the amino acid sequence set forth as SEQ ID NO:76 as CDR1; SEQ ID NO:78 as CDR2; and SEQ ID NO:80 as CDR3;

(2) an amino acid sequence comprising the amino acid sequence set forth as SEQ ID NO:82 as CDR1; SEQ ID NO:84 as CDR2; and SEQ ID NO:86 as CDR3;

(3) an amino acid sequence comprising the amino acid sequence set forth as SEQ ID NO:88 as CDR1; SEQ ID NO:90 as CDR2; and SEQ ID NO:92 as CDR3;

(4) an amino acid sequence comprising the amino acid sequence set forth as SEQ ID NO:94 as CDR1; SEQ ID NO:96 as CDR2; and SEQ ID NO:98 as CDR3;

(5) an amino acid sequence comprising the amino acid sequence set forth as SEQ ID NO:100 as CDR1; SEQ ID NO: 102 as CDR2; and SEQ ID NO: 104 as CDR3;

(6) an amino acid sequence comprising the amino acid sequence set forth as SEQ ID NO:106 as CDR1; SEQ ID NO: 108 as CDR2; and SEQ ID NO: 109 as CDR3;

(7) an amino acid sequence comprising the amino acid sequence set forth as SEQ ID NO:111 as CDR1; SEQ ID NO:113 as CDR2; and SEQ ID NO: 115 as CDR3;

(8) an amino acid sequence comprising the amino acid sequence set forth as SEQ ID NO:117 as CDR1; SEQ ID NO:119 as CDR2; and SEQ ID NO: 120 as CDR3;

(9) an amino acid sequence comprising the amino acid sequence set forth as SEQ ID NO: 122 as CDR1; SEQ ID NO: 124 as CDR2; and SEQ ID NO: 126 as CDR3;

(10) an amino acid sequence comprising the amino acid sequence set forth as SEQ ID NO:128 as CDR1; SEQ ID NO:130 as CDR2; and SEQ ID NO: 132 as CDR3;

(11) an amino acid sequence comprising the amino acid sequence set forth as SEQ ID NO:134 as CDR1; SEQ ID NO:136 as CDR2; and SEQ ID NO: 138 as CDR3;

(12) an amino acid sequence comprising the amino acid sequence set forth as SEQ ID NO:140 as CDR1; SEQ ID NO:142 as CDR2; and SEQ ID NO: 144 as CDR3;

(13) an amino acid sequence comprising the amino acid sequence set forth as SEQ ID NO:146 as CDR1; SEQ ID NO:148 as CDR2; and SEQ ID NO:150 as CDR3; and

(14) an amino acid sequence comprising the amino acid sequence set forth as SEQ ID NO:152 as CDR1; SEQ ID NO:154 as CDR2; and SEQ ID NO:156 as CDR3.

Examples of preferable combinations of the light chain and heavy chain of the antibody having affinity to hTfR, which is to be fused with BDNF, include those as CDRs according to one of (1) to (14) below:

(1) a combination of the light chain having the amino acid sequence set forth as SEQ ID NO:6 or SEQ ID NO:7 as CDR1; the amino acid sequence set forth as SEQ ID NO:8 or SEQ ID NO:9 or the amino acid sequence Trp-Thr-Ser as CDR2; and the amino acid sequence set forth as SEQ ID NO:10 as CDR3; and the heavy chain having the amino acid sequence set forth as SEQ ID NO:76 or SEQ ID NO:77 as CDR1; the amino acid sequence set forth as SEQ ID NO:78 or SEQ ID NO:79 as CDR2; and the amino acid sequence set forth as SEQ ID NO:80 or SEQ ID NO:81 as CDR3;

(2) a combination of the light chain having the amino acid sequence set forth as SEQ ID NO:11 or SEQ ID NO:12 as CDR1; the amino acid sequence set forth as SEQ ID NO: 13 or SEQ ID NO: 14 or the amino acid sequence Tyr-Ala-Ser as CDR2; and the amino acid sequence set forth as SEQ ID NO: 15 as CDR3; and the heavy chain having the amino acid sequence set forth as SEQ ID NO:82 or SEQ ID NO:83 as CDR1; the amino acid sequence set forth as SEQ ID NO:84 or SEQ ID NO:85 as CDR2; and the amino acid sequence set forth as SEQ ID NO:86 or SEQ ID NO:87 as CDR3;

(3) a combination of the light chain having the amino acid sequence set forth as SEQ ID NO:16 or SEQ ID NO:17 as CDR1; the amino acid sequence set forth as SEQ ID NO: 18 or SEQ ID NO: 19 or the amino acid sequence Lys-Val-Ser as CDR2; and the amino acid sequence set forth as SEQ ID NO:20 as CDR3; and the heavy chain having the amino acid sequence set forth as SEQ ID NO:88 or SEQ ID NO:89 as CDR1; the amino acid sequence set forth as SEQ ID NO:90 or SEQ ID NO:91 as CDR2; and the amino acid sequence set forth as SEQ ID NO:92 or SEQ ID NO:93 as CDR3;

(4) a combination of the light chain having the amino acid sequence set forth as SEQ ID NO:21 or SEQ ID NO:22 as CDR1; the amino acid sequence set forth as SEQ ID NO:23 or SEQ ID NO:24 or the amino acid sequence Asp-Thr-Ser as CDR2; and the amino acid sequence set forth as SEQ ID NO:25 as CDR3; and the heavy chain having the amino acid sequence set forth as SEQ ID NO:94 or SEQ ID NO:95 as CDR1; the amino acid sequence set forth as SEQ ID NO:96 or SEQ ID NO:97 as CDR2; and the amino acid sequence set forth as SEQ ID NO:98 or SEQ ID NO:99 as CDR3;

(5) a combination of the light chain having the amino acid sequence set forth as SEQ ID NO:26 or SEQ ID NO:27 as CDR1; the amino acid sequence set forth as SEQ ID NO:28 or SEQ ID NO:29 or the amino acid sequence Asp-Thr-Ser as CDR2; and the amino acid sequence set forth as SEQ ID NO:30 as CDR3;

the heavy chain having the amino acid sequence set forth as SEQ ID NO: 100 or SEQ ID NO:101 as CDR1; the amino acid sequence set forth as SEQ ID NO:102 or SEQ ID NO:103 as CDR2; and the amino acid sequence set forth as SEQ ID NO: 104 or SEQ ID NO: 105 as CDR3;

(6) a combination of the light chain having the amino acid sequence set forth as SEQ ID NO:31 or SEQ ID NO:32 as CDR1; the amino acid sequence set forth as SEQ ID NO:33 or SEQ ID NO:34 or the amino acid sequence Ala-Ala-Ser as CDR2; and the amino acid sequence set forth as SEQ ID NO:35 as CDR3; and the heavy chain having the amino acid sequence set forth as SEQ ID NO: 106 or SEQ ID NO: 107 as CDR1; the amino acid sequence set forth as SEQ ID NO:108 or SEQ ID NO:266 as CDR2; and the amino acid sequence set forth as SEQ ID NO: 109 or SEQ ID NO: 110 as CDR3;

(7) a combination of the light chain having the amino acid sequence set forth as SEQ ID NO:36 or SEQ ID NO:37 as CDR1; the amino acid sequence set forth as SEQ ID NO:38 or SEQ ID NO:39 or the amino acid sequence Gln-Thr-Ser as CDR2; and the amino acid sequence set forth as SEQ ID NO:40 as CDR3; and the heavy chain having the amino acid sequence set forth as SEQ ID NO:111 or SEQ ID NO:112 as CDR1; the amino acid sequence set forth as SEQ ID NO:113 or SEQ ID NO:114 as CDR2; and the amino acid sequence set forth as SEQ ID NO:115 or SEQ ID NO:116 as CDR3;

(8) a combination of the light chain having the amino acid sequence set forth as SEQ ID NO:41 or SEQ ID NO:42 as CDR1; the amino acid sequence set forth as SEQ ID NO:43 or SEQ ID NO:44 or the amino acid sequence Gly-Thr-Ser as CDR2; and the amino acid sequence set forth as SEQ ID NO:45 as CDR3; and the heavy chain having the amino acid sequence set forth as SEQ ID NO:117 or SEQ ID NO:118 as CDR1; the amino acid sequence set forth as SEQ ID NO:119 or SEQ ID NO:267 as CDR2; and the amino acid sequence set forth as SEQ ID NO: 120 or SEQ ID NO: 121 as CDR3;

(9) a combination of the light chain having the amino acid sequence set forth as SEQ ID NO:46 or SEQ ID NO:47 as CDR1; the amino acid sequence set forth as SEQ ID NO:48 or SEQ ID NO:49 or the amino acid sequence Phe-Thr-Ser as CDR2; and the amino acid sequence set forth as SEQ ID NO:50 as CDR3; and the heavy chain having the amino acid sequence set forth as SEQ ID NO: 122 or SEQ ID NO: 123 as CDR1; the amino acid sequence set forth as SEQ ID NO:124 or SEQ ID NO:125 as CDR2; and the amino acid sequence set forth as SEQ ID NO: 126 or SEQ ID NO: 127 as CDR3;

(10) a combination of the light chain having the amino acid sequence set forth as SEQ ID NO:51 or SEQ ID NO:52 as CDR1; the amino acid sequence set forth as SEQ ID NO:53 or SEQ ID NO:54 or the amino acid sequence Ala-Ala-Ser as CDR2; and the amino acid sequence set forth as SEQ ID NO:55 as CDR3; and the heavy chain having the amino acid sequence set forth as SEQ ID NO: 128 or SEQ ID NO: 129 as CDR1; the amino acid sequence set forth as SEQ ID NO:130 or SEQ ID NO:131 as CDR2; and the amino acid sequence set forth as SEQ ID NO: 132 or SEQ ID NO: 133 as CDR3;

(11) a combination of the light chain having the amino acid sequence set forth as SEQ ID NO:56 or SEQ ID NO:57 as CDR1; the amino acid sequence set forth as SEQ ID NO:58 or SEQ ID NO:59 or the amino acid sequence Tyr-Ala-Ser as CDR2; and the amino acid sequence set forth as SEQ ID NO:60 as CDR3; and the heavy chain having the amino acid sequence set forth as SEQ ID NO: 134 or SEQ ID NO:135 as CDR1; the amino acid sequence set forth as SEQ ID NO:136 or SEQ ID NO:137 as CDR2; and the amino acid sequence set forth as SEQ ID NO: 138 or SEQ ID NO: 139 as CDR3;

(12) a combination of the light chain having the amino acid sequence set forth as SEQ ID NO:61 or SEQ ID NO:62 as CDR1; the amino acid sequence set forth as SEQ ID NO:63 or SEQ ID NO:64 or the amino acid sequence Trp-Ser-Ser as CDR2; and the amino acid sequence set forth as SEQ ID NO:65 as CDR3; and the heavy chain having the amino acid sequence set forth as SEQ ID NO: 140 or SEQ ID NO: 141 as CDR1; the amino acid sequence set forth as SEQ ID NO:142 or SEQ ID NO:143 as CDR2; and the amino acid sequence set forth as SEQ ID NO: 144 or SEQ ID NO: 145 as CDR3;

(13) a combination of the light chain having the amino acid sequence set forth as SEQ ID NO:66 or SEQ ID NO:67 as CDR1; the amino acid sequence set forth as SEQ ID NO:68 or SEQ ID NO:69 or the amino acid sequence Tyr-Ala-Ser as CDR2; and the amino acid sequence set forth as SEQ ID NO:70 as CDR3; and the heavy chain having the amino acid sequence set forth as SEQ ID NO: 146 or SEQ ID NO: 147 as CDR1; the amino acid sequence set forth as SEQ ID NO:148 or SEQ ID NO: 149 as CDR2; and the amino acid sequence set forth as SEQ ID NO: 150 or SEQ ID NO: 151 as CDR3;

(14) a combination of the light chain having the amino acid sequence set forth as SEQ ID NO:71 or SEQ ID NO:72 as CDR1; the amino acid sequence set forth as SEQ ID NO:73 or SEQ ID NO:74 or the amino acid sequence Asp-Thr-Ser as CDR2; and the amino acid sequence set forth as SEQ ID NO:75 as CDR3; and the heavy chain having the amino acid sequence set forth as SEQ ID NO:152 or SEQ ID NO:153 as CDR1; the amino acid sequence set forth as SEQ ID NO:154 or SEQ ID NO:155 as CDR2; and the amino acid sequence set forth as SEQ ID NO: 156 or SEQ ID NO: 157 as CDR3.

Examples of specific embodiments of combinations of the light chain and heavy chain of the antibody having affinity to hTfR, which is to be fused with BDNF, include those having combinations of the amino acid sequences as CDRs according to one of (1) to (14) below:

(1) a combination of the light chain having the amino acid sequence set forth as SEQ ID NO:6 as CDR1; SEQ ID NO:8 as CDR2; and SEQ ID NO:10 as CDR3; and the heavy chain having the amino acid sequence set forth as SEQ ID NO:76 as CDR1; SEQ ID NO:78 as CDR2; and SEQ ID NO:80 as CDR3;

(2) a combination of the light chain having the amino acid sequence set forth as SEQ ID NO:11 as CDR1; SEQ ID NO:13 as CDR2; and SEQ ID NO:15 as CDR3; and the heavy chain having the amino acid sequence set forth as SEQ ID NO:82 as CDR1; SEQ ID NO:84 as CDR2; and SEQ ID NO:86 as CDR3;

(3) a combination of the light chain having the amino acid sequence set forth as SEQ ID NO:16 as CDR1; SEQ ID NO:18 as CDR2; and SEQ ID NO:20 as CDR3; and the heavy chain having the amino acid sequence set forth as SEQ ID NO:88 as CDR1; SEQ ID NO:90 as CDR2; and SEQ ID NO:92 as CDR3;

(4) a combination of
the light chain having the amino acid sequence set forth as SEQ ID NO:21 as CDR1; SEQ ID NO:23 as CDR2; and SEQ ID NO:25 as CDR3; and
the heavy chain having the amino acid sequence set forth as SEQ ID NO:94 as CDR1; SEQ ID NO:96 as CDR2; and SEQ ID NO:98 as CDR3;

(5) a combination of
the light chain having the amino acid sequence set forth as SEQ ID NO:26 as CDR1; SEQ ID NO:28 as CDR2; and SEQ ID NO:30 as CDR3; and
the heavy chain having the amino acid sequence set forth as SEQ ID NO:100 as CDR1; SEQ ID NO:102 as CDR2; and SEQ ID NO: 104 as CDR3;

(6) a combination of
the light chain having the amino acid sequence set forth as SEQ ID NO:31 as CDR1; SEQ ID NO:33 as CDR2; and SEQ ID NO:35 as CDR3; and
the heavy chain having the amino acid sequence set forth as SEQ ID NO:106 as CDR1; SEQ ID NO:108 as CDR2; and SEQ ID NO: 109 as CDR3;

(7) a combination of
the light chain having the amino acid sequence set forth as SEQ ID NO:36 as CDR1; SEQ ID NO:38 as CDR2; and SEQ ID NO:40 as CDR3; and
the heavy chain having the amino acid sequence set forth as SEQ ID NO:111 as CDR1; SEQ ID NO:113 as CDR2; and SEQ ID NO:115 as CDR3;

(8) a combination of
the light chain having the amino acid sequence set forth as SEQ ID NO:41 as CDR1; SEQ ID NO:43 as CDR2; and SEQ ID NO:45 as CDR3; and
the heavy chain having the amino acid sequence set forth as SEQ ID NO:117 as CDR1; SEQ ID NO:119 as CDR2; and SEQ ID NO: 120 as CDR3;

(9) a combination of
the light chain having the amino acid sequence set forth as SEQ ID NO:46 as CDR1; SEQ ID NO:48 as CDR2; and SEQ ID NO:50 as CDR3; and
the heavy chain having the amino acid sequence set forth as SEQ ID NO:122 as CDR1; SEQ ID NO:124 as CDR2; and SEQ ID NO: 126 as CDR3;

(10) a combination of
the light chain having the amino acid sequence set forth as SEQ ID NO:51 as CDR1; SEQ ID NO:53 as CDR2; and SEQ ID NO:55 as CDR3; and
the heavy chain having the amino acid sequence set forth as SEQ ID NO:128 as CDR1; SEQ ID NO:130 as CDR2; and SEQ ID NO: 132 as CDR3;

(11) a combination of
the light chain having the amino acid sequence set forth as SEQ ID NO:56 as CDR1; SEQ ID NO:58 as CDR2; and SEQ ID NO:60 as CDR3; and
the heavy chain having the amino acid sequence set forth as SEQ ID NO:134 as CDR1; SEQ ID NO:136 as CDR2; and SEQ ID NO: 138 as CDR3;

(12) a combination of
the light chain having the amino acid sequence set forth as SEQ ID NO:61 as CDR1; SEQ ID NO:63 as CDR2; and SEQ ID NO:65 as CDR3; and
the heavy chain having the amino acid sequence set forth as SEQ ID NO:140 as CDR1; SEQ ID NO:142 as CDR2; and SEQ ID NO: 144 as CDR3;

(13) a combination of
the light chain having the amino acid sequence set forth as SEQ ID NO:66 as CDR1; SEQ ID NO:68 as CDR2; and SEQ ID NO:70 as CDR3; and
the heavy chain having the amino acid sequence set forth as SEQ ID NO:146 as CDR1; SEQ ID NO:148 as CDR2; and SEQ ID NO: 150 as CDR3; and

(14) a combination of
the light chain having the amino acid sequence set forth as SEQ ID NO:71 as CDR1; SEQ ID NO:73 as CDR2; and SEQ ID NO:75 as CDR3; and
the heavy chain having the amino acid sequence set forth as SEQ ID NO:152 as CDR1; SEQ ID NO:154 as CDR2; and SEQ ID NO:156 as CDR3.

As preferred embodiments of humanized antibodies having affinity to hTfR, which are to be fused with BDNF, there are humanized antibodies produced using the amino acid sequences of the light chain variable region and the heavy chain variable region of the mouse anti-human TfR antibody set forth as SEQ ID NO:218 to SEQ ID NO:245 as CDRs. The humanized antibodies are produced by grafting the amino acid sequences of CDRs of the light chain variable region and the heavy chain variable region of mouse anti-human TfR antibody into proper positions of a human antibody variable region.

For example, the light chain of a humanized antibody can be made by replacing the amino acid sequences of corresponding CDRs of the light chain of a human antibody with an amino acid sequence consisting of not less than 3, or not less than 6, consecutive amino acids at the positions 24th to 34th of the amino acid sequence set forth as SEQ ID NO:218 as CDR1; with an amino acid sequence consisting of not less than 3, or not less than 6, consecutive amino acids at the positions 50th to 56th of the amino acid sequence set forth as SEQ ID NO:218 as CDR2; and with an amino acid sequence consisting of not less than 3, or not less than 8, consecutive amino acids at the positions 89th to 97th of the amino acid sequence set forth as SEQ ID NO:218 as CDR3. Moreover, the heavy chain of a humanized antibody can be made by replacing the amino acid sequences of corresponding CDRs of the heavy chain of a human antibody with an amino acid sequence consisting of not less than 3 consecutive amino acids at the positions 26th to 35th of the amino acid sequence set forth as SEQ ID NO:219 as CDR1; with an amino acid sequence consisting of not less than 3, or not less than 8, consecutive amino acids at the positions 50th to 66th of the amino acid sequence set forth as SEQ ID NO:219 as CDR2; with an amino acid sequence consisting of not less than 3, or not less than 7, consecutive amino acids at the positions 97th to 105th of the amino acid sequence set forth as SEQ ID NO:219 as CDR3.

By combining the light chain and the heavy chain of the humanized antibody thus obtained, the humanized antibody can be prepared.

Moreover, for example, the light chain of a humanized antibody can be made by replacing the amino acid sequences of corresponding CDRs of the light chain of a human antibody with an amino acid sequence consisting of not less than 3, or not less than 6, consecutive amino acids at the positions 24th to 34th of the amino acid sequence set forth as SEQ ID NO:220 as CDR1; with an amino acid sequence consisting of not less than 3, or not less than 6, consecutive amino acids at the positions 50th to 56th of the amino acid sequence set forth as SEQ ID NO:220 as CDR2; and with an amino acid sequence consisting of not less than 3, or not less than 8, consecutive amino acids at the positions 89th to 97th of the amino acid sequence set forth as SEQ ID NO:220 as CDR3. Moreover, the heavy chain of a humanized antibody can be made by replacing the amino acid sequences of corresponding CDRs of the heavy chain of a human antibody with an amino acid sequence consisting of not less than 3 consecutive amino acids at the positions 26th to 35th of the amino acid sequence set forth as SEQ ID NO:221 as CDR1; with an amino acid sequence consisting of not less than 3, or not less than 8, consecutive amino acids at the positions 50th to 66th of the amino acid sequence set forth as SEQ ID NO:221 as CDR2; with an amino acid sequence consisting of not less than 3, or not less than 14, consecutive amino acids at the positions 97th to 112nd of the amino acid sequence set forth as SEQ ID NO:221 as CDR3.

By combining the light chain and the heavy chain of the humanized antibody thus obtained, the humanized antibody can be prepared.

Further, for example, the light chain of a humanized antibody can be made by replacing the amino acid sequences of corresponding CDRs of the light chain of a human antibody with an amino acid sequence consisting of not less than 3, or not less than 11, consecutive amino acids at the positions 24th to 39th of the amino acid sequence set forth as SEQ ID NO:222 as CDR1; with an amino acid sequence consisting of not less than 3, not less than 6, consecutive amino acids at the positions 55th to 61st of the amino acid sequence set forth as SEQ ID NO:222 as CDR2; and with an amino acid sequence consisting of not less than 3, or not less than 8, consecutive amino acids at the positions 94th to 102nd of the amino acid sequence set forth as SEQ ID NO:222 as CDR3; and the heavy chain of a humanized antibody can be made by replacing the amino acid sequences of corresponding CDRs of the heavy chain of a human antibody with an amino acid sequence consisting of not less than 3 consecutive amino acids at the positions 26th to 35th of the amino acid sequence set forth as SEQ ID NO:223 as CDR1; with an amino acid sequence consisting of not less than 3, or not less than 8, consecutive amino acids at the positions 50th to 66th of the amino acid sequence set forth as SEQ ID NO:223 as CDR2; and with an amino acid sequence consisting of not less than 3, or not less than 9 consecutive amino acids at the positions 97th to 107th of the amino acid sequence set forth as SEQ ID NO:223 as CDR3.

By combining the light chain and the heavy chain of the humanized antibody thus obtained, the humanized antibody can be prepared.

Further, for example, the light chain of a humanized antibody can be made by replacing the amino acid sequences of corresponding CDRs of the light chain of a human antibody with an amino acid sequence consisting of not less than 3, or not less than 5, consecutive amino acids at the positions 24th to 33rd of the amino acid sequence set forth as SEQ ID NO:224 as CDR1; with an amino acid sequence consisting of not less than 3, or not less than 6, consecutive amino acids at the positions 49th to 55th of the amino acid sequence set forth as SEQ ID NO:224 as CDR2; and with an amino acid sequence consisting of not less than 3, or not less than 8, consecutive amino acids at the positions 88th to 96th of the amino acid sequence set forth as SEQ ID NO:224 as CDR3. Moreover, the heavy chain of a humanized antibody can be made by replacing the amino acid sequences of corresponding CDRs of the heavy chain of a human antibody with an amino acid sequence consisting of not less than 3 consecutive amino acids at the positions 26th to 35th of the amino acid sequence set forth as SEQ ID NO:225 as CDR1; with an amino acid sequence consisting of not less than 3, or not less than 8, consecutive amino acids at the positions 51st to 66th of the amino acid sequence set forth as SEQ ID NO:225 as CDR2; with an amino acid sequence consisting of not less than 3, or not less than 13, consecutive amino acids at the positions 97th to 111st of the amino acid sequence set forth as SEQ ID NO:225 as CDR3.

By combining the light chain and the heavy chain of the humanized antibody thus obtained, the humanized antibody can be prepared.

Further, for example, the light chain of a humanized antibody can be made by replacing the amino acid sequences of corresponding CDRs of the light chain of a human antibody with an amino acid sequence consisting of not less than 3, or not less than 5, consecutive amino acids at the positions 24th to 33rd of the amino acid sequence set forth as SEQ ID NO:226 as CDR1; with an amino acid sequence consisting of not less than 3, or not less than 6, consecutive amino acids at the positions 49th to 55th of the amino acid sequence set forth as SEQ ID NO:226 as CDR2; and with an amino acid sequence consisting of not less than 3, or not less than 7, consecutive amino acids at the positions 88th to 95th of the amino acid sequence set forth as SEQ ID NO:226 as CDR3. The heavy chain of a humanized antibody can be made by replacing the amino acid sequences of corresponding CDRs of the heavy chain of a human antibody with an amino acid sequence consisting of not less than 3 consecutive amino acids at the positions 26th to 35th of the amino acid sequence set forth as SEQ ID NO:227 as CDR1; with an amino acid sequence consisting of not less than 3, or not less than 8, consecutive amino acids at the positions 51st to 66th of the amino acid sequence set forth as SEQ ID NO:227 as CDR2; with an amino acid sequence consisting of not less than 3, or not less than 9, consecutive amino acids at the positions 97th to 107th of the amino acid sequence set forth as SEQ ID NO:227 as CDR3.

By combining the light chain and the heavy chain of the humanized antibody thus obtained, the humanized antibody can be prepared.

Further, for example, the light chain of a humanized antibody can be made by replacing the amino acid sequences of corresponding CDRs of the light chain of a human antibody with an amino acid sequence consisting of not less than 3, or not less than 6, consecutive amino acids at the positions 24th to 34th of the amino acid sequence set forth as SEQ ID NO:228 as CDR1; with an amino acid sequence consisting of not less than 3, or not less than 6, consecutive amino acids at the positions 50th to 56th of the amino acid sequence set forth as SEQ ID NO:228 as CDR2; and with an amino acid sequence consisting of not less than 3, or not less than 8, consecutive amino acids at the positions 89th to 97th of the amino acid sequence set forth as SEQ ID NO:228 as CDR3. Moreover, the heavy chain of a humanized antibody can be made by replacing the amino acid sequences of corresponding CDRs of the heavy chain of a human antibody with an amino acid sequence consisting of not less than 3 consecutive amino acids at the positions 26th to 35th of the amino acid sequence set forth as SEQ ID NO:229 as CDR1; with an amino acid sequence consisting of not less than 3, or not less than 7, consecutive amino acids at the positions 50th to 65th of the amino acid sequence set forth as SEQ ID NO:229 as CDR2; with an amino acid sequence consisting of not less than 3, or not less than 4, consecutive amino acids at the positions 96th to 101st of the amino acid sequence set forth as SEQ ID NO:229 as CDR3.

By combining the light chain and the heavy chain of the humanized antibody thus obtained, the humanized antibody can be prepared.

Further, for example, the light chain of a humanized antibody can be made by replacing the amino acid sequences of corresponding CDRs of the light chain of a human antibody with an amino acid sequence consisting of not less than 3, or not less than 5, consecutive amino acids at the positions 24th to 33rd of the amino acid sequence set forth as SEQ ID NO:230 as CDR1; with an amino acid sequence consisting of not less than 3, or not less than 6, consecutive amino acids at the positions 49th to 55th of the amino acid sequence set forth as SEQ ID NO:230 as CDR2; and with an amino acid sequence consisting of not less than 3, or not less than 8, consecutive amino acids at the positions 88th to 96th of the amino acid sequence set forth as SEQ ID NO:230 as CDR3. Moreover, the heavy chain of a humanized antibody can be made by replacing the amino acid sequences of corresponding CDRs of the heavy chain of a human antibody with an amino acid sequence consisting of not less than 3 consecutive amino acids at the positions 26th to 35th of the amino acid sequence set forth as SEQ ID NO:231 as CDR1; with an amino acid sequence consisting of not less than 3, or not less than 8, consecutive amino acids at the positions 51st to 66th of the amino acid sequence set forth as SEQ ID NO:231 as CDR2; with an amino acid sequence consisting of not less than 3, or not less than 11, consecutive amino acids at the positions 97th to 109th of the amino acid sequence set forth as SEQ ID NO:231 as CDR3.

By combining the light chain and the heavy chain of the humanized antibody thus obtained, the humanized antibody can be prepared.

Further, for example, the light chain of a humanized antibody can be made by replacing the amino acid sequences of corresponding CDRs of the light chain of a human antibody with an amino acid sequence consisting of not less than 3, or not less than 5, consecutive amino acids at the positions 24th to 33rd of the amino acid sequence set forth as SEQ ID NO:232 as CDR1; with an amino acid sequence consisting of not less than 3, or not less than 6, consecutive amino acids at the positions 49th to 55th of the amino acid sequence set forth as SEQ ID NO:232 as CDR2; and with an amino acid sequence consisting of not less than 3, or not less than 8, consecutive amino acids at the positions 88th to 96th of the amino acid sequence set forth as SEQ ID NO:232 as CDR3. Moreover, the heavy chain of a humanized antibody can be made by replacing the amino acid sequences of corresponding CDRs of the heavy chain of a human antibody with an amino acid sequence consisting of not less than 3 consecutive amino acids at the positions 26th to 35th of the amino acid sequence set forth as SEQ ID NO:233 as CDR1; with an amino acid sequence consisting of not less than 3, or not less than 7, consecutive amino acids at the positions 50th to 65th of the amino acid sequence set forth as SEQ ID NO:233 as CDR2; with an amino acid sequence consisting of not less than 3, or not less than 4, consecutive amino acids at the positions 96th to 101st of the amino acid sequence set forth as SEQ ID NO:233 as CDR3.

By combining the light chain and the heavy chain of the humanized antibody thus obtained, the humanized antibody can be prepared.

Further, for example, the light chain of a humanized antibody can be made by replacing the amino acid sequences of corresponding CDRs of the light chain of a human antibody with an amino acid sequence consisting of not less than 3, or not less than 5, consecutive amino acids at the positions 24th to 33rd of the amino acid sequence set forth as SEQ ID NO:234 as CDR1; with an amino acid sequence consisting of not less than 3, or not less than 6, consecutive amino acids at the positions 49th to 55th of the amino acid sequence set forth as SEQ ID NO:234 as CDR2; and with an amino acid sequence consisting of not less than 3, or not less than 8, consecutive amino acids at the positions 88th to 96th of the amino acid sequence set forth as SEQ ID NO:234 as CDR3. Moreover, the heavy chain of a humanized antibody can be made by replacing the amino acid sequences of corresponding CDRs of the heavy chain of a human antibody with an amino acid sequence consisting of not less than 3 consecutive amino acids at the positions 26th to 35th of the amino acid sequence set forth as SEQ ID NO:235 as CDR1; with an amino acid sequence consisting of not less than 3, or not less than 8, consecutive amino acids at the positions 51st to 66th of the amino acid sequence set forth as SEQ ID NO:235 as CDR2; with an amino acid sequence consisting of not less than 3, or not less than 8, consecutive amino acids at the positions 97th to 106th of the amino acid sequence set forth as SEQ ID NO:235 as CDR3.

By combining the light chain and the heavy chain of the humanized antibody thus obtained, the humanized antibody can be prepared.

Further, for example, the light chain of a humanized antibody can be made by replacing the amino acid sequences of corresponding CDRs of the light chain of a human antibody with an amino acid sequence consisting of not less than 3, or not less than 6, consecutive amino acids at the positions 24th to 34th of the amino acid sequence set forth as SEQ ID NO:236 as CDR1; with an amino acid sequence consisting of not less than 3, or not less than 6, consecutive amino acids at the positions 50th to 56th of the amino acid sequence set forth as SEQ ID NO:236 as CDR2; and with an amino acid sequence consisting of not less than 3, or not less than 8, consecutive amino acids at the positions 89th to 97th of the amino acid sequence set forth as SEQ ID NO:236 as CDR3. Moreover, the heavy chain of a humanized antibody can be made by replacing the amino acid sequences of corresponding CDRs of the heavy chain of a human antibody with an amino acid sequence consisting of not less than 3 consecutive amino acids at the positions 26th to 35th of the amino acid sequence set forth as SEQ ID NO:237 as CDR1; with an amino acid sequence consisting of not less than 3, or not less than 8, consecutive amino acids at the positions 51st to 66th of the amino acid sequence set forth as SEQ ID NO:237 as CDR2; with an amino acid sequence consisting of not less than 3, or not less than 11, consecutive amino acids at the positions 97th to 109th of the amino acid sequence set forth as SEQ ID NO:237 as CDR3.

By combining the light chain and the heavy chain of the humanized antibody thus obtained, the humanized antibody can be prepared.

Further, for example, the light chain of a humanized antibody can be made by replacing the amino acid sequences of corresponding CDRs of the light chain of a human antibody with an amino acid sequence consisting of not less than 3, or not less than 6, consecutive amino acids at the positions 24th to 34th of the amino acid sequence set forth as SEQ ID NO:238 as CDR1; with an amino acid sequence consisting of not less than 3, or not less than 6, consecutive amino acids at the positions 50th to 56th of the amino acid sequence set forth as SEQ ID NO:238 as CDR2; and with an amino acid sequence consisting of not less than 3, or not less than 8, consecutive amino acids at the positions 89th to 97th of the amino acid sequence set forth as SEQ ID NO:238 as CDR3. Moreover, the heavy chain of a humanized antibody can be made by replacing the amino acid sequences of corresponding CDRs of the heavy chain of a human antibody with an amino acid sequence consisting of not less than 3 consecutive amino acids at the positions 26th to 35th of the amino acid sequence set forth as SEQ ID NO:239 as CDR1; with an amino acid sequence consisting of not less than 3, or not less than 8, consecutive amino acids at the positions 51st to 66th of the amino acid sequence set forth as SEQ ID NO:239 as CDR2; with an amino acid sequence consisting of not less than 3, or not less than 9, consecutive amino acids at the positions 97th to 107th of the amino acid sequence set forth as SEQ ID NO:239 as CDR3.

By combining the light chain and the heavy chain of the humanized antibody thus obtained, the humanized antibody can be prepared.

Further, for example, the light chain of a humanized antibody can be made by replacing the amino acid sequences of corresponding CDRs of the light chain of a human antibody with an amino acid sequence consisting of not less than 3, or not less than 6, consecutive amino acids at the positions 24th to 34th of the amino acid sequence set forth as SEQ ID NO:240 as CDR1; with an amino acid sequence consisting of not less than 3, or not less than 6, consecutive amino acids at the positions 50th to 56th of the amino acid sequence set forth as SEQ ID NO:240 as CDR2; and with an amino acid sequence consisting of not less than 3, or not less than 8, consecutive amino acids at the positions 89th to 97th of the amino acid sequence set forth as SEQ ID NO:240 as CDR3. Moreover, the heavy chain of a humanized antibody can be made by replacing the amino acid sequences of corresponding CDRs of the heavy chain of a human antibody with an amino acid sequence consisting of not less than 3 consecutive amino acids at the positions 26th to 35th of the amino acid sequence set forth as SEQ ID NO:241 as CDR1; with an amino acid sequence consisting of not less than 3, or not less than 8, consecutive amino acids at the positions 51st to 66th of the amino acid sequence set forth as SEQ ID NO:241 as CDR2; with an amino acid sequence consisting of not less than 3, or not less than 10, consecutive amino acids at the positions 97th to 108th of the amino acid sequence set forth as SEQ ID NO:241 as CDR3.

By combining the light chain and the heavy chain of the humanized antibody thus obtained, the humanized antibody can be prepared.

Further, for example, the light chain of a humanized antibody can be made by replacing the amino acid sequences of corresponding CDRs of the light chain of a human antibody with an amino acid sequence consisting of not less than 3, or not less than 6, consecutive amino acids at the positions 24th to 34th of the amino acid sequence set forth as SEQ ID NO:242 as CDR1; with an amino acid sequence consisting of not less than 3, or not less than 6, consecutive amino acids at the positions 50th to 56th of the amino acid sequence set forth as SEQ ID NO:242 as CDR2; and with an amino acid sequence consisting of not less than 3, or not less than 8, consecutive amino acids at the positions 89th to 97th of the amino acid sequence set forth as SEQ ID NO:242 as CDR3. Moreover, the heavy chain of a humanized antibody can be made by replacing the amino acid sequences of corresponding CDRs of the heavy chain of a human antibody with an amino acid sequence consisting of not less than 3 consecutive amino acids at the positions 26th to 35th of the amino acid sequence set forth as SEQ ID NO:243 as CDR1; with an amino acid sequence consisting of not less than 3, or not less than 8, consecutive amino acids at the positions 51st to 66th of the amino acid sequence set forth as SEQ ID NO:243 as CDR2; with an amino acid sequence consisting of not less than 3, or not less than 9, consecutive amino acids at the positions 97th to 107th of the amino acid sequence set forth as SEQ ID NO:243 as CDR3.

By combining the light chain and the heavy chain of the humanized antibody thus obtained, the humanized antibody can be prepared.

Further, for example, the light chain of a humanized antibody can be made by replacing the amino acid sequences of corresponding CDRs of the light chain of a human antibody with an amino acid sequence consisting of not less than 3, or not less than 5, consecutive amino acids at the positions 24th to 33rd of the amino acid sequence set forth as SEQ ID NO:244 as CDR1; with an amino acid sequence consisting of not less than 3, or not less than 6, consecutive amino acids at the positions 49th to 55th of the amino acid sequence set forth as SEQ ID NO:244 as CDR2; and with an amino acid sequence consisting of not less than 3, or not less than 9, consecutive amino acids at the positions 88th to 96th of the amino acid sequence set forth as SEQ ID NO:244 as CDR3. Moreover, the heavy chain of a humanized antibody can be made by replacing the amino acid sequences of corresponding CDRs of the heavy chain of a human antibody with an amino acid sequence consisting of not less than 3 consecutive amino acids at the positions 26th to 35th of the amino acid sequence set forth as SEQ ID NO:245 as CDR1; with an amino acid sequence consisting of not less than 3, or not less than 8, consecutive amino acids at the positions 51st to 66th of the amino acid sequence set forth as SEQ ID NO:245 as CDR2; with an amino acid sequence consisting of not less than 3, or not less than 9, consecutive amino acids at the positions 97th to 107th of the amino acid sequence set forth as SEQ ID NO:245 as CDR3.

By combining the light chain and the heavy chain of the humanized antibody thus obtained, the humanized antibody can be prepared.

Examples of preferred embodiments of the humanized antibody having affinity to hTfR, which is to be fused with BDNF, include those having an amino acid sequence according to one of (1) to (3) below:

(1) An anti-hTfR antibody,
wherein the light chain variable region thereof comprises an amino acid sequence selected from the group consisting of the amino acid sequences set forth as SEQ ID NO:158, SEQ ID NO:159, SEQ ID NO: 160, SEQ ID NO:161, SEQ ID NO: 162, and SEQ ID NO: 163, and
wherein the heavy chain variable region thereof comprises an amino acid sequence selected from the group consisting of the amino acid sequences set forth as SEQ ID NO: 166, SEQ ID NO: 167, SEQ ID NO: 168, SEQ ID NO: 169, SEQ ID NO: 170, and SEQ ID NO: 171.

(2) an anti-hTfR antibody,
wherein the light chain variable region thereof comprises an amino acid sequence selected from the group consisting of the amino acid sequences set forth as SEQ ID NO: 174, SEQ ID NO: 175, SEQ ID NO: 176, SEQ ID NO: 177, SEQ ID NO: 178, and SEQ ID NO: 179, and
wherein the heavy chain variable region thereof comprises an amino acid sequence selected from the group consisting of the amino acid sequences set forth as SEQ ID NO: 182, SEQ ID NO: 183, SEQ ID NO: 184, SEQ ID NO: 185, SEQ ID NO: 186, and SEQ ID NO: 187.

(3) anti-hTfR antibody,
wherein the light chain variable region thereof comprises an amino acid sequence selected from the group consisting of the amino acid sequences set forth as SEQ ID NO: 190, SEQ ID NO: 191, SEQ ID NO: 192, SEQ ID NO: 193, SEQ ID NO: 194, and SEQ ID NO: 195, and
wherein the heavy chain variable region thereof comprises an amino acid sequence selected from the group consisting of the amino acid sequences set forth as SEQ ID NO:204, SEQ ID NO:205, SEQ ID NO:206, SEQ ID NO:207, SEQ ID NO:208 and SEQ ID NO:209.

The amino acid sequences of the light chain variable region set forth as SEQ ID NO:158, SEQ ID NO:159, SEQ ID NO: 160, SEQ ID NO:161, SEQ ID NO:162 and SEQ ID NO:163 comprise the amino acid sequence set forth as SEQ ID NO:6 or 7 in CDR1; SEQ ID NO:8 or 9 in CDR2; and SEQ ID NO: 10 in CDR3. However, the term CDRs as used above in regard to the amino acid sequences of the light chain variable region set forth as SEQ ID NOs: 158 to 162 is not limited to those specific sequences but may also include a region containing the amino acid sequences of one of the CDRs or include an amino acid sequence comprising not less than 3 consecutive amino acids of one of the above CDRs.

The amino acid sequences of the heavy chain variable region set forth as SEQ ID NO: 166, SEQ ID NO: 167, SEQ ID NO: 168, SEQ ID NO:169, SEQ ID NO:170, and SEQ ID NO:171 comprise the amino acid sequence set forth as SEQ ID NO:76 or 77 in CDR1; SEQ ID NO:78 or 79 in CDR2; and SEQ ID NO:80 or 81 in CDR3. However, the term CDRs used above in regard to the amino acid sequences of the heavy chain variable region set forth as SEQ ID NOs: 166 to 171 is not limited to those specific sequences but may also include a region containing the amino acid sequences of one of the CDRs or include an amino acid sequence comprising not less than 3 consecutive amino acids of one of the above CDRs.

The amino acid sequences of the light chain variable region set forth as SEQ ID NO:174, SEQ ID NO:175, SEQ ID NO:176, SEQ ID NO:177, SEQ ID NO:178, and SEQ ID NO:179 comprise the amino acid sequence set forth as SEQ ID NO:11 or 12 in CDR1; SEQ ID NO:13 or 14 in CDR2; and SEQ ID NO:15 in CDR3. However, the term CDRs as used above in regard to the amino acid sequences of the light chain variable region set forth as SEQ ID NOs: 174 to 179 is not limited to those specific sequences but may also include a region containing the amino acid sequences of one of the CDRs or include an amino acid sequence comprising not less than 3 consecutive amino acids of one of the above CDRs.

The amino acid sequences of the heavy chain variable region set forth as SEQ ID NO:182, SEQ ID NO:183, SEQ ID NO:184, SEQ ID NO:185, SEQ ID NO:186, and SEQ ID NO:187 comprise the amino acid sequence set forth as SEQ ID NO:82 or 83 in CDR1; SEQ ID NO:84 or 85 in CDR2; and SEQ ID NO:86 or 87 in CDR3. However, the term CDRs used above in regard to the amino acid sequences of the heavy chain variable region set forth as SEQ ID NOs: 182 to 187 is not limited to those specific sequences but may also include a region containing the amino acid sequences of one of the CDRs or include an amino acid sequence comprising not less than 3 consecutive amino acids of one of the above CDRs.

The amino acid sequences of the light chain variable region set forth as SEQ ID NO: 190, SEQ ID NO:191, SEQ ID NO: 192, SEQ ID NO:193, SEQ ID NO:194, and SEQ ID NO:195 comprise the amino acid sequence set forth as SEQ ID NO:16 or 17 in CDR1, SEQ ID NO:18 or 19 in CDR2, and SEQ ID NO:20 in CDR3. However, the term CDRs as used above in regard to the amino acid sequences of the light chain variable region set forth as SEQ ID NOs: 190 to 195 is not limited to those specific sequences but may also include a region containing the amino acid sequences of one of the CDRs or include an amino acid sequence comprising not less than 3 consecutive amino acids of one of the above CDRs.

The amino acid sequences of the heavy chain variable region set forth as SEQ ID NO:204, SEQ ID NO:205, SEQ ID NO:206, SEQ ID NO:207, SEQ ID NO:208 and SEQ ID NO:209 comprise the amino acid sequence set forth as SEQ ID NO:88 or 89 in CDR1; SEQ ID NO:90 or 91 in CDR2, and SEQ ID NO:92 or 93 in CDR3. However, the term CDRs used above in regard to the amino acid sequences of the heavy chain variable region set forth as SEQ ID NOs:204 to 209 is not limited to those specific sequences but may also include a region containing the amino acid sequences of one of the CDRs or include an amino acid sequence comprising not less than 3 consecutive amino acids of one of the above CDRs.

Examples of more specific embodiments of the humanized antibody having affinity to hTfR, which is to be fused with BDNF, include:

(1a) the one that comprises the amino acid sequence set forth as SEQ ID NO: 163 in the light chain variable region and comprises the amino acid sequence set forth as SEQ ID NO:171 in the heavy chain variable region, (2a) the one that comprises the amino acid sequence set forth as SEQ ID NO: 179 in the light chain variable region and comprises the amino acid sequence set forth as SEQ ID NO:187 in the heavy chain variable region, (3a) the one that comprises the amino acid sequence set forth as SEQ ID NO:191 in the light chain variable region and comprises the amino acid sequence set forth as SEQ ID NO:205 in the heavy chain variable region, (3b) the one that comprises the amino acid sequence set forth as SEQ ID NO: 193 in the light chain variable region and comprises the amino acid sequence set forth as SEQ ID NO:205 in the heavy chain variable region, (3c) the one that comprises the amino acid sequence set forth as SEQ ID NO: 194 in the light chain variable region and comprises the amino acid sequence set forth as SEQ ID NO:205 in the heavy chain variable region, and (3d) the one that comprises the amino acid sequence set forth as SEQ ID NO: 195 in the light chain variable region and comprises the amino acid sequence set forth as SEQ ID NO:205 in the heavy chain variable region.

Examples of more specific embodiments of the humanized antibody having affinity to hTfR, which is to be fused with BDNF, include:

(1b) the one that comprises the amino acid sequence set forth as SEQ ID NO: 164 in the light chain and the amino acid sequence set forth as SEQ ID NO: 172 in the heavy chain, (2b) the one that comprises the amino acid sequence set forth as SEQ ID NO: 180 in the light chain and the amino acid sequence set forth as SEQ ID NO: 188, in the heavy chain, (3e) the one that comprises the amino acid sequence set forth as SEQ ID NO: 196 in the light chain and the amino acid sequence set forth as SEQ ID NO:210 in the heavy chain, (3f) the one that comprises the amino acid sequence set forth as SEQ ID NO: 198 in the light chain and the amino acid sequence set forth as SEQ ID NO:210 in the heavy chain, (3g) the one that comprises the amino acid sequence set forth as SEQ ID NO:200 in the light chain and the amino acid sequence set forth as SEQ ID NO:210 in the heavy chain, (3h) the one that comprises the amino acid sequence set forth as SEQ ID NO:202 in the light chain and the amino acid sequence set forth as SEQ ID NO:210 in the heavy chain, (3i) the one that comprises the amino acid sequence set forth as SEQ ID NO: 196 in the light chain and the amino acid sequence set forth as SEQ ID NO:212 in the heavy chain, (3j) the one that comprises the amino acid sequence set forth as SEQ ID NO: 198 in the light chain and the amino acid sequence set forth as SEQ ID NO:212 in the heavy chain, (3k) the one that comprises the amino acid sequence set forth as SEQ ID NO:200 in the light chain and the amino acid sequence set forth as SEQ ID NO:212 in the heavy chain, and (3l) the one that comprises the amino acid sequence set forth as SEQ ID NO:202 in the light chain and the amino acid sequence set forth as SEQ ID NO:212 in the heavy chain.

Preferred embodiments of the humanized antibody having affinity to hTfR, which is to be fused with BDNF, have been exemplified above. The light chain and heavy chain of those anti-hTfR antibodies may be mutated as desired, by substitution, deletion, addition and the like, in their variable-region amino acid sequences in order to adjust the affinity of the anti-hTfR antibody to hTfR to a suitable level. Moreover, hBDNF may be mutated as desired, by substitution, deletion, addition and the like, in order to adjust the function of hBDNF and the like to desired function and the like.

When replacing on or more amino acids of the light chain variable-region amino acid sequence with other amino acids, the number of amino acids to be replaced is preferably 1 to 10, more preferably 1 to 5, still more preferably 1 to 3, and even more preferably 1 to 2. When deleting one or more amino acids of the light chain variable to region amino acid sequence, the number of amino acids to be deleted is preferably 1 to 10, more preferably 1 to 5, still more preferably 1 to 3, and even more preferably 1 to 2. Introduction of a combined mutation of such substitution and deletion of amino acids is also allowed.

When adding one or more amino acids to the light chain variable region, they may be added inside, or on the N-terminal side or the C-terminal side of, the light chain variable-region amino acid sequence, and preferably 1 to 10, more preferably 1 to 5, still more preferably 1 to 3, and even more preferably 1 to 2, in number. Introduction of a combined mutation of such addition, substitution, and deletion of amino acids is also allowed. Such a mutated light chain variable-region amino acid sequence has a homology preferably not lower than 80%, more preferably not lower than 90%, still more preferably not lower than 95%, to the amino acid sequence of the original light chain variable-region.

In particular, when replacing one or more amino acids of the amino acid sequence of respective CDRs in the light chain with other amino acids, the number of amino acids to be replaced is preferably 1 to 5, more preferably 1 to 3, still more preferably 1 to 2, and even more preferably 1. When deleting one or more amino acid of the amino acid sequence of the respective CDRs, the number of amino acids to be deleted is preferably 1 to 5, more preferably 1 to 3, still more preferably 1 to 2, and even more preferably 1. Introduction of a combined mutation of such substitution and deletion of amino acids is also allowed.

When adding one or more amino acids to the amino acid sequence of respective CDRs in the light chain, they are added inside, or on the N-terminal side or the C-terminal side of, the amino acid sequence, and preferably 1 to 5, more preferably 1 to 3, still more preferably 1 to 2, and even more preferably 1, in number. Introduction of a combined mutation of such addition, substitution, and deletion of amino acids is also allowed. The amino acid sequence of each of such mutated CDRs has a homology preferably not lower than 80%, more preferably not lower than 90%, and still more preferably not lower than 95%, to the amino acid sequence of the respective original CDRs.

When replacing one or more amino acids of the heavy chain variable-region amino acid sequence with other amino acids, the number of amino acids to be replaced is preferably 1 to 10, more preferably 1 to 5, still more preferably 1 to 3, and even more preferably 1 to 2. When deleting one or more amino acids of the heavy chain variable to region amino acid sequence, the number of amino acids to be deleted is preferably 1 to 10, more preferably 1 to 5, still more preferably 1 to 3, and even more preferably 1 to 2. Introduction of a combined mutation of such substitution and deletion of amino acids is also allowed.

When adding one or more amino acids to the heavy chain variable region, they may be added inside, or on the N-terminal side or the C-terminal side of, the heavy chain variable-region amino acid sequence, and preferably 1 to 10, more preferably 1 to 5, still more preferably 1 to 3, and even more preferably 1 to 2, in number. Introduction of a combined mutation of such addition, substitution, and deletion of amino acids is also allowed. Such a mutated heavy chain variable-region amino acid sequence has a homology preferably not lower than 80%, more preferably not lower than 90%, still more preferably not lower than 95%, to the amino acid sequence of the original heavy chain variable-region.

In particular, when replacing one or more amino acids of the amino acid sequence of respective CDRs in the heavy chain with other amino acids, the number of amino acids to be replaced is preferably 1 to 5, more preferably 1 to 3, still more preferably 1 to 2, and even more preferably 1. When deleting one or more amino acid of the amino acid sequence of the respective CDRs, the number of amino acids to be deleted is preferably 1 to 5, more preferably 1 to 3, still more preferably 1 to 2, and even more preferably 1. Introduction of a combined mutation of such substitution and deletion of amino acids is also allowed.

When adding one or more amino acids to the amino acid sequence of respective CDRs in the heavy chain, they are added inside, or on the N-terminal side or the C-terminal side of, the amino acid sequence, and preferably 1 to 5, more preferably 1 to 3, and still more preferably 1 to 2, in number. Introduction of a combined mutation of such addition, substitution, and deletion of amino acids is also allowed. The amino acid sequence of each of such mutated CDRs has a homology preferably not lower than 80%, more preferably not lower than 90%, and still more preferably not lower than 95%, to the amino acid sequence of the respective original CDRs.

By combining a mutation to the above described anti-hTfR antibody light chain variable region with a mutation to the above described anti-hTfR antibody heavy chain variable region, both the light chain and heavy chain variable regions of the anti-hTfR antibody can be mutated.

Examples of the above mentioned substitution of one or more amino acids in the amino acid sequence of the light chain and the heavy chain of the anti-hTfR antibody with other amino acids are exemplified by interchange between acidic amino acids, i.e., aspartic acid and glutamic acid; interchange between amide-type amino acids, i.e., asparagine and glutamine; interchange between basic amino acids, i.e., lysine and arginine, interchange between branched amino acids, i.e., valine, leucine and isoleucine; interchange between aliphatic amino acids, i.e., glycine and alanine, interchange between hydroxyamino acids, i.e., serine and threonine, and interchange between aromatic amino acids, i.e., phenylalanine and tyrosine.

Besides, in the case where introducing a mutation into the anti-hTfR antibody or hBDNF by adding one or more amino acids on its C-terminus or the N-terminus, if the added amino acids are positioned between the anti-hTfR antibody and BDNF when they are fused, the added amino acids constitute part of a linker.

The fusion protein of the present invention can be produced by the methods described in the after-mentioned Examples or methods publicly known in the present technical field.

For example, as described in Examples 16 and 17 of the present specification, an expression vector having DNA encoding a fusion protein formed by fusing the N-terminus or C-terminus of BDNF, directly or a via linker (e.g., Gly-Ser), with the C-terminus of the heavy chain of the obtained anti-human transferrin antibody, and a vector for expression of animal and plant cells, having DNA encoding the light chain of the antibody, are each constructed, and these expression vectors are then introduced together into suitable host cells, so as to obtain cells or transgenic animals or plants producing the fusion protein of the present invention. Alternatively, an expression vector having DNA encoding a fusion protein formed by fusing the N-terminus or C-terminus of BDNF, directly or a via linker (e.g., Gly-Ser), with the C-terminus of the light chain of the obtained anti-human transferrin antibody, and an expression vector having DNA encoding the heavy chain of the antibody, are each constructed, and these expression vectors are then introduced together into suitable host cells, so as to obtain cells or transgenic animals or plants producing the fusion protein of the present invention.

The thus constructed fusion protein gene can be expressed and obtained according to a conventional method. In order to maximize the expression level of the fusion protein, the nucleotide sequence of the fusion protein gene may be optimized depending on the frequency of using the codons of cells or animal species used in the expression of the fusion protein. In the case of mammalian cells, the fusion protein can be expressed using a commonly used useful promoter, an antibody gene to be expressed, DNA comprising a poly A signal operably linked downstream of the 3'-side thereof, or a vector comprising it. Examples of the promoter/enhancer include human cytomegalovirus immediate early promoter/enhancer.

Examples of other promoters/enhancers, which can be used for the expression of the antibody in the present invention, include virus promoters/enhancers, such as retrovirus, polyoma virus, adenovirus, and simian virus 40 (SV40), and mammalian cell-derived promoters/enhancers, such as human elongation factor 1α (hEF1α).

For example, in the case of using the SV40 promoter/enhancer, the method of Mulligan et al. (Mulligan, R. C. et al., Nature (1979) 277, 108-114) is applied, and in the case of using the hEF1α promoter/enhancer, the method of Mizushima et al. (Mizushima, S. and Nagata, S. Nucleic Acids Res. (1990) 18, 5322) is applied, so that the antibody gene can be easily expressed.

In the case of E. coli, a commonly used useful promoter, a signal sequence for antibody secretion, and an antibody gene to be expressed, are operably linked to one another, so that the antibody gene can be expressed. Examples of the promoter include a lacZ promoter and an araB promoter. In the case of using the lacZ promoter, the method of Ward et al. (Ward, E. S. et al., Nature (1989) 341, 544-546; Ward, E. S. et al., FASEB J. (1992) 6, 2422-2427) may be applied, and in the case of using the araB promoter, the method of Better et al. (Better, M. et al., Science (1988) 240, 1041-1043) may be applied.

As a signal sequence for antibody secretion, in the case where the periplasm of E. coli is allowed to produce the antibody, a pelB signal sequence (Lei, S. P. et al., J. Bacteriol. (1987) 169, 4379-4383) may be used (see, for example, WO 96/30394).

As a replication origin, one derived from SV40, polyoma virus, adenovirus, bovine papillomavirus (BPV), and the like can be used. Further, in order to increase the gene copy number in a host cell system, the expression vector can comprise, as a selective marker, an aminoglycoside phosphotransferase (APH) gene, a thymidine kinase (TK) gene, an E. coli xanthine guanine phosphoribosyl transferase (Ecogpt) gene, a dihydrofolate reductase (dhfr) gene, or the like.

In the case of using eukaryotic cells, there is a production system of using animal cells, plant cells, or fungal cells. Examples of the known animal cells include (1) mammalian cells, such as CHO, HEK293, COS, myeloma, BHK (baby hamster kidney), HeLa, and Vero, (2) amphibian cells, such as Xenopus oocytes, or (3) insect cells, such as sf9, sf21, and Tn5. Examples of the known plant cells include cells derived from Nicotiana tabacum, and these plant cells may be subjected to callus culture. Examples of the known fungal cells include: yeasts, for example, genus Saccharomyces such as Saccharomyces cerevisiae; and Filamentous fungi, for example, genus Aspergillus such as Aspergillus niger.

In the case of using prokaryotic cells, there is a production system of using bacterial cells. As such bacterial cells, E. coli and Bacillus subtilis are known.

An antibody gene of interest is introduced to these cells by transformation, and the transformed cells were then cultured in vitro to obtain the antibody. The culture is carried out according to a conventional method. For example, DMEM, MEM, RPMI1640, or IMDM can be used as a culture medium, and further, serum supplement such as fetal calf serum (FCS) can also be used in combination. Alternatively, antibody gene-introduced cells are transferred into the abdominal cavity of an animal or the like, so that the antibody may be produced in vivo.

The in vivo production system can be a production system of using animals or a production system of using plants. In the case of using animals, there is a production system of using mammals or insects or the like.

Examples of the mammal, which can be used, include a goat, a pig, a sheep, a mouse, and a bovine (Vicki Glaser, SPECTRUM Biotechnology Applications, 1993). In addition, as an insect, silkworm can be used. In the case of using plants, tobacco can be used, for example.

A fusion protein gene is introduced into such an animal or a plant, and a fusion protein is produced in the body of the animal or plant and is then recovered. For example, a fusion protein gene is inserted into a gene encoding a protein specifically produced in milk such as goat β-casein, so as to prepare a fusion gene. A DNA fragment comprising a fusion gene into which an antibody gene has been inserted is injected into the embryo of a goat, and this embryo is then introduced into a female goat. A desired fusion protein is obtained from milk produced from a transgenic goat, which was born from the embryo-received goat, or a progeny thereof. In order to increase the amount of milk comprising the desired fusion protein produced from the transgenic goat, hormone may be used for the transgenic goat, as appropriate (Ebert, K. M. et al., Bio/Technology (1994) 12, 699-702).

Moreover, in the case of using silkworm, a silkworm is infected with baculovirus, into which a fusion protein gene of interest has been inserted, and a desired antibody is then obtained from the body fluid of the silkworm (Maeda, S. et al., Nature (1985) 315, 592-594). Furthermore, in the case of using tobacco, a fusion protein gene of interest is inserted into a plant expression vector such as pMON 530, and this vector is then introduced into bacteria such as *Agrobacterium tumefaciens*. Thereafter, a tobacco plant, such as *Nicotiana tabacum*, is infected with the bacteria, and a desired fusion protein is then obtained from the leaves of the tobacco (Julian, K.-C. Ma et al., Eur. J. Immunol. (1994) 24, 131-138).

The thus produced and expressed fusion protein can be separated from inside or outside of cells and host cells, and can be purified to a homogeneous state. The fusion protein used in the present invention can be separated and purified by affinity chromatography. Examples of a column used in such affinity chromatography include a protein A column, a protein G column, and a protein L column. Examples of a carrier used in the protein A column include Hyper D, POROS, and Sepharose F. F. Other than these methods, separation and purification methods used for ordinary proteins may be used, and are not limited at all. As necessary, by combining chromatography other than the above described affinity chromatography, filtration, ultrafiltration, salting-out, dialysis, etc., the antibody used in the present invention can be separated and purified. Examples of the chromatography include ion exchange chromatography, hydrophobic chromatography, and gel filtration. These chromatographic methods can be applied to HPLC (High performance liquid chromatography). In addition, reverse phase HPLC may also be used.

BDNF specifically binds, in the form of a homodimer, to a BDNF receptor (TrkB) on the surface of a target cell, and plays an important role in differentiation of cells, function maintenance, synaptogenesis, and regeneration and damage repair when damaged, etc. in the central and peripheral nervous systems (Non-patent Document 1 and Non-patent Document 2). Because of such actions, BDNF has been focused as a protein, which can be widely applied to the treatment of diseases associated with damage of the central and peripheral nerves.

Moreover, it has been reported that a reduction in the expression level or amount of BDNF occurs in various diseases associated with the nervous system, such as Huntington's disease, Parkinson's disease, and Alzheimer's disease (Nuerosci. Lett. (1999) 270: 45-48), and it has been known that, when BDNF is continuously injected into the brain or medullary cavity of these disease model animals, using an osmotic pump or the like, it exhibits effects, such as suppression of the neuron death of the striatum, the improvement of movement disorder, and the improvement of memory (J. Nuerosci. (2004) 24: 7727-7739, Proc. Nati. Acad. Sci. USA (1992) 89: 11347-11351), Nat. Med. (2009) 15: 331-337).

Furthermore, it has also been known that BDNF has a variety of actions, such as promotion of proliferation and differentiation of tooth-related cells or vascular endothelial cells, food intake regulation, and glucose metabolism (Tissue Eng. (2005) 11: 1618-629, *Himan Kenkyu* (Obesity Studies) (2009) 15: 97-99).

For these reasons, it is anticipated that BDNF will be developed as a therapeutic agent for various diseases including neurodegenerative diseases such as Alzheimer's disease, Parkinson's disease and Huntington's disease, spinal degenerative diseases such as amyotrophic lateral sclerosis, and further, diabetic neuropathy, cerebral ischemic disease, developmental disorder, schizophrenia, depression, and Rett syndrome (Non-patent Document 3, Non-patent Document 4, Non-patent Document 5, Non-patent Document 6, Non-patent Document 7, Non-patent Document 8, and WO 91/03568).

BDNF cannot pass through the blood-brain barrier (BBB), but the fusion protein of the present invention (hBDNF-anti-hTfR antibody fusion protein) can pass through the BBB. Accordingly, the fusion protein of the present invention, which has been peripherally administered, transfers into the brain, and can exhibit the intrinsic effects of BDNF. Such functions of BDNF can be confirmed by the following methods.

The function of BDNF can be evaluated in vitro by examining binding affinity to a BDNF receptor (TrkB) (Eur J Neurosci (1994) 6: 1389-1405), activation of a BDNF receptor using the phosphorylation thereof as an indicator (Biochim Biophys Acta (2015) 1852: 862-872), intracellular signaling enhancing activity such as intracellular calcium increase associated with activation of a BDNF receptor (Nature Reviews Neuroscience (2009)10: 850-860), action to promote the growth of TrkB-expressing neurons (Bulletin of Gifu Pharmaceutical University (2006) 55: 53-54), survival action (Prog Neuropsychopharmacol Biol Psychiatry (2015) 60: 11-17), neurite outgrowth action (J Biol Chem (2007) 282: 34525-34534), etc. The cells used in vitro may be either cells endogenously expressing TrkB, or cells in which TrkB has been exogenously forcibly expressed. For example, cells prepared by introducing a TrkB gene into BAF cells, CHO cells, PC-12 cells, etc., and then allowing the gene to forcibly express therein, and primary culture neurons of the hippocampus, the striatum, etc. can be used.

Moreover, the function of BDNF can be evaluated in vivo by examining the therapeutic effects of BDNF on disease model animals having diseases such as Parkinson's disease, Huntington's disease or Alzheimer's disease (Proc. Nati. Acad. Sci. USA (1994) 91: 8920-8924). For example, the in vivo biological activity of BDNF comprised in the fusion protein of the present invention (a TfR antibody-BDNF fusion protein) can be evaluated by examining the action to improve movement function disorder, the effect of recovering striatal dopamine amount, the effect of regenerating striatal dopamine neurons, etc. in Parkinson's disease model animals, using the methods as described in Examples 2-5. As Parkinson's disease models, mice and monkeys, which have been subjected to an MPTP treatment known as a treatment of specifically destroying dopamine neurons, can be utilized.

It is to be noted that the improvement of the disease or disorder of a certain disease model animal, for example, a Parkinson's disease model animal, by peripheral administration of the fusion protein of the present invention (hBDNF-anti-hTfR antibody fusion protein), demonstrates that the fusion protein of the present invention has reached a necessary site (e.g., in the brain) to such an extent that BDNF can exhibit its intrinsic effects. This means that the fusion protein of the present invention can be widely used, not only for the aforementioned diseases, but also for treating diseases and disorders benefiting from the exposure to BDNF.

The present invention can be used to treat diseases or disorders benefiting from the exposure to BDNF by administration of a pharmaceutical composition comprising, as an active ingredient, a therapeutically effective amount of the fusion protein of the present invention. Accordingly, the present invention also provides an agent for preventing and/or treating diseases or disorders benefiting from the exposure to BDNF, comprising, as an active ingredient, the fusion protein of the present invention. Herein, the term "treat" means not only complete cure, but also symptom improvement.

Examples of the diseases or disorders benefiting from the exposure to the fusion protein of the present invention include not only diseases or disorders developed by a reduction in the expression level or amount of BDNF, but also diseases or disorders, which can be treated by the action of BDNF. Examples of such diseases or disorders include nervous system diseases or disorders (neurodegenerative disease, depression, schizophrenia, epilepsy, autism, Rett syndrome, West syndrome, neonatal convulsion, problematic behaviors associated with dementia (e.g., wandering, aggressive behavior, etc.), anxiety, pain, Hirschsprung's disease, REM sleep behavior disorder, etc.), and other disease or disorders. Examples of the neurodegenerative disease include the below-mentioned cerebral neurodegenerative disease, spinal degenerative disease, retinal degenerative disease, and peripheral neurodegenerative disease.

Examples of the cerebral neurodegenerative disease include neurodegenerative diseases of cranial nervous system (Alzheimer's disease, Parkinson's disease, Huntington's disease, dementia with Lewy bodies, Pick's disease, multiple system atrophy, progressive ascending paralysis, Down's syndrome, etc.), cerebral ischemic diseases (stroke, cerebral infarction, transient ischemic attack, subarachnoid hemorrhage, ischemic encephalopathy, cerebral infarction (lacunar infarction, atherothrombotic cerebral infarction, cardiogenic cerebral infarction, hemorrhagic stroke, other infarctions), etc.), traumatic brain injury, leukoencephalopathy, and multiple sclerosis.

Examples of the spinal degenerative disease include amyotrophic lateral sclerosis (ALS), spinal cord injury, and spinal cord disorder developed by various causes, spinal progressive muscular atrophy and spinocerebellar degeneration.

Examples of the retinal degenerative disease include age-related macular degeneration (AMD), diabetic retinopathy, retinitis pigmentosa, hypertensive retinopathy, and glaucoma.

Examples of the peripheral neurodegenerative disease include diabetic neuropathy, peripheral nerve injury, traumatic peripheral neuropathy, peripheral neuropathy caused by poisoning or other toxic substances, peripheral neuropathy caused by cancer chemotherapy, Guillain-Barre syndrome, peripheral neuropathy caused by deficiency of vitamin and the like, amyloid peripheral neuropathy, ischemic peripheral neuropathy, peripheral neuropathy associated with malignant tumor, uremic peripheral neuropathy, peripheral neuropathy due to physical causes, Charcot-Marie-Tooth disease, alcoholic peripheral neuropathy, dysautonomia (hypoglycemia unawareness, gastroparesis, neuropathic diarrhea and constipation, erectile dysfunction, orthostatic hypotension, arrhythmia, heart failure, painless myocardial infarction, sweating abnormality, neurogenic bladder, etc.), and bladder dysfunction (e.g., uninhibited bladder, reflex bladder, autonomic bladder, sensory paralytic bladder, motor paralytic bladder, etc.).

Examples of other diseases or disorders include periodontal disease, diabetes, diabetic cardiomyopathy, diabetic foot lesions, inflammatory bowel disease (e.g., ulcerative colitis, Crohn's disease, etc.), hearing impairments, and bone disease (e.g., osteoporosis, etc.), and joint disease (e.g., Charcot joint, osteoarthritis, arthritis, etc.).

The fusion protein of the present invention can be used as a pharmaceutical agent, which is to exhibit its functions in the central nervous system (CNS) after administered into the blood. Such pharmaceutical agents may be administered to patients generally by intravenous injection such as intravenous infusion and the like, subcutaneous injection, intramuscular injection, though there is no particular limitation as to the route of their administration.

The fusion protein of the present invention can be provided to medical facilities as pharmaceutical agents in such a form of as a lyophilized product or an aqueous preparation. In the case of an aqueous preparation, it can be provided in the form of preparations in which one of the pharmaceutical agents is dissolved in a solution containing a stabilizer, buffer, and an isotonizer in advance, and sealed in vials or syringes. A type of preparations sealed in a syringe is generally called a prefilled syringe-type preparation. Taking the form of a prefilled syringe-type preparation facilitates patients' self-administration of the pharmaceutical agent.

Where an aqueous preparation is provided, the concentration of BDNF conjugated with the anti-hTfR antibody in the aqueous preparation is, e.g., 0.01 to 5 mg/mL, though it is to be adjusted as desired in accordance with the dosage. Where there is no particular limitation as to stabilizers to be contained in the aqueous preparation insofar as they are pharmaceutically available, nonionic surfactants may preferably be used. Examples of such nonionic surfactants include polysorbate and poloxamer, either of which may be used alone or in combination. Among polysorbates, polysorbate 20 and polysorbate 80 are preferably used. As poloxamer, poloxamer 188 (polyoxyethylene (160) polyoxypropylene (30) glycol) is particularly preferred. Further, the concentration of nonionic surfactant contained in the aqueous preparation is preferably 0.01 to 1 mg/mL, more preferably, 0.01 to 0.5 mg/mL, and still more preferably 0.1 to 0.5 mg/mL. As stabilizers, amino acids such as histidine, arginine, methionine, and glycine may also be used. Where employed as a stabilizer, the concentration of an amino acid in the aqueous preparation is preferably 0.1 to 40 mg/mL, more preferably 0.2 to 5 mg/mL, and still more preferably 0.5 to 4 mg/mL. While there is no particular limitation as to a buffer to be contained in the aqueous preparation insofar as it is pharmaceutically available, phosphate buffer is preferred, and more preferred is sodium phosphate buffer. Where used as a buffer, the concentration of sodium phosphate is preferably 0.01 to 0.04 M. The pH of the aqueous preparation adjusted with a buffer is preferably 5.5 to 7.2. While there is no particular limitation as to an isotonizer to be contained in the aqueous preparation insofar as it is pharmaceutically available, sodium chloride or mannitol may be preferably used alone or in combination as an isotonizer.

The applied dose of the above described pharmaceutical agent comprising the fusion protein of the present invention is different depending on an administration target, a target disease, symptoms, an administration route, etc. For example, in the case where the pharmaceutical agent is used to treat and/or prevent neurodegenerative disease, with regard to the dose thereof, an effective amount thereof, for example, a therapeutically effective amount thereof is determined, such that the concentration of BDNF in the brain is, at least, not less than approximately 0.001 ng/g, and preferably more than 0.01, 0.1, 1, 10 or 100 ng/g per brain. In addition, the increased BDNF level in the brain is preferably maintained even several days (1, 2, 3, 4, 5, 6, or 7 days), 2 weeks, or further 1 month had passed after an administration, and BDNF is preferably maintained at a BDNF concentration maintained in the brain of, for example, approximately 1 ng/g per brain, approximately 10 ng/g per brain, approximately 100 ng/g per brain, or more than approximately 100 ng/g per brain.

For example, the applied dose can be selected within the range of 0.0001 to 1000 mg/kg of body weight, as a single dose, in several embodiments, but is not limited thereto. Alternatively, the dose can also be selected within the range of 0.001 to 100000 mg per patient. In general, the pharmaceutical agent comprising the fusion protein of the present invention is administered to a patient, for example, by intravenous administration, at a dose of approximately 0.01 to 1000 mg, approximately 0.1 to 100 mg, approximately 1 to 100 mg, approximately 0.05 to 500 mg, approximately 0.5 to 50 mg, or approximately 5 mg to 50 mg. In the case where a patient has particularly severe symptoms, the dose may be increased depending on the symptoms.

The composition of the present invention, for example, the fusion protein of the present invention may be used alone, or it may also be administered to a patient, as necessary, together with other pharmaceutical products or other treatment methods, in the range that does not impair the effects of the present invention, in the form of a single formulation or as different compositions. Examples of a pharmaceutical agent used for Alzheimer dementia in combination with the pharmaceutical composition of the present invention include therapeutic agents for Alzheimer's disease including acetylcholinesterase inhibitors such as donepezil hydrochloride, rivastigmine or galanthamine hydrobromide, and memantine hydrochloride. In addition, other examples of such a pharmaceutical agent include anti-Aβ antibodies which are currently at the clinical development stage, such as Solanezumab (N Engl J Med. (2014) 370: 311-21) and Gantenerumab (Arch Neurol. (2012) 69: 198-207), and β-amyloid production inhibitors such as Verubecestat (AAIC 2013, Boston: Abs 01-06-05, July 2013) and AZD-3293 (AAIC 2014, Copenhagen: Abs P1-363, July 2014). An example of the treatment method used for Alzheimer dementia in combination with the pharmaceutical composition of the present invention is brain active rehabilitation therapy. Examples of the pharmaceutical agent used for Parkinson's disease in combination with the pharmaceutical composition of the present invention include therapeutic agents for Parkinson's disease including drugs for dopamine replacement therapy such as Levodopa, dopamine receptor agonists such as Talipexole, Pramipexole or Bromocriptine, dopamine-degrading enzyme inhibitors such as MAO-B inhibitors or COMT inhibitors, and dopamine release promoters such as Amantadine or Nouriast. Examples of the treatment method used for Parkinson's disease in combination with the pharmaceutical composition of the present invention include thalamic stimulation surgery, globus pallidus stimulation surgery, and subthalamic nucleus stimulation surgery. Examples of the pharmaceutical agent used for Huntington's disease in combination with the pharmaceutical composition of the present invention include therapeutic agents for Huntington's disease including monoamine vesicular transporter 2 inhibitors such as Tetrabenazine. Examples of the pharmaceutical agent used for cerebral ischemic disease in combination with the pharmaceutical composition of the present invention include brain-protecting drugs such as Radicut. Examples of the treatment method used for cerebral ischemic disease in combination with the pharmaceutical composition of the present invention include thrombolytic therapy and rehabilitation therapy.

The timing of administration of the pharmaceutical composition of the present invention is not particularly limited, and the present pharmaceutical composition may be administered, as appropriate, before or after, or simultaneously with the administration of other pharmaceutical agents or other treatments.

EXAMPLES

Though the present invention is described in further detail below with reference to examples, it is not intended that the present invention be limited to those examples.

[Example 1] Construction of hTfR Expression Vector

Employing human spleen Quick Clone cDNA (Clontech Inc.) as a template and using primer hTfR5' (SEQ ID NO:214) and primer hTfR3' (SEQ ID NO:215), PCR was performed to amplify the gene fragment encoding human transferrin receptor (hTfR). The amplified fragment encoding hTfR was digested with MluI and NotI, and then inserted between MluI and NotI sites of vector pCI-neo (Promega Corp.). The vector thus prepared was designated pCI-neo (hTfR). This vector then was digested with MluI and NotI to cut out the gene fragment encoding hTfR, and this fragment was inserted between MluI and NotI sites of pE-mIRES-GS-puro, an expression vector disclosed in an international publication WO 2012/063799 to construct an hTfR expression vector, pE-mIRES-GS-puro(hTfR).

[Example 2] Preparation of Recombinant hTfR

Into CHO-K1 cells was introduced pE-mIRES-GS-puro (hTfR) by electroporation, and the cells then were subjected to selection culture in a CD OPTICHO medium (Invitrogen Inc.) containing methionine sulfoximine (MSX) and puromycin to prepare recombinant hTfR expressing cells. The recombinant hTfR expressing cells were cultured, and recombinant hTfR was prepared.

[Example 3] Immunization of Mouse with Recombinant hTfR

Mice were immunized with recombinant hTfR prepared in Example 2 as antigen. Immunization was carried out by intravenously or intraperitoneally injecting the mice with the antigen.

[Example 4] Preparation of Hybridoma Cells

About one week after the last injection, the spleens of the mice were excised and homogenized to isolate spleen cells. The spleen cells thus obtained were fused with cells of mouse myeloma cell line (P3.X63.Ag8.653) by the polyethylene glycol method. After cell fusion, the cells were suspended in a RPMI 1640 medium containing (1×) HAT supplement (Life Technologies Inc.) and 10% Ultra low IgG fetal bovine serum (Life Technologies Inc.), and the cell suspension was dispensed to twenty 96-well plates, each at 200 µL/well. After the cells were cultured for 10 days in a carbon dioxide gas incubator (37° C., 5% $CO_2$), each well was examined under a microscope, and the wells that contain a single colony were selected.

When the cells in each well reached near confluence, the culture supernatant was collected as a culture supernatant of hybridoma, and subjected to the following screening process.

[Example 5] Screening of High Affinity Antibody Producing Cell Line

The recombinant hTfR solution (Sino Biologics Inc.) was diluted with 50 mM sodium phosphate buffer (pH 9.5 to 9.6) to 5 µg/mL to prepare a solid phase solution. After 50 µL of the solid phase solution was added to each well of a Nunc MAXISORP flat-bottom 96-well plate (substrate: polystyrene, mfd. by Nunc Inc.), the plate was left to stand for one hour at room temperature to let the recombinant hTfR adhere to the plate and become immobilized. The solid phase solution was discarded, each well was washed three times with 2501 µL of washing solution (PBS containing 0.05% Tween20), 200 µL of a blocking solution (PBS containing 1% BSA) then was added to each well, and the plate was left to stand for one hour at room temperature. The blocking solution was discarded, and each well was washed three times with 250 µL washing solution (PBS containing 0.05% Tween20). To each well was added 50 µL of the hybridoma culture supernatant producing mouse anti-human transferrin receptor antibody (mouse anti-hTfR antibody), and the plate was left to stand for one hour at room temperature to let the mouse anti-hTfR antibody contained in the culture supernatant bind to the recombinant hTfR. At the same time, to some wells was added 50 µL of culture supernatant of a hybridoma that did not produce mouse anti-hTfR antibody, as a control. In addition, 50 µL of the medium for hybridoma culture was added to the wells, as mock wells, beside those wells to which the culture supernatant was added. Measurement was conducted in an n=2 fashion. Then, the solution was discarded, and each well was washed three times with 250 µL of washing solution (PBS containing 0.05% Tween20).

To each of the above wells was added 100 µL of HRP-labelled goat anti-mouse immunoglobulin antibody solution (Promega Inc.), and the plate was left to stand for one minute at room temperature. The solution then was discarded, and each well was washed three times with 250 µL of washing solution (PBS containing 0.05% Tween20). To each well as added 50 µL of a chromogenic substrate solution, TMB Stabilized Substrate for Horseradish Peroxidase (Promega Inc.), and the wells were left to stand for 10 to 20 minutes at room temperature. Then, following addition of 100 µL of a stop solution (2N sulfuric acid), the absorbance of each well was measured on a plate reader at 450 nm. Of the two wells for each of the culture supernatant and control, the mean values were taken, respectively, and from each of the mean values, the respective mean value for the two mock wells placed corresponding to each of the culture supernatant and the control, was subtracted, giving the measurement.

Fourteen types of hybridoma cells corresponding to culture supernatants added to the wells which exhibited the higher measurements were selected as the cell lines (high affinity antibody producing cell line) that produce antibodies exhibiting high affinities to hTfR (high affinity anti-hTfR antibody). These fourteen types of cell lines were designated as Clone 1 line to Clone 14 line. Further, the anti-hTfR antibodies produced by Clone 1 line to Clone 14 line were designated as anti-hTfR antibodies Nos. 1 to 14, respectively.

[Example 6] Analysis of the Variable-Region Amino Acid Sequence of the High Affinity Anti-hTfR Antibodies From each of the Clone 1 line to Clone 14 line selected in Example 5, cDNA were prepared, using which as a template the genes encoding the light chain and the heavy chain of the antibody were amplified. By translating the nucleotide sequence of the amplified genes, the respective amino acid sequences of the light chain and heavy chain variable regions were determined for the anti-hTfR antibodies Nos. 1 to 14 produced by the cell lines.

The anti-hTfR antibody No. 1 was found to include the amino acid sequence set forth as SEQ ID NO:218 as the light chain variable region, and the amino acid sequence set forth as SEQ ID NO:219 as the heavy chain variable region. The light chain variable region was found to include the amino acid sequence set forth as SEQ ID NO:6 or 7 as CDR1; SEQ ID NO:8 or 9 as CDR2, and SEQ ID NO:10 as CDR3; and the heavy chain variable region to include the amino acid sequence set forth as SEQ ID NO:76 or 77 as CDR1, SEQ ID NO:78 or 79 as CDR2, and SEQ ID NO:80 or 81 as CDR3. However, it was also considered that CDRs are not limited to those which consist of these amino acid sequences, but they can also either be regions of amino acid sequences that include any of the above sequences, or amino acid sequences consisting of not less than three consecutive amino acids containing part of the above sequences.

The anti-hTfR antibody No. 2 was found to include the amino acid sequence set forth as SEQ ID NO:220 as the light chain variable region, and the amino acid sequence set forth as SEQ ID NO:221 as the heavy chain variable region. The light chain variable region was found to include the amino acid sequence set forth as SEQ ID NO: 11 or 12 as CDR1; SEQ ID NO:13 or 14 as CDR2, and SEQ ID NO:15 as CDR3; and the heavy chain variable region to include the amino acid sequence set forth as SEQ ID NO:82 or 83 as CDR1, SEQ ID NO:84 or 85 as CDR2, and SEQ ID NO:86 or 87 as CDR3. However, it was also considered that CDRs are not limited to those which consist of these amino acid sequences, but they can also either be regions of amino acid sequences that include any of the above sequences, or amino acid sequences consisting of not less than three consecutive amino acids containing part of the above sequences.

The anti-hTfR antibody No. 3 was found to include the amino acid sequence set forth as SEQ ID NO:222 as the light chain variable region, and the amino acid sequence set forth as SEQ ID NO:223 as the heavy chain variable region. The light chain variable region was found to include the amino acid sequence set forth as SEQ ID NO: 16 or 17 as CDR1; SEQ ID NO:18 or 19 as CDR2, and SEQ ID NO:20 as CDR3; and the heavy chain variable region to include the amino acid sequence set forth as SEQ ID NO:88 or 89 as CDR1, SEQ ID NO:90 or 91 as CDR2, and SEQ ID NO:92 or 93 as CDR3. However, it was also considered that CDRs are not limited to those which consist of these amino acid sequences, but they can also either be regions of amino acid sequences that include any of the above sequences, or amino acid sequences consisting of not less than three consecutive amino acids containing part of the above sequences.

The anti-hTfR antibody No. 4 was found to include the amino acid sequence set forth as SEQ ID NO:224 as the light chain variable region, and the amino acid sequence set forth as SEQ ID NO:225 as the heavy chain variable region. The light chain variable region was found to include the amino acid sequence set forth as SEQ ID NO:21 or 22 as CDR1; SEQ ID NO:23 or 24 as CDR2, and SEQ ID NO:25 as CDR3; and the heavy chain variable region to include the amino acid sequence set forth as SEQ ID NO:94 or 95 as CDR1, SEQ ID NO:96 or 97 as CDR2, and SEQ ID NO:98 or 99 as CDR3. However, it was also considered that CDRs are not limited to those which consist of these amino acid sequences, but they can also either be regions of amino acid sequences that include any of the above sequences, or amino acid sequences consisting of not less than three consecutive amino acids containing part of the above sequences.

The anti-hTfR antibody No. 5 was found to include the amino acid sequence set forth as SEQ ID NO:226 as the light chain variable region, and the amino acid sequence set forth as SEQ ID NO:227 as the heavy chain variable region. The light chain variable region was found to include the amino acid sequence set forth as SEQ ID NO:26 or 27 as CDR1; SEQ ID NO:28 or 29 as CDR2, and SEQ ID NO:30 as CDR3; and the heavy chain variable region to include the amino acid sequence set forth as SEQ ID NO: 100 or 101 as CDR1, SEQ ID NO: 102 or 103 as CDR2, and SEQ ID NO: 104 or 105 as CDR3. However, it was also considered that CDRs are not limited to those which consist of these amino acid sequences, but they can also either be regions of amino acid sequences that include any of the above sequences, or amino acid sequences consisting of not less than three consecutive amino acids containing part of the above sequences.

The anti-hTfR antibody No. 6 was found to include the amino acid sequence set forth as SEQ ID NO:228 as the light chain variable region, and the amino acid sequence set forth as SEQ ID NO:229 as the heavy chain variable region. The light chain variable region was found to include the amino acid sequence set forth as SEQ ID NO:31 or 32 as CDR1; SEQ ID NO:33 or 34 as CDR2, and SEQ ID NO:35 as CDR3; and the heavy chain variable region to include the amino acid sequence set forth as SEQ ID NO:106 or 107 as CDR1, SEQ ID NO: 108 or 266 as CDR2, and SEQ ID NO: 109 or 110 as CDR3. However, it was also considered that CDRs are not limited to those which consist of these amino acid sequences, but they can also either be regions of amino acid sequences that include any of the above sequences, or amino acid sequences consisting of not less than three consecutive amino acids containing part of the above sequences.

The anti-hTfR antibody No. 7 was found to include the amino acid sequence set forth as SEQ ID NO:230 as the light chain variable region, and the amino acid sequence set forth as SEQ ID NO:231 as the heavy chain variable region. The light chain variable region was found to include the amino acid sequence set forth as SEQ ID NO:36 or 37 as CDR1; SEQ ID NO:38 or 39 as CDR2, and SEQ ID NO:40 as CDR3; and the heavy chain variable region to include the amino acid sequence set forth as SEQ ID NO:111 or 112 as CDR1, SEQ ID NO:113 or 114 as CDR2, and SEQ ID NO:115 or 116 as CDR3. However, it was also considered that CDRs are not limited to those which consist of these amino acid sequences, but they can also either be regions of amino acid sequences that include any of the above sequences, or amino acid sequences consisting of not less than three consecutive amino acids containing part of the above sequences.

The anti-hTfR antibody No. 8 was found to include the amino acid sequence set forth as SEQ ID NO:232 as the light chain variable region, and the amino acid sequence set forth as SEQ ID NO:233 as the heavy chain variable region. The light chain variable region was found to include the amino acid sequence set forth as SEQ ID NO:41 or 42 as CDR1; SEQ ID NO:43 or 44 as CDR2, and SEQ ID NO:45 as CDR3; and the heavy chain variable region to include the amino acid sequence set forth as SEQ ID NO:117 or 118 as CDR1, SEQ ID NO:119 or 267 as CDR2, and SEQ ID NO:120 or 121 as CDR3. However, it was also considered that CDRs are not limited to those which consist of these amino acid sequences, but they can also either be regions of amino acid sequences that include any of the above sequences, or amino acid sequences consisting of not less than three consecutive amino acids containing part of the above sequences.

The anti-hTfR antibody No. 9 was found to include the amino acid sequence set forth as SEQ ID NO:234 as the light chain variable region, and the amino acid sequence set forth as SEQ ID NO:235 as the heavy chain variable region. The light chain variable region was found to include the amino acid sequence set forth as SEQ ID NO:46 or 47 as CDR1; SEQ ID NO:48 or 49 as CDR2, and SEQ ID NO:50 as CDR3; and the heavy chain variable region to include the amino acid sequence set forth as SEQ ID NO: 122 or 123 as CDR1, SEQ ID NO: 124 or 125 as CDR2, and SEQ ID NO: 126 or 127 as CDR3. However, it was also considered that CDRs are not limited to those which consist of these amino acid sequences, but they can also either be regions of amino acid sequences that include any of the above sequences, or amino acid sequences consisting of not less than three consecutive amino acids containing part of the above sequences.

The anti-hTfR antibody No. 10 was found to include the amino acid sequence set forth as SEQ ID NO:236 as the light chain variable region, and the amino acid sequence set forth as SEQ ID NO:237 as the heavy chain variable region. The light chain variable region was found to include the amino acid sequence set forth as SEQ ID NO:51 or 52 as CDR1; SEQ ID NO:53 or 54 as CDR2, and SEQ ID NO:55 as CDR3; and the heavy chain variable region to include the amino acid sequence set forth as SEQ ID NO: 128 or 129 as CDR1, SEQ ID NO: 130 or 131 as CDR2, and SEQ ID NO: 132 or 133 as CDR3. However, it was also considered that CDRs are not limited to those which consist of these amino acid sequences, but they can also either be regions of amino acid sequences that include any of the above sequences, or amino acid sequences consisting of not less than three consecutive amino acids containing part of the above sequences.

The anti-hTfR antibody No. 11 was found to include the amino acid sequence set forth as SEQ ID NO:238 as the light chain variable region, and the amino acid sequence set forth as SEQ ID NO:239 as the heavy chain variable region. The light chain variable region was found to include the amino acid sequence set forth as SEQ ID NO:56 or 57 as CDR1; SEQ ID NO:58 or 59 as CDR2, and SEQ ID NO:60 as CDR3; and the heavy chain variable region to include the amino acid sequence set forth as SEQ ID NO: 134 or 135 as CDR1, SEQ ID NO: 136 or 137, as CDR2, and SEQ ID NO: 138 or 139 as CDR3. However, it was also considered that CDRs are not limited to those which consist of these amino acid sequences, but they can also either be regions of amino acid sequences that include any of the above sequences, or amino acid sequences consisting of not less than three consecutive amino acids containing part of the above sequences.

The anti-hTfR antibody No. 12 was found to include the amino acid sequence set forth as SEQ ID NO:240 as the light chain variable region, and the amino acid sequence set forth as SEQ ID NO:241 as the heavy chain variable region. The light chain variable region was found to include the amino acid sequence set forth as SEQ ID NO:61 or 62 as CDR1; SEQ ID NO:63 or 64 as CDR2, and SEQ ID NO:65 as CDR3; and the heavy chain variable region to include the amino acid sequence set forth as SEQ ID NO: 140 or 141 as CDR1, SEQ ID NO: 142 or 143 as CDR2, and SEQ ID NO: 144 or 145 as CDR3. However, it was also considered that CDRs are not limited to those which consist of these amino acid sequences, but they can also either be regions of amino acid sequences that include any of the above sequences, or amino acid sequences consisting of not less than three consecutive amino acids containing part of the above sequences.

The anti-hTfR antibody No. 13 was found to include the amino acid sequence set forth as SEQ ID NO:242 as the light chain variable region, and the amino acid sequence set forth as SEQ ID NO:243 as the heavy chain variable region. The light chain variable region was found to include the amino acid sequence set forth as SEQ ID NO:66 or 67 as CDR1; SEQ ID NO:68 or 69 as CDR2, and SEQ ID NO:70 as CDR3; and the heavy chain variable region to include the amino acid sequence set forth as SEQ ID NO: 146 or 147 as CDR1, SEQ ID NO: 148 or 149 as CDR2, and SEQ ID NO: 150 or 151 as CDR3. However, it was also considered that CDRs are not limited to those which consist of these amino acid sequences, but they can also either be regions of amino acid sequences that include any of the above sequences, or amino acid sequences consisting of not less than three consecutive amino acids containing part of the above sequences.

The anti-hTfR antibody No. 14 was found to include the amino acid sequence set forth as SEQ ID NO:244 as the light chain variable region, and the amino acid sequence set forth as SEQ ID NO:245 as the heavy chain variable region. The light chain variable region was found to include the amino acid sequence set forth as SEQ ID NO:71 or 72 as CDR1; SEQ ID NO:73 or 74 as CDR2, and SEQ ID NO:75 as CDR3; and the heavy chain variable region to include the amino acid sequence set forth as SEQ ID NO: 152 or 153 as CDR1, SEQ ID NO: 154 or 155 as CDR2, and SEQ ID NO: 156 or 157 as CDR3. However, it was also considered that CDRs are not limited to those which consist of these amino acid sequences, but they can also either be regions of amino acid sequences that include any of the above sequences, or amino acid sequences consisting of not less than three consecutive amino acids containing part of the above sequences.

Table 1 shows collectively the SEQ ID NOs of the respective amino acid sequences included in the light chain and the heavy chain variable regions of the anti-hTfR antibody Nos. 1 to 14.

TABLE 1

Sequence numbers of respective amino acid sequences included in the light and the heavy chain variable regions of the anti-hTfR antibodies Nos. 1 to 14

| Antibody No. | light chain variable region | heavy chain variable region |
|---|---|---|
| 1 | 218 | 219 |
| 2 | 220 | 221 |
| 3 | 222 | 223 |
| 4 | 224 | 225 |
| 5 | 226 | 227 |
| 6 | 228 | 229 |
| 7 | 230 | 231 |
| 8 | 232 | 233 |
| 9 | 234 | 235 |
| 10 | 236 | 237 |
| 11 | 238 | 239 |
| 12 | 240 | 241 |
| 13 | 242 | 243 |
| 14 | 244 | 245 |

Table 2 shows collectively the SEQ ID NOs of the respective amino acid sequences contained in CDR1 to CDR3 of the light chain variable region and CDR1 to CDR3 of the heavy chain variable region of anti-hTfR antibodies Nos. 1 to 14. However, Table 2 shows those amino acid sequence only as examples and does not limit the amino acid sequence of each CDR to those in Table 2, but it was considered that CDRs are not limited to those which consist of these amino acid sequences, but they can also either be regions of amino acid sequences that include any of the above sequences, or amino acid sequences consisting of not less than three consecutive amino acids containing part of the above sequences.

TABLE 2

Sequence numbers of respective amino acid sequences contained in CDR1 to CDR3 of the light chain and the heavy chain variable regions of anti-hTfR antibodies Nos. 1 to 14

| Antibody No. | light chain variable region | | | heavy chain variable region | | |
|---|---|---|---|---|---|---|
| | CDR1 | CDR2 | CDR3 | CDR1 | CDR2 | CDR3 |
| 1 | 6, 7 | 8, 9 | 10 | 76, 77 | 78, 79 | 80, 81 |
| 2 | 11, 12 | 13, 14 | 15 | 82, 83 | 84, 85 | 86, 87 |
| 3 | 16, 17 | 18, 19 | 20 | 88, 89 | 90, 91 | 92, 93 |
| 4 | 21, 22 | 23, 24 | 25 | 94, 95 | 96, 97 | 98, 99 |
| 5 | 26, 27 | 28, 29 | 30 | 100, 101 | 102, 103 | 104, 105 |
| 6 | 31, 32 | 33, 34 | 35 | 106, 107 | 108, 278 | 109, 110 |
| 7 | 36, 37 | 38, 29 | 40 | 111, 112 | 113, 114 | 115, 116 |
| 8 | 41, 42 | 43, 44 | 45 | 117, 118 | 119, 279 | 120, 121 |
| 9 | 46, 47 | 48, 49 | 50 | 122, 123 | 124, 125 | 126, 127 |
| 10 | 51, 52 | 53, 54 | 55 | 128, 129 | 130, 131 | 132, 133 |
| 11 | 56, 57 | 58, 59 | 60 | 134, 135 | 136, 137 | 138, 139 |
| 12 | 61, 62 | 63, 64 | 65 | 140, 141 | 142, 143 | 144, 145 |
| 13 | 66, 67 | 68, 69 | 70 | 146, 147 | 148, 149 | 150, 151 |
| 14 | 71, 72 | 73, 74 | 75 | 152, 153 | 154, 155 | 156, 157 |

[Example 7] Measurement of the Affinity of Anti-hTfR Antibody to Human and Monkey TfRs The affinity of the anti-hTfR antibody to human and monkey TfRs were measured on Octet RED96 (ForteBio Inc., a division of Pall Corporation), a system for analysis of interactions between biomolecules utilizing bio-layer interferometry (BLI). The basic principles of bio-layer interferometry are briefly explained below. When a layer of a biomolecule immobilized on the surface of a sensor tip is irradiated with light of a certain wavelength, the light is reflected from two of the surfaces, the one of the biomolecule and the other of inner, reference layer, producing interfering light waves. A molecule in the sample being measured binds to the biomolecule on the surface of the sensor tip and thus increases the thickness of the layers on the sensor tip, which results in a shift between the interfering waves. By measuring the variations of this shift between the interfering waves, determination of the number of the molecules bound to the layer of the biomolecules immobilized to the sensor tip surface and kinetic analysis of it can be performed in real time. The measurement was performed according generally to the operating manual attached to Octet RED96. As a human TfR, a recombinant human TfR (r human TfR: Sino Biological Inc.) was used, which had the amino acid sequence of the hTfR extracellular region, i.e., the cysteine residue at the position 89th from the N-terminal side to the phenylalanine at the C-terminus, of the amino acid sequence set forth as SEQ ID NO:1, with a histidine tag attached to the N-terminus. As a monkey TfR, a recombinant monkey TfR (r monkey TfR: Sino Biological Inc.) was used, which had the amino acid sequence of the cynomolgus monkey TfR extracellular region, i.e., the cysteine residue at the position 89th from the N-terminal side to the phenylalanine at the C-terminus, of the amino acid sequence set forth as SEQ ID NO:2, with a histidine tag attached to the N-terminus.

Clone 1 line to Clone 14 line selected in Example 5 were respectively diluted with a RPMI 1640 medium containing (1×) HAT Supplement (Life Technologies Inc.) and 10% Ultra low IgG fetal bovine serum (Life Technologies Inc.) so as to adjust the cell density to approximately $2 \times 10^5$ cells/mL. To a 1-L conical flask were added 200 mL of each cell suspension, and the culture was performed for 6 to 7 days in a humid environment at 37° C., 5% $CO_2$ and 95% air, with stirring at a rate of about 70 rpm. The culture supernatant was collected by centrifugation, and filtered through a 0.22 m filter (Millipore Inc.) to prepare the culture supernatant. The culture supernatant thus collected was loaded onto a Protein G column (column volume: 1 mL, GE Healthcare Inc.) that had been equilibrated in advance with three column volumes of 20 mM Tris buffer (pH 8.0) containing 150 mM NaCl. After the column was washed with 5 column volumes of the same buffer, adsorbed antibody was eluted with 4 column volumes of 50 mM glycine buffer (pH 2.8) containing 150 mM NaCl, and eluted fractions were collected. The eluted fractions were adjusted to pH 7.0 by addition of 1 M Tris buffer (pH 8.0). These were used as purified products of anti-hTfR antibodies Nos. 1 to 14 in the experiments described below.

Each of the antibodies (anti-hTfR antibody Nos. 1 to 14) purified above was subjected to 2-fold dilution steps with HBS-P+ (10 mM HEPES containing 150 mM NaCl, 50 μM EDTA and 0.05% Surfactant P20) to prepare antibody solutions of 7 different concentrations, 0.78125 to 50 nM (0.117 to 7.5 μg/mL). These antibody solutions were used as the sample solutions. The r human and r monkey TfRs were respectively diluted with HBS-P+ to prepare 25 μg/mL solutions, which were used as r human TfR-ECD (Histag) solution and r monkey TfR-ECD (Histag) solution, respectively.

Each of the sample solutions prepared above by 2-fold dilution steps was added, 200 μL/well, to a 96-well plate, black (Greiner Bio-One Inc.). Each of the r human TfR-ECD (Histag) solution and the r monkey TfR-ECD (Histag) solutions prepared above was added, 200 μL/well, to predetermined wells. To respective wells for baseline, dissociation and washing were added HBS-P+, 200 μL/well. To wells for regeneration were added 10 mM Glycine-HCl, pH 1.7, 200 μL/well. To wells for activation was added 0.5 mM $NiCl_2$ solution, 200 μL/well. The plate and biosensor (Biosensor/Ni-NTA: ForteBio Inc., a division of Pall Corporation) were set in the prescribed positions of Octet RED96.

Octet RED96 was run under the conditions shown in Table 3 below to collect data, on which then, using the analyzing software attached to Octet RED96, and fitting the binding reaction curve to 1:1 binding model or 2:1 binding model, the association rate constant ($k_{on}$) and dissociation rate constant ($k_{off}$) of anti-hTfR antibody to r human TfR and r monkey TfR were measured and the dissociation constant ($K_D$) was calculated. The measurement was performed at 25 to 30° C.

TABLE 3

Operating conditions of Octet RED96

| | Step | Contact time (sec) | Rate (rpm) | Threshold |
|---|---|---|---|---|
| 1 | Baseline 1 | 60 | 1000 | — |
| 2 | Load | 600 | 1000 | 1.5-2.0 |

TABLE 3-continued

Operating conditions of Octet RED96

| | Step | Contact time (sec) | Rate (rpm) | Threshold |
|---|---|---|---|---|
| 3 | Baseline 2 | 60 | 1000 | |
| 4 | Association | 180 | 1000 | |
| 5 | Dissociation | 540 | 1000 | |
| 6 | Regeneration | 5 | 1000 | |
| 7 | Washing | 5 | 1000 | |
| | Steps 6-7 repeated 6 to 7 times | | | |
| 8 | Activation | 60 | 1000 | — |
| | Steps 1-8 repeated until all the samples measured | | | |

Table 4 shows the results of measurement of association rate constant ($k_{on}$), dissociation rate constant ($k_{off}$) of anti-hTfR antibody Nos. 1-14 (corresponding to antibody Nos. 1-14, respectively, in the table), and dissociation constant ($K_D$) to human TfR.

TABLE 4

Affinity of anti-hTfR antibodies to human TfR

| Antibody No. | kon ($M^{-1}s^{-1}$) | koff ($s^{-1}$) | $K_D$ (M) |
|---|---|---|---|
| 1 | $5.00 \times 10^5$ | $2.55 \times 10^{-6}$ | $5.09 \times 10^{-12}$ |
| 2 | $1.11 \times 10^6$ | $1.23 \times 10^{-5}$ | $1.12 \times 10^{-11}$ |
| 3 | $6.53 \times 10^5$ | $<1.0 \times 10^{-7}$ | $<1.0 \times 10^{-12}$ |
| 4 | $1.91 \times 10^6$ | $2.29 \times 10^{-4}$ | $1.20 \times 10^{-10}$ |
| 5 | $6.71 \times 10^5$ | $2.44 \times 10^{-5}$ | $3.64 \times 10^{-11}$ |
| 6 | $7.54 \times 10^5$ | $7.23 \times 10^{-4}$ | $9.58 \times 10^{-10}$ |
| 7 | $3.69 \times 10^5$ | $3.03 \times 10^{-5}$ | $8.22 \times 10^{-11}$ |
| 8 | $6.96 \times 10^5$ | $<1.0 \times 10^{-7}$ | $<1.0 \times 10^{-12}$ |
| 9 | $7.82 \times 10^5$ | $9.46 \times 10^{-5}$ | $1.21 \times 10^{-10}$ |
| 10 | $6.79 \times 10^5$ | $7.66 \times 10^{-4}$ | $1.13 \times 10^{-9}$ |
| 11 | $2.72 \times 10^5$ | $2.28 \times 10^{-5}$ | $8.37 \times 10^{-11}$ |
| 12 | $7.54 \times 10^5$ | $7.23 \times 10^{-4}$ | $4.32 \times 10^{-10}$ |
| 13 | $8.35 \times 10^5$ | $<1.0 \times 10^{-7}$ | $<1.0 \times 10^{-12}$ |
| 14 | $9.61 \times 10^5$ | $<1.0 \times 10^{-7}$ | $<1.0 \times 10^{-12}$ |

Table 5 shows the results of measurement of association rate constant ($k_{on}$), dissociation rate constant ($k_{off}$) of anti-hTfR antibody Nos. 1-14 (corresponding to Nos. 1-14, respectively, in the table), and dissociation constant ($K_D$) to monkey TfR.

TABLE 5

Affinity of anti-hTfR antibodies to monkey TfR

| Antibody No. | kon ($M^{-1}s^{-1}$) | koff ($s^{-1}$) | $K_D$ (M) |
|---|---|---|---|
| 1 | $2.80 \times 10^5$ | $<1.0 \times 10^{-7}$ | $<1.0 \times 10^{-12}$ |
| 2 | $4.18 \times 10^5$ | $1.75 \times 10^{-6}$ | $4.18 \times 10^{-11}$ |
| 3 | $3.89 \times 10^5$ | $<1.0 \times 10^{-7}$ | $<1.0 \times 10^{-12}$ |
| 4 | $7.54 \times 10^5$ | $1.21 \times 10^{-4}$ | $1.61 \times 10^{-10}$ |
| 5 | $5.19 \times 10^5$ | $7.58 \times 10^{-4}$ | $1.46 \times 10^{-9}$ |
| 6 | $4.95 \times 10^5$ | $2.36 \times 10^{-4}$ | $1.23 \times 10^{-10}$ |
| 7 | $2.66 \times 10^5$ | $4.54 \times 10^{-6}$ | $1.71 \times 10^{-11}$ |
| 8 | $5.52 \times 10^5$ | $5.07 \times 10^{-3}$ | $9.18 \times 10^{-9}$ |
| 9 | $6.99 \times 10^5$ | $1.47 \times 10^{-4}$ | $2.10 \times 10^{-9}$ |
| 10 | $3.87 \times 10^5$ | $1.22 \times 10^{-2}$ | $3.16 \times 10^{-8}$ |
| 11 | $1.24 \times 10^5$ | $4.21 \times 10^{-4}$ | $3.38 \times 10^{-9}$ |
| 12 | $5.05 \times 10^5$ | $1.26 \times 10^{-4}$ | $2.49 \times 10^{-10}$ |
| 13 | $5.91 \times 10^5$ | $7.29 \times 10^{-5}$ | $1.23 \times 10^{-10}$ |
| 14 | $7.00 \times 10^5$ | $3.61 \times 10^{-5}$ | $5.16 \times 10^{-11}$ |

As a result of the affinity measurement of those anti-hTfR antibodies to human TfR, the dissociation constant with human TfR was not more than $1 \times 10^{-8}$ M for all the antibodies; and for 13 antibodies except antibody No. 10, the dissociation constant with human TfR was not more than $1×10^{-9}$ M; and for antibodies Nos. 3, 8, 13 and 14, in particular, the dissociation constant was not more than $1×10^{-12}$ M (Table 4). The result demonstrates that all of the 14 antibodies are antibodies having a high-affinity antibody to human TfR. Then looking to the result of the measurement of the affinity of the anti-hTfR antibodies to monkey TfR, the dissociation constant with monkey TfR was not more than $5×10^{-8}$ M for all the antibodies, and for antibodies Nos. 1 and 3, in particular, the dissociation constant with monkey TfR was not more than $1×10^{-12}$ M (Table 5). The result shows that all the 14 antibodies are antibodies having a high-affinity antibody not only to human TfR but also to monkey TfR.

[Example 7-2] Evaluation of Brain Uptake of the Anti-hTfR Antibodies Using Mice

Then, for 13 antibodies, anti-hTfR antibodies Nos. 1 to 9 and 11 to 14, evaluation was performed about their transfer into the brain through the BBB, by using hTfR knock-in mice (hTfR-KI mice) in which the gene encoding the extracellular region of mouse transferrin receptor has been replaced with a gene encoding the extracellular region of human transferrin receptor. The hTfR-KI mice were produced by the method described below as a whole. Besides, the purified products of Example 7 were used as the anti-hTfR antibodies.

A DNA fragment having a nucleotide sequence set forth as SEQ ID NO:253 was chemically synthesized, in which a neomycin resistance gene flanked by loxP sequences was placed on the 3'-side of a cDNA encoding a chimeric hTfR whose intracellular region consisted of the amino acid sequence of mouse TfR and the extracellular region consisted of the amino acid sequence of human TfR sequence. This DNA fragment was inserted by a conventional method into a targeting vector having as the 5'-arm sequence a nucleotide sequence set forth as SEQ ID NO:254 and as the 3'-arm sequence a nucleotide sequence set forth as SEQ ID NO:255, and the construct was introduced into mouse ES cells by electroporation. The mouse ES cells to which the gene had been introduced were subjected to selection culture in a medium in the presence of neomycin to select those mouse ES cells in which the targeting vector had been incorporated into the chromosome through homologous recombination. The recombinant mouse ES cells thus obtained were injected into 8-cell stage embryos (host embryos) of ICR mice, and the embryos thus prepared were implanted into pseudo pregnant mice (recipient mice) which had been obtained through mating with mice having undergone vasoligation. The offspring (chimeric mice) obtained were examined by their hair color, and those mice which had the higher proportion of white hairs in their total body hairs were selected, i.e., those mice in which the ES cells had contributed at the higher rates in the development of the individual organisms. Each of these chimeric mice was mated with ICR mice to generate F1 mice. F1 mice with white hair were selected, the DNAs extracted from their tail tissue were analyzed, and those mice whose mouse TfR gene on their chromosomes had been replaced with chimeric hTfR, were regarded as hTfR-KI mice.

The above 13 anti-hTfR antibodies were fluorescently labeled with fluorescein isothiocyanate (FITC) using Fluorescein Labeling Kit-NH$_2$ (Dojindo Laboratories) according to the attached manual. PBS solutions were prepared each containing one of the FITC fluorescent labeled 13 anti-hTfR antibodies. Each of these PBS antibody solutions was intravenously injected to an hTfR-KI mouse (male, 10 to 12-week old), at the anti-hTfR antibody dosage of 3 mg/kg. As a control, a PBS solution containing mouse IgG1 (Sigma Inc.), fluorescently labeled with FITC in the same manner as above, was intravenously injected to an hTfR-KI mouse (male, 10 to 12-week old), at the dose of 3 mg/kg. About eight hours after the intravenous injection, the whole body was perfused with saline, and brain (part including the cerebrum and the cerebellum) was obtained. The brain thus excised was weighed (wet weight), and then the brain tissues were homogenized with T-PER (Thermo Fisher Scientific Inc.) containing Protease Inhibitor Cocktail (Sigma Inc.). The homogenate was centrifuged, the supernatant was collected, and the amount of the FITC fluorescent labeled antibody contained in the supernatant was measured in the following manner. First, 10 μL of anti-FITC Antibody (Bethyl Inc.) was added to each well of a High Bind Plate (Meso Scale Diagnostics Inc.) and left to stand for one hour so as to immobilize it to the plate. Then, the plate was blocked by addition of 150 μL of SuperBlock Blocking buffer in PBS (Thermo Fisher Scientific Inc.) to each well and shaking of the plate for one hour. Then, 25 μL of the supernatant of a brain tissue homogenate was added to each well, and the plate was shaken for one hour. Then, 25 μL of SULFO-TAG Anti-Mouse Antibody(Goat)(Meso Scale Diagnostics Inc.) were added to each well, and shaking was continued for one hour. Then, to each well was added 150 μL of Read buffer T (Meso Scale Diagnostics Inc.), and the amount of luminescence from each well was read on a Sector™ Imager 6000 reader. The amount of the antibody contained per one gram brain (wet weight) (the concentration of the anti-hTfR antibody in the brain tissues) was calculated, by producing a standard curve based on measurements of standard samples containing known concentrations of fluorescently FITC-labeled anti-hTfR antibody, and then interpolating the measurement of each of the samples with reference to the standard. The results are shown in Table 5-2.

The concentration of any of the antibodies designated anti-hTfR antibodies Nos. 1 to 9 and 11 to 14 in brain tissues was over 25 times greater than that of the control. The concentration of anti-hTfR antibodies Nos. 5 and 6 was both over 100 times greater than that of the control, with anti-hTfR antibody No. 6, in particular, the value reached approximately 160 times as high as that of the control. The results indicate that the antibodies designated anti-hTfR antibody Nos. 1 to 9 and 11 to 14 transfers into the brain, actively passing through the BBB.

TABLE 5-2

Concentration of anti-hTfR antibodies in brain tissues

| Antibody No. | Brain tissues (μg/g wet weight) | Relative value to the control |
|---|---|---|
| Control | 0.003 | 1 |
| 1 | 0.141 | 47.0 |
| 2 | 0.126 | 42.0 |
| 3 | 0.0833 | 27.8 |
| 4 | 0.221 | 73.7 |
| 5 | 0.335 | 112 |
| 6 | 0.492 | 164 |
| 7 | 0.0855 | 28.5 |
| 8 | 0.133 | 44.3 |
| 9 | 0.112 | 37.3 |
| 11 | 0.103 | 34.3 |
| 12 | 0.215 | 71.7 |

TABLE 5-2-continued

Concentration of anti-hTfR antibodies in brain tissues

| Antibody No. | Brain tissues (μg/g wet weight) | Relative value to the control |
|---|---|---|
| 13 | 0.127 | 42.3 |
| 14 | 0.213 | 71.0 |

[Example 8] Pharmacokinetic Analysis of Anti-hTfR Antibodies in Monkey

Each of anti-hTfR antibodies Nos. 1 to 3 was intravenously administered once to a male cynomolgus monkey at a dosage of 5.0 mg/kg, and 8 hours after the administration, whole body irrigation was carried out with physiological saline. As a negative control, a monkey which had not received anti-hTfR antibody was subjected to whole body irrigation in the same manner. After the irrigation, brain tissues including the medulla oblongata were excised. Using the brain tissues, the concentration of the anti-hTfR antibody was measured, and immunohistochemical staining was performed. Besides, the anti-hTfR antibodies employed were purified products described in Example 7.

Measurement of the concentration of anti-hTfR antibodies in brain tissues were carried out largely following the procedure described below. Collected brain tissues were divided into the cerebrum, the cerebellum, the hippocampus, and the medulla oblongata, and they were respectively homogenized with RIPA Buffer (Wako Pure Chemical Industries Inc.) containing Protease Inhibitor Cocktail (Sigma-Aldrich Inc.), and centrifuged to collect the supernatant. Affinipure Goat Anti mouse IgG Fcγ pAb (Jackson ImmunoResearch Inc.) was added, 10 μL each, to the wells of a High Bind Plate (Meso Scale Diagnostics Inc.), and the plate was left to stand for one hour to immobilize the antibody. Then, the plate was blocked by addition of 150 μL of SuperBlock Blocking buffer in PBS (Thermo Fisher Scientific Inc.) to each well and shaken for one hour. Then, 25 μL of the supernatant of a brain tissue homogenate was added to each well, and the plate was shaken for one hour. Then, 25 μL of Affinipure Goat Anti mouse IgG Fab-Biotin (Jackson ImmunoResearch Inc.) was added to each well, and shaking was continued for one hour. Then, 25 μL or SULFO-Tag-Streptavidin (Meso Scale Diagnostics Inc.) was added to each well, and shaking was continued for half an hour. To each well was added 150 μL of Read buffer T (Meso Scale Diagnostics Inc.), and the amount of luminescence from each well was read on a Sector™ Imager 6000 reader (Meso Scale Diagnostics). The amount of the antibody contained per one gram of brain (wet weight) (the concentration of the anti-hTfR antibody in brain tissues) was calculated, by producing a standard curve based on measurements of standard samples containing known concentrations of the anti-hTfR antibody, and then interpolating the measurement of each of the samples with reference to the standard.

The result of the measurement of the concentration of the anti-hTfR antibodies in brain tissues is shown in Table 6. Though any of anti-hTfR antibodies Nos. 1 to 3 was observed to accumulate in the cerebrum, the cerebellum, the hippocampus and the medulla oblongata, in their amount there was a relation of anti-hTfR antibody No. 1<anti-hTfR antibody No. 3<anti-hTfR antibody No. 2, showing the lowest with anti-hTfR antibody No. 1 and highest in anti-hTfR antibody No. 2. In comparison with anti-hTfR antibody No. 1, the accumulation of anti-hTfR antibody No. 2 was approximately 4.3 times in the cerebrum, approximately 6.6 times in the cerebellum, approximately 4.6 times in the hippocampus, and approximately 2 times in the medulla oblongata. These results demonstrate that these 3 types of antibodies have the property of passing through the blood-brain barrier and being accumulated in brain tissues, and thus that BDNF as a drug to be allowed to function in such brain tissues is linked to these antibodies, so that the drug can be efficiently accumulated in the brain tissues.

TABLE 6

Concentration of anti-hTfR antibodies in brain tissues (μg/g wet weight)

| Antibody No. | Cerebrum | Cerebellum | Hippocampus | Medulla oblongata |
|---|---|---|---|---|
| 1 | 0.18 | 0.15 | 0.12 | 0.22 |
| 2 | 0.78 | 0.99 | 0.56 | 0.43 |
| 3 | 0.82 | 0.6 | 0.33 | 0.31 |

Immunohistochemical staining of the anti-hTfR antibodies in these brain tissues was carried out using the following procedures described below basically. The collected tissues were rapidly frozen to −80° C. in a Tissue-Tek Cryo 3DM (Sakura Finetek Inc.) to prepare frozen blocks of tissues. The frozen blocks were sliced into 4-μm sections, and which were affixed to MAS coated glass slides (Matsunami Glass Inc.). The tissue sections were reacted with 4% paraformaldehyde (Wako Pure Chemical Industries Inc.) for 5 minutes at 4° C. and fixed to glass slides. Then, the tissue sections were reacted with methanol solution containing 0.3% hydrogen peroxide (Wako Pure Chemical Industries Inc.) for 30 min to inactivate endogenous peroxidases. Then, the glass slides were blocked by reacting SuperBlock blocking buffer in PBS for 30 min at room temperature. Then, the tissue sections were reacted with Mouse IgG-heavy and light chain Antibody (Bethyl Laboratories Inc.) for one hour at room temperature. The tissue sections were allowed to visualize with DAB substrate (3,3'-diaminobenzidine, Vector Laboratories Inc.), counterstained with Mayer's hematoxylin solution (Merck Inc.), embedded after dehydration and clearing, and observed under an optical microscope.

FIG. 1 shows the result of the immunohistochemical staining of the anti-hTfR antibodies in the cerebral cortex. In the cerebral cortex of monkeys administered anti-hTfR antibodies Nos. 1 to 3, specific staining in the blood vessels were observed (FIG. 1, panels b to d, respectively). In particular, in the cerebral cortex of the monkeys administered anti-hTfR antibodies No. 2 or 3, specific staining was also observed extensively in the brain parenchyma region, outside the blood vessels (FIG. 1, panels c and d, respectively). Besides, no staining was observed in the cerebral cortex of the control monkey non-administered anti-hTfR antibody, indicating that there was almost no background staining (FIG. 1, panel a).

Figure 2:
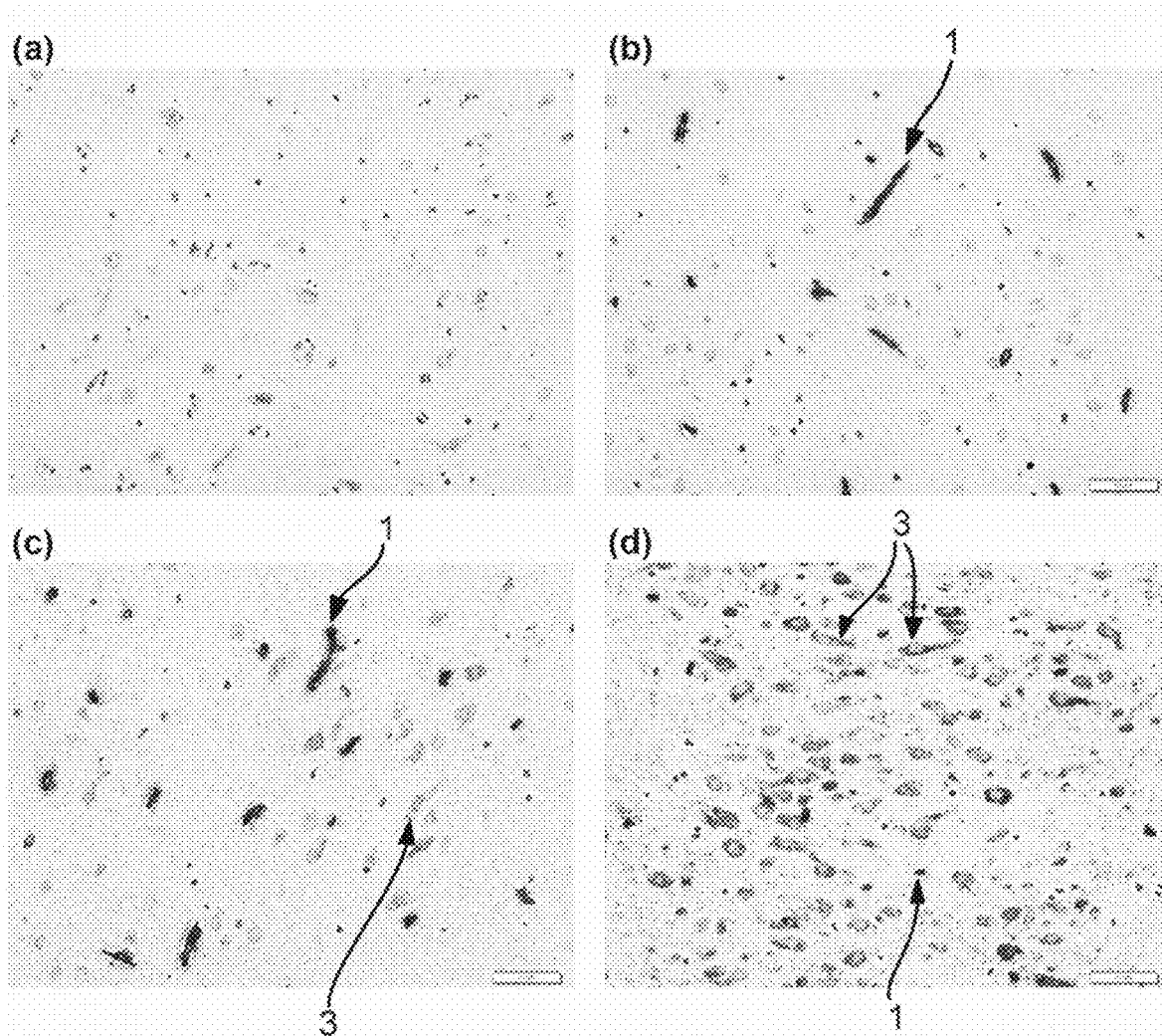
FIG. 2 Substitute photographs for drawings showing the result of the immunohistochemical staining of the anti-hTfR antibody in the hippocampus of a cynomolgus monkey after a single intravenous administration of the anti-hTfR antibody. Staining photographs of the hippocampus: (a) anti-hTfR antibody not administered, (b) anti-hTfR antibody No. 1 administered, (c) anti-hTfR antibody No. 2 administered, (d) anti-hTfR antibody No. 3 administered. The bar at the bottom right in each photograph is a 50-µm gauge.

FIG. 2 shows the result of immunohistochemical staining of anti-hTfR antibodies in the hippocampus. In the cerebrum of monkeys administered anti-hTfR antibodies Nos. 1 to 3, specific staining of blood vessels were observed (FIG. 2, panels b to d, respectively). In particular, in the hippocampus of the monkeys administered anti-hTfR antibodies No. 2 or 3, specific staining of neuron-like cells was also observed (FIG. 2, panels c and d, respectively), and specific and extensive staining of the brain parenchyma region, outside the blood vessels, was also observed. Besides, no staining was observed in the hippocampus of the control monkey non-administered anti-hTfR antibody, indicating that there was almost no background staining (FIG. 2, panel a).

Figure 3:
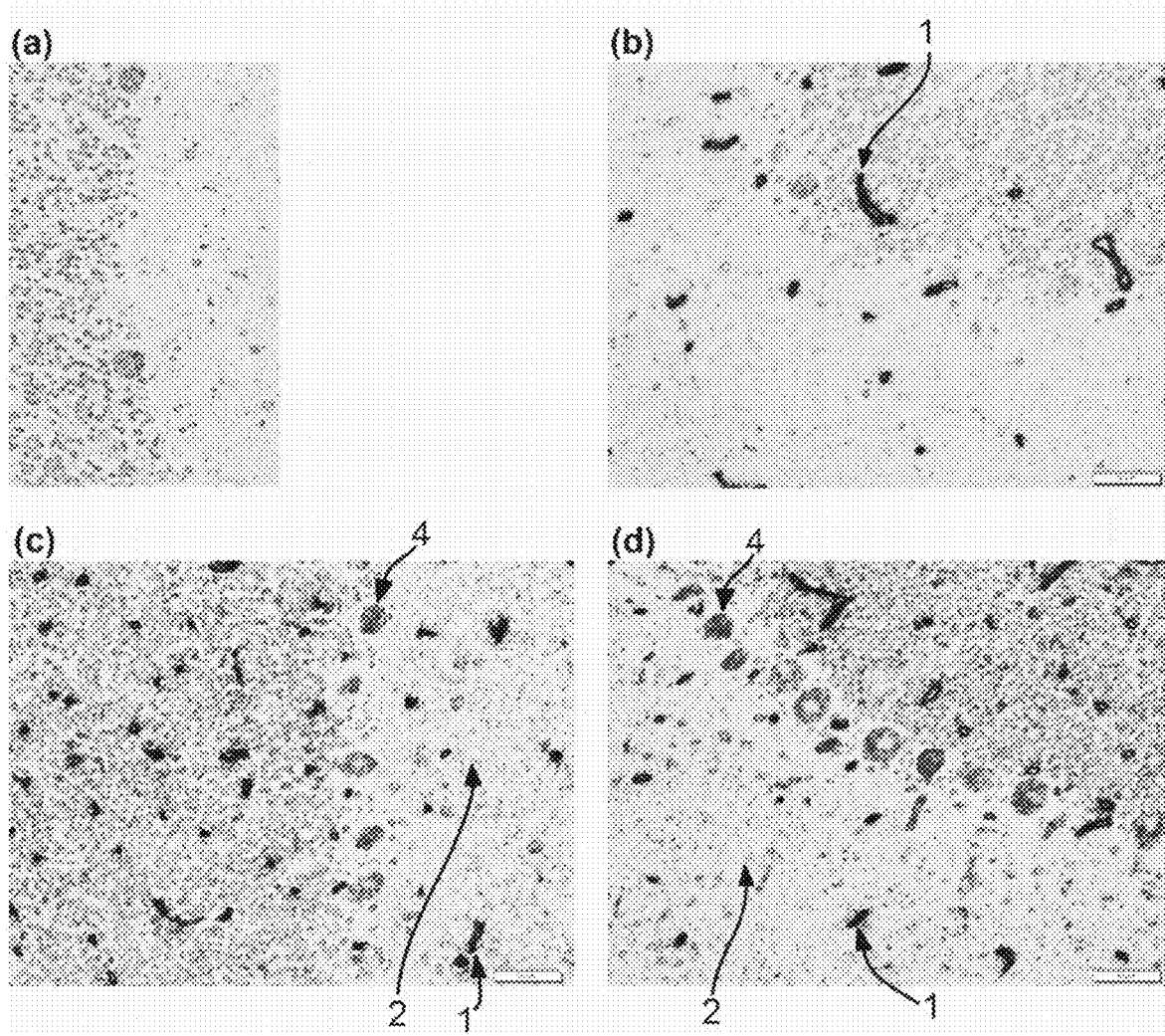
FIG. 3 Substitute photographs for drawings showing the result of the immunohistochemical staining of the anti-hTfR antibody in the cerebellum of a cynomolgus monkey after a single intravenous administration of the anti-hTfR antibody. Staining photographs of the cerebellum: (a) anti-hTfR antibody not administered, (b) anti-hTfR antibody No. 1 administered, (c) anti-hTfR antibody No. 2 administered, (d) anti-hTfR antibody No. 3 administered. The bar at the bottom right in each photograph is a 50-µm gauge.

FIG. 3 shows the result of immunohistochemical staining of the anti-hTfR antibodies in the cerebellum. In the cerebellum of monkeys administered anti-hTfR antibodies Nos. 1 to 3, specific staining of blood vessels were observed (FIG. 3, panels b to d, respectively). In particular, in the cerebellum of the monkeys administered anti-hTfR antibodies No. 2 or 3, specific staining of Purkinje cells was also observed (FIG. 3, panels c and d, respectively). Besides, no staining was observed in the cerebellum of the control with no anti-hTfR antibody administered, indicating that there was almost no background staining (FIG. 3, panel a).

From the above results of immunohistochemical staining in the cerebrum, the hippocampus, and the cerebellum, it was considered that while anti-hTfR antibody No. 1 can bind to hTfR existing on the endothelium of blood vessels in the brain, relatively small amount of it transfers to the brain parenchyma compared with anti-hTfR antibodies Nos. 2 and 3. On the other hand, it was found that anti-hTfR antibodies Nos. 2 and 3 can bind to hTfR existing on the endothelium of blood vessels of the brain, and after binding to hTfR, they pass through the blood-brain barrier and transfer into the brain parenchyma, and further, are taken up into the brain parenchyma and neuron-like cells in the hippocampus, and are taken up by Purkinje cells in the cerebellum.

[Example 9] Preparation of Humanized Anti-hTfR Antibodies

Humanization was tried of the amino acid sequence included in the light chain and the heavy chain variable regions of anti-hTfR antibodies Nos. 1 to 3 shown in Table 1. From anti-hTfR antibody No. 1 were obtained a humanized light chain variable region having one of the amino acid sequences set forth as SEQ ID NO:158 to SEQ ID NO: 163, and a humanized heavy chain variable region having one of the amino acid sequences set forth as SEQ ID NO:166 to SEQ ID NO:171. From anti-hTfR antibody No. 2 were obtained a humanized light chain variable region having one of the amino acid sequences set forth as SEQ ID NO: 174 to SEQ ID NO: 179, and a humanized heavy chain variable region having one of the amino acid sequences set forth as SEQ ID NO:182 to SEQ ID NO:187. From anti-hTfR antibody No. 3 were obtained a humanized light chain variable region having one of the amino acid sequences set forth as SEQ ID NO:190 to SEQ ID NO: 195, and a humanized heavy chain variable region having one of the amino acid sequences set forth as SEQ ID NO:204 to SEQ ID NO:209.

[Example 10] Construction of Genes Encoding Humanized Anti-hTfR Antibodies

For each of anti-hTfR antibodies Nos. 1 to 3 above, DNA fragments were artificially synthesized which contained a gene encoding the full length of the light chain, and of the heavy chain, having humanized anti-hTfR antibody light chain and heavy chain variable regions, respectively. In doing this, a MluI sequences and a sequence encoding a leader peptide was added, in this order from the 5' end, on the 5' side of the gene encoding the full length of the light chain, and on the 3' side was added a NotI sequence. And, a MluI sequences and a sequence encoding a leader peptide was added, in this order from the 5' end, on the 5' side of the gene encoding the full length of the heavy chain, and on the 3' side was added a NotI sequence. The leader peptide introduced above is to function as secretion signal when the light chain and heavy chain of the humanized antibody is expressed in mammalian cells as host cells so that the light chain and the heavy chain are secreted out of the cells.

For the light chain of anti-hTfR antibody No. 1, a DNA fragment (SEQ ID NO: 165) was synthesized, which included a gene encoding the full length of the light chain (the light chain of humanized anti-hTfR antibody No. 1) consisting of the amino acid sequence set forth as SEQ ID NO: 164, which had in the variable region the amino acid sequence set forth as SEQ ID NO: 163.

For the heavy chain of anti-hTfR antibody No. 1, a DNA fragment (SEQ ID NO:173) was synthesized, which included a gene encoding the full length of the heavy chain (the heavy chain of humanized anti-hTfR antibody No. 1) consisting of the amino acid sequence set forth as SEQ ID NO: 172, which had in the variable region the amino acid sequence set forth as SEQ ID NO: 171.

The heavy chain of the humanized anti-hTfR antibody encoded by the DNA fragment set forth as SEQ ID NO: 173 is IgG1.

For the light chain of anti-hTfR antibody No. 2, a DNA fragment (SEQ ID NO: 181) was synthesized, which included a gene encoding the full length of the light chain (the light chain of humanized anti-hTfR antibody No. 2) consisting of the amino acid sequence set forth as SEQ ID NO: 180, which had in the variable region the amino acid sequence set forth as SEQ ID NO: 179.

For the heavy chain of anti-hTfR antibody No. 2, a DNA fragment (SEQ ID NO:189) was synthesized, which included a gene encoding the full length of the heavy chain (the heavy chain of humanized anti-hTfR antibody No. 2) consisting of the amino acid sequence set forth as SEQ ID NO: 188, which had in the variable region the amino acid sequence set forth as SEQ ID NO: 187.

The heavy chain of the humanized anti-hTfR antibody encoded by the DNA fragment set forth as SEQ ID NO: 189 is IgG1.

For the light chain of anti-hTfR antibody No. 3, a DNA fragment (SEQ ID NO: 197) was synthesized, which included a gene encoding the full length of the light chain (the light chain of humanized anti-hTfR antibody No. 3) consisting of the amino acid sequence set forth as SEQ ID NO: 196, which had in the variable region the amino acid sequence set forth as SEQ ID NO: 191.

As to the light chain of anti-hTfR antibody No. 3, also synthesized were, a DNA fragment (SEQ ID NO:199) encoding the full length amino acid sequence of the light chain (the light chain of humanized anti-hTfR antibody No. 3-2) consisting of the amino acid sequence set forth as SEQ ID NO:198, which had in the variable region the amino acid sequence set forth as SEQ ID NO: 193;

a DNA fragment (SEQ ID NO:201) encoding the full length amino acid sequence of the light chain (the light chain of humanized anti-hTfR antibody No. 3-3) consisting of the amino acid sequence set forth as SEQ ID NO:200, which had in the variable region the amino acid sequence set forth as SEQ ID NO: 194;

a DNA fragment (SEQ ID NO:203) encoding the full length amino acid sequence of the light chain (the light chain of humanized anti-hTfR antibody No. 3-4) consisting of the amino acid sequence set forth as SEQ ID NO:202, which had in the variable region the amino acid sequence set forth as SEQ ID NO: 195.

For the heavy chain of anti-hTfR antibody No. 3, a DNA fragment (SEQ ID NO:211) was synthesized, which included a gene encoding the full length of the heavy chain (the heavy chain of humanized anti-hTfR antibody No. 3) consisting of the amino acid sequence set forth as SEQ ID NO:210, which had in the variable region the amino acid sequence set forth as SEQ ID NO:205.

The heavy chain of the humanized anti-hTfR antibody encoded by the DNA fragment set forth as SEQ ID NO:211 is IgG1.

Further, for the heavy chain of anti-hTfR antibody No. 3, also synthesized was a DNA fragment (SEQ ID NO:213) encoding the full length amino acid sequence of the heavy chain (the heavy chain IgG4 of humanized anti-hTfR antibody No. 3) consisting of the amino acid sequence set forth as SEQ NO:212, which had in the variable region the amino acid sequence set forth as SEQ ID NO:205;

The heavy chain of the humanized anti-hTfR antibody encoded by the DNA fragment set forth as SEQ ID NO:213 is IgG4.

[Example 11] Construction of Humanized Anti-hTfR Antibody Expression Vector

Vector pEF/myc/nuc (Invitrogen Inc.) was digested with KpnI and NcoI to cut out a region including EF-1α promoter and its first intron, and this was blunt-ended with T4 DNA polymerase. A region including the CMV enhancer/promoter and intron was removed from pCI-neo (Invitrogen Inc.) by digesting it with BglII and EcoRI, and the remaining fragment thus left was blunt-ended with T4 DNA polymerase. To this was inserted the above-mentioned region including EF-1α promoter and its first intron to construct pE-neo vector. This vector, pE-neo, was digested with SfiI and BstXI to remove a region of approximately 1 kb including a neomycin resistance gene. PCR was performed employing pcDNA3.1/Hygro(+)(Invitrogen) as a template and using primer Hyg-Sfi5' (SEQ ID NO:216) and primer Hyg-BstX3' (SEQ ID NO:217) to amplify hygromycin gene. The hygromycin gene thus amplified was digested with SfiI and BstXI and inserted into the above pE-neo vector from which neomycin resistance gene had been removed to construct a vector pE-hygr.

Vectors pE-hygr and pE-neo were both digested with MluI and NotI. The DNA fragment (SEQ ID NO: 165) encoding the light chain of humanized anti-hTfR antibody No. 1 and the DNA fragment (SEQ ID NO: 173) encoding the heavy chain of the antibody, both synthesized in Example 10, were digested with MluI and NotI, and the fragments thus obtained were inserted into vector pE-hygr and vector pE-neo, respectively, between their MluI and NotI sites. The vectors thus obtained were used as an expression vector for the light chain of humanized anti-hTfR antibody No. 1, pE-hygr(LC1), and as an expression vector for the heavy chain of the antibody, pE-neo(HC1), in the experiments described below.

In an analogous manner, the DNA fragment (SEQ ID NO:181) encoding the light chain of humanized anti-hTfR antibody No. 2 and the DNA fragment (SEQ ID NO:189) encoding the heavy chain of the antibody, both synthesized in Example 10, were both digested with MluI and NotI, and the fragments thus obtained were inserted into vector pE-hygr and vector pE-neo, respectively, between their MluI and NotI sites. The vectors thus obtained were used as an expression vector for the light chain of humanized anti-hTfR antibody No. 2, pE-hygr(LC2), and as an expression vector for the heavy chain of humanized anti-hTfR antibody No. 2, pE-neo(HC2), in the experiments described below.

Further, in the same manner as above, the DNA fragment (SEQ ID NO: 197) encoding the light chain of humanized anti-hTfR antibody No. 3 and the DNA fragment (SEQ ID NO:211) encoding the heavy chain of the antibody, both synthesized in Example 10, were both digested with MluI and NotI, and the fragments thus obtained were inserted into vector pE-hygr and vector pE-neo, respectively, between their MluI and NotI sites. The vectors thus obtained were used as an expression vector for the light chain of humanized anti-hTfR antibody No. 3, pE-hygr(LC3), and as an expression vector for the heavy chain of humanized anti-hTfR antibody No. 3, pE-neo(HC3), in the experiments described below.

Further, as to the light chain of anti-hTfR antibody No. 3, the following fragments synthesized in Example 10, namely:
the DNA fragment (SEQ ID NO: 199) encoding the light chain of humanized anti-hTfR antibody No. 3-2,
the DNA fragment (SEQ ID NO:201) encoding the light chain of humanized anti-hTfR antibody No. 3-3, and
the DNA fragment (SEQ ID NO:203) encoding the light chain of humanized anti-hTfR antibody No. 3-4,
were digested with MluI and NotI, and inserted into the vector pE-hygr between the MluI and NotI sites thereof to construct
pE-hygr(LC3-2), an expression vector for the light chain of humanized anti-hTfR antibody No. 3-2,
pE-hygr(LC3-3), an expression vector for the light chain of humanized anti-hTfR antibody No. 3-3, and
pE-hygr(LC3-4), an expression vector for the light chain of humanized anti-hTfR antibody No. 3-4, respectively.

Further, in the same manner as above, as to the heavy chain of anti-hTfR antibody No. 3, the DNA fragment (SEQ ID NO:213) encoding the heavy chain IgG4 of humanized anti-hTfR antibody No. 3 synthesized in Example 10 was digested with MluI and NotI, and inserted into the vector pE-neo between the MluI and NotI sites thereof to construct pE-neo(HC3-IgG4), an expression vector for the heavy chain IgG4 of humanized anti-hTfR antibody No. 3.

[Example 12] Construction of Cells for Expression of Humanized Anti-hTfR Antibody CHO cells (CHO-K1: obtained from American Type Culture Collection) were transformed with pE-hygr(LC1), the vector for light chain expression, and pE-neo(HC1), the vector for heavy chain expression, both constructed in Example 11, as follows, using GenePulser (Bio-Rad Inc.). Transformation of the cells was performed in the following manner as a whole. $5 \times 10^5$ of CHO-K1 cells were seeded in a 3.5-cm culture dish containing CD OPTICHO medium (Life Technologies Inc.) and cultured overnight at 37° C., 5% $CO_2$. The medium was replaced with Opti-MEM™ I medium (Life Technologies Inc.), and the cells were suspended at the density of $5 \times 10^6$ cells/mL. 100 μL of the cell suspension were taken, to which was added 5 μL each of a pE-hygr(LC1) and a pE-neo(HC1) plasmid DNA solution both having been diluted with Opti-MEM™ I medium to 100 μg/mL. These plasmids were introduced into the cells by electroporation using GenePulser (Bio-Rad Inc.). The cells then were cultured overnight under the condition of 37° C., 5% $CO_2$, and subjected to selection culture in CD OPTICHO medium supplemented with 0.5 mg/mL of hygromycin and 0.8 mg/m L of G418.

The ELISA above was conducted as follows in general. To each well of 96-well microtiter plates (Nunc Inc.) were added 100 μL of a goat anti-human IgG polyclonal antibody solution diluted with 0.05 M sodium bicarbonate buffer (pH 9.6) to 4 µg/mL, and the plate was left to stand for at least one hour at room temperature so as to allow the antibody to be adsorbed by the plates. Then, after each well was washed three times with a phosphate-buffered saline (pH 7.4) supplemented with 0.05% Tween20 (PBS-T), 200 µL of Starting Block (PBS) Blocking Buffer (Thermo Fisher Scientific Inc.) was added to each well, and the plates were left to stand for 30 minutes at room temperature. After each well was washed with PBS-T three times, the culture supernatant or the human IgG reference standard product which had been diluted with a PBS supplemented with 0.5% BSA and 0.05% Tween20 (PBS-BT) to appropriate concentrations, was added to each well, in the amount of 100 µL, and the plates were left to stand for at least one hour at room temperature. After the plates were washed three times with PBS-T, 100 µL of HRP-labeled anti-human IgG polyclonal antibody solution which had been diluted with PBS-BT, was added to each well, and the plates were left to stand for at least one hour at room temperature. After the wells were washed three times with PBS-T, 0.4 mg/mL o-phenylenediamine in citrate-phosphate buffer (pH 5.0) was added to each well, in the amount of 100 µL, and the wells were left to stand for 8 to 20 minutes at room temperature. Then, 1 mol/L sulfuric acid was added to each well, in the amount of 100 µL to terminate the reaction, and the absorbance for each well was measured at 490 nm using a 96-well plate reader. The cells corresponding to the wells which exhibited the higher measurements were regarded as a high-expressing cell line for humanized anti-hTfR antibody No. 1. This was designated antibody No. 1 expressing cell line.

In the same manner, CHO cells were transformed with the light chain expression vector pE-hygr(LC2) and the heavy chain expression vector pE-neo(HC2), both constructed in Example 11, and a high-expressing cell line for humanized anti-hTfR antibody No. 2 was obtained. This was designated antibody No. 2 expressing cell line.

Further, in the same manner, CHO cells were transformed with the light chain expression vector pE-hygr(LC3) and the heavy chain expression vector pE-neo(HC3), both constructed in Example 11, and a high-expressing cell line for humanized anti-hTfR antibody No. 3 was obtained. This was designated antibody No. 3 expressing cell line.

Further, in the same manner, CHO cells were transformed with the light chain expression vector pE-hygr(LC3-2) and the heavy chain expression vector pE-neo(HC3), both constructed in Example 11, and a high-expressing cell line for humanized anti-hTfR antibody No. 3-2 was obtained. This was designated antibody No. 3-2 expressing cell line.

Further, in the same manner, CHO cells were transformed with the light chain expression vector pE-hygr(LC3-3) and the heavy chain expression vector pE-neo(HC3), both constructed in Example 11, and a high-expressing cell line for humanized anti-hTfR antibody No. 3-3 was obtained. This was designated antibody No. 3-3 expressing cell line.

Further, in the same manner, CHO cells were transformed with the light chain expression vector pE-hygr(LC3-4) and the heavy chain expression vector pE-neo(HC3) both constructed in Example 11, and a high-expressing cell line for humanized anti-hTfR antibody No. 3-4 was obtained. This was designated antibody No. 3-4 expressing cell line.

Further, in the same manner, CHO cells were transformed with the light chain expression vector pE-hygr(LC3) and the heavy chain expression vector pE-neo(HC3-IgG4) both constructed in Example 11, and a high-expressing cell line for humanized anti-hTfR antibody No. 3(IgG4) was obtained. This was designated antibody No. 3(IgG4) expressing cell line.

Further, in the same manner, CHO cells were transformed with the light chain expression vector pE-hygr(LC3-2) and the heavy chain expression vector pE-neo(HC3-IgG4) both constructed in Example 11, and a high-expressing cell line for humanized anti-hTfR antibody No. 3-2 (IgG4) was obtained. This was designated antibody No. 3-2 (IgG4) expressing cell line.

[Example 13] Purification of Humanized Anti-hTfR Antibodies

Antibody No. 1 expressing cell line, antibody No. 2 expressing cell line, antibody No. 3 expressing cell line, antibody No. 3-2 expressing cell line, antibody No. 3-3 expressing cell line and antibody No. 3-4 expressing cell line obtained in Example 12 were respectively diluted with CD OPTICHO medium to the density of approximately $2 \times 10^5$ cells/mL. The cell suspensions, 200 mL, was added to a 1 L-conical flask, and cultured for 6 to 7 days in a humid environment at 37° C., 5% $CO_2$, 95% air, with stirring at a rate of about 70 rpm. Each culture supernatant was collected by centrifugation, and filtered through a 0.22 µm filter (Millipore Inc.) to prepare the culture supernatant. To each culture supernatant thus obtained was added five volumes of 20 mM Tris buffer (pH 8.0) containing 150 mM NaCl, and loaded onto a Protein A column (column volume: 1 mL, Bio-Rad Inc.) which had been equilibrated in advance with three column volumes of 20 mM Tris buffer (pH 8.0) containing 150 mM NaCl. Then, the column was washed with five column volumes of the same buffer, and the adsorbed humanized anti-hTfR antibody was eluted with four column volumes of 50 mM glycine buffer (pH 2.8) containing 150 mM NaCl and used as the purified antibody preparation.

In the above, the antibody purified from the culture supernatant of antibody No. 1 expressing cell line was designated humanized anti-hTfR antibody No. 1. The antibody purified from the culture supernatant of antibody No. 2 expressing cell line was designated humanized anti-hTfR antibody No. 2. The antibody purified from the culture supernatant of antibody No. 3 expressing cell line was designated humanized anti-hTfR antibody No. 3. The antibody purified from the culture supernatant of antibody No. 3-2 expressing cell line was designated humanized anti-hTfR antibody No. 3-2. The antibody purified from the culture supernatant of antibody No. 3-3 expressing cell line was designated humanized anti-hTfR antibody No. 3-3. The antibody purified from the culture supernatant of antibody No. 3-4 expressing cell line was designated humanized anti-hTfR antibody No. 3-4.

Further, antibody No. 3(IgG4) expressing cell line and antibody No. 3-2 (IgG4) expressing cell line obtained in Example 12 also were cultured in the same manner as above, and from their culture supernatants were obtained purified humanized anti-hTfR antibody No. 3(IgG4) and humanized anti-hTfR antibody No. 3-2 (IgG4), respectively. These two antibodies were employed in the pharmacokinetic analysis using monkeys described in Example 15.

[Example 14] Measurement of Affinity of Humanized Anti-hTfR Antibodies to Human TfR and Monkey TfR The affinity of the humanized anti-hTfR antibodies obtained in Example 13 to human and monkey TfRs was measured by the method described in Example 7. Table 7 shows the result of the measurement of the association rate constant ($k_{on}$), dissociation rate constant ($k_{off}$), and dissociation constant ($K_D$) of humanized anti-hTfR antibodies Nos. 1 to 3-4 (corresponding to Nos. 1 to 3-4, respectively, in the table) to human TfR.

TABLE 7

Affinity of humanized anti-hTfR antibodies to human TfR

| Antibody No. | kon ($M^{-1}s^{-1}$) | koff ($s^{-1}$) | $K_D$ (M) |
|---|---|---|---|
| 1 | $3.93 \times 10^5$ | $<1.0 \times 10^{-7}$ | $<1.0 \times 10^{-12}$ |
| 2 | $1.97 \times 10^5$ | $<1.0 \times 10^{-7}$ | $<1.0 \times 10^{-12}$ |
| 3 | $1.19 \times 10^6$ | $<1.0 \times 10^{-7}$ | $<1.0 \times 10^{-12}$ |
| 3-2 | $6.06 \times 10^5$ | $1.45 \times 10^{-5}$ | $2.39 \times 10^{-11}$ |
| 3-3 | $6.00 \times 10^5$ | $1.25 \times 10^{-5}$ | $2.09 \times 10^{-11}$ |
| 3-4 | $1.01 \times 10^6$ | $<1.0 \times 10^{-7}$ | $<1.0 \times 10^{-12}$ |

Table 8 shows the result of the measurement of the association rate constant ($k_{on}$), dissociation rate constant ($k_{off}$), and dissociation constant ($K_D$) of humanized anti-hTfR antibodies Nos. 1 to 3-4 (corresponding to Nos. 1 to 3-4, respectively, in the table) to monkey TfR.

TABLE 8

Affinity of humanized anti-hTfR antibodies to monkey TfR

| Antibody No. | kon ($M^{-1}s^{-1}$) | koff ($s^{-1}$) | $K_D$ (M) |
|---|---|---|---|
| 1 | $2.53 \times 10^5$ | $<1.0 \times 10^{-7}$ | $<1.0 \times 10^{-12}$ |
| 2 | $4.87 \times 10^5$ | $3.67 \times 10^{-5}$ | $7.55 \times 10^{-11}$ |
| 3 | $6.03 \times 10^5$ | $6.76 \times 10^{-4}$ | $1.12 \times 10^{-9}$ |
| 3-2 | $4.95 \times 10^5$ | $8.76 \times 10^{-4}$ | $1.77 \times 10^{-9}$ |
| 3-3 | $4.88 \times 10^5$ | $9.32 \times 10^{-4}$ | $1.91 \times 10^{-9}$ |
| 3-4 | $5.19 \times 10^5$ | $1.35 \times 10^{-4}$ | $2.60 \times 10^{-10}$ |

The result of the measurement of the affinity of humanized anti-hTfR antibody Nos. 1 to 3-4 to human TfR showed that the dissociation constant between humanized anti-hTfR antibodies Nos. 1, 2, 3, and 3-4 and human TfR was less than $1 \times 10^{-12}$ M (Table 7). And the dissociation constant between humanized anti-hTfR antibodies Nos. 3-2 and 3-3 and human TfR was $2.39 \times 10^{-11}$ M and $2.09 \times 10^{-11}$ M, respectively. At the same time, the dissociation constant between the pre-humanized anti-hTfR antibodies corresponding to those antibodies and human TfR was: $5.09 \times 10^{-12}$ M for antibody No. 1, $1.12 \times 10^{-11}$ M for antibody No. 2, and less than $1 \times 10^{-12}$ M for antibody No. 3 (Table 4). These results demonstrate that the high affinity of those pre-humanized anti-hTfR antibodies to human TfR was maintained after humanization of the antibodies, and indicate that anti-hTfR antibodies Nos. 4 to 14 would also maintain their affinity to human TfR after their humanization.

Then, looking to the result of measurement of the affinity of humanized anti-hTfR antibodies to monkey TfR, it is seen that the dissociation constant of humanized anti-hTfR antibody No. 1 was less than $1 \times 10^{-12}$ M, indicating that the pre-humanized affinity was maintained after humanization, and also with regard to humanized anti-hTfR antibody No. 2, the dissociation constant was $4.18 \times 10^{-11}$ M before humanization and $7.55 \times 10^{-11}$ M after humanization, indicating the affinity was maintained (Table 5, Table 8). On the other hand, regarding to humanized anti-hTfR antibodies Nos. 3 to 3-4, while the dissociation constant of anti-hTfR antibody No. 3, the pre-humanized antibody corresponding to them, to monkey TfR was less than $1 \times 10^{-12}$ M, their dissociation constant after humanization was $2.60 \times 10^{-10}$ M to $1.91 \times 10^{-9}$ M, showing a lowering of the affinity to monkey TfR. As to the humanized anti-hTfR antibody No. 3, although a lowering of affinity to monkey TfR was observed, the result indicates that the pre-humanized high affinity of anti-hTfR antibody to monkey TfR was not lost after its humanization but was maintained as a whole. It indicates that as to humanized anti-hTfR antibodies Nos. 4 to 14, too, the pre-humanized affinity to monkey TfR could be maintained after their humanization.

[Example 15] Pharmacokinetic Analysis of Humanized Anti-hTfR Antibody in Monkey

Using monkeys, pharmacokinetic analysis was performed with four antibodies: humanized anti-hTfR antibody No. 3, humanized anti-hTfR antibody No. 3-2, humanized anti-hTfR antibody No. 3 (IgG4), and humanized anti-hTfR antibody No. 3-2 (IgG4). Besides, the heavy chain of humanized anti-hTfR antibody No. 3 was IgG1, while in humanized anti-hTfR antibody No. 3 (IgG4), the heavy chain of humanized anti-hTfR antibody No. 3 had been converted into IgG4, with its variable region kept intact. Further, the heavy chain of humanized anti-hTfR antibody No. 3-2 was IgG1, while in humanized anti-hTfR antibody No. 3-2 (IgG4), the heavy chain of humanized anti-hTfR antibody No. 3-2 had been converted into IgG4 with its variable region kept intact. These four antibodies were respectively intravenously administered once to male cynomolgus monkeys, at a dosage of 5.0 mg/kg, and their peripheral blood was sampled before the administration, 2 minutes, 30 minutes, 2 hours, 4 hours and 8 hours after the administration, and then they were subjected to whole body irrigation. As a negative control, trastuzumab (Herceptin™, Chugai Pharmaceutical Co., Ltd.), a humanized anti-hTfR antibody to HER2 protein, was intravenously administered once to a single monkey in the same manner, and its peripheral blood was sampled before the administration, 2 minutes, 30 minutes, 2 hours, 4 hours and 8 hours after the administration, and then it was subjected to the whole body irrigation. After the irrigation, the brain and spine tissues including the medulla oblongata and other tissues (liver, heart, spleen and bone marrow) were excised. Using these brain and spinal tissues and other tissues, the concentration of the humanized anti-hTfR antibodies was measured and immunohistochemical staining was carried out.

Measurement of the concentration of humanized anti-hTfR antibodies in tissues and peripheral blood was carried out largely following the procedure described below. Besides, as to the brain, the collected tissues were separated into the cerebral cortex, the cerebellum, the hippocampus and the medulla oblongata, and then the concentration of the humanized anti-hTfR antibodies were measured. The respective tissues thus obtained were homogenized with RIPA Buffer (Wako Pure Chemical Industries Inc.) containing Protease Inhibitor Cocktail (Sigma-Aldrich Inc.), centrifuged, and the supernatant collected. From the above peripheral blood, serum was separated. To each well of High Bind Plate (Meso Scale Diagnostics) was added 10 µL of Affinipure Goat Anti mouse IgG Fcγ pAb (Jackson ImmunoResearch Inc.), and the plate was left to stand for one hour to provide a solid phase. Then, 150 µL of SuperBlock blocking buffer in PBS (Thermo Fisher Scientific Inc.) was added to each well, and the plate was blocked by one-hour shaking. Then, 25 µL of the supernatant of the homogenate or the serum was added to each well, and the wells were shaken for one hour. Then, 25 µL of Affinipure Goat Anti mouse IgG Fab-Biotin (Jackson ImmunoResearch Inc.) was added to each well, and shaking was continued for one hour.

Then, 25 μL of SULFO-Tag-Streptavidin (Meso Scale Diagnostics Inc.) was added to each well, followed by shaking for half an hour. To each well was added 150 μL of Read buffer T (Meso Scale Diagnostics Inc.), and the amount of luminescence from each well was read on a Sector™ Imager 6000 reader. The amount of the antibody contained in each tissue and the peripheral blood was calculated by producing a standard curve based on measurements of standard samples containing known concentrations of the anti-hTfR antibody, and then interpolating the measurement of each of the samples with reference to the standard. Measurement of concentration was repeated three times for each sample.

The result of measurement of the concentration of humanized anti-hTfR antibodies in the brain and spinal tissues is shown in Table 9.

TABLE 9

Concentration of humanized anti-hTfR antibodies in brain tissues (μg/g wet weight)

| Antibody No. | Cerebral cortex | Cerebellum | Hippocampus | Medulla oblongata | Spinal cord |
| --- | --- | --- | --- | --- | --- |
| 3 | 0.67 ± 0.12 | 0.61 ± 0.02 | 0.49 ± 0.02 | 0.59 ± 0.10 | 0.46 ± 0.17 |
| 3-2 | 1.05 ± 0.07 | 0.72 ± 0.04 | 0.72 ± 0.07 | 0.69 ± 0.03 | 0.46 ± 0.02 |
| 3 (IgG4) | 0.65 ± 0.05 | 0.59 ± 0.03 | 0.56 ± 0.02 | 0.59 ± 0.02 | 0.46 ± 0.07 |
| 3-2 (IgG4) | 0.76 ± 0.02 | 0.57 ± 0.07 | 0.62 ± 0.05 | 0.73 ± 0.16 | 0.48 ± 0.03 |
| Negative control | 0.0082 ± 0.0032 | 0.0090 ± 0.0067 | 0.0053 ± 0.0009 | 0.011 ± 0.003 | 0.15 ± 0.04 |

TABLE 10

Amount of humanized anti-hTfR antibodies accumulated in brain tissues (factors in comparison with negative control)

| Antibody No. | Cerebral cortex | Cerebellum | Hippocampus | Medulla oblongata | Spinal cord |
| --- | --- | --- | --- | --- | --- |
| 3 | 82 | 68 | 92 | 54 | 3.1 |
| 3-2 | 128 | 80 | 136 | 63 | 3.1 |
| 3 (IgG4) | 79 | 66 | 106 | 54 | 3.1 |
| 3-2 (IgG4) | 93 | 63 | 117 | 66 | 3.2 |
| Negative control | 1 | 1 | 1 | 1 | 1 |

All the antibodies, i.e., humanized anti-hTfR antibody No. 3, humanized anti-hTfR antibody No. 3-2, humanized anti-hTfR antibody No. 3 (IgG4) and humanized anti-hTfR antibody No. 3-2 (IgG4), were observed to accumulate in the cerebral cortex, cerebellum, hippocampus, medulla oblongata and spinal cord (Table 9). The respective amount accumulated was as follow:

with humanized anti-hTfR antibody No. 3, approximately 82 times in the cerebral cortex, approximately 68 times in the cerebellum, approximately 92 times in the hippocampus, approximately 54 times in the medulla oblongata, and approximately 3.1 times in the spinal cord, in comparison with the negative control, trastuzumab (Herceptin™), with humanized anti-hTfR antibody No. 3-2, approximately 128 times in the cerebral cortex, approximately 80 times in the cerebellum, approximately 136 times in the hippocampus, approximately 63 times in the medulla oblongata, approximately 3.1 times in the spinal cord, in comparison with the negative control, trastuzumab, with humanized anti-hTfR antibody No. 3 (IgG4), approximately 79 times in the cerebral cortex, approximately 66 times in the cerebellum, approximately 106 times in the hippocampus, approximately 54 times in the medulla oblongata, approximately 3.1 times in the spinal cord, in comparison with the negative control, trastuzumab, and with humanized anti-hTfR antibody No. 3-2 (IgG4), approximately 93 times in the cerebral cortex, approximately 63 times in the cerebellum, approximately 117 times in the hippocampus, approximately 66 times in the medulla oblongata, approximately 3.2 times in the spinal cord, in comparison with the negative control, trastuzumab (Table 10).

These results indicate that these four humanized anti-hTfR antibodies have a property that allows them to pass through the blood-brain barrier and accumulate in the brain tissues, and thus that BDNF as a drug to be allowed to function in such brain tissues is linked to these antibodies, so that the drug can be efficiently accumulated in the brain tissues.

Figure 4:
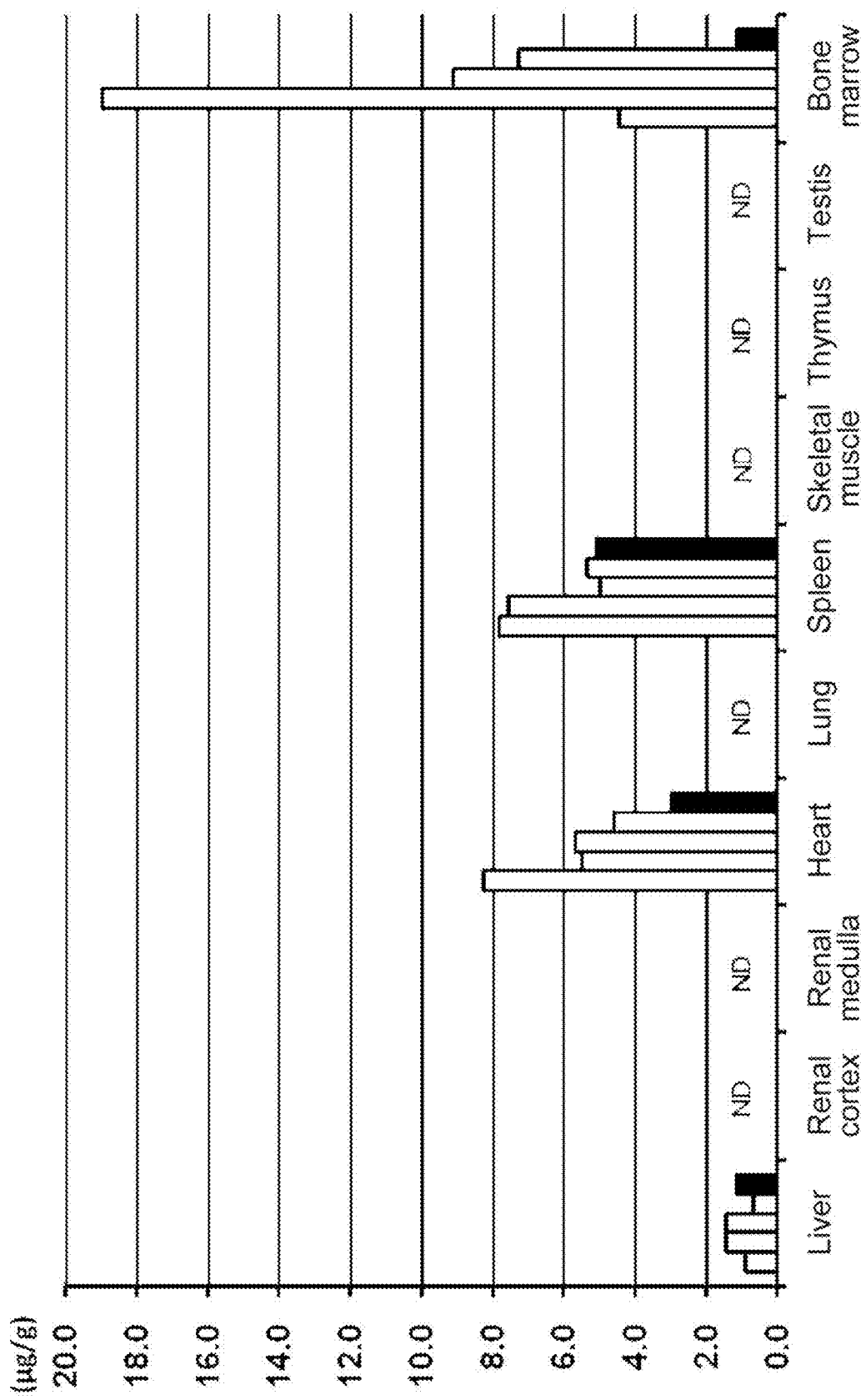
FIG. 4 A figure showing the amount of a humanized anti-hTfR antibody accumulated in various organs other than the brain of a cynomolgus monkey after a single intravenous administration. The vertical axis indicates the amount of the humanized anti-hTfR antibody (μg/g wet weight) per wet weight of each organ. The white bars represent, from the left, the amount accumulated in each organ of the monkey after administration of humanized anti-hTfR antibody No. 3, humanized anti-hTfR antibody No. 3-2, humanized anti-hTfR antibody No. 3 (IgG4), and humanized anti-hTfR antibody No. 3-2 (IgG4), respectively, and the black bars represent the amount accumulated in respective organs of the monkey after administration of trastuzumab (Herceptin™). "ND" denotes "not detected".

Then, FIG. 4 shows the result of measurement of the concentration of the humanized anti-hTfR antibodies in the tissues of the liver, heart, spleen and bone marrow. The four humanized anti-hTfR antibodies, as well as the negative control, trastuzumab, were observed to accumulate in the liver and spleen, and their amount accumulated was equal between the four humanized anti-hTfR antibodies and trastuzumab. In the heart, the humanized anti-hTfR antibodies tended to accumulate more than trastuzumab, the negative control, but the amount was only about 1.5 to 2.8 times that of the negative control. In bone marrow, the humanized anti-hTfR antibodies tended to accumulate markedly more than trastuzumab, the negative control, and the amount was 3.5 to 16 times that of the negative control. The cause of this accumulation of the humanized anti-hTfR antibodies in bone marrow is thought to be that TfR is expressed at high levels in bone marrow, hematopoietic organ, and more humanized anti-hTfR antibodies, therefore, accumulate through binding to TfR, than the negative control. These data indicate that the four humanized anti-hTfR antibodies has a property that allows them to specifically accumulate the cerebrum, cerebellum, hippocampus and medulla oblongata, which constitute the central nervous system, and thus that BDNF as a drug to be allowed to function in such brain tissues is linked to these antibodies, so that the drug can be efficiently accumulated in the brain tissues.

Then, Table 11 shows the result of pharmacokinetic measurement of the humanized anti-hTfR antibodies in the blood. As that of the negative control, trastuzumab, the blood concentration of the four humanized anti-hTfR antibodies was maintained at high levels, higher than 60 μg/mL, even eight hours after administration, indicating that they are stable in the blood (Table 11).

TABLE 11

Pharmacokinetics of humanized anti-hTfR antibodies in blood (μg/mL blood( )

| Antibody No. | Time after administration | | | | |
|---|---|---|---|---|---|
| | 2 min | 30 min | 2 hr | 4 hr | 8 hr |
| 3 | 173 | 147 | 128 | 117 | 97.5 |
| 3-2 | 124 | 99.5 | 78.5 | 76.5 | 61 |
| 3 (IgG4) | 141 | 113 | 99 | 95 | 83 |
| 3-2 (IgG4) | 132 | 111 | 98.5 | 99 | 95.5 |
| Negative control | 124 | 92.5 | 96 | 75.5 | 60.5 |

Immunohistochemical staining of the humanized anti-hTfR antibodies in brain tissues was performed in the following manner. The collected tissues were rapidly frozen to −80° C. in a Tissue-Tek Cryo 3DM (Sakura Finetek Inc.) to prepare frozen blocks of tissues. The frozen blocks were sliced into 4 μm sections, which were affixed to MAS coated glass slides (Matsunami Glass Inc.). The tissue sections were reacted with 4% paraformaldehyde (Wako Pure Chemical Industries Inc.) for 5 minutes at 4° C. and fixed to glass slides. Then, the tissue sections were reacted with methanol solution containing 0.3% hydrogen peroxide (Wako Pure Chemical Industries Inc.) for 30 min to inactivate endogenous peroxidases. Then, the glass slides were blocked by reacting SuperBlock blocking buffer in PBS for 30 min at room temperature. Then, the tissue sections were reacted with Mouse IgG-heavy and light chain Antibody (Bethyl Laboratories) for one hour at room temperature. The tissue sections were allowed to visualize with DAB substrate (3,3'-diaminobenzidine, Vector Laboratories Inc.), counterstained with Mayer's hematoxylin solution (Merck Inc.), embedded after dehydration and clearing, and observed under a optical microscope.

Figure 5:
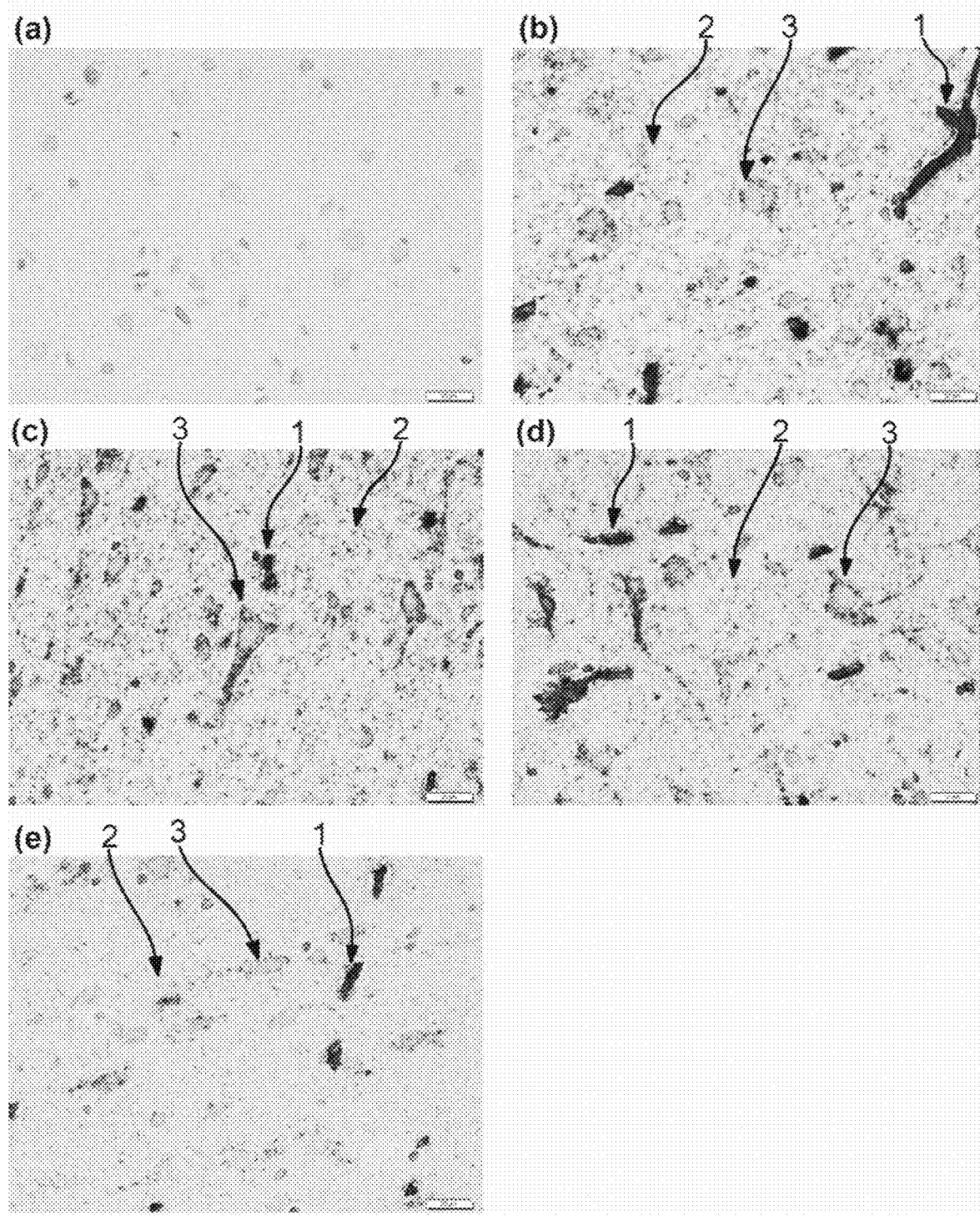
FIG. 5 Substitute photographs for drawings showing the result of immunohistochemical staining of a humanized anti-hTfR antibody in the cerebral cortex of a cynomolgus monkey after a single intravenous administration. Staining photographs of the cerebral cortex: (a) Herceptin administered, (b) humanized anti-hTfR antibody No. 3 administered, (c) humanized anti-hTfR antibody No. 3-2 administered, (d) humanized anti-hTfR antibody No. 3 (IgG4) administered, (e) humanized anti-hTfR antibody No. 3-2 (IgG4) administered. The bar at the bottom right in each photograph is a 20-μm gauge.

FIG. 5 shows the result of immunohistochemical staining of the humanized anti-hTfR antibodies in the cerebral cortex. Specific staining of blood vessels and neuron-like cells were observed in the cerebral cortex of the monkeys administered humanized anti-hTfR antibody No. 3, humanized anti-hTfR antibody No. 3-2, humanized anti-hTfR antibody No. 3 (IgG4), and humanized anti-hTfR antibody No. 3-2 (IgG4) (FIG. 5, panels b to e, respectively). In the cerebral cortex of the monkey administered humanized anti-hTfR antibody No. 3-2, in particular, (FIG. 5, panels c), the brain parenchyma region, outside the blood vessels, was also observed specifically stained extensively. Besides, no staining was observed in the cerebral cortex of the monkey administered Herceptin as a control, indicating that the tissue staining observed in FIG. 5, panels b to e was specific for the humanized anti-hTfR antibodies (FIG. 5, panels a).

Figure 6:
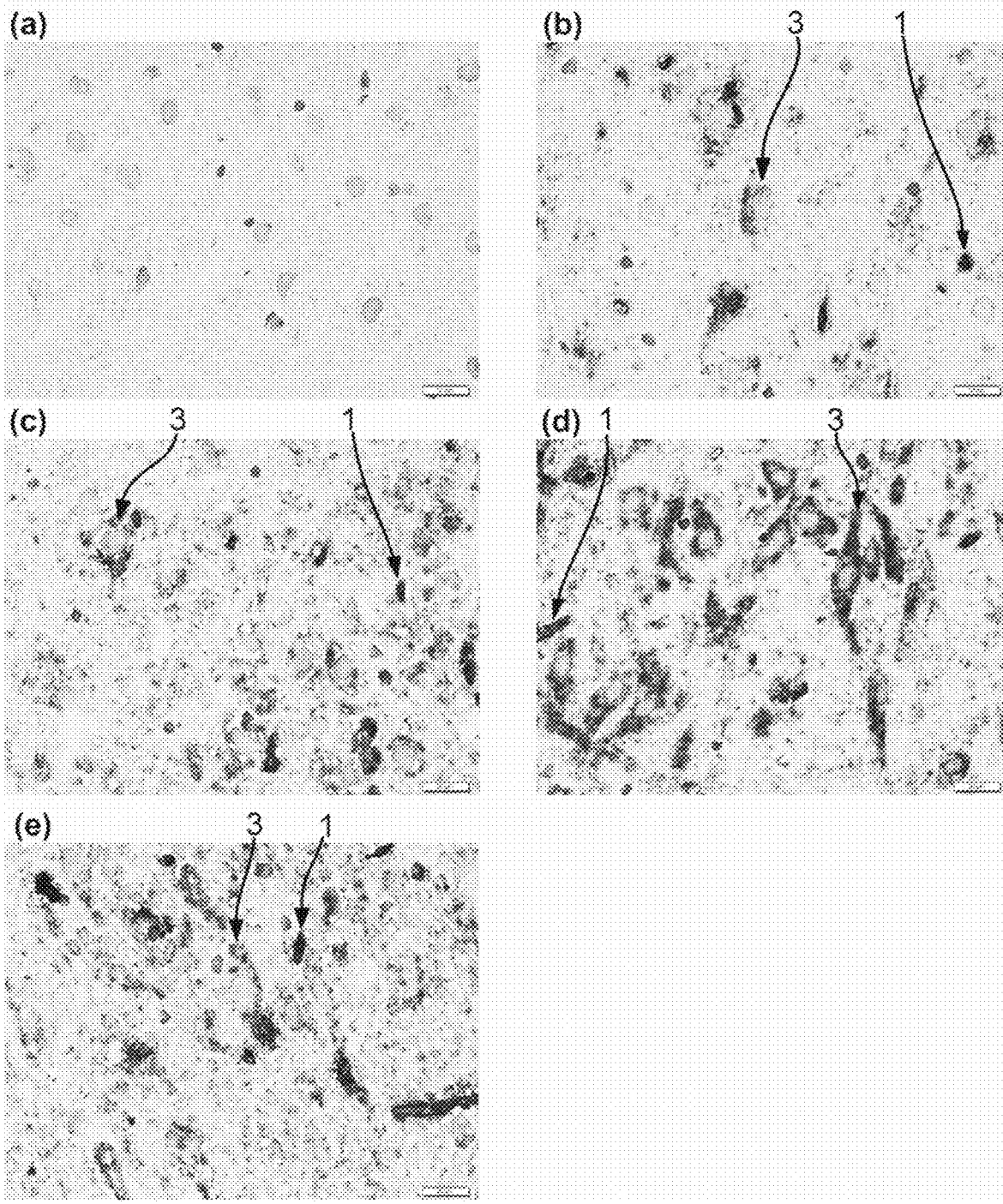
FIG. 6 Substitute photographs for drawing showing the result of immunohistochemical staining of a humanized anti-hTfR antibody in the hippocampus of a cynomolgus monkey after a single intravenous administration. Staining photographs of the hippocampus: (a) Herceptin administered, (b) humanized anti-hTfR antibody No. 3 administered, (c) humanized anti-hTfR antibody No. 3-2 administered, (d) humanized anti-hTfR antibody No. 3 (IgG4) administered, (e) humanized anti-hTfR antibody No. 3-2 (IgG4) administered. The bar at the bottom right at each photograph is a 20-μm gauge.

FIG. 6 shows the result of immunohistochemical staining of the humanized anti-hTfR antibodies in the hippocampus. Specific staining of blood vessels and neuron-like cells were observed in the hippocampus of the monkeys administered humanized anti-hTfR antibody No. 3, humanized anti-hTfR antibody No. 3-2, humanized anti-hTfR antibody No. 3(IgG4), and humanized anti-hTfR antibody No. 3-2 (IgG4) (FIG. 6, panels b to e, respectively). Besides, no staining was observed in the hippocampus of the monkey administered Herceptin as a control, indicating that the tissue staining observed in FIG. 6b to 6e was specific for the humanized anti-hTfR antibodies (FIG. 6, panel a).

Figure 7:
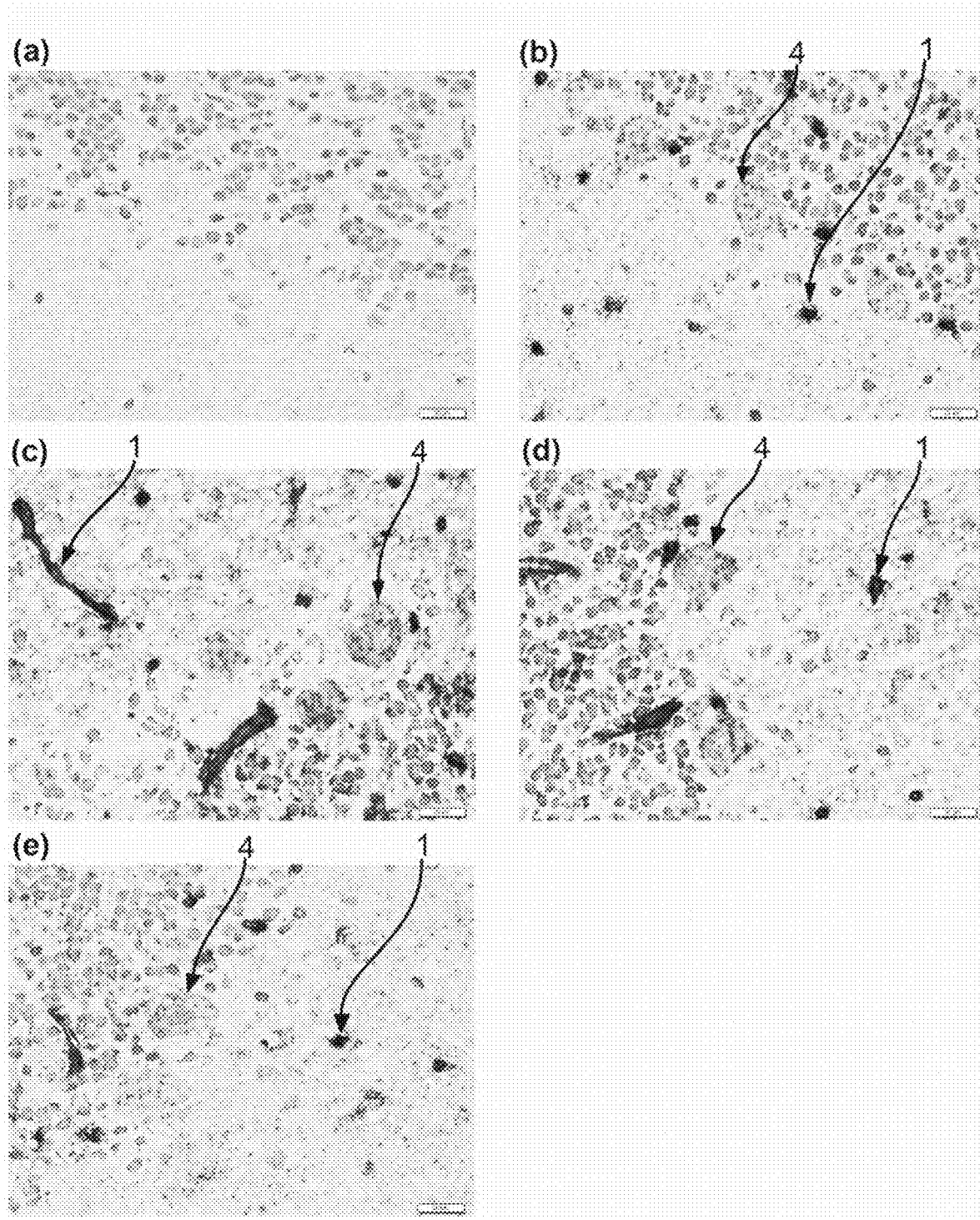
FIG. 7 A figure showing the result of immunohistochemical staining of humanized anti-hTfR antibody in the cerebellum of a cynomolgus monkey after a single intravenous administration. Staining photographs of the cerebellum: (a) Herceptin administered, (b) humanized anti-hTfR antibody No. 3 administered, (c) humanized anti-hTfR antibody No. 3-2 administered, (d) humanized anti-hTfR antibody No. 3 (IgG4) administered, (e) humanized anti-hTfR antibody No. 3-2 (IgG4) administered. The bar at the bottom right at each photograph is a 20-μm gauge.

FIG. 7 shows the result of immunohistochemical staining of the humanized anti-hTfR antibodies in the cerebellum. Specific staining of blood vessels and Purkinje cells were observed in the cerebellum of the monkeys administered humanized anti-hTfR antibody No. 3, humanized anti-hTfR antibody No. 3-2, humanized anti-hTfR antibody No. 3(IgG4), and humanized anti-hTfR antibody No. 3-2 (IgG4) (FIG. 7, panels b to e, respectively). Besides, no staining was observed in the cerebellum of the monkey administered Herceptin as a control, indicating that the tissue staining observed in FIG. 7, panels b to e was specific for the humanized anti-hTfR antibodies (FIG. 7, panel a).

Figure 8:
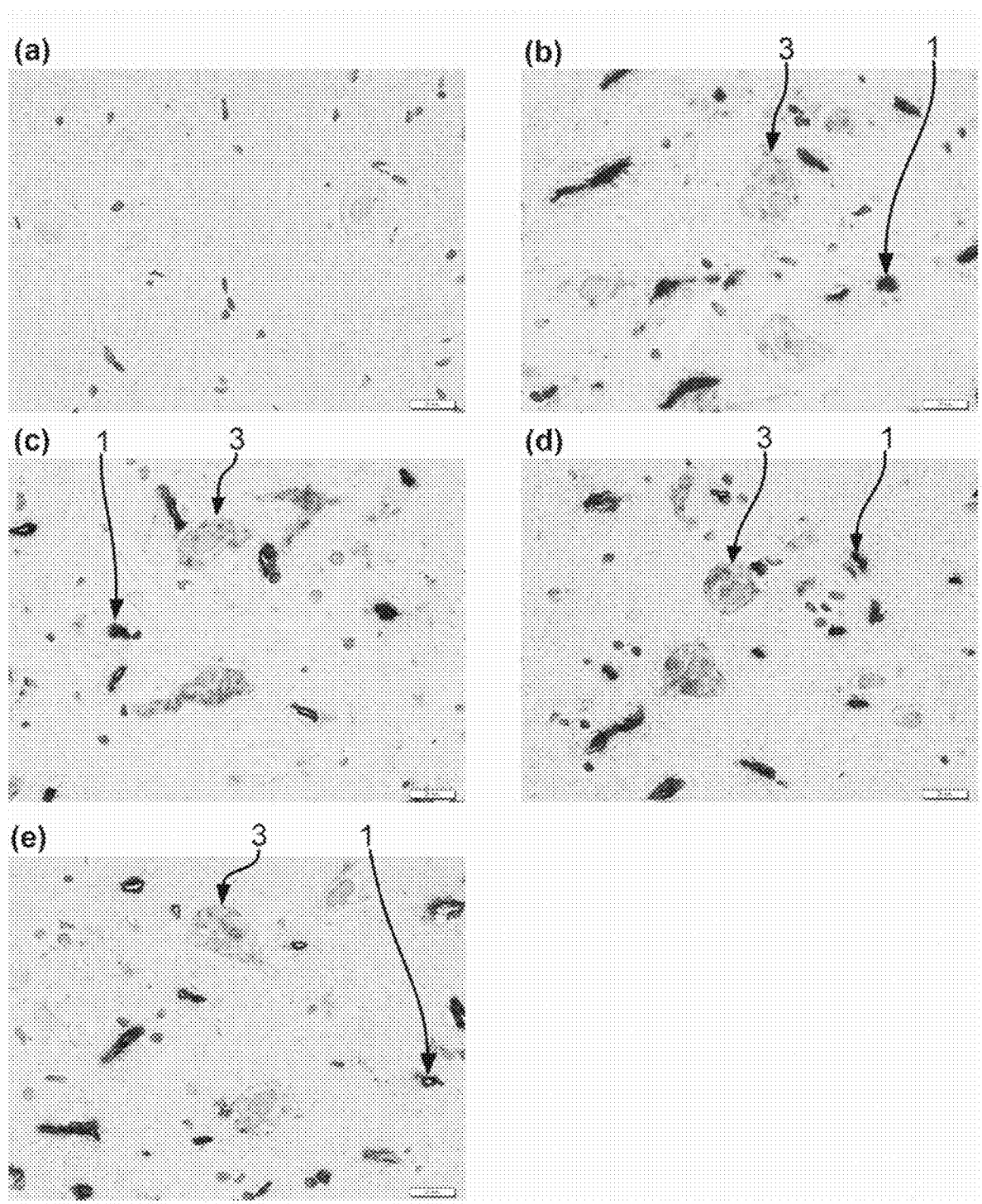
FIG. 8 Substitute photographs for drawings showing the result of immunohistochemical staining of humanized anti-hTfR antibody in the medulla oblongata of a cynomolgus monkey after a single intravenous administration. Staining photographs of the medulla oblongata: (a) Herceptin administered, (b) humanized anti-hTfR antibody No. 3 administered, (c) humanized anti-hTfR antibody No. 3-2 administered, (d) humanized anti-hTfR antibody No. 3 (IgG4) administered, (e) humanized anti-hTfR antibody No. 3-2 (IgG4) administered. The bar at the bottom right at each photograph is a 20-μm gauge.

FIG. 8 shows the result of immunohistochemical staining of the humanized anti-hTfR antibodies in the medulla oblongata. Specific staining of blood vessels and neuron-like cells were observed in the medulla oblongata of the monkeys administered humanized anti-hTfR antibody No. 3, humanized anti-hTfR antibody No. 3-2, humanized anti-hTfR antibody No. 3(IgG4), and humanized anti-hTfR antibody No. 3-2 (IgG4) (FIG. 8, panels b to e, respectively). Besides, no staining was observed in the medulla oblongata of the monkey administered Herceptin as a control, indicating that the tissue staining observed in FIG. 8, panels b to e was specific for the humanized anti-hTfR antibodies (FIG. 8, panel a).

From the result of immunohistochemical staining of the cerebrum and cerebellum in Example 8, it had been anticipated that though the anti-hTfR antibody No. 1, a pre-humanized mouse antibody, can bind to hTfR existing on the endothelium of blood vessel in the brain, the amount transferring to the brain parenchyma would be small. On the other hand, it was shown that anti-hTfR antibodies Nos. 2 and 3, pre-humanized mouse antibodies, can bind to hTfR existing on the endothelium of blood vessel in the brain, and after binding to hTfR, pass through the blood-brain barrier into the brain parenchyma, and further be taken up into the brain parenchyma and neuron-like cells in the hippocampus, and into Purkinje cells in the cerebellum.

From the result of immunohistochemical staining in the cerebrum, hippocampus, cerebellum, and medulla oblongata in Example 15, it was revealed that the tested four humanized anti-hTfR antibodies obtained by humanizing anti-hTfR antibody No. 3 subjected to the experiment can bind to hTfR existing on the endothelium of blood vessels of the brain, and after binding to hTfR, pass through the blood-brain barrier and transfer into the brain parenchyma, and further, be taken up into neuron-like cells in the cerebral cortex; into the brain parenchyma and the neuron-like cells in the hippocampus; into Purkinje cells in the cerebellum; and into neuron-like cells in the medulla oblongata.

[Example 16] Production of Cells for Use in Expression of hBDNF-Humanized Anti-hTfR Antibody Fusion Protein (hBDNF-Anti-hTfR Antibody Fusion Protein)

By digesting pEF/myc/nucvector (Invitrogen Inc.) with KpnI and NcoI, a region including EF-1α promoter and its first intron was cut out, which then was blunt-ended with T4 DNA polymerase. After digesting pCI-neo (Invitrogen Inc.) with BglII and EcoRI to remove a region including the enhancer/promoter and intron of CMV, the vector was blunt-ended with T4 DNA polymerase, and into which the above mentioned region including EF-1α promoter and its first intron was inserted to construct a vector pE-neo. The vector pE-neo was digested with SfiI and BstXI to cut out a region of approximately 1 kbp including a neomycin resistance gene. Employing pcDNA3.1/Hygro(+) (Invitrogen Inc.) as a template and using primer Hyg-Sfi5' (SEQ ID NO:216) and primer Hyg-BstX3' (SEQ ID NO:217), PCR was performed to amplify the hygromycin gene. The hygromycin gene thus amplified was digested with SfiI and BstXI and inserted into the above vector pE-neo, of which the neomycin resistance gene had been removed, to construct vector pE-hygr.

A DNA fragment was artificially synthesized having the nucleotide sequence set forth as SEQ ID NO:249, which included a gene encoding a protein in which the humanized anti-hTfR antibody heavy chain having the amino acid sequence set forth as SEQ ID NO:172 was linked, on the C-terminal side thereof and via a linker sequence (Gly-Ser), to hBDNF having the amino acid sequence set forth as SEQ ID NO:247. This DNA fragment encoded a protein having the amino acid sequence set forth as SEQ ID NO:248, in which humanized anti-hTfR antibody heavy chain was linked, via a linker sequence (Gly-Ser), to hBDNF. This DNA fragment had, on its 5' side, a MluI sequence, and a sequence encoding a leader peptide acting as a secretion signal in this order from the 5' end, and a NotI sequence on its 3' side. The DNA fragment was digested with MluI and NotI, and inserted into the vector pE-neo, between the MluI and NotI thereof, to construct pE-neo(HC-BDNF-1).

A DNA fragment was artificially synthesized having the nucleotide sequence set forth as SEQ ID NO:251, which included a gene encoding a protein in which the humanized anti-hTfR antibody heavy chain having the amino acid sequence set forth as SEQ ID NO:188 was linked, on the C-terminal side thereof and via a linker sequence (Gly-Ser), to hBDNF having the amino acid sequence set forth as SEQ ID NO:247. This DNA fragment encoded a protein having the amino acid sequence set forth as SEQ ID NO:250, in which humanized anti-hTfR antibody heavy chain was linked, via a linker sequence (Gly-Ser), to hBDNF. This DNA fragment had, on its 5' side, a MluI sequence and a sequence encoding a leader peptide acting as a secretion signal in this order from the 5' end, and a NotI sequence on its 3' side. The DNA fragment was digested with MluI and NotI, and inserted into the vector pE-neo, between the MluI and NotI thereof, to construct pE-neo(HC-BDNF-2).

A DNA fragment was artificially synthesized having the nucleotide sequence set forth as SEQ ID NO:253, which included a gene encoding a protein in which the humanized anti-hTfR antibody heavy chain having the amino acid sequence set forth as SEQ ID NO:210 was linked, on the C-terminal side thereof and via a linker sequence (Gly-Ser), to hBDNF having the amino acid sequence set forth as SEQ ID NO:247. This DNA fragment encoded a protein having the amino acid sequence set forth as SEQ ID NO:252, in which humanized anti-hTfR antibody heavy chain was linked, via a linker sequence (Gly-Ser), to hBDNF. This DNA fragment had, on its 5' side, a MluI sequence and a sequence encoding a leader peptide acting as a secretion signal in this order from the 5' end, and a NotI sequence on its 3' side. The DNA fragment was digested with MluI and NotI, and inserted into the vector pE-neo, between the MluI and NotI thereof, to construct pE-neo(HC-BDNF-3).

A DNA fragment was artificially synthesized having the nucleotide sequence set forth as SEQ ID NO:255, which included a gene encoding a fusion protein in which the humanized anti-hTfR antibody heavy chain having the amino acid sequence set forth as SEQ ID NO:210 was fused, on the C-terminal side thereof and via a linker sequence consisting of 27 amino acids that is composed of Gly-Ser followed by consecutively linked five copies of the amino acid sequence Gly-Gly-Gly-Gly-Ser set forth as SEQ ID NO:3, with hBDNF having the amino acid sequence set forth as SEQ ID NO:247. This DNA fragment encoded a protein having the amino acid sequence set forth as SEQ ID NO:254, in which humanized anti-hTfR antibody heavy chain was linked, via the above described linker sequence, to hBDNF. The DNA fragment has in the 5' side a MluI sequence and a sequence encoding a leader peptide acting as a secretion signal, in this order from the 5' end, and a NotI sequence in the 3' side. The DNA fragment was digested with MluI and NotI, and inserted into the vector pE-neo between MluI and NotI sites to construct pE-neo(HC-BDNF-4).

A DNA fragment was artificially synthesized having the nucleotide sequence set forth as SEQ ID NO:258, which included a gene encoding a fusion protein in which the humanized anti-hTfR antibody (scFv) having the amino acid sequence set forth as SEQ ID NO:257 was fused, via a linker sequence consisting of 27 amino acids that is composed of Gly-Ser followed by consecutively linked five copies of the amino acid sequence Gly-Gly-Gly-Gly-Ser set forth as SEQ ID NO:3, with hBDNF pro form having the amino acid sequence set forth as SEQ ID NO:256, on the C-terminal side thereof. Herein, in the amino acid sequence set forth as SEQ ID NO:257, the amino acid sequence at the positions 1st to 118th from the N-terminal side corresponds to the amino acid sequence set forth as SEQ ID NO:205, the amino acid sequence at the positions 119th to 133rd corresponds to a linker sequence, and the amino acid sequence at the position 134th to the C-terminus corresponds to the amino acid sequence set forth as SEQ ID NO:191, respectively. That is to say, the humanized anti-hTfR antibody scFv portion of this fusion protein was formed by fusing SEQ ID NO: 191 (amino acid sequence 2 of the light chain variable region of humanized anti-hTfR antibody No. 3), via a linker sequence consisting of 15 amino acids consisting of consecutively linked three copies of the amino acid sequence Gly-Gly-Gly-Gly-Ser set forth as SEQ ID NO:3, with SEQ ID NO:205 (amino acid sequence 2 of the heavy chain variable region of humanized anti-hTfR antibody No. 3), on the C-terminal side thereof. This DNA fragment encoded a fusion protein of a hBDNF pro form and a humanized anti-hTfR antibody (scFv), having the amino acid sequence set forth as SEQ ID NO:259. The fusion protein having the amino acid sequence set forth as SEQ ID NO:259 is subjected to processing after the expression thereof, so that it becomes a fusion protein of hBDNF and a humanized anti-hTfR antibody scFv, having the amino acid sequence set forth as SEQ ID NO:260. In the amino acid sequence set forth as SEQ ID NO:259, the amino acid sequence at the positions 1st to 110th from the N-terminal side corresponds to a portion, which is removed during the processing of hBDNF pro form into mature hBDNF. This DNA fragment was digested with MluI and NotI, and was incorporated between the MluI and NotI of a pE-neo vector to construct pE-neo (BDNF-scFv). In the fusion protein of BDNF and a humanized anti-hTfR antibody, encoded by pE-neo (BDNF-scFv), the linker sequence between BDNF and scFv is a first linker sequence, and the linker sequence between the heavy chain and the light chain in scFv is a second linker sequence.

A DNA fragment was artificially synthesized having the nucleotide sequence set forth as SEQ ID NO:262, which included a gene encoding a protein in which the humanized anti-hTfR antibody Fab heavy chain having the amino acid sequence set forth as SEQ ID NO:261 was fused, via a linker sequence consisting of 27 amino acids that is composed of Gly-Ser followed by consecutively linked five copies of the amino acid sequence Gly-Gly-Gly-Gly-Ser set forth as SEQ ID NO:3, with hBDNF pro form having the amino acid sequence set forth as SEQ ID NO:256, on the C-terminal side thereof. Herein, the amino acid sequence set forth as SEQ ID NO:261 corresponds to positions 1 to 226 from the N-terminal side of the amino acid sequence set forth as SEQ ID NO:210. Herein, the amino acid sequence at the positions 1st to 118th from the N-terminal side corresponds to SEQ ID NO:205 (amino acid sequence 2 of the heavy chain variable region of humanized anti-hTfR antibody No. 3), the amino acid sequence at the positions 119th to 216th corresponds to a $C_H 1$ region, and the amino acid sequence at the positions 217th to 226th corresponds to a hinge region.

This DNA fragment encoded a fusion protein of a hBDNF pro form and a humanized anti-hTfR antibody Fab heavy chain, having the amino acid sequence set forth as SEQ ID NO:263. The fusion protein having the amino acid sequence set forth as SEQ ID NO:263 is subjected to processing after the expression thereof, so that it becomes a fusion protein of hBDNF and a humanized anti-hTfR antibody Fab heavy chain, having the amino acid sequence set forth as SEQ ID NO:264. In the amino acid sequence set forth as SEQ ID NO:259, the amino acid sequence at the positions 1st to 110th from the N-terminal side corresponds to a portion, which is removed during the processing of hBDNF pro form into mature hBDNF. This DNA fragment was digested with MluI and NotI, and was incorporated between the MluI and NotI of a pE-neo vector to construct pE-neo (BDNF-Fab HC-1).

A DNA fragment was artificially synthesized having the nucleotide sequence set forth as SEQ ID NO:265, which included a gene encoding a fusion protein in which the humanized anti-hTfR antibody Fab heavy chain having the amino acid sequence set forth as SEQ ID NO:261 was fused, via a linker sequence consisting of 27 amino acids that is composed of Gly-Ser followed by consecutively linked five copies of the amino acid sequence Gly-Gly-Gly-Gly-Ser set forth as SEQ ID NO:3, with hBDNF having the amino acid sequence set forth as SEQ ID NO:247, on the C-terminal side thereof. Herein, the amino acid sequence set forth as SEQ ID NO:261 corresponds to positions 1 to 226 from the N-terminal side of the amino acid sequence set forth as SEQ ID NO:210. Herein, the amino acid sequence at the positions 1st to 118th from the N-terminal side corresponds to SEQ ID NO:205 (amino acid sequence 2 of the heavy chain variable region of humanized anti-hTfR antibody No. 3), the amino acid sequence at the positions 119th to 216th corresponds to a $C_H 1$ region, and the amino acid sequence at the positions 217th to 226th corresponds to a hinge region.

This DNA fragment encoded a fusion protein of a hBDNF and a humanized anti-hTfR antibody Fab heavy chain, having the amino acid sequence set forth as SEQ ID NO:264. This DNA fragment was digested with MluI and NotI, and was incorporated between the MluI and NotI of a pE-neo vector to construct pE-neo (BDNF-Fab HC-2).

CHO cells (CHO-K1: obtained from American Type Culture Collection) was transformed with pE-neo (HC-BDNF-1) and pE-hygr (LC1) which had been constructed in Example 11 according to the method described in Example 12, so as to obtain a cell line expressing a fusion protein of hBDNF and a humanized anti-hTfR antibody. This cell line was designated hBDNF-anti-hTfR antibody-expressing cell line 1. The fusion protein of hBDNF and a humanized anti-hTfR antibody expressed by this cell line was designated hBDNF-anti-hTfR antibody 1.

In the same manner, CHO cells were transformed with pE-neo (HC-BDNF-2) and the pE-hygr (LC2) which had been constructed in Example 11, so as to obtain a cell line expressing a fusion protein of hBDNF and a humanized anti-hTfR antibody. This cell line was designated hBDNF-anti-hTfR antibody-expressing cell line 2. The fusion protein of hBDNF and a humanized anti-hTfR antibody expressed by this cell line was designated hBDNF-anti-hTfR antibody 2.

Further, in the same manner, CHO cells were transformed with pE-neo (HC-BDNF-3) and the pE-hygr (LC3) which had been constructed in Example 11, so as to obtain a cell line expressing a fusion protein of hBDNF and a humanized anti-hTfR antibody. This cell line was designated hBDNF-anti-hTfR antibody-expressing cell line 3. The fusion protein of hBDNF and a humanized anti-hTfR antibody expressed by this cell line was designated hBDNF-anti-hTfR antibody 3.

Further, in the same manner, CHO cells were transformed with pE-neo (HC-BDNF-4) and the pE-hygr (LC3) which had been constructed in Example 11, so as to obtain a cell line expressing a fusion protein of hBDNF and a humanized anti-hTfR antibody. This cell line was designated hBDNF-anti-hTfR antibody-expressing cell line 4. The fusion protein of hBDNF and a humanized anti-hTfR antibody expressed by this cell line was designated hBDNF-anti-hTfR antibody 4.

Further, in the same manner, CHO cells were transformed with pE-neo (BDNF-scFv) to obtain a cell line expressing a fusion protein of hBDNF and a humanized anti-hTfR antibody. This cell line was designated hBDNF-anti-hTfR antibody-expressing cell line 5. The fusion protein of hBDNF and a humanized anti-hTfR antibody expressed by this cell line was designated hBDNF-anti-hTfR antibody 5.

In the same manner, CHO cells were transformed with pE-neo (BDNF-Fab HC-1) and the pE-hygr (LC3) which had been constructed in Example 11, so as to obtain a cell line expressing a fusion protein of hBDNF and a humanized anti-hTfR antibody. This cell line was designated hBDNF-anti-hTfR antibody-expressing cell line 6. The fusion protein of hBDNF and a humanized anti-hTfR antibody expressed by this cell line was designated hBDNF-anti-hTfR antibody 6.

Further, in the same manner, CHO cells were transformed with pE-neo (BDNF-Fab HC-2) and the pE-hygr (LC3) which had been constructed in Example 11, so as to obtain a cell line expressing a fusion protein of hBDNF and a humanized anti-hTfR antibody. This cell line was designated hBDNF-anti-hTfR antibody-expressing cell line 7. The fusion protein of hBDNF and a humanized anti-hTfR antibody expressed by this cell line was designated hBDNF-anti-hTfR antibody 7.

[Example 17] Production of hBDNF-humanized Anti-hTfR Antibody Fusion Protein

A hBDNF-humanized anti-hTfR antibody fusion protein could be produced by the following method. The hBDNF-anti-hTfR antibody-expressing cell lines 5, 6 and 7 obtained in Example 16 were each diluted with CD OPTICHO medium to have a cell concentration of approximately $2\times10^5$ cells/mL, and 200 mL of each cell suspension was then added to a 1-L conical flask. Thereafter, the cell suspension was cultured at 37° C. in a humid environment consisting of 5% $CO_2$ and 95% air, at a stirring rate of approximately 70 rpm for 6 to 7 days. Thereafter, a culture supernatant was recovered by centrifugation, and was then filtrated through a 0.22 μm filter (Millipore Inc.) to obtain a culture supernatant. To the above-recovered culture supernatant was added five column volumes of 20 mM Tris buffer (pH 8.0)

containing 150 mL NaCl, and the obtained mixture was then loaded on a Protein A column (Bio-Rad Inc.) or a Protein L column (column volume: 1 mL, GE Healthcare Inc.), which had been equilibrated in advance with three column volumes of 20 mM Tris buffer (pH 8.0) containing 150 mM NaCl. Herein, the Protein A column was used for the hBDNF-anti-hTfR antibody-expressing cell lines 1, 2, 3 and 6, whereas the Protein L column was used for the hBDNF-anti-hTfR antibody-expressing cell lines 4, 5 and 7. Then, the column was washed with five column volumes of the same buffer, and the adsorbed hBDNF-anti-hTfR antibody was eluted with four column volumes of 50 mM glycine buffer (pH 2.8) containing 150 mM NaCl. Immediately after completion of the elution, the pH of the hBDNF-anti-hTfR antibody was adjusted to pH 7.0 with 1 M Tris buffer (pH 8.0). The resultants were used as purified products of the hBDNF-anti-hTfR antibody fusion proteins (hBDNF-anti-hTfR antibodies 5, 6 and 7) in the subsequent tests.

[Example 18] Evaluation of BDNF Activity in hBDNF-Anti-hTfR Antibody Fusion Proteins, Using BDNF Receptor (TrkB)-Expressing Cells The biological activity of BDNF possessed by the hBDNF-anti-hTfR antibody fusion proteins produced in Example 17 was evaluated by measuring intracellular signaling-enhancing activity, using, as an indicator, a change in the Ca concentration in CHO-TrkB cells prepared by introducing a TrkB gene into Chinese hamster ovary cells (CHO cells).

CHO cells were cultured in a medium for subculture (Nutrient Mixture F-12 Ham, 10% fetal bovine serum). Thereafter, the medium was exchanged with a medium for evaluation (Nutrient Mixture F-12 Ham, 3% fetal bovine serum, 10 mM Hepes (pH 7.4)) to produce a cell suspension. Viruses expressing Apoaequorin and human TrkB (GenBank Acc. No. NP_001018074.1) were introduced into the cells, and the resulting cells were then seeded on a black colored 384 bottom clear plate for cell culture, to a cell density of $2 \times 10^3$ cells/well. Thereafter, the cells were subjected to a static culture overnight in a $CO_2$ incubator (37° C., 95% Air, 5% $CO_2$).

HHBS solution (1× Hanks' Balanced Salt Solution, 20 mM HEPES (pH 7.4)) containing 1 μM Viviren (Promega Inc.) was added in an amount of 20 μL/well to the cultured cells, and the obtained mixture was then left to stand at room temperature for 4 hours. Thereafter, BDNF and hBDNF-anti-hTfR antibody fusion proteins (hBDNF-anti-hTfR antibodies 5, 6 and 7) were each diluted with HHBS solution containing 0.10% bovine serum albumin to obtain concentrations of interest, and the thus diluted solutions were each added to the reaction mixture. Thereafter, emission intensity was measured over time, using FDSS7000 (Hamamatsu Photonics K. K.). The emission intensity indicated by 111 ng/mL BDNF (#450-02, Peprotech Inc.) was set at 100%, and a relative TrkB agonistic activity was calculated from the obtained emission intensity. From the dose-response curve, EC50 was calculated, and the obtained value was defined as BDNF activity.

The results obtained by evaluating the hBDNF-anti-hTfR antibody fusion proteins are shown in Table 12.

TABLE 12

BDNF activity in hBDNF-anti-hTfR antibody fusion proteins

| (No.) Name | BDNF activity (TrkB agonistic EC50, nmol/L) |
|---|---|
| hBDNF-anti-hTfR antibody 5 | 0.092 |
| hBDNF-anti-hTfR antibody 6 | 0.16 |
| hBDNF-anti-hTfR antibody 7 | 0.23 |

[Example 18-2] Measurement of Affinity of hBDNF-Anti-hTfR Antibody Fusion Protein to hTfR The affinity of the hBDNF-anti-hTfR antibody fusion protein to hTfR was measured using an ELISA method. The measurement by the ELISA method was generally carried out by the following method. As human TfR, recombinant human TfR (r human TfR: Sino Biological Inc.) having the amino acid sequence of the extracellular region of hTfR, ranging from the cysteine residue at the position 89th from the N-terminal side to the phenylalanine at the C-terminus in the amino acid sequence set forth as SEQ ID NO:1, to the N-terminus of which a histidine tag was added, was used. As monkey TfR, recombinant monkey TfR (r monkey TfR: Sino Biological Inc.) having the amino acid sequence of the extracellular region of cynomolgus monkey hTfR, ranging from the cysteine residue at the position 89th from the N-terminal side to the phenylalanine at the C-terminus in the amino acid sequence set forth as SEQ ID NO:2, to the N-terminus of which a histidine tag was added, was used. The measurement was carried out on the hBDNF-anti-hTfR antibodies 3, 4 and 6 among the hBDNF-humanized anti-hTfR antibody fusion proteins obtained in Example 17.

Recombinant human and monkey TfR (Sino Biological Inc.) were each diluted to 0.5 ug/mL, and the diluted solution was then added in an amount of 100 μL to each well of a 96-well plate (Nunc Inc), followed by leaving it to stand for 1 hour. Thereafter, the solid phase solution was discarded, and 300 μL of Block Ace (DS Pharma Biomedical Inc.) was then added to each well, followed by leaving it to stand for 1 hour. The hBDNF-anti-hTfR antibody 6 was diluted with TBS-T (Sigma Aldrich Inc.) to a concentration of 20 nmol/L, and 9 stages of 3-fold dilution were carried out to obtain a sample solution. Thereafter, Block Ace was discarded, and 100 μL of the sample solution was then added to each well, followed by leaving it to stand for 1 hour. In doing this, to the blank well, 100 μL of TBS-T was added. The solution was discarded, the well was then washed with TBS-T three times, and thereafter, 100 μL of biotin-labeled rabbit anti-BDNF antibody (PeproTech Inc.), which had been diluted with TBS-T to a concentration of 0.5 μg/mL, was added to each well, followed by leaving it to stand for 1 hour. Thereafter, the solution was discarded, the well was then washed with TBS-T three times, and 100 μL of streptavidin solution (Streptavidin-HRP (R & D system Inc.)), which had been 200-fold diluted with TBS-T, was added to each well, followed by leaving it to stand for 1 hour. Thereafter, the solution was discarded, the well was then washed with TBS-T three times, and thereafter, 50 μL of TMB substrate solution (Nacalai Tesque Inc.) was added to each well, followed by performing a reaction at room temperature for 5 minutes. Subsequently, 100 μL of 0.5 N HCl was added to each well to terminate the reaction. Using a plate reader, the absorbance at 450 nm was measured. A curve was drawn by four parameter analysis, and the $EC_{50}$ of the hBDNF-anti-hTfR antibody 6 to human and monkey TfR was calculated from this curve.

The $EC_{50}$ of the hBDNF-anti-hTfR antibody 3 to human TfR was $1.6 \times 10^{-9}$ M, the binding activity to monkey TfR ($EC_{50}$) was $2.0 \times 10^{-9}$ M. The $EC_{50}$ of the hBDNF-anti-hTfR antibody 4 to human TfR was $8.3 \times 10^{-10}$ M, and the binding activity to monkey TfR ($EC_{50}$) was $2.1 \times 10^{-9}$ M. Moreover, the $EC_{50}$ of the hBDNF-anti-hTfR antibody 6 to human TfR was $6.3 \times 10^{-10}$ M, and the binding activity to monkey TfR ($EC_{50}$) was $2.3 \times 10^{-9}$ M.

Herein, the hBDNF-anti-hTfR antibody 3 is a hBDNF-anti-hTfR antibody consisting of a protein having the amino acid sequence set forth as SEQ ID NO:252, which is formed by linking a humanized anti-hTfR antibody heavy chain, on the C-terminal side thereof and via a linker sequence (Gly-Ser), to hBDNF, and a humanized anti-hTfR antibody light chain having the amino acid sequence set forth as SEQ ID NO:196. In addition, the hBDNF-anti-hTfR antibody 4 is a hBDNF-anti-hTfR antibody consisting of a protein having the amino acid sequence set forth as SEQ ID NO:254, which is formed by linking a humanized anti-hTfR antibody heavy chain, on the C-terminal side thereof and via a linker sequence consisting of 27 amino acids that is composed of Gly-Ser followed by consecutively linked five copies of the amino acid sequence Gly-Gly-Gly-Gly-Ser set forth as SEQ ID NO:3, to hBDNF, and a humanized anti-hTfR antibody light chain having the amino acid sequence set forth as SEQ ID NO:196. Moreover, the hBDNF-anti-hTfR antibody 6 is a hBDNF-anti-hTfR antibody consisting of: a protein formed by fusing hBDNF, on the C-terminal side thereof and via a linker sequence consisting of 27 amino acids that is composed of Gly-Ser followed by consecutively linked five copies of the amino acid sequence Gly-Gly-Gly-Gly-Ser set forth as SEQ ID NO:3, with a humanized anti-hTfR antibody Fab heavy chain having the amino acid sequence set forth as SEQ ID NO:261, wherein the protein in which the hBDNF and the humanized anti-hTfR antibody Fab heavy chain is linked together, having as a whole the amino acid sequence set forth as SEQ ID NO:263; and a humanized anti-hTfR antibody light chain having the amino acid sequence set forth as SEQ ID NO: 196. Accordingly, the obtained measurement results demonstrate that a fusion protein of hBDNF and an anti-hTfR antibody, which has high affinity to both human TfR and monkey TfR, can be obtained by linking an anti-hTfR antibody heavy chain, on the C-terminal side thereof, and directly or via a linker sequence, to hBDNF, or by linking hBDNF, on the C-terminal side thereof and via a linker sequence, to a humanized anti-hTfR antibody Fab heavy chain. Moreover, the obtained measurement results also demonstrate that a humanized anti-hTfR antibody heavy chain obtained by grafting of mouse antibody CDRs set forth as SEQ ID NOS:218 to 245 is linked, on the C-terminal side thereof, and directly or via a linker sequence, to hBDNF, or a humanized anti-hTfR antibody Fab heavy chain is linked, on the N-terminal side thereof and via a linker sequence, to hBDNF, so as to produce a fusion protein, so that the hBDNF can be linked, as a fusion protein with high affinity, to human TfR, and further, so that the hBDNF can pass through the BBB and can exhibit its function in the brain.

Besides, the affinity of the humanized anti-hTfR antibody No. 3, which corresponds to a humanized antibody portion of the hBDNF-anti-hTfR antibody 3, to hTfR was measured by the present measurement method. As a result, the $EC_{50}$ thereof to human TfR was found to be $9.0 \times 10^{-11}$ M, and the binding activity ($EC_{50}$) to monkey TfR was found to be $2.5 \times 10^{-10}$ M. The dissociation constant ($K_D$) of the humanized anti-hTfR antibody No. 3 to human TfR, which was measured by the method described in Example 7, was less than $1.0 \times 10^{-12}$ M, and the dissociation constant ($K_D$) thereof to monkey TfR was $1.12 \times 10^{-9}$ M (Example 14).

[Example 19] Pharmacokinetic Analysis of hBDNF-Humanized Anti-hTfR Antibody Fusion Protein Using KI Mice and Monkeys The in vivo brain uptake of the hBDNF-anti-hTfR antibody fusion protein produced in Example 17 could be evaluated, for example, by administering the fusion protein to hTfR knock-in mice or cynomolgus monkeys in the same manner as the methods described in Examples 7-2, 8, and 15, then subjecting the mice or monkeys to systemic perfusion with a normal saline after a certain period of time has passed, and then measuring the concentration of the hBDNF-humanized anti-hTfR antibody fusion protein and hBDNF in the brain tissues. The hBDNF-humanized anti-hTfR antibody fusion protein may be fluorescently labeled with FITC or the like, as necessary, before administration, in the same manner as that in Example 7-2.

In the case where the concentration of the hBDNF-humanized anti-hTfR antibody fusion protein in brain tissues is measured, the measurement is generally carried out by the following procedures. The collected tissues are divided into the cerebrum, the cerebellum, the hippocampus and the medulla oblongata, and each portion was homogenized using RIPA Buffer (Nacalai Tesque Inc.) comprising Protease Inhibitor Cocktail and was then centrifuged, so as to recover a supernatant. Anti-Human IgG H & L pre-adsorbed (abcam Inc.) was added to each well of Normal Plate (Meso Scale Diagnostics Inc.), and it was then left to stand for 1 hour, so that it was immobilized on the plate. Subsequently, SuperBlocking buffer in PBS (Thermo Fisher Scientific Inc.) was added to each well, and was then shaken for 1 hour, so that the plate was blocked. After that, the supernatant of the homogenate of brain tissues was added to the plate, and was then shaken for 1 hour. Subsequently, SULFO-Tag-Anti-BDNF antibody [35928.11] (abcam Inc.) was added thereto, and it was then shaken for 1 hour. Thereafter, Read buffer T (Meso Scale Diagnostics Inc.) was added to the plate, and using Sector Imager 6000 reader (Meso Scale Diagnostics Inc.), the light emission amount was measured. A calibration curve was produced from the measurement value of a standard sample having a known concentration, and the measurement value of each specimen was then interpolate in the curve, so as to calculate the amount of the antibody contained per gram weight (wet weight) of individual brain tissues (the concentration of the anti-hTfR antibody in the brain tissues).

Moreover, in the case of measuring the concentration of hBDNF in the brain tissues, the measurement is generally carried out by the following procedures.

The supernatant of the homogenate of brain tissues was added to each well of Human BDNF Assay kit (Meso Scale Diagnostics Inc.), and was then shaken for 1 hour. Subsequently, SULFO-Tag-Human BDNF Detection (Meso Scale Diagnostics Inc.) was added to the plate, and was then shaken for 1 hour. Thereafter, Read buffer T (Meso Scale Diagnostics) was added to the plate, and using Sector Imager 6000 reader (Meso Scale Diagnostics Inc.), the light emission amount was measured. A calibration curve was produced from the measurement value of a standard sample having a known concentration, and the measurement value of each specimen was then interpolate in the curve, so as to calculate the concentration of BDNF contained per gram weight (wet weight) of individual brain tissues.

[Example 19-2] Studies Regarding the Movement Dysfunction-Improving Action of the Fusion Protein of the Present Invention, Using Parkinson's Disease Model Mice Treated with 1-methyl-4-phenyl-1,2,3,6-tetrahydropyridine (MPTP)

The in vivo biological activity of BDNF in the hBDNF-anti-hTfR antibody fusion protein produced in Example 17 could be evaluated based on the Parkinson's disease symptom-improving effect of the fusion protein in MPTP-treated mice, for example, by applying the below-mentioned method.

(1) Production of Parkinson's Disease Model Mice

C57BL/6 male mice (8 to 15-week old) were used after the completion of quarantine and acclimatization. The thus prepared mice were intraperitoneally administered saline or MPTP (25 or 30 mg/kg) dissolved in saline, once a day for 5 days. Otherwise, the mice were intraperitoneally administered therewith at a single dose of 20 mg/kg, every 2 hours, 4 times in a day.

Three days after the final administration, bradykinesia symptoms were evaluated by a Pole test, or a decrease in motor incoordination was evaluated by a Rota-rod test.

(2) Pole Test

MPTP-treated mice were allowed to hold a portion around 5 cm from the top of a vertical wooden bar, with the heads of the mice upward. The time required for the mice from holding the bar to changing the direction downward ($T_{turn}$), and the time required for the mice from holding the bar to going down to the floor ($T_{LA}$) were measured. In addition, the movement of the mice was observed, and the symptoms thereof were scored as follows.

0: Going down to the floor using four limbs well/normal movement.

1: Awkwardness is observed when changed the direction at the upper portion of the bar.

2: The mouse cannot straddle the bar and moves like side-slipping.

3: The mouse falls down from the bar.

First, training was carried out once, and the test was then carried out repeatedly, once every 5 minutes, a total of three times. A mean time from the three trials was used as data for grouping. Based on the body weight and the data from the Pole test, the MPTP-treated mice were assigned to 3 or 4 groups according to the multivariable completely randomized allocation.

Repeated intravenous administration was carried out on a total of 4 to 5 groups consisting of normal saline-treated mice (a solvent-treated group), MPTP-treated mice (a solvent-treated group, and groups treated with 0.1 to 10 mg/kg of the fusion protein of the present invention), once or twice a week, for 4 to 8 weeks. One week after the final administration, a Pole test was carried out again (with the same protocols as those applied upon obtaining the above described data for grouping), and the action to improve bradykinesia symptoms was evaluated. The intravenously administered fusion protein of the present invention has transferred into the brain, and it has then exerted BDNF activity therein, so that it could improve disorders of movement dysfunctions, such as bradykinesia, in the Parkinson's disease model animals.

Thus, it could be confirmed that the intravenously administered fusion protein of the present invention has transferred into the brain of disease model animals (mice) and can exert BDNF activity therein.

(3) Rota-Rod Test

Mice were placed on a rotation axis of a Rota-rod apparatus (MK-610A, Muromachi Kikai Co., Ltd.) (a single mouse in each lane on the rotation axis), and they were then left to stand for 30 seconds. Thereafter, the mice were acclimatized to the rotation of the axis at 8 rpm for 1 minute, and were then trained under conditions where the rotation speed was increased to 25 rpm for 3 minutes. One hour after completion of the training, the following evaluation test was carried out.

In the test, the mice were acclimatized for 30 seconds to the movement of the axis rotating at 8 rpm, and thereafter, the time required until the mice fell from the axis under conditions where the rotation speed was increased to 40 rpm for 5 minutes was measured. The test was repeatedly carried out three times at intervals of 1 hour, and a mean time from the three trials was used as data for grouping. Based on the body weight and the data from the Rota-rod test, the MPTP-treated mice were assigned to 4 groups according to multivariable completely randomized allocation.

Repeated intravenous administration was carried out on a total of 5 groups consisting of normal saline-treated mice (a solvent-treated group), MPTP-treated mice (a solvent-treated group, and groups treated with 0.3, 1, and 3 mg/kg of the fusion protein of the present invention), once a week, for 4 to 8 weeks. One week after the final administration, a Rota-rod test was carried out again (with the same protocols as those applied upon performing the grouping in the above (1)), and the action to improve motor incoordination was evaluated. The intravenously administered fusion protein of the present invention has transferred into the brain, and it has then exerted BDNF activity therein, so that it could improve movement dysfunctions, such as motor incoordination, in the Parkinson's disease model animals.

Thus, it could be confirmed that the intravenously administered fusion protein of the present invention has transferred into the brain of disease model animals (mice) and can exhibit BDNF activity therein.

(3) Rota-Rod Test

Mice were each placed on a rotation axis of a Rota-rod apparatus (MK-610A, Muromachi Kikai Co., Ltd.), and they were then left to stand for 30 seconds. Thereafter, the mice were acclimatized to the rotation of the axis at 8 rpm for 1 minute, and were then trained under conditions where the rotation speed was increased to 25 rpm for 3 minutes. One hour after completion of the training, the following evaluation test was carried out.

In the test, the mice were acclimatized for 30 seconds to the movement of the axis rotating at 8 rpm, and thereafter, the time required until the mice fell from the axis under conditions where the rotation speed was increased to 40 rpm for 5 minutes was measured. The test was repeatedly carried out three times at intervals of 1 hour, and a mean time from the three trials was used as data for grouping. Based on the body weight and the data from the Rota-rod test, the MPTP-treated mice were assigned to 4 groups according to multivariable completely randomized allocation using SAS (SAS Institute Inc., Ver. 9.2) and Stat Preclinica (Takumi Information Technology Inc., Ver. 1.2).

Repeated intravenous administration was carried out on a total of 5 groups consisting of normal saline-treated mice (a solvent-treated group), MPTP-treated mice (a solvent-treated group, and groups treated with 0.3, 1, and 3 mg/kg of the fusion protein of the present invention), once a week, for 4 to 8 weeks. One week after the final administration, a Rota-rod test was carried out again (with the same protocols as those applied upon performing the grouping in the above (1)), and the action to improve motor incoordination was evaluated. The intravenously administered fusion protein of the present invention has transferred into the brain, and it has then exerted BDNF activity therein, so that it could improve movement dysfunctions, such as motor incoordination, in the Parkinson's disease model animals.

Thus, it could be confirmed that the intravenously administered fusion protein of the present invention has transferred into the brain of disease model animals (mice) and can exert BDNF activity therein.

[Example 20] Studies Regarding the Movement Dysfunction-Improving Effect of the Fusion Protein of the Present Invention, Using Parkinson's Disease Model Monkeys Treated with 1-methyl-4-phenyl-1,2,3,6-tetrahydropyridine (MPTP)

The in vivo biological activity of BDNF in the hBDNF-anti-hTfR antibody fusion protein produced in Example 17 could be evaluated based on the Parkinson's disease-like symptom improving effect of the fusion protein in MPTP-treated monkeys, for example, by applying the below-mentioned method.

For five days before the treatment with MPTP, male rhesus monkeys (5 to 8 years old) or cynomolgus monkeys (4 to 8 years old), which had previously been evaluated to do normal behavior, were administered MPTP (at a dose of 0.2 mg/kg or more, and at a upper limit of 2 mg/kg) during at maximum 5 consecutive days in a week, for 4 or more weeks, by intravenous, intramuscular or subcutaneous administration, and thereafter, a reduction in the UPDRS scores or a reduction in the momentum was confirmed. Otherwise, MPTP (at a dose of 0.2 mg/kg or more, and at an upper limit of 2 mg/kg) was administered into either one internal carotid artery, once or twice, and thereafter, using UPDRS scores (J Neurosci Methods. 2000; 96: 71-76), momentum, and turning momentum as indicators, Parkinson's disease-like symptoms were confirmed, and the MPTP treatment was then terminated.

After confirming that Parkinson's disease-like symptoms were stabilized 1 week after the final administration of MPTP, the hBDNF-anti-hTfR antibody fusion protein (0.03 to 10 mg/kg) was intravenously administered to the monkeys once a week, and the improvement factor of movement functions was evaluated based on the evaluation of UPDRS, momentum, or turning movement. The intravenously administered hBDNF-anti-hTfR antibody fusion protein has transferred into the brain, and it has then exerted BDNF activity therein, so that it could improve movement dysfunctions in the Parkinson's disease model animals.

Thus, it could be confirmed that the intravenously administered fusion protein of the present invention has transferred into the brain of disease model animals (monkeys) and can exert BDNF activity therein.

[Example 21] Studies Regarding the Striatal Dopamine Amount-Recovering Effect of the Fusion Protein of the Present Invention, Using Parkinson's Disease Model Mice Treated with 1-methyl-4-phenyl-1,2,3,6-tetrahydropyridine (MPTP)

The striatal dopamine amount-recovering effect of the hBDNF-anti-hTfR antibody fusion protein produced in Example 17 could be evaluated, for example, by measuring the amount of dopamine in the striatum of an animal treated with MPTP, by applying the below-mentioned method.

According to the method of Example 19-2, Parkinson's disease models were produced by the MPTP treatment, and the produced models were then administered a solvent or a hBDNF-anti-hTfR antibody fusion protein (wherein the dose providing the improvement of movement functions was applied) once a week, for 4 to 8 weeks, by repeated intravenous administration. Seven to ten days after the final administration, microwave (5.0 to 5.2 kw, 1.0 to 1.1 seconds) was applied to the heads of the models, using a microwave apparatus (TMW-6402, Toshiba). The striatum was excised, was then frozen on dry ice, and preserved at −80° C. before being subjected to an operation of extracting a neurotransmitter.

The frozen striatum was added to 1 M formic acid-acetone (15: 85) solution containing 0.01% (w/v) EDTA-2Na and 20 ng/mL 5-hydroxy-tryptophol (internal standard substance) (in an amount of 50 times greater than the wet weight of the striatum), followed by homogenization. The homogenate was centrifuged (4° C., 10000 rpm×15 minutes), and 100 μL of supernatant was fractionated and was then dried and solidified by being evaporated with a centrifugal evaporator (CE1D, TP-80, Hitachi) for 90 minutes. Thereafter, the resultant was preserved at −20° C. before being subjected to a quantification operation.

100 μL each of 0.01 M acetic acid solution (containing 0.01% (w/v) EDTA-2Na) was added to the evaporated and dried and solidified sample, so that the sample was dissolved in the solution. The obtained solution was centrifuged (4° C., 9,000 rpm×15 minutes), and dopamine and dopamine metabolites (DL-3,4-dihydroxyphenyl glycol and homovanillic acid) in the supernatant were measured by HPLC.

As a result, it could be confirmed that the function of BDNF, such as the recovery of a dopamine amount in the striatum of a disease model animal, can be exhibited by intravenous administration of the fusion protein of the present invention.

[Example 22] Studies Regarding the Nigrostriatal Dopamine Neuron-Regenerating Effect of the Fusion Protein of the Present Invention, Using Parkinson's Disease Model Mice/Monkeys Treated with 1-methyl-4-phenyl-1,2,3,6-tetrahydropyridine (MPTP)

The dopamine neuron-regenerating effect of the hBDNF-anti-hTfR antibody fusion protein produced in Example 17 could be evaluated according to a histopathological studies, in which dopamine neurons in the nigrostriatum of an animal treated with MPTP are stained using an antibody against tyrosine hydroxylase (TH) as a marker for the cells, for example, by applying the below-mentioned method.

According to the methods of Examples 19-2 and 20, Parkinson's disease models were produced by the MPTP treatment, and the produced models were then administered a solvent or a hBDNF-anti-hTfR antibody fusion protein, once a week, for 4 to 8 weeks, by repeated intravenous administration.

Seven to ten days after the final administration, the models were subjected to perfusion fixation using 4% paraformaldehyde (PFA), and the brain was then excised. A post-fixation was carried out using 4% PFA, and a portion containing the substantia nigra and/or the striatum was excised (wherein a brain slicer was used in the case of mice) and was then fixed again with 10% neutral buffered formalin overnight. Thereafter, a paraffin block was prepared. The paraffin block was sliced to a thickness of approximately 4 μm, was then adhered to a slide glass coated with MAS-GP Type A, and was then subjected to immunostaining.

For antigen activation, an enzyme treatment or a heat treatment was carried out, as necessary. For example, a paraffin section of the substantia nigra and/or striatum portion was immersed in an antigen-activating reagent such as SEROTEC TARGET UNMASKING FLUID MARK2 (UNIVERSAL) (BUF025B, AbD Serotec), which had been 10-fold diluted and had been then warmed to approximately 60° C., and it was then placed in a steamed pressure cooker. After that, it was treated in a high pressure mode for 10 minutes to carry out antigen activation. Thereafter, a mouse tissue section was blocked in 3% $H_2O_2$ using a blocking reagent A of a mouse stain kit (414322, NICHIREI BIOSCIENCE INC.), whereas a monkey tissue section was blocked in 3% $H_2O_2$ using 4% Block Ace (DS Pharma Biomedical). Thereafter, each tissue section was allowed to react with a primary antibody (anti-TH antibody, clone LNC1, MAB318, Millipore), which had been appropriately diluted with an antibody diluting solution having activating effects (IMMUNO SHOT immunostaining, Mild, IS-M-20, COSMO BIO CO., LTD.), at room temperature for 30 minutes, or at 4° C. overnight. After completion of the reaction, each tissue section was washed with PBS-T (0.05% TWEEN 20-containing PBS). Then, the mouse tissue section was treated with a blocking reagent B of the mouse stain kit for 10 minutes, and a secondary antibody (Histofine Simple Stain Mouse MAX-PO (M) of the mouse stain kit) was added dropwise to the section, followed by performing a reaction for 10 minutes. On the other hand, with regard to the monkey tissue section, a secondary antibody (Histofine Simple Stain MAX-PO (M)) was added dropwise thereto, and a reaction was performed for 30 minutes. Thereafter, each tissue section was washed with PBS-T (0.05% Tween 20-containing PBS), and was then immersed in DAB solution (DAB substrate kit, 425011, NICHIREI BIOSCIENCE INC.) for 10 minutes for visualization.

The stained sections were each air-dried, and were then enclosed. Thereafter, using Aperio (registered trademark) AT2 (Leica Biosystems), the sections were scanned and digitized. The thus digitized sections were analyzed using image analysis software ImageScope (Leica Biosystems), and the area of a TH-positive region was then quantified.

Thus, it could be confirmed that the intravenously administered fusion protein of the present invention has transferred into the brain of disease model animals and can exhibit the function of BDNF of regenerating the nigrostriatal dopamine neuron therein.

[Example 23] Studies Regarding the Disease Progression-Suppressing Effect of the Fusion Protein of the Present Invention, Using Huntington's Disease Model Mice (R6/2 Mice)

The in vivo biological activity of BDNF in the hBDNF-anti-hTfR antibody fusion protein produced in Example 17 could be evaluated based on the disease progression-suppressing effect of the fusion protein in R6/2 mice (Mangiarini L, et al., 1996 Cell 87; 493-506), for example, by applying a behavioral pharmacological method as reported in the non-patent documents (Giralt A. et al., 2011. Mol Neurodegener. 6; 71-86, DeMarch Z. et al., 2008. Neurobiol Dis. 30; 375-387.).

(1) Change in Body Weight and Survival Rate

Wild-type mice (a solvent-treated group) and R6/2 mice (one solvent-treated group, and two or three hBDNF-anti-hTfR antibody fusion protein-treated groups) were subjected to repeated intravenous administration once a week, after they had become 4 weeks old.

The solvent-treated R6/2 mouse group was compared with the hBDNF-anti-hTfR antibody fusion protein-treated R6/2 mouse groups, in terms of a change in the body weight and survival rate, so that the disease progression-suppressing effect of the fusion protein in Huntington's disease model animals could be evaluated.

(2) Rota-Rod Test

Wild-type mice (a solvent-treated group) and R6/2 mice (one solvent-treated group, and two or three hBDNF-anti-hTfR antibody fusion protein-treated groups) were subjected to repeated intravenous administration once a week, after they had become 4 weeks old. Rota-rod test was carried out once a week or once two weeks, and the effect of the hBDNF-anti-hTfR antibody fusion protein to suppress a progressive reduction over time in motor incoordination was evaluated.

Mice were placed on a rotation axis of a Rota-rod apparatus (MK-610A, Muromachi Kikai Co., Ltd.) (a single mouse in each lane on the rotation axis), and they were then left to stand for 30 seconds. Thereafter, the mice were acclimatized to the rotation of the axis at 2 rpm for 1 minute, and were then trained under conditions where the rotation speed was increased to 15 rpm for 3 minutes. One hour after completion of the training, the test was carried out. In the test, the mice were acclimatized for 30 seconds to the movement of the axis rotating at 4 rpm, and thereafter, the time required until the mice fell from the axis under conditions where the rotation speed was increased to 30 rpm for 5 minutes was measured. The test was repeatedly carried out three times at intervals of 1 hour, and a mean time from the three trials was used as data for individual mice. The solvent-treated R6/2 mouse group was compared with the hBDNF-anti-hTfR antibody fusion protein-treated R6/2 mouse groups, so that the effect of the hBDNF-anti-hTfR antibody fusion protein to suppress a progressive reduction in the motor incoordination in Huntington's disease model animals could be evaluated.

(3) Clasping Test

Wild-type mice (a solvent-treated group) and R6/2 mice (one solvent-treated group, and two or three hBDNF-anti-hTfR antibody fusion protein-treated groups) were subjected to repeated intravenous administration once a week, after they had become 4 weeks old. Clasping test was carried out once a week, and the effect of the hBDNF-anti-hTfR antibody fusion protein to suppress the progression of central nerve degeneration was evaluated by evaluating the expression time or the presence or absence of limb reflex abnormality (limb crossing).

The tail of a mouse was grabbed, and the mouse was then hanged from a height of approximately 40 cm, grabbing the tail thereof. After it had hanged for 1 minute, the time at which the mouse showed limb reflex abnormality (limb crossing) was measured with a stopwatch. The measurement was carried out three times, and a mean value thereof was used as data. The solvent-treated R6/2 mouse group was compared with the hBDNF-anti-hTfR antibody fusion protein-treated R6/2 mouse groups, so that the effect of the hBDNF-anti-hTfR antibody fusion protein to suppress the progression of central nerve degeneration in Huntington's disease model animals could be evaluated. In addition, as reported in the non-patent document (Guyenet S. J. et al., 2010. J. Vis. Exp. 21; pii: 1787), the appearance of limb abnormality immediately after completion of the hanging (within 10 seconds), was scored, for example, based on the following scoring: 0: no particular movement; 1: the mouse draws one hind leg; 2: the mouse draws both hind legs; and 3: the mouse draws all of the limb, so that the efficiencies of the hBDNF-anti-hTfR antibody fusion protein could also be evaluated.

(4) Novel Object Recognition Test

Wild-type mice (a solvent-treated group) and R6/2 mice (one solvent-treated group, and two or three hBDNF-anti-hTfR antibody fusion protein-treated groups) were subjected to repeated intravenous administration once a week, after they had become 4 weeks old. Novel object recognition test was carried out once one or two weeks. Lengths of exploring times for a familiar object and a novel object in the second trial, and a discrimination index (DI) calculated from the exploring times were evaluated, so that the cognitive function-enhancing effect of the hBDNF-anti-hTfR antibody fusion protein was evaluated.

A mouse was placed in a test box containing two objects having the same shape, and was allowed to freely explore for 5 minutes (first trial). The exploring time for the objects was measured, and one hour after the first trial, the second trial was carried out. In the second trial, an object which the mouse explored for a longer time in the first trial was left in the box, and the other object was exchanged with a novel object. The exploring times for familiar and novel objects in the second trial (5 minutes) were measured, and DI was then calculated (DI=(novel object exploring time−familiar object exploring time)/(novel object exploring time+familiar object exploring time)). In terms of DI, the solvent-treated R6/2 mouse group was compared with the hBDNF-anti-hTfR antibody fusion protein-treated R6/2 mouse groups, so that the cognitive function-enhancing effect of the hBDNF-anti-hTfR antibody fusion protein in Huntington's disease model animals could be evaluated.

[Example 24] Studies Regarding the Disease Progression-Suppressing Effect of the Fusion Protein of the Present Invention, Using Amyotrophic Lateral Sclerosis (ALS) Model Mice (Wobbler Mice)

The in vivo biological activity of BDNF in the hBDNF-anti-hTfR antibody fusion protein produced in Example 17 could be evaluated based on the effect of the hBDNF-anti-hTfR antibody fusion protein to suppress a progressive reduction in the neuromuscular function of Wobbler mice, for example, by applying a behavioral pharmacological method as reported in the non-patent document (Ishiyama T. et al., 2004. Brain Res. 1019; 226-236.).

(1) Grip Test

Wild-type mice (a solvent-treated group) and Wobbler mice (one solvent-treated group, and two or three hBDNF-anti-hTfR antibody fusion protein-treated groups) were subjected to repeated intravenous administration once a week, after they had become 3 to 4 weeks old. Grip test was carried out once a week, and by evaluating grip strength, the effect of the hBDNF-anti-hTfR antibody fusion protein to suppress a progressive reduction in the neuromuscular function could be evaluated.

A mouse was allowed to grab a bar of a dynamometer (NS-TRM-M, Neuroscience), and the tail thereof was then pulled. The power required until the mouse left the bar was recorded as grip strength, and a mean value from five times of measurements was used as data for individual mice. The solvent-treated Wobbler mouse group was compared with the hBDNF-anti-hTfR antibody fusion protein-treated Wobbler mouse groups, so that the effect of the hBDNF-anti-hTfR antibody fusion protein to suppress a progressive reduction in the neuromuscular function of ALS model animals could be evaluated.

(2) Rota-Rod Test

Wild-type mice (a solvent-treated group) and Wobbler mice (one solvent-treated group, and two or three hBDNF-anti-hTfR antibody fusion protein-treated groups) were subjected to repeated intravenous administration once a week, after they had become 3 to 4 weeks old. Rota-rod test was carried out once a week or once two weeks, and the effect of the hBDNF-anti-hTfR antibody fusion protein to suppress a progressive reduction over time in motor incoordination was evaluated.

Mice were placed on a rotation axis of a Rota-rod apparatus (MK-610A, Muromachi Kikai Co., Ltd.) (a single mouse in each lane on the rotation axis), and they were then left to stand for 30 seconds. Thereafter, the mice were acclimatized to the rotation of the axis at 2 rpm for 1 minute, and were then trained under conditions where the rotation speed was increased to 15 rpm for 3 minutes. One hour after completion of the training, the test was carried out. In the test, the mice were acclimatized for 30 seconds to the movement of the axis rotating at 4 rpm, and thereafter, the time required until the mice fell from the axis under conditions where the rotation speed was increased to 30 rpm for 5 minutes was measured. The test was repeatedly carried out three times at intervals of 1 hour, and a mean time from the three trials was used as data for individual mice. The solvent-treated Wobbler mouse group was compared with the hBDNF-anti-hTfR antibody fusion protein-treated Wobbler mouse groups, so that the effect of the hBDNF-anti-hTfR antibody fusion protein to suppress a progressive reduction in the neuromuscular function in ALS model animals could be evaluated.

[Example 25] Studies Regarding the Disease-Improving Effect of the Fusion Protein of the Present Invention, Using Rett Syndrome Model Mice (MeCP2 (Methyl-CpG Binding Protein 2) Knockout Mice)

The in vivo biological activity of BDNF in the hBDNF-anti-hTfR antibody fusion protein produced in Example 17 could be evaluated based on the disease-improving effect of the hBDNF-anti-hTfR antibody fusion protein in MeCP2 knockout (KO) mice, for example, by applying a behavioral pharmacological method as reported in the non-patent document (Derecki N. C. et al., 2012. Nature 484; 105-109.).

(1) Change in Body Weight and Survival Rate

Wild-type mice (a solvent-treated group) and MeCP2 KO mice (one solvent-treated group, and two or three hBDNF-anti-hTfR antibody fusion protein-treated groups) were subjected to repeated intravenous administration once a week, after they had become 3 to 4 weeks old.

The solvent-treated MeCP2 KO mouse group was compared with the hBDNF-anti-hTfR antibody fusion protein-treated MeCP2 KO mouse groups, in terms of a change in the body weight and survival rate, so that the disease-improving effect of the hBDNF-anti-hTfR antibody fusion protein in Rett syndrome model animals could be evaluated.

(2) Evaluation of Respiratory Function

Wild-type mice (a solvent-treated group) and MeCP2 KO mice (one solvent-treated group, and two or three hBDNF-anti-hTfR antibody fusion protein-treated groups) were subjected to repeated intravenous administration once a week, after they had become 3 to 4 weeks old. The evaluation of respiratory function was carried out once a week, and the respiratory function-improving effect of the hBDNF-anti-hTfR antibody fusion protein could be evaluated by evaluating the number of apnea.

A mouse was placed in a chamber of a respiratory function measurement apparatus (Biosystem XA, Buxco), and spontaneous respiration was measured for 1 hour. The number of apnea (the number of an apnea condition continued for 1 second or more) in the time at which no body motion was observed was used as data. The solvent-treated MeCP2 KO mouse group was compared with the hBDNF-anti-hTfR antibody fusion protein-treated MeCP2 KO mouse groups, so that the respiratory function-improving effect of the hBDNF-anti-hTfR antibody fusion protein in Rett syndrome model animals could be evaluated.

(3) Clasping Test

Wild-type mice (a solvent-treated group) and MeCP2 KO mice (one solvent-treated group, and two or three hBDNF-anti-hTfR antibody fusion protein-treated groups) were subjected to repeated intravenous administration once a week, after they had become 3 to 4 weeks old. Clasping test was carried out once a week, and the effect of the hBDNF-anti-hTfR antibody fusion protein to suppress the progression of central nerve degeneration was evaluated by evaluating the expression time or the presence or absence of limb reflex abnormality (limb crossing).

The tail of a mouse was grabbed, and the mouse was then hanged from a height of approximately 40 cm, grabbing the tail thereof. The time at which the mouse showed limb reflex abnormality during the hanging condition for 1 minute was measured with a stopwatch. The measurement was carried out three times, and a mean value thereof was used as data. The solvent-treated MeCP2 KO mouse group was compared with the hBDNF-anti-hTfR antibody fusion protein-treated MeCP2 KO mouse groups, so that the effect of the hBDNF-anti-hTfR antibody fusion protein to suppress the progression of central nerve degeneration in Rett syndrome model animals could be evaluated. In addition, as reported in the non-patent document (Guyenet S. J. et al., 2010. J. Vis. Exp. 21; pii: 1787), the appearance of limb abnormality immediately after completion of the hanging (within 10 seconds), was scored, for example, based on the following scoring: 0: no particular movement; 1: the mouse draws one hind leg; 2: the mouse draws both hind legs; and 3: the mouse draws all of the limbs, so that the medicinal effects of the hBDNF-anti-hTfR antibody fusion protein could also be evaluated.

[Example 26] Studies Regarding the Cognitive Function-Improving Effect of the Fusion Protein of the Present Invention, Using Alzheimer's Disease Model Mice (Tg2576 Mice)

The in vivo biological activity of BDNF in the hBDNF-anti-hTfR antibody fusion protein produced in Example 17 could be evaluated based on the cognitive function impairment-improving effect of the hBDNF-anti-hTfR antibody fusion protein in Tg2576 mice, for example, by applying a behavioral pharmacological method as reported in the non-patent document (Iwasaki Y. et al., 2012. J Neurosci. Res. 90; 981-989. Cuadrado-Tejedor M. et al., 2010. Br. J. Pharmacol. 164; 2029-2041.).

(1) Morris Water Maze Test

Wild-type mice (a solvent-treated group) and Tg2576 mice (one solvent-treated group, and two or three hBDNF-anti-hTfR antibody fusion protein-treated groups) were subjected to repeated intravenous administration once a week, after they had become 14 to 16 months old. A water maze test was carried out after the repeated intravenous administration for four weeks or more, and the cognitive function-enhancing effect of the hBDNF-anti-hTfR antibody fusion protein was evaluated by evaluating the shortness of the reaching time to a platform in a training trial and the length of the residence time in a region, in which the platform had been present in a training trial, in a probe test.

A mouse was placed in a round pool with a diameter of 1.2 m, which was filled with water, and it was then trained 8 trials a day for 3 days under conditions where there were no landmarks around the pool and a platform was seen. Subsequently, the mouse was trained 4 trials a day for 8 days under conditions where there were landmarks around the pool and a platform was immersed in water. On the 9th day, a probe test was carried out. In the probe test, the platform was removed, and the time at which the mouse swam in a region corresponding to one quarter of the pool in which the platform had been present in a training trial. The solvent-treated Tg2576 mouse group was compared with the hBDNF-anti-hTfR antibody fusion protein-treated Tg2576 mouse groups, in terms of the platform-reaching time in the training and the swimming time in the probe test, so that the cognitive function-enhancing effect of the hBDNF-anti-hTfR antibody fusion protein in Alzheimer's disease model animals could be evaluated.

[Example 27] Studies Regarding the Nerve Regeneration/Nerve Degeneration Progression-Suppressing Effect of the Fusion Protein of the Present Invention, Using Nerve Degeneration Model Mice The in vivo biological activity of BDNF in the hBDNF-anti-hTfR antibody fusion protein produced in Example 17 could be evaluated based on the nerve regeneration effect or nerve degeneration progression-suppressing effect of the hBDNF-anti-hTfR antibody fusion protein, for example, by applying an immunohistological method or a Western blotting method as reported in the non-patent documents (Giralt A. et al., 2011. Mol Neurodegener. 6; 71-86, DeMarch Z. et al., 2008. Neurobiol Dis. 30; 375-387) in the case of using Huntington's disease model mice, or as reported in the non-patent document (Ishiyama T. et al., 2004. Brain Res. 1019; 226-236) in the case of amyotrophic lateral sclerosis (ALS) model mice, or as reported in the non-patent document (Iwasaki Y. et al., 2012. J Neurosci. Res. 90; 981-989. Cuadrado-Tejedor M. et al., 2010. Br. J. Pharmacol. 164; 2029-2041) in the case of Alzheimer's disease model mice.

Wild-type mice (a solvent-treated group) and model mice (one solvent-treated group, and two or three hBDNF-anti-hTfR antibody fusion protein-treated groups) were subjected to repeated intravenous administration once a week. The fusion protein was continuously administered to the mice for a certain period of time. Thereafter, for immunohistological evaluation, the mice were sacrificed by exsanguination, and were then subjected to perfusion fixation with 4% paraformaldehyde, and a brain sample was then collected from each mouse. For evaluation by Western blotting, the brain was excised from each mouse, after it had been sacrificed by decapitation, and a necessary area was then cut out to collect a sample. As reported in the aforementioned non-patent documents, examples of the evaluation target include VGLUT1, PSD-95, Calbindin, DARPP32, enkephalin-containing neurons, Synaptophysin, NeuN, SMI-32, choline acetyltransferase, and tyrosine hydroxylase. The solvent-treated model mouse group was compared with the hBDNF-anti-hTfR antibody fusion protein-treated model mouse groups, so that the nerve regeneration effect/nerve degeneration progression-suppressing effect of the hBDNF-anti-hTfR antibody fusion protein could be evaluated.

INDUSTRIAL APPLICABILITY

The fusion protein of the present invention consisting of hBDNF and an anti-hTfR antibody allow them to pass through the blood-brain barrier, and is, therefore, highly useful in providing means to allow hBDNF to act on the central nervous system.

REFERENCE SIGNS LIST

1 Blood vessel
2 Brain parenchyma
3 Neuron-like cells
4 Purkinje cells

Sequence Listing Free Text

SEQ ID NO:3: Amino acid sequence of exemplified linker 1
SEQ ID NO:4: Amino acid sequence of exemplified linker 2
SEQ ID NO:5: Amino acid sequence of exemplified linker 3
SEQ ID NO:6: Amino acid sequence 1 of CDR1 in the light chain of mouse anti-hTfR antibody No. 1
SEQ ID NO:7: Amino acid sequence 2 of CDR1 in the light chain of mouse anti-hTfR antibody No. 1
SEQ ID NO:8: Amino acid sequence 1 of CDR2 in the light chain of mouse anti-hTfR antibody No. 1
SEQ ID NO:9: Amino acid sequence 2 of CDR2 in the light chain of mouse anti-hTfR antibody No. 1
SEQ ID NO:10: Amino acid sequence of CDR3 in the light chain of mouse anti-hTfR antibody No. 1
SEQ ID NO: 11: Amino acid sequence 1 of CDR1 in the light chain of mouse anti-hTfR antibody No. 2
SEQ ID NO: 12: Amino acid sequence 2 of CDR1 in the light chain of mouse anti-hTfR antibody No. 2 SEQ ID NO:13: Amino acid sequence 1 of CDR2 in the light chain of mouse anti-hTfR antibody No. 2
SEQ ID NO: 14: Amino acid sequence 2 of CDR2 in the light chain of mouse anti-hTfR antibody No. 2 SEQ ID NO:15: Amino acid sequence of CDR3 in the light chain of mouse anti-hTfR antibody No. 2
SEQ ID NO: 16: Amino acid sequence 1 of CDR1 in the light chain of mouse anti-hTfR antibody No. 3
SEQ ID NO: 17: Amino acid sequence 2 of CDR1 in the light chain of mouse anti-hTfR antibody No. 3
SEQ ID NO:18: Amino acid sequence 1 of CDR2 in the light chain of mouse anti-hTfR antibody No. 3
SEQ ID NO: 19: Amino acid sequence 2 of CDR2 in the light chain of mouse anti-hTfR antibody No. 3
SEQ ID NO:20: Amino acid sequence of CDR3 in the light chain of mouse anti-hTfR antibody No. 3
SEQ ID NO:21: Amino acid sequence 1 of CDR1 in the light chain of mouse anti-hTfR antibody No. 4
SEQ ID NO:22: Amino acid sequence 2 of CDR1 in the light chain of mouse anti-hTfR antibody No. 4
SEQ ID NO:23: Amino acid sequence 1 of CDR2 in the light chain of mouse anti-hTfR antibody No. 4
SEQ ID NO:24: Amino acid sequence 2 of CDR2 in the light chain of mouse anti-hTfR antibody No. 4
SEQ ID NO:25: Amino acid sequence of CDR3 in the light chain of mouse anti-hTfR antibody No. 4
SEQ ID NO:26: Amino acid sequence 1 of CDR1 in the light chain of mouse anti-hTfR antibody No. 5
SEQ ID NO:27: Amino acid sequence 2 of CDR1 in the light chain of mouse anti-hTfR antibody No. 5
SEQ ID NO:28: Amino acid sequence 1 of CDR2 in the light chain of mouse anti-hTfR antibody No. 5
SEQ ID NO:29: Amino acid sequence 2 of CDR2 in the light chain of mouse anti-hTfR antibody No. 5
SEQ ID NO:30: Amino acid sequence of CDR3 in the light chain of mouse anti-hTfR antibody No. 5
SEQ ID NO:31: Amino acid sequence 1 of CDR1 in the light chain of mouse anti-hTfR antibody No. 6
SEQ ID NO:32: Amino acid sequence 2 of CDR1 in the light chain of mouse anti-hTfR antibody No. 6
SEQ ID NO:33: Amino acid sequence 1 of CDR2 in the light chain of mouse anti-hTfR antibody No. 6
SEQ ID NO:34: Amino acid sequence 2 of CDR2 in the light chain of mouse anti-hTfR antibody No. 6
SEQ ID NO:35: Amino acid sequence of CDR3 in the light chain of mouse anti-hTfR antibody No. 6
SEQ ID NO:36: Amino acid sequence 1 of CDR1 in the light chain of mouse anti-hTfR antibody No. 7
SEQ ID NO:37: Amino acid sequence 2 of CDR1 in the light chain of mouse anti-hTfR antibody No. 7
SEQ ID NO:38: Amino acid sequence 1 of CDR2 in the light chain of mouse anti-hTfR antibody No. 7
SEQ ID NO:39: Amino acid sequence 2 of CDR2 in the light chain of mouse anti-hTfR antibody No. 7
SEQ ID NO:40: Amino acid sequence of CDR3 in the light chain of mouse anti-hTfR antibody No. 7
SEQ ID NO:41: Amino acid sequence 1 of CDR1 in the light chain of mouse anti-hTfR antibody No. 8
SEQ ID NO:42: Amino acid sequence 2 of CDR1 in the light chain of mouse anti-hTfR antibody No. 8
SEQ ID NO:43: Amino acid sequence 1 of CDR2 in the light chain of mouse anti-hTfR antibody No. 8
SEQ ID NO:44: Amino acid sequence 2 of CDR2 in the light chain of mouse anti-hTfR antibody No. 8
SEQ ID NO:45: Amino acid sequence of CDR3 in the light chain of mouse anti-hTfR antibody No. 8
SEQ ID NO:46: Amino acid sequence 1 of CDR1 in the light chain of mouse anti-hTfR antibody No. 9
SEQ ID NO:47: Amino acid sequence 2 of CDR1 in the light chain of mouse anti-hTfR antibody No. 9
SEQ ID NO:48: Amino acid sequence 1 of CDR2 in the light chain of mouse anti-hTfR antibody No. 9
SEQ ID NO:49: Amino acid sequence 2 of CDR2 in the light chain of mouse anti-hTfR antibody No. 9
SEQ ID NO:50: Amino acid sequence of CDR3 in the light chain of mouse anti-hTfR antibody No. 9
SEQ ID NO:51: Amino acid sequence 1 of CDR1 in the light chain of mouse anti-hTfR antibody No. 10
SEQ ID NO:52: Amino acid sequence 2 of CDR1 in the light chain of mouse anti-hTfR antibody No. 10
SEQ ID NO:53: Amino acid sequence 1 of CDR2 in the light chain of mouse anti-hTfR antibody No. 10
SEQ ID NO:54: Amino acid sequence 2 of CDR2 in the light chain of mouse anti-hTfR antibody No. 10
SEQ ID NO:55: Amino acid sequence of CDR3 in the light chain of mouse anti-hTfR antibody No. 10
SEQ ID NO:56: Amino acid sequence 1 of CDR1 in the light chain of mouse anti-hTfR antibody No. 11
SEQ ID NO:57: Amino acid sequence 2 of CDR1 in the light chain of mouse anti-hTfR antibody No. 11
SEQ ID NO:58: Amino acid sequence 1 of CDR2 in the light chain of mouse anti-hTfR antibody No. 11

SEQ ID NO:59: Amino acid sequence 2 of CDR2 in the light chain of mouse anti-hTfR antibody No. 11
SEQ ID NO:60: Amino acid sequence of CDR3 in the light chain of mouse anti-hTfR antibody No. 11
SEQ ID NO:61: Amino acid sequence 1 of CDR1 in the light chain of mouse anti-hTfR antibody No. 12
SEQ ID NO:62: Amino acid sequence 2 of CDR1 in the light chain of mouse anti-hTfR antibody No. 12
SEQ ID NO:63: Amino acid sequence 1 of CDR2 in the light chain of mouse anti-hTfR antibody No. 12
SEQ ID NO:64: Amino acid sequence 2 of CDR2 in the light chain of mouse anti-hTfR antibody No. 12
SEQ ID NO:65: Amino acid sequence of CDR3 in the light chain of mouse anti-hTfR antibody No. 12
SEQ ID NO:66: Amino acid sequence 1 of CDR1 in the light chain of mouse anti-hTfR antibody No. 13
SEQ ID NO:67: Amino acid sequence 2 of CDR1 in the light chain of mouse anti-hTfR antibody No. 13
SEQ ID NO:68: Amino acid sequence 1 of CDR2 in the light chain of mouse anti-hTfR antibody No. 13
SEQ ID NO:69: Amino acid sequence 2 of CDR2 in the light chain of mouse anti-hTfR antibody No. 13
SEQ ID NO:70: Amino acid sequence of CDR3 in the light chain of mouse anti-hTfR antibody No. 13
SEQ ID NO:71: Amino acid sequence 1 of CDR1 in the light chain of mouse anti-hTfR antibody No. 14
SEQ ID NO:72: Amino acid sequence 2 of CDR1 in the light chain of mouse anti-hTfR antibody No. 14
SEQ ID NO:73: Amino acid sequence 1 of CDR2 in the light chain of mouse anti-hTfR antibody No. 14
SEQ ID NO:74: Amino acid sequence 2 of CDR2 in the light chain of mouse anti-hTfR antibody No. 14
SEQ ID NO:75: Amino acid sequence of CDR3 in the light chain of mouse anti-hTfR antibody No. 14
SEQ ID NO:76: Amino acid sequence 1 of CDR1 in the heavy chain of mouse anti-hTfR antibody No. 1
SEQ ID NO:77: Amino acid sequence 2 of CDR1 in the heavy chain of mouse anti-hTfR antibody No. 1
SEQ ID NO:78: Amino acid sequence 1 of CDR2 in the heavy chain of mouse anti-hTfR antibody No. 1
SEQ ID NO:79: Amino acid sequence 2 of CDR2 in the heavy chain of mouse anti-hTfR antibody No. 1
SEQ ID NO:80: Amino acid sequence 1 of CDR3 in the heavy chain of mouse anti-hTfR antibody No. 1
SEQ ID NO:81: Amino acid sequence 2 of CDR3 in the heavy chain of mouse anti-hTfR antibody No. 1
SEQ ID NO:82: Amino acid sequence 1 of CDR1 in the heavy chain of mouse anti-hTfR antibody No. 2
SEQ ID NO:83: Amino acid sequence 2 of CDR1 in the heavy chain of mouse anti-hTfR antibody No. 2
SEQ ID NO:84: Amino acid sequence 1 of CDR2 in the heavy chain of mouse anti-hTfR antibody No. 2
SEQ ID NO:85: Amino acid sequence 2 of CDR2 in the heavy chain of mouse anti-hTfR antibody No. 2
SEQ ID NO:86: Amino acid sequence 1 of CDR3 in the heavy chain of mouse anti-hTfR antibody No. 2
SEQ ID NO:87: Amino acid sequence 2 of CDR3 in the heavy chain of mouse anti-hTfR antibody No. 2
SEQ ID NO:88: Amino acid sequence 1 of CDR1 in the heavy chain of mouse anti-hTfR antibody No. 3
SEQ ID NO:89: Amino acid sequence 2 of CDR1 in the heavy chain of mouse anti-hTfR antibody No. 3
SEQ ID NO:90: Amino acid sequence 1 of CDR2 in the heavy chain of mouse anti-hTfR antibody No. 3
SEQ ID NO:91: Amino acid sequence 2 of CDR2 in the heavy chain of mouse anti-hTfR antibody No. 3
SEQ ID NO:92: Amino acid sequence 1 of CDR3 in the heavy chain of mouse anti-hTfR antibody No. 3
SEQ ID NO:93: Amino acid sequence 2 of CDR3 in the heavy chain of mouse anti-hTfR antibody No. 3
SEQ ID NO:94: Amino acid sequence 1 of CDR1 in the heavy chain of mouse anti-hTfR antibody No. 4
SEQ ID NO:95: Amino acid sequence 2 of CDR1 in the heavy chain of mouse anti-hTfR antibody No. 4
SEQ ID NO:96: Amino acid sequence 1 of CDR2 in the heavy chain of mouse anti-hTfR antibody No. 4
SEQ ID NO:97: Amino acid sequence 2 of CDR2 in the heavy chain of mouse anti-hTfR antibody No. 4
SEQ ID NO:98: Amino acid sequence 1 of CDR3 in the heavy chain of mouse anti-hTfR antibody No. 4
SEQ ID NO:99: Amino acid sequence 2 of CDR3 in the heavy chain of mouse anti-hTfR antibody No. 4
SEQ ID NO: 100: Amino acid sequence 1 of CDR1 in the heavy chain of mouse anti-hTfR antibody No. 5
SEQ ID NO:101: Amino acid sequence 2 of CDR1 in the heavy chain of mouse anti-hTfR antibody No. 5
SEQ ID NO: 102: Amino acid sequence 1 of CDR2 in the heavy chain of mouse anti-hTfR antibody No. 5
SEQ ID NO: 103: Amino acid sequence 2 of CDR2 in the heavy chain of mouse anti-hTfR antibody No. 5
SEQ ID NO: 104: Amino acid sequence 1 of CDR3 in the heavy chain of mouse anti-hTfR antibody No. 5
SEQ ID NO: 105: Amino acid sequence 2 of CDR3 in the heavy chain of mouse anti-hTfR antibody No. 5
SEQ ID NO: 106: Amino acid sequence 1 of CDR1 in the heavy chain of mouse anti-hTfR antibody No. 6
SEQ ID NO:107: Amino acid sequence 2 of CDR1 in the heavy chain of mouse anti-hTfR antibody No. 6
SEQ ID NO: 108: Amino acid sequence of CDR2 in the heavy chain of mouse anti-hTfR antibody No. 6
SEQ ID NO: 109: Amino acid sequence 1 of CDR3 in the heavy chain of mouse anti-hTfR antibody No. 6
SEQ ID NO: 110: Amino acid sequence 2 of CDR3 in the heavy chain of mouse anti-hTfR antibody No. 6
SEQ ID NO: 111: Amino acid sequence 1 of CDR1 in the heavy chain of mouse anti-hTfR antibody No. 7
SEQ ID NO: 112: Amino acid sequence 2 of CDR1 in the heavy chain of mouse anti-hTfR antibody No. 7
SEQ ID NO: 113: Amino acid sequence 1 of CDR2 in the heavy chain of mouse anti-hTfR antibody No. 7
SEQ ID NO:114: Amino acid sequence 2 of CDR2 in the heavy chain of mouse anti-hTfR antibody No. 7
SEQ ID NO: 115: Amino acid sequence 1 of CDR3 in the heavy chain of mouse anti-hTfR antibody No. 7
SEQ ID NO: 116: Amino acid sequence 2 of CDR3 in the heavy chain of mouse anti-hTfR antibody No. 7
SEQ ID NO:117: Amino acid sequence 1 of CDR1 in the heavy chain of mouse anti-hTfR antibody No. 8
SEQ ID NO: 118: Amino acid sequence 2 of CDR1 in the heavy chain of mouse anti-hTfR antibody No. 8
SEQ ID NO: 119: Amino acid sequence of CDR2 in the heavy chain of mouse anti-hTfR antibody No. 8
SEQ ID NO: 120: Amino acid sequence 1 of CDR3 in the heavy chain of mouse anti-hTfR antibody No. 8
SEQ ID NO: 121: Amino acid sequence 2 of CDR3 in the heavy chain of mouse anti-hTfR antibody No. 8
SEQ ID NO: 122: Amino acid sequence 1 of CDR1 in the heavy chain of mouse anti-hTfR antibody No. 9
SEQ ID NO: 123: Amino acid sequence 2 of CDR1 in the heavy chain of mouse anti-hTfR antibody No. 9
SEQ ID NO: 124: Amino acid sequence 1 of CDR2 in the heavy chain of mouse anti-hTfR antibody No. 9

SEQ ID NO: 125: Amino acid sequence 2 of CDR2 in the heavy chain of mouse anti-hTfR antibody No. 9
SEQ ID NO: 126: Amino acid sequence 1 of CDR3 in the heavy chain of mouse anti-hTfR antibody No. 9
SEQ ID NO: 127: Amino acid sequence 2 of CDR3 in the heavy chain of mouse anti-hTfR antibody No. 9
SEQ ID NO: 128: Amino acid sequence 1 of CDR1 in the heavy chain of mouse anti-hTfR antibody No. 10
SEQ ID NO: 129: Amino acid sequence 2 of CDR1 in the heavy chain of mouse anti-hTfR antibody No. 10
SEQ ID NO: 130: Amino acid sequence 1 of CDR2 in the heavy chain of mouse anti-hTfR antibody No. 10
SEQ ID NO: 131: Amino acid sequence 2 of CDR2 in the heavy chain of mouse anti-hTfR antibody No. 10
SEQ ID NO: 132: Amino acid sequence 1 of CDR3 in the heavy chain of mouse anti-hTfR antibody No. 10
SEQ ID NO: 133: Amino acid sequence 2 of CDR3 in the heavy chain of mouse anti-hTfR antibody No. 10
SEQ ID NO: 134: Amino acid sequence 1 of CDR1 in the heavy chain of mouse anti-hTfR antibody No. 11
SEQ ID NO: 135: Amino acid sequence 2 of CDR1 in the heavy chain of mouse anti-hTfR antibody No. 11
SEQ ID NO: 136: Amino acid sequence 1 of CDR2 in the heavy chain of mouse anti-hTfR antibody No. 11
SEQ ID NO: 137: Amino acid sequence 2 of CDR2 in the heavy chain of mouse anti-hTfR antibody No. 11
SEQ ID NO: 138: Amino acid sequence 1 of CDR3 in the heavy chain of mouse anti-hTfR antibody No. 11
SEQ ID NO: 139: Amino acid sequence 2 of CDR3 in the heavy chain of mouse anti-hTfR antibody No. 11
SEQ ID NO: 140: Amino acid sequence 1 of CDR1 in the heavy chain of mouse anti-hTfR antibody No. 12
SEQ ID NO: 141: Amino acid sequence 2 of CDR1 in the heavy chain of mouse anti-hTfR antibody No. 12
SEQ ID NO: 142: Amino acid sequence 1 of CDR2 in the heavy chain of mouse anti-hTfR antibody No. 12
SEQ ID NO: 143: Amino acid sequence 2 of CDR2 in the heavy chain of mouse anti-hTfR antibody No. 12
SEQ ID NO: 144: Amino acid sequence 1 of CDR3 in the heavy chain of mouse anti-hTfR antibody No. 12
SEQ ID NO: 145: Amino acid sequence 2 of CDR3 in the heavy chain of mouse anti-hTfR antibody No. 12
SEQ ID NO: 146: Amino acid sequence 1 of CDR1 in the heavy chain of mouse anti-hTfR antibody No. 13
SEQ ID NO: 147: Amino acid sequence 2 of CDR1 in the heavy chain of mouse anti-hTfR antibody No. 13
SEQ ID NO: 148: Amino acid sequence 1 of CDR2 in the heavy chain of mouse anti-hTfR antibody No. 13
SEQ ID NO: 149: Amino acid sequence 2 of CDR2 in the heavy chain of mouse anti-hTfR antibody No. 13
SEQ ID NO: 150: Amino acid sequence 1 of CDR3 in the heavy chain of mouse anti-hTfR antibody No. 13
SEQ ID NO: 151: Amino acid sequence 2 of CDR3 in the heavy chain of mouse anti-hTfR antibody No. 13
SEQ ID NO: 152: Amino acid sequence 1 of CDR1 in the heavy chain of mouse anti-hTfR antibody No. 14
SEQ ID NO:153: Amino acid sequence 2 of CDR1 in the heavy chain of mouse anti-hTfR antibody No. 14
SEQ ID NO:154: Amino acid sequence 1 of CDR2 in the heavy chain of mouse anti-hTfR antibody No. 14
SEQ ID NO: 155: Amino acid sequence 2 of CDR2 in the heavy chain of mouse anti-hTfR antibody No. 14
SEQ ID NO: 156: Amino acid sequence 1 of CDR3 in the heavy chain of mouse anti-hTfR antibody No. 14
SEQ ID NO: 157: Amino acid sequence 2 of CDR3 in the heavy chain of mouse anti-hTfR antibody No. 14
SEQ ID NO:158: Amino acid sequence 1 of the light chain variable region of humanized anti-hTfR antibody No. 1
SEQ ID NO:159: Amino acid sequence 2 of the light chain variable region of humanized anti-hTfR antibody No. 1
SEQ ID NO:160: Amino acid sequence 3 of the light chain variable region of humanized anti-hTfR antibody No. 1
SEQ ID NO:161: Amino acid sequence 4 of the light chain variable region of humanized anti-hTfR antibody No. 1
SEQ ID NO:162: Amino acid sequence 5 of the light chain variable region of humanized anti-hTfR antibody No. 1
SEQ ID NO:163: Amino acid sequence 6 of the light chain variable region of humanized anti-hTfR antibody No. 1
SEQ ID NO:164: Amino acid sequence of the light chain of humanized anti-hTfR antibody No. 1 containing amino acid sequence 6 as the variable region, synthetic sequence
SEQ ID NO: 165: Nucleotide sequence encoding the amino acid sequence of the light chain of humanized anti-hTfR antibody No. 1 containing amino acid sequence 6 as the variable region, synthetic sequence
SEQ ID NO:166: Amino acid sequence 1 of the heavy chain variable region of humanized anti-hTfR antibody No. 1
SEQ ID NO:167: Amino acid sequence 2 of the heavy chain variable region of humanized anti-hTfR antibody No. 1
SEQ ID NO:168: Amino acid sequence 3 of the heavy chain variable region of humanized anti-hTfR antibody No. 1
SEQ ID NO:169: Amino acid sequence 4 of the heavy chain variable region of humanized anti-hTfR antibody No. 1
SEQ ID NO:170: Amino acid sequence 5 of the heavy chain variable region of humanized anti-hTfR antibody No. 1
SEQ ID NO:171: Amino acid sequence 6 of the heavy chain variable region of humanized anti-hTfR antibody No. 1
SEQ ID NO:172: Amino acid sequence of the heavy chain of humanized anti-hTfR antibody No. 1 containing amino acid sequence 6 as the variable region
SEQ ID NO: 173: Nucleotide sequence encoding the amino acid sequence of the heavy chain of humanized anti-hTfR antibody No. 1 containing amino acid sequence 6 as the variable region, synthetic sequence
SEQ ID NO:174: Amino acid sequence 1 of the light chain variable region of humanized anti-hTfR antibody No. 2
SEQ ID NO:175: Amino acid sequence 2 of the light chain variable region of humanized anti-hTfR antibody No. 2
SEQ ID NO:176: Amino acid sequence 3 of the light chain variable region of humanized anti-hTfR antibody No. 2
SEQ ID NO:177: Amino acid sequence 4 of the light chain variable region of humanized anti-hTfR antibody No. 2
SEQ ID NO:178: Amino acid sequence 5 of the light chain variable region of humanized anti-hTfR antibody No. 2

SEQ ID NO:179: Amino acid sequence 6 of the light chain variable region of humanized anti-hTfR antibody No. 2

SEQ ID NO:180: Amino acid sequence of the light chain of humanized anti-hTfR antibody No. 2 containing amino acid sequence 6 as the variable region SEQ ID NO:181: Nucleotide sequence comprising a nucleotide sequence encoding the amino acid sequence of the light chain of humanized anti-hTfR antibody No. 2 containing amino acid sequence 6 as the variable region, synthetic sequence SEQ ID NO:182: Amino acid sequence 1 of the heavy chain variable region of humanized anti-hTfR antibody No. 2

SEQ ID NO:183: Amino acid sequence 2 of the heavy chain variable region of humanized anti-hTfR antibody No. 2

SEQ ID NO:184: Amino acid sequence 3 of the heavy chain variable region of humanized anti-hTfR antibody No. 2

SEQ ID NO:185: Amino acid sequence 4 of the heavy chain variable region of humanized anti-hTfR antibody No. 2

SEQ ID NO:186: Amino acid sequence 5 of the heavy chain variable region of humanized anti-hTfR antibody No. 2

SEQ ID NO:187: Amino acid sequence 6 of the heavy chain variable region of humanized anti-hTfR antibody No. 2

SEQ ID NO:188: Amino acid sequence of the heavy chain of humanized anti-hTfR antibody No. 2 containing amino acid sequence 6 as the variable region SEQ ID NO: 189: Nucleotide sequence comprising a nucleotide sequence encoding the amino acid sequence of the heavy chain of humanized anti-hTfR antibody No. 2 containing amino acid sequence 6 as the variable region, synthetic sequence SEQ ID NO:190: Amino acid sequence 1 of the light chain variable region of humanized anti-hTfR antibody No. 3

SEQ ID NO:191: Amino acid sequence 2 of the light chain variable region of humanized anti-hTfR antibody No. 3

SEQ ID NO:192: Amino acid sequence 3 of the light chain variable region of humanized anti-hTfR antibody No. 3

SEQ ID NO:193: Amino acid sequence 4 of the light chain variable region of humanized anti-hTfR antibody No. 3

SEQ ID NO:194: Amino acid sequence 5 of the light chain variable region of humanized anti-hTfR antibody No. 3

SEQ ID NO:195: Amino acid sequence 6 of the light chain variable region of humanized anti-hTfR antibody No. 3

SEQ ID NO:196: Amino acid sequence of the light chain of humanized anti-hTfR antibody No. 3 containing amino acid sequence 2 as the variable region SEQ ID NO: 197: Nucleotide sequence encoding the amino acid sequence of the light chain of humanized anti-hTfR antibody No. 3 containing amino acid sequence 2 as the variable region, synthetic sequence SEQ ID NO:198: Amino acid sequence of the light chain of humanized anti-hTfR antibody No. 3 containing amino acid sequence 4 as the variable region SEQ ID NO: 199: Nucleotide sequence encoding the amino acid sequence of the light chain of humanized anti-hTfR antibody No. 3 containing amino acid sequence 4 as the variable region, synthetic sequence SEQ ID NO:200: Amino acid sequence of the light chain of humanized anti-hTfR antibody No. 3 containing amino acid sequence 5 as the variable region SEQ ID NO:201: Nucleotide sequence encoding the amino acid sequence of the light chain of humanized anti-hTfR antibody No. 3 containing amino acid sequence 5 as the variable region, synthetic sequence SEQ ID NO:202: Humanized anti-hTfR antibody No. 3 containing amino acid sequence 6 as the variable region SEQ ID NO:203: Nucleotide sequence encoding the amino acid sequence of the light chain of humanized anti-hTfR antibody No. 3 containing amino acid sequence 6 as the variable region, synthetic sequence SEQ ID NO:204: Amino acid sequence 1 of the heavy chain variable region of humanized anti-hTfR antibody No. 3

SEQ ID NO:205: Amino acid sequence 2 of the heavy chain variable region of humanized anti-hTfR antibody No. 3

SEQ ID NO:206: Amino acid sequence 3 of the heavy chain variable region of humanized anti-hTfR antibody No. 3

SEQ ID NO:207: Amino acid sequence 4 of the heavy chain variable region of humanized anti-hTfR antibody No. 3

SEQ ID NO:208: Amino acid sequence 5 of the heavy chain variable region of humanized anti-hTfR antibody No. 3

SEQ ID NO:209: Amino acid sequence 6 of the heavy chain variable region of humanized anti-hTfR antibody No. 3

SEQ ID NO:210: Amino acid sequence of the heavy chain of humanized anti-hTfR antibody No. 3 containing amino acid sequence 2 as the variable region SEQ ID NO:211: Nucleotide sequence encoding the amino acid sequence of the heavy chain of humanized anti-hTfR antibody No. 3 containing amino acid sequence 2 as the variable region, synthetic sequence SEQ ID NO:212: Amino acid sequence of the heavy chain (IgG4) of humanized anti-hTfR antibody No. 3 containing amino acid sequence 2 as the variable region SEQ ID NO:213: Nucleotide sequence encoding the amino acid sequence of the heavy chain (IgG4) of humanized anti-hTfR antibody No. 3 containing amino acid sequence 2 as the variable region, synthetic sequence SEQ ID NO:214: Primer hTfR5', synthetic sequence SEQ ID NO:215: Primer hTfR3', synthetic sequence SEQ ID NO:216: Primer Hyg-Sfi5', synthetic sequence SEQ ID NO:217: Primer Hyg-BstX3', synthetic sequence SEQ ID NO:218: Amino acid sequence of the light chain variable region of anti-hTfR antibody No. 1

SEQ ID NO:219: Amino acid sequence of the heavy chain variable region of anti-hTfR antibody No. 1

SEQ ID NO:220: Amino acid sequence of the light chain variable region of anti-hTfR antibody No. 2

SEQ ID NO:221: Amino acid sequence of the heavy chain variable region of anti-hTfR antibody No. 2

SEQ ID NO:222: Amino acid sequence of the light chain variable region of anti-hTfR antibody No. 3

SEQ ID NO:223: Amino acid sequence of the heavy chain variable region of anti-hTfR antibody No. 3

SEQ ID NO:224: Amino acid sequence of the light chain variable region of anti-hTfR antibody No. 4

SEQ ID NO:225: Amino acid sequence of the heavy chain variable region of anti-hTfR antibody No. 4

SEQ ID NO:226: Amino acid sequence of the light chain variable region of anti-hTfR antibody No. 5
SEQ ID NO:227: Amino acid sequence of the heavy chain variable region of anti-hTfR antibody No. 5
SEQ ID NO:228: Amino acid sequence of the light chain variable region of anti-hTfR antibody No. 6
SEQ ID NO:229: Amino acid sequence of the heavy chain variable region of anti-hTfR antibody No. 6
SEQ ID NO:230: Amino acid sequence of the light chain variable region of anti-hTfR antibody No. 7
SEQ ID NO:231: Amino acid sequence of the heavy chain variable region of anti-hTfR antibody No. 7
SEQ ID NO:232: Amino acid sequence of the light chain variable region of anti-hTfR antibody No. 8
SEQ ID NO:233: Amino acid sequence of the heavy chain variable region of anti-hTfR antibody No. 8
SEQ ID NO:234: Amino acid sequence of the light chain variable region of anti-hTfR antibody No. 9
SEQ ID NO:235: Amino acid sequence of the heavy chain variable region of anti-hTfR antibody No. 9
SEQ ID NO:236: Amino acid sequence of the light chain variable region of anti-hTfR antibody No. 10
SEQ ID NO:237: Amino acid sequence of the heavy chain variable region of anti-hTfR antibody No. 10
SEQ ID NO:238: Amino acid sequence of the light chain variable region of anti-hTfR antibody No. 11
SEQ ID NO:239: Amino acid sequence of the heavy chain variable region of anti-hTfR antibody No. 11
SEQ ID NO:240: Amino acid sequence of the light chain variable region of anti-hTfR antibody No. 12
SEQ ID NO:241: Amino acid sequence of the heavy chain variable region of anti-hTfR antibody No. 12
SEQ ID NO:242: Amino acid sequence of the light chain variable region of anti-hTfR antibody No. 13
SEQ ID NO:243: Amino acid sequence of the heavy chain variable region of anti-hTfR antibody No. 13
SEQ ID NO:244: Amino acid sequence of the light chain variable region of anti-hTfR antibody No. 14
SEQ ID NO:245: Amino acid sequence of the heavy chain variable region of anti-hTfR antibody No. 14
SEQ ID NO:248: Amino acid sequence of the fusion protein of heavy chain of anti-hTfR antibody No. 1 (humanized 6) and hBDNF
SEQ ID NO:249: Nucleotide sequence encoding the amino acid sequence of fusion protein of heavy chain of anti-hTfR antibody No. 1 (humanized 6) and hBDNF, synthetic sequence
SEQ ID NO:250: Amino acid sequence of the fusion protein of heavy chain of anti-hTfR antibody No. 2 (humanized 6) and hBDNF
SEQ ID NO:251: Nucleotide sequence encoding the amino acid sequence of fusion protein of heavy chain of anti-hTfR antibody No. 2 (humanized 6) and hBDNF, synthetic sequence
SEQ ID NO:252: Amino acid sequence of fusion protein of heavy chain of anti-hTfR antibody No. 3 (humanized 2) and hBDNF, synthetic sequence
SEQ ID NO:253: Nucleotide sequence encoding the amino acid sequence of fusion protein of heavy chain of anti-hTfR antibody No. 3 (humanized 2) and hBDNF, synthetic sequence
SEQ ID NO:254: Amino acid sequence of the fusion protein of heavy chain of anti-hTfR antibody No. 3 (humanized 2) and hBDNF
SEQ ID NO:255: Nucleotide sequence encoding the amino acid sequence of fusion protein of heavy chain of anti-hTfR antibody No. 3 (humanized 2) and hBDNF, synthetic sequence
SEQ ID NO:256: Amino acid sequence of hBDNF pro form
SEQ ID NO:257: Amino acid sequence of anti-hTfR single-chain antibody
SEQ ID NO:258: Nucleotide sequence encoding the amino acid sequence of fusion protein of hBDNF pro form and single-chain anti-hTfR antibody, synthetic sequence
SEQ ID NO:259: Amino acid sequence of fusion protein of hBDNF pro form and single-chain anti-hTfR antibody
SEQ ID NO:260: Amino acid sequence of fusion protein of hBDNF and single-chain anti-hTfR antibody
SEQ ID NO:261: Amino acid sequence of humanized anti-hTfR antibody Fab heavy chain
SEQ ID NO:262: Nucleotide sequence encoding the amino acid sequence of fusion protein of hBDNF pro form and humanized anti-hTfR antibody Fab heavy chain, synthetic sequence
SEQ ID NO:263: Amino acid sequence of fusion protein of hBDNF pro form and humanized anti-hTfR antibody Fab heavy chain
SEQ ID NO:264: Amino acid sequence of fusion protein of hBDNF and humanized anti-hTfR antibody Fab heavy chain
SEQ ID NO:265: Nucleotide sequence encoding the amino acid sequence of fusion protein of hBDNF and humanized anti-hTfR antibody Fab heavy chain, synthetic sequence
SEQ ID NO:266: Amino acid sequence 2 of CDR2 in the heavy chain of mouse anti-hTfR antibody No. 6
SEQ ID NO:267: Amino acid sequence 2 of CDR2 in the heavy chain of mouse anti-hTfR antibody No. 8

SEQUENCE LISTING

```
<160> NUMBER OF SEQ ID NOS: 267

<210> SEQ ID NO 1
<211> LENGTH: 760
<212> TYPE: PRT
<213> ORGANISM: Homo sapiens

<400> SEQUENCE: 1

Met Met Asp Gln Ala Arg Ser Ala Phe Ser Asn Leu Phe Gly Gly Glu
1               5                   10                  15

Pro Leu Ser Tyr Thr Arg Phe Ser Leu Ala Arg Gln Val Asp Gly Asp
            20                  25                  30
```

-continued

```
Asn Ser His Val Glu Met Lys Leu Ala Val Asp Glu Glu Asn Ala
         35                  40                  45
Asp Asn Asn Thr Lys Ala Asn Val Thr Lys Pro Lys Arg Cys Ser Gly
 50                  55                  60
Ser Ile Cys Tyr Gly Thr Ile Ala Val Ile Val Phe Phe Leu Ile Gly
 65                  70                  75                  80
Phe Met Ile Gly Tyr Leu Gly Tyr Cys Lys Gly Val Glu Pro Lys Thr
                 85                  90                  95
Glu Cys Glu Arg Leu Ala Gly Thr Glu Ser Pro Val Arg Glu Glu Pro
             100                 105                 110
Gly Glu Asp Phe Pro Ala Ala Arg Arg Leu Tyr Trp Asp Asp Leu Lys
             115                 120                 125
Arg Lys Leu Ser Glu Lys Leu Asp Ser Thr Asp Phe Thr Gly Thr Ile
         130                 135                 140
Lys Leu Leu Asn Glu Asn Ser Tyr Val Pro Arg Glu Ala Gly Ser Gln
145                 150                 155                 160
Lys Asp Glu Asn Leu Ala Leu Tyr Val Glu Asn Gln Phe Arg Glu Phe
                 165                 170                 175
Lys Leu Ser Lys Val Trp Arg Asp Gln His Phe Val Lys Ile Gln Val
             180                 185                 190
Lys Asp Ser Ala Gln Asn Ser Val Ile Ile Val Asp Lys Asn Gly Arg
             195                 200                 205
Leu Val Tyr Leu Val Glu Asn Pro Gly Gly Tyr Val Ala Tyr Ser Lys
         210                 215                 220
Ala Ala Thr Val Thr Gly Lys Leu Val His Ala Asn Phe Gly Thr Lys
225                 230                 235                 240
Lys Asp Phe Glu Asp Leu Tyr Thr Pro Val Asn Gly Ser Ile Val Ile
                 245                 250                 255
Val Arg Ala Gly Lys Ile Thr Phe Ala Glu Lys Val Ala Asn Ala Glu
             260                 265                 270
Ser Leu Asn Ala Ile Gly Val Leu Ile Tyr Met Asp Gln Thr Lys Phe
         275                 280                 285
Pro Ile Val Asn Ala Glu Leu Ser Phe Phe Gly His Ala His Leu Gly
290                 295                 300
Thr Gly Asp Pro Tyr Thr Pro Gly Phe Pro Ser Phe Asn His Thr Gln
305                 310                 315                 320
Phe Pro Pro Ser Arg Ser Ser Gly Leu Pro Asn Ile Pro Val Gln Thr
                 325                 330                 335
Ile Ser Arg Ala Ala Ala Glu Lys Leu Phe Gly Asn Met Glu Gly Asp
             340                 345                 350
Cys Pro Ser Asp Trp Lys Thr Asp Ser Thr Cys Arg Met Val Thr Ser
             355                 360                 365
Glu Ser Lys Asn Val Lys Leu Thr Val Ser Asn Val Leu Lys Glu Ile
         370                 375                 380
Lys Ile Leu Asn Ile Phe Gly Val Ile Lys Gly Phe Val Glu Pro Asp
385                 390                 395                 400
His Tyr Val Val Val Gly Ala Gln Arg Asp Ala Trp Gly Pro Gly Ala
                 405                 410                 415
Ala Lys Ser Gly Val Gly Thr Ala Leu Leu Lys Leu Ala Gln Met
             420                 425                 430
Phe Ser Asp Met Val Leu Lys Asp Gly Phe Gln Pro Ser Arg Ser Ile
         435                 440                 445
Ile Phe Ala Ser Trp Ser Ala Gly Asp Phe Gly Ser Val Gly Ala Thr
```

```
            450                 455                 460
Glu Trp Leu Glu Gly Tyr Leu Ser Ser Leu His Leu Lys Ala Phe Thr
465                 470                 475                 480

Tyr Ile Asn Leu Asp Lys Ala Val Leu Gly Thr Ser Asn Phe Lys Val
                485                 490                 495

Ser Ala Ser Pro Leu Leu Tyr Thr Leu Ile Glu Lys Thr Met Gln Asn
            500                 505                 510

Val Lys His Pro Val Thr Gly Gln Phe Leu Tyr Gln Asp Ser Asn Trp
        515                 520                 525

Ala Ser Lys Val Glu Lys Leu Thr Leu Asp Asn Ala Ala Phe Pro Phe
    530                 535                 540

Leu Ala Tyr Ser Gly Ile Pro Ala Val Ser Phe Cys Phe Cys Glu Asp
545                 550                 555                 560

Thr Asp Tyr Pro Tyr Leu Gly Thr Thr Met Asp Thr Tyr Lys Glu Leu
                565                 570                 575

Ile Glu Arg Ile Pro Glu Leu Asn Lys Val Ala Arg Ala Ala Ala Glu
            580                 585                 590

Val Ala Gly Gln Phe Val Ile Lys Leu Thr His Asp Val Glu Leu Asn
        595                 600                 605

Leu Asp Tyr Glu Arg Tyr Asn Ser Gln Leu Leu Ser Phe Val Arg Asp
    610                 615                 620

Leu Asn Gln Tyr Arg Ala Asp Ile Lys Glu Met Gly Leu Ser Leu Gln
625                 630                 635                 640

Trp Leu Tyr Ser Ala Arg Gly Asp Phe Phe Arg Ala Thr Ser Arg Leu
                645                 650                 655

Thr Thr Asp Phe Gly Asn Ala Glu Lys Thr Asp Arg Phe Val Met Lys
            660                 665                 670

Lys Leu Asn Asp Arg Val Met Arg Val Glu Tyr His Phe Leu Ser Pro
        675                 680                 685

Tyr Val Ser Pro Lys Glu Ser Pro Phe Arg His Val Phe Trp Gly Ser
    690                 695                 700

Gly Ser His Thr Leu Pro Ala Leu Leu Glu Asn Leu Lys Leu Arg Lys
705                 710                 715                 720

Gln Asn Asn Gly Ala Phe Asn Glu Thr Leu Phe Arg Asn Gln Leu Ala
                725                 730                 735

Leu Ala Thr Trp Thr Ile Gln Gly Ala Ala Asn Ala Leu Ser Gly Asp
            740                 745                 750

Val Trp Asp Ile Asp Asn Glu Phe
        755                 760

<210> SEQ ID NO 2
<211> LENGTH: 760
<212> TYPE: PRT
<213> ORGANISM: Macaca fascicularis

<400> SEQUENCE: 2

Met Met Asp Gln Ala Arg Ser Ala Phe Ser Asn Leu Phe Gly Gly Glu
1               5                   10                  15

Pro Leu Ser Tyr Thr Arg Phe Ser Leu Ala Arg Gln Val Asp Gly Asp
                20                  25                  30

Asn Ser His Val Glu Met Lys Leu Ala Val Asp Glu Glu Asn Ala
            35                  40                  45

Asp Asn Asn Thr Lys Ala Asn Gly Thr Lys Pro Lys Arg Cys Gly Gly
        50                  55                  60
```

-continued

```
Asn Ile Cys Tyr Gly Thr Ile Ala Val Ile Ile Phe Phe Leu Ile Gly
 65                  70                  75                  80

Phe Met Ile Gly Tyr Leu Gly Tyr Cys Lys Gly Val Glu Pro Lys Thr
                 85                  90                  95

Glu Cys Glu Arg Leu Ala Gly Thr Glu Ser Pro Ala Arg Glu Glu Pro
            100                 105                 110

Glu Glu Asp Phe Pro Ala Ala Pro Arg Leu Tyr Trp Asp Asp Leu Lys
        115                 120                 125

Arg Lys Leu Ser Glu Lys Leu Asp Thr Thr Asp Phe Thr Ser Thr Ile
130                 135                 140

Lys Leu Leu Asn Glu Asn Leu Tyr Val Pro Arg Glu Ala Gly Ser Gln
145                 150                 155                 160

Lys Asp Glu Asn Leu Ala Leu Tyr Ile Glu Asn Gln Phe Arg Glu Phe
                165                 170                 175

Lys Leu Ser Lys Val Trp Arg Asp Gln His Phe Val Lys Ile Gln Val
            180                 185                 190

Lys Asp Ser Ala Gln Asn Ser Val Ile Ile Val Asp Lys Asn Gly Gly
        195                 200                 205

Leu Val Tyr Leu Val Glu Asn Pro Gly Gly Tyr Val Ala Tyr Ser Lys
210                 215                 220

Ala Ala Thr Val Thr Gly Lys Leu Val His Ala Asn Phe Gly Thr Lys
225                 230                 235                 240

Lys Asp Phe Glu Asp Leu Asp Ser Pro Val Asn Gly Ser Ile Val Ile
                245                 250                 255

Val Arg Ala Gly Lys Ile Thr Phe Ala Glu Lys Val Ala Asn Ala Glu
            260                 265                 270

Ser Leu Asn Ala Ile Gly Val Leu Ile Tyr Met Asp Gln Thr Lys Phe
        275                 280                 285

Pro Ile Val Lys Ala Asp Leu Ser Phe Phe Gly His Ala His Leu Gly
290                 295                 300

Thr Gly Asp Pro Tyr Thr Pro Gly Phe Pro Ser Phe Asn His Thr Gln
305                 310                 315                 320

Phe Pro Pro Ser Gln Ser Ser Gly Leu Pro Asn Ile Pro Val Gln Thr
                325                 330                 335

Ile Ser Arg Ala Ala Ala Glu Lys Leu Phe Gly Asn Met Glu Gly Asp
            340                 345                 350

Cys Pro Ser Asp Trp Lys Thr Asp Ser Thr Cys Lys Met Val Thr Ser
        355                 360                 365

Glu Asn Lys Ser Val Lys Leu Thr Val Ser Asn Val Leu Lys Glu Thr
370                 375                 380

Lys Ile Leu Asn Ile Phe Gly Val Ile Lys Gly Phe Val Glu Pro Asp
385                 390                 395                 400

His Tyr Val Val Val Gly Ala Gln Arg Asp Ala Trp Gly Pro Gly Ala
                405                 410                 415

Ala Lys Ser Ser Val Gly Thr Ala Leu Leu Leu Lys Leu Ala Gln Met
            420                 425                 430

Phe Ser Asp Met Val Leu Lys Asp Gly Phe Gln Pro Ser Arg Ser Ile
        435                 440                 445

Ile Phe Ala Ser Trp Ser Ala Gly Asp Phe Gly Ser Val Gly Ala Thr
450                 455                 460

Glu Trp Leu Glu Gly Tyr Leu Ser Ser Leu His Leu Lys Ala Phe Thr
465                 470                 475                 480

Tyr Ile Asn Leu Asp Lys Ala Val Leu Gly Thr Ser Asn Phe Lys Val
```

```
                485                 490                 495
Ser Ala Ser Pro Leu Leu Tyr Thr Leu Ile Glu Lys Thr Met Gln Asp
            500                 505                 510

Val Lys His Pro Val Thr Gly Arg Ser Leu Tyr Gln Asp Ser Asn Trp
            515                 520                 525

Ala Ser Lys Val Glu Lys Leu Thr Leu Asp Asn Ala Ala Phe Pro Phe
            530                 535                 540

Leu Ala Tyr Ser Gly Ile Pro Ala Val Ser Phe Cys Phe Cys Glu Asp
545                 550                 555                 560

Thr Asp Tyr Pro Tyr Leu Gly Thr Thr Met Asp Thr Tyr Lys Glu Leu
                565                 570                 575

Val Glu Arg Ile Pro Glu Leu Asn Lys Val Ala Arg Ala Ala Ala Glu
            580                 585                 590

Val Ala Gly Gln Phe Val Ile Lys Leu Thr His Asp Thr Glu Leu Asn
            595                 600                 605

Leu Asp Tyr Glu Arg Tyr Asn Ser Gln Leu Leu Leu Phe Leu Arg Asp
            610                 615                 620

Leu Asn Gln Tyr Arg Ala Asp Val Lys Glu Met Gly Leu Ser Leu Gln
625                 630                 635                 640

Trp Leu Tyr Ser Ala Arg Gly Asp Phe Phe Arg Ala Thr Ser Arg Leu
                645                 650                 655

Thr Thr Asp Phe Arg Asn Ala Glu Lys Arg Asp Lys Phe Val Met Lys
            660                 665                 670

Lys Leu Asn Asp Arg Val Met Arg Val Glu Tyr Tyr Phe Leu Ser Pro
            675                 680                 685

Tyr Val Ser Pro Lys Glu Ser Pro Phe Arg His Val Phe Trp Gly Ser
            690                 695                 700

Gly Ser His Thr Leu Ser Ala Leu Leu Glu Ser Leu Lys Leu Arg Arg
705                 710                 715                 720

Gln Asn Asn Ser Ala Phe Asn Glu Thr Leu Phe Arg Asn Gln Leu Ala
                725                 730                 735

Leu Ala Thr Trp Thr Ile Gln Gly Ala Ala Asn Ala Leu Ser Gly Asp
            740                 745                 750

Val Trp Asp Ile Asp Asn Glu Phe
            755                 760

<210> SEQ ID NO 3
<211> LENGTH: 5
<212> TYPE: PRT
<213> ORGANISM: Artificial Sequence
<220> FEATURE:
<223> OTHER INFORMATION: Amino acid sequence of exemplified linker 1

<400> SEQUENCE: 3

Gly Gly Gly Gly Ser
1               5

<210> SEQ ID NO 4
<211> LENGTH: 6
<212> TYPE: PRT
<213> ORGANISM: Artificial Sequence
<220> FEATURE:
<223> OTHER INFORMATION: Amino acid sequence of exemplified linker 2

<400> SEQUENCE: 4

Gly Gly Gly Gly Gly Ser
1               5
```

<210> SEQ ID NO 5
<211> LENGTH: 5
<212> TYPE: PRT
<213> ORGANISM: Artificial Sequence
<220> FEATURE:
<223> OTHER INFORMATION: Amino acid sequence of exemplified linker 3

<400> SEQUENCE: 5

Ser Gly Gly Gly Gly
1               5

<210> SEQ ID NO 6
<211> LENGTH: 6
<212> TYPE: PRT
<213> ORGANISM: Artificial Sequence
<220> FEATURE:
<223> OTHER INFORMATION: Amino acid sequence 1 of CDR 1 in the light
      chain of mouse anti-hTfR antibody No.1

<400> SEQUENCE: 6

Gln Asp Val Asn Ser Ala
1               5

<210> SEQ ID NO 7
<211> LENGTH: 11
<212> TYPE: PRT
<213> ORGANISM: Artificial Sequence
<220> FEATURE:
<223> OTHER INFORMATION: Amino acid sequence 2 of CDR 1 in the light
      chain of mouse anti-hTfR antibody No.1

<400> SEQUENCE: 7

Lys Ala Ser Gln Asp Val Asn Ser Ala Val Ala
1               5                   10

<210> SEQ ID NO 8
<211> LENGTH: 6
<212> TYPE: PRT
<213> ORGANISM: Artificial Sequence
<220> FEATURE:
<223> OTHER INFORMATION: Amino acid sequence 1 of CDR 2 in the light
      chain of mouse anti-hTfR antibody No.1

<400> SEQUENCE: 8

Trp Thr Ser Thr Arg His
1               5

<210> SEQ ID NO 9
<211> LENGTH: 7
<212> TYPE: PRT
<213> ORGANISM: Artificial Sequence
<220> FEATURE:
<223> OTHER INFORMATION: Amino acid sequence 2 of CDR 2 in the light
      chain of mouse anti-hTfR antibody No.1

<400> SEQUENCE: 9

Trp Thr Ser Thr Arg His Thr
1               5

<210> SEQ ID NO 10
<211> LENGTH: 9
<212> TYPE: PRT
<213> ORGANISM: Artificial Sequence
<220> FEATURE:
<223> OTHER INFORMATION: Amino acid sequence of CDR 3 in the light chain
      of mouse anti-hTfR antibody No.1

<400> SEQUENCE: 10

```
Gln Gln His Tyr Ser Thr Pro Arg Thr
1               5

<210> SEQ ID NO 11
<211> LENGTH: 6
<212> TYPE: PRT
<213> ORGANISM: Artificial Sequence
<220> FEATURE:
<223> OTHER INFORMATION: Amino acid sequence 1 of CDR 1 in the light
      chain of mouse anti-hTfR antibody No.2

<400> SEQUENCE: 11

Gln Ser Ile Ser Asn Asn
1               5

<210> SEQ ID NO 12
<211> LENGTH: 11
<212> TYPE: PRT
<213> ORGANISM: Artificial Sequence
<220> FEATURE:
<223> OTHER INFORMATION: Amino acid sequence 2 of CDR 1 in the light
      chain of mouse anti-hTfR antibody No.2

<400> SEQUENCE: 12

Arg Ala Ser Gln Ser Ile Ser Asn Asn Leu Gln
1               5                   10

<210> SEQ ID NO 13
<211> LENGTH: 6
<212> TYPE: PRT
<213> ORGANISM: Artificial Sequence
<220> FEATURE:
<223> OTHER INFORMATION: Amino acid sequence 1 of CDR 2 in the light
      chain of mouse anti-hTfR antibody No.2

<400> SEQUENCE: 13

Tyr Ala Ser Gln Ser Ile
1               5

<210> SEQ ID NO 14
<211> LENGTH: 7
<212> TYPE: PRT
<213> ORGANISM: Artificial Sequence
<220> FEATURE:
<223> OTHER INFORMATION: Amino acid sequence 2 of CDR 2 in the light
      chain of mouse anti-hTfR antibody No.2

<400> SEQUENCE: 14

Tyr Ala Ser Gln Ser Ile Ser
1               5

<210> SEQ ID NO 15
<211> LENGTH: 9
<212> TYPE: PRT
<213> ORGANISM: Artificial Sequence
<220> FEATURE:
<223> OTHER INFORMATION: Amino acid sequence of CDR 3 in the light chain
      of mouse anti-hTfR antibody No.2

<400> SEQUENCE: 15

Gln Gln Ser Asn Ser Trp Pro Arg Thr
1               5

<210> SEQ ID NO 16
<211> LENGTH: 11
<212> TYPE: PRT
<213> ORGANISM: Artificial Sequence
```

```
<220> FEATURE:
<223> OTHER INFORMATION: Amino acid sequence 1 of CDR 1 in the light
      chain of mouse anti-hTfR antibody No.3

<400> SEQUENCE: 16

Gln Ser Leu Val His Ser Asn Gly Asn Thr Tyr
1               5                   10

<210> SEQ ID NO 17
<211> LENGTH: 16
<212> TYPE: PRT
<213> ORGANISM: Artificial Sequence
<220> FEATURE:
<223> OTHER INFORMATION: Amino acid sequence 2 of CDR 1 in the light
      chain of mouse anti-hTfR antibody No.3

<400> SEQUENCE: 17

Arg Ser Ser Gln Ser Leu Val His Ser Asn Gly Asn Thr Tyr Leu His
1               5                   10                  15

<210> SEQ ID NO 18
<211> LENGTH: 6
<212> TYPE: PRT
<213> ORGANISM: Artificial Sequence
<220> FEATURE:
<223> OTHER INFORMATION: Amino acid sequence 1 of CDR 2 in the light
      chain of mouse anti-hTfR antibody No.3

<400> SEQUENCE: 18

Lys Val Ser Asn Arg Phe
1               5

<210> SEQ ID NO 19
<211> LENGTH: 7
<212> TYPE: PRT
<213> ORGANISM: Artificial Sequence
<220> FEATURE:
<223> OTHER INFORMATION: Amino acid sequence 2 of CDR 2 in the light
      chain of mouse anti-hTfR antibody No.3

<400> SEQUENCE: 19

Lys Val Ser Asn Arg Phe Ser
1               5

<210> SEQ ID NO 20
<211> LENGTH: 9
<212> TYPE: PRT
<213> ORGANISM: Artificial Sequence
<220> FEATURE:
<223> OTHER INFORMATION: Amino acid sequence of CDR 3 in the light chain
      of mouse anti-hTfR antibody No.3

<400> SEQUENCE: 20

Ser Gln Ser Thr His Val Pro Trp Thr
1               5

<210> SEQ ID NO 21
<211> LENGTH: 5
<212> TYPE: PRT
<213> ORGANISM: Artificial Sequence
<220> FEATURE:
<223> OTHER INFORMATION: Amino acid sequence 1 of CDR 1 in the light
      chain of mouse anti-hTfR antibody No.4

<400> SEQUENCE: 21

Ser Asn Val Asn Tyr
1               5
```

<210> SEQ ID NO 22
<211> LENGTH: 10
<212> TYPE: PRT
<213> ORGANISM: Artificial Sequence
<220> FEATURE:
<223> OTHER INFORMATION: Amino acid sequence 2 of CDR 1 in the light
      chain of mouse anti-hTfR antibody No.4

<400> SEQUENCE: 22

Ser Ala Ser Ser Asn Val Asn Tyr Met His
1               5                   10

<210> SEQ ID NO 23
<211> LENGTH: 6
<212> TYPE: PRT
<213> ORGANISM: Artificial Sequence
<220> FEATURE:
<223> OTHER INFORMATION: Amino acid sequence 1 of CDR 2 in the light
      chain of mouse anti-hTfR antibody No.4

<400> SEQUENCE: 23

Asp Thr Ser Lys Leu Ala
1               5

<210> SEQ ID NO 24
<211> LENGTH: 7
<212> TYPE: PRT
<213> ORGANISM: Artificial Sequence
<220> FEATURE:
<223> OTHER INFORMATION: Amino acid sequence 2 of CDR 2 in the light
      chain of mouse anti-hTfR antibody No.4

<400> SEQUENCE: 24

Asp Thr Ser Lys Leu Ala Ser
1               5

<210> SEQ ID NO 25
<211> LENGTH: 9
<212> TYPE: PRT
<213> ORGANISM: Artificial Sequence
<220> FEATURE:
<223> OTHER INFORMATION: Amino acid sequence of CDR 3 in the light chain
      of mouse anti-hTfR antibody No.4

<400> SEQUENCE: 25

Phe Gln Gly Asn Gly Asn Pro Tyr Thr
1               5

<210> SEQ ID NO 26
<211> LENGTH: 5
<212> TYPE: PRT
<213> ORGANISM: Artificial Sequence
<220> FEATURE:
<223> OTHER INFORMATION: Amino acid sequence 1 of CDR 1 in the light
      chain of mouse anti-hTfR antibody No.5

<400> SEQUENCE: 26

Ser Ser Ile Ser Ser
1               5

<210> SEQ ID NO 27
<211> LENGTH: 10
<212> TYPE: PRT
<213> ORGANISM: Artificial Sequence
<220> FEATURE:
<223> OTHER INFORMATION: Amino acid sequence 2 of CDR 1 in the light
      chain of mouse anti-hTfR antibody No.5

```
<400> SEQUENCE: 27

Ser Ala Ser Ser Ser Ile Ser Ser Ile His
1               5                   10

<210> SEQ ID NO 28
<211> LENGTH: 6
<212> TYPE: PRT
<213> ORGANISM: Artificial Sequence
<220> FEATURE:
<223> OTHER INFORMATION: Amino acid sequence 1 of CDR 2 in the light
      chain of mouse anti-hTfR antibody No.5

<400> SEQUENCE: 28

Asp Thr Ser Thr Leu Ala
1               5

<210> SEQ ID NO 29
<211> LENGTH: 7
<212> TYPE: PRT
<213> ORGANISM: Artificial Sequence
<220> FEATURE:
<223> OTHER INFORMATION: Amino acid sequence 2 of CDR 2 in the light
      chain of mouse anti-hTfR antibody No.5

<400> SEQUENCE: 29

Asp Thr Ser Thr Leu Ala Ser
1               5

<210> SEQ ID NO 30
<211> LENGTH: 8
<212> TYPE: PRT
<213> ORGANISM: Artificial Sequence
<220> FEATURE:
<223> OTHER INFORMATION: Amino acid sequence of CDR 3 in the light chain
      of mouse anti-hTfR antibody No.5

<400> SEQUENCE: 30

His Gln Arg Ser Ser Tyr Pro Thr
1               5

<210> SEQ ID NO 31
<211> LENGTH: 6
<212> TYPE: PRT
<213> ORGANISM: Artificial Sequence
<220> FEATURE:
<223> OTHER INFORMATION: Amino acid sequence 1 of CDR 1 in the light
      chain of mouse anti-hTfR antibody No.6

<400> SEQUENCE: 31

Gln Glu Ile Ser Gly Tyr
1               5

<210> SEQ ID NO 32
<211> LENGTH: 11
<212> TYPE: PRT
<213> ORGANISM: Artificial Sequence
<220> FEATURE:
<223> OTHER INFORMATION: Amino acid sequence 2 of CDR 1 in the light
      chain of mouse anti-hTfR antibody No.6

<400> SEQUENCE: 32

Arg Ala Ser Gln Glu Ile Ser Gly Tyr Leu Ser
1               5                   10

<210> SEQ ID NO 33
<211> LENGTH: 6
<212> TYPE: PRT
```

```
<213> ORGANISM: Artificial Sequence
<220> FEATURE:
<223> OTHER INFORMATION: Amino acid sequence 1 of CDR 2 in the light
      chain of mouse anti-hTfR antibody No.6

<400> SEQUENCE: 33

Ala Ala Ser Thr Leu Asp
1               5

<210> SEQ ID NO 34
<211> LENGTH: 7
<212> TYPE: PRT
<213> ORGANISM: Artificial Sequence
<220> FEATURE:
<223> OTHER INFORMATION: Amino acid sequence 2 of CDR 2 in the light
      chain of mouse anti-hTfR antibody No.6

<400> SEQUENCE: 34

Ala Ala Ser Thr Leu Asp Ser
1               5

<210> SEQ ID NO 35
<211> LENGTH: 9
<212> TYPE: PRT
<213> ORGANISM: Artificial Sequence
<220> FEATURE:
<223> OTHER INFORMATION: Amino acid sequence of CDR 3 in the light chain
      of mouse anti-hTfR antibody No.6

<400> SEQUENCE: 35

Leu Gln Tyr Ser Ser Tyr Pro Arg Thr
1               5

<210> SEQ ID NO 36
<211> LENGTH: 5
<212> TYPE: PRT
<213> ORGANISM: Artificial Sequence
<220> FEATURE:
<223> OTHER INFORMATION: Amino acid sequence 1 of CDR 1 in the light
      chain of mouse anti-hTfR antibody No.7

<400> SEQUENCE: 36

Ser Ser Val Asn Tyr
1               5

<210> SEQ ID NO 37
<211> LENGTH: 10
<212> TYPE: PRT
<213> ORGANISM: Artificial Sequence
<220> FEATURE:
<223> OTHER INFORMATION: Amino acid sequence 2 of CDR 1 in the light
      chain of mouse anti-hTfR antibody No.7

<400> SEQUENCE: 37

Ser Ala Ser Ser Ser Val Asn Tyr Ile His
1               5                   10

<210> SEQ ID NO 38
<211> LENGTH: 6
<212> TYPE: PRT
<213> ORGANISM: Artificial Sequence
<220> FEATURE:
<223> OTHER INFORMATION: Amino acid sequence 1 of CDR 2 in the light
      chain of mouse anti-hTfR antibody No.7

<400> SEQUENCE: 38

Gln Thr Ser Asn Leu Ala
1               5
```

<210> SEQ ID NO 39
<211> LENGTH: 7
<212> TYPE: PRT
<213> ORGANISM: Artificial Sequence
<220> FEATURE:
<223> OTHER INFORMATION: Amino acid sequence 2 of CDR 2 in the light
      chain of mouse anti-hTfR antibody No.7

<400> SEQUENCE: 39

Gln Thr Ser Asn Leu Ala Ser
1               5

<210> SEQ ID NO 40
<211> LENGTH: 9
<212> TYPE: PRT
<213> ORGANISM: Artificial Sequence
<220> FEATURE:
<223> OTHER INFORMATION: Amino acid sequence of CDR 3 in the light chain
      of mouse anti-hTfR antibody No.7

<400> SEQUENCE: 40

His Gln Trp Ser Ser Tyr Pro Trp Thr
1               5

<210> SEQ ID NO 41
<211> LENGTH: 5
<212> TYPE: PRT
<213> ORGANISM: Artificial Sequence
<220> FEATURE:
<223> OTHER INFORMATION: Amino acid sequence 1 of CDR 1 in the light
      chain of mouse anti-hTfR antibody No.8

<400> SEQUENCE: 41

Ser Ser Val Ser Tyr
1               5

<210> SEQ ID NO 42
<211> LENGTH: 10
<212> TYPE: PRT
<213> ORGANISM: Artificial Sequence
<220> FEATURE:
<223> OTHER INFORMATION: Amino acid sequence 2 of CDR 1 in the light
      chain of mouse anti-hTfR antibody No.8

<400> SEQUENCE: 42

Ser Ala Ser Ser Ser Val Ser Tyr Met His
1               5                   10

<210> SEQ ID NO 43
<211> LENGTH: 6
<212> TYPE: PRT
<213> ORGANISM: Artificial Sequence
<220> FEATURE:
<223> OTHER INFORMATION: Amino acid sequence 1 of CDR 2 in the light
      chain of mouse anti-hTfR antibody No.8

<400> SEQUENCE: 43

Gly Thr Ser Asn Leu Ala
1               5

<210> SEQ ID NO 44
<211> LENGTH: 7
<212> TYPE: PRT
<213> ORGANISM: Artificial Sequence
<220> FEATURE:
<223> OTHER INFORMATION: Amino acid sequence 2 of CDR 2 in the light
      chain of mouse anti-hTfR antibody No.8

```
<400> SEQUENCE: 44

Gly Thr Ser Asn Leu Ala Ser
1               5

<210> SEQ ID NO 45
<211> LENGTH: 9
<212> TYPE: PRT
<213> ORGANISM: Artificial Sequence
<220> FEATURE:
<223> OTHER INFORMATION: Amino acid sequence of CDR 3 in the light chain
      of mouse anti-hTfR antibody No.8

<400> SEQUENCE: 45

His Gln Trp Ser Ser Tyr Pro Trp Thr
1               5

<210> SEQ ID NO 46
<211> LENGTH: 5
<212> TYPE: PRT
<213> ORGANISM: Artificial Sequence
<220> FEATURE:
<223> OTHER INFORMATION: Amino acid sequence 1 of CDR 1 in the light
      chain of mouse anti-hTfR antibody No.9

<400> SEQUENCE: 46

Ser Ser Val Ser Leu
1               5

<210> SEQ ID NO 47
<211> LENGTH: 10
<212> TYPE: PRT
<213> ORGANISM: Artificial Sequence
<220> FEATURE:
<223> OTHER INFORMATION: Amino acid sequence 2 of CDR 1 in the light
      chain of mouse anti-hTfR antibody No.9

<400> SEQUENCE: 47

Ser Ala Ser Ser Ser Val Ser Leu Met Phe
1               5                   10

<210> SEQ ID NO 48
<211> LENGTH: 6
<212> TYPE: PRT
<213> ORGANISM: Artificial Sequence
<220> FEATURE:
<223> OTHER INFORMATION: Amino acid sequence 1 of CDR 2 in the light
      chain of mouse anti-hTfR antibody No.9

<400> SEQUENCE: 48

Phe Thr Ser Tyr Arg Ala
1               5

<210> SEQ ID NO 49
<211> LENGTH: 7
<212> TYPE: PRT
<213> ORGANISM: Artificial Sequence
<220> FEATURE:
<223> OTHER INFORMATION: Amino acid sequence 2 of CDR 2 in the light
      chain of mouse anti-hTfR antibody No.9

<400> SEQUENCE: 49

Phe Thr Ser Tyr Arg Ala Ser
1               5

<210> SEQ ID NO 50
<211> LENGTH: 9
```

-continued

```
<212> TYPE: PRT
<213> ORGANISM: Artificial Sequence
<220> FEATURE:
<223> OTHER INFORMATION: Amino acid sequence of CDR 3 in the light chain
      of mouse anti-hTfR antibody No.9

<400> SEQUENCE: 50

Gln Gln Trp Thr Ser Asp Pro Pro Thr
1               5

<210> SEQ ID NO 51
<211> LENGTH: 6
<212> TYPE: PRT
<213> ORGANISM: Artificial Sequence
<220> FEATURE:
<223> OTHER INFORMATION: Amino acid sequence 1 of CDR 1 in the light
      chain of mouse anti-hTfR antibody No.10

<400> SEQUENCE: 51

Gln Glu Ile Ser Gly Tyr
1               5

<210> SEQ ID NO 52
<211> LENGTH: 11
<212> TYPE: PRT
<213> ORGANISM: Artificial Sequence
<220> FEATURE:
<223> OTHER INFORMATION: Amino acid sequence 2 of CDR 1 in the light
      chain of mouse anti-hTfR antibody No.10

<400> SEQUENCE: 52

Arg Pro Ser Gln Glu Ile Ser Gly Tyr Leu Ser
1               5                   10

<210> SEQ ID NO 53
<211> LENGTH: 6
<212> TYPE: PRT
<213> ORGANISM: Artificial Sequence
<220> FEATURE:
<223> OTHER INFORMATION: Amino acid sequence 1 of CDR 2 in the light
      chain of mouse anti-hTfR antibody No.10

<400> SEQUENCE: 53

Ala Ala Ser Thr Leu Asp
1               5

<210> SEQ ID NO 54
<211> LENGTH: 7
<212> TYPE: PRT
<213> ORGANISM: Artificial Sequence
<220> FEATURE:
<223> OTHER INFORMATION: Amino acid sequence 2 of CDR 2 in the light
      chain of mouse anti-hTfR antibody No.10

<400> SEQUENCE: 54

Ala Ala Ser Thr Leu Asp Ser
1               5

<210> SEQ ID NO 55
<211> LENGTH: 9
<212> TYPE: PRT
<213> ORGANISM: Artificial Sequence
<220> FEATURE:
<223> OTHER INFORMATION: Amino acid sequence of CDR 3 in the light chain
      of mouse anti-hTfR antibody No.10

<400> SEQUENCE: 55

Leu Gln Tyr Ala Ser Tyr Pro Arg Thr
```

<210> SEQ ID NO 56
<211> LENGTH: 6
<212> TYPE: PRT
<213> ORGANISM: Artificial Sequence
<220> FEATURE:
<223> OTHER INFORMATION: Amino acid sequence 1 of CDR 1 in the light
      chain of mouse anti-hTfR antibody No.11

<400> SEQUENCE: 56

Gln Ser Ile Arg Asn Tyr
1               5

<210> SEQ ID NO 57
<211> LENGTH: 11
<212> TYPE: PRT
<213> ORGANISM: Artificial Sequence
<220> FEATURE:
<223> OTHER INFORMATION: Amino acid sequence 2 of CDR 1 in the light
      chain of mouse anti-hTfR antibody No.11

<400> SEQUENCE: 57

Arg Ala Ser Gln Ser Ile Arg Asn Tyr Leu His
1               5                   10

<210> SEQ ID NO 58
<211> LENGTH: 6
<212> TYPE: PRT
<213> ORGANISM: Artificial Sequence
<220> FEATURE:
<223> OTHER INFORMATION: Amino acid sequence 1 of CDR 2 in the light
      chain of mouse anti-hTfR antibody No.11

<400> SEQUENCE: 58

Tyr Ala Ser Gln Ser Ile
1               5

<210> SEQ ID NO 59
<211> LENGTH: 7
<212> TYPE: PRT
<213> ORGANISM: Artificial Sequence
<220> FEATURE:
<223> OTHER INFORMATION: Amino acid sequence 2 of CDR 2 in the light
      chain of mouse anti-hTfR antibody No.11

<400> SEQUENCE: 59

Tyr Ala Ser Gln Ser Ile Ser
1               5

<210> SEQ ID NO 60
<211> LENGTH: 9
<212> TYPE: PRT
<213> ORGANISM: Artificial Sequence
<220> FEATURE:
<223> OTHER INFORMATION: Amino acid sequence of CDR 3 in the light chain
      of mouse anti-hTfR antibody No.11

<400> SEQUENCE: 60

Gln Gln Thr Asn Ser Trp Pro Tyr Thr
1               5

<210> SEQ ID NO 61
<211> LENGTH: 6
<212> TYPE: PRT
<213> ORGANISM: Artificial Sequence
<220> FEATURE:
<223> OTHER INFORMATION: Amino acid sequence 1 of CDR 1 in the light chain of mouse anti-hTfR antibody No.12

<400> SEQUENCE: 61

His Asp Val Lys Thr Ala
1               5

<210> SEQ ID NO 62
<211> LENGTH: 11
<212> TYPE: PRT
<213> ORGANISM: Artificial Sequence
<220> FEATURE:
<223> OTHER INFORMATION: Amino acid sequence 2 of CDR 1 in the light
      chain of mouse anti-hTfR antibody No.12

<400> SEQUENCE: 62

Lys Ala Ser His Asp Val Lys Thr Ala Val Ala
1               5                   10

<210> SEQ ID NO 63
<211> LENGTH: 6
<212> TYPE: PRT
<213> ORGANISM: Artificial Sequence
<220> FEATURE:
<223> OTHER INFORMATION: Amino acid sequence 1 of CDR 2 in the light
      chain of mouse anti-hTfR antibody No.12

<400> SEQUENCE: 63

Trp Ser Ser Thr Arg His
1               5

<210> SEQ ID NO 64
<211> LENGTH: 7
<212> TYPE: PRT
<213> ORGANISM: Artificial Sequence
<220> FEATURE:
<223> OTHER INFORMATION: Amino acid sequence 2 of CDR 2 in the light
      chain of mouse anti-hTfR antibody No.12

<400> SEQUENCE: 64

Trp Ser Ser Thr Arg His Thr
1               5

<210> SEQ ID NO 65
<211> LENGTH: 9
<212> TYPE: PRT
<213> ORGANISM: Artificial Sequence
<220> FEATURE:
<223> OTHER INFORMATION: Amino acid sequence of CDR 3 in the light chain
      of mouse anti-hTfR antibody No.12

<400> SEQUENCE: 65

Gln Gln His Phe Ser Thr Pro Leu Thr
1               5

<210> SEQ ID NO 66
<211> LENGTH: 6
<212> TYPE: PRT
<213> ORGANISM: Artificial Sequence
<220> FEATURE:
<223> OTHER INFORMATION: Amino acid sequence 1 of CDR 1 in the light
      chain of mouse anti-hTfR antibody No.13

<400> SEQUENCE: 66

Gln Ser Ile Arg Asn Tyr
1               5

<210> SEQ ID NO 67

```
<211> LENGTH: 11
<212> TYPE: PRT
<213> ORGANISM: Artificial Sequence
<220> FEATURE:
<223> OTHER INFORMATION: Amino acid sequence 2 of CDR 1 in the light
      chain of mouse anti-hTfR antibody No.13

<400> SEQUENCE: 67

Arg Ala Ser Gln Ser Ile Arg Asn Tyr Leu His
1               5                   10

<210> SEQ ID NO 68
<211> LENGTH: 6
<212> TYPE: PRT
<213> ORGANISM: Artificial Sequence
<220> FEATURE:
<223> OTHER INFORMATION: Amino acid sequence 1 of CDR 2 in the light
      chain of mouse anti-hTfR antibody No.13

<400> SEQUENCE: 68

Tyr Ala Ser Gln Ser Ile
1               5

<210> SEQ ID NO 69
<211> LENGTH: 7
<212> TYPE: PRT
<213> ORGANISM: Artificial Sequence
<220> FEATURE:
<223> OTHER INFORMATION: Amino acid sequence 2 of CDR 2 in the light
      chain of mouse anti-hTfR antibody No.13

<400> SEQUENCE: 69

Tyr Ala Ser Gln Ser Ile Ser
1               5

<210> SEQ ID NO 70
<211> LENGTH: 9
<212> TYPE: PRT
<213> ORGANISM: Artificial Sequence
<220> FEATURE:
<223> OTHER INFORMATION: Amino acid sequence of CDR 3 in the light chain
      of mouse anti-hTfR antibody No.13

<400> SEQUENCE: 70

Gln Gln Thr Asn Ser Trp Pro Tyr Thr
1               5

<210> SEQ ID NO 71
<211> LENGTH: 5
<212> TYPE: PRT
<213> ORGANISM: Artificial Sequence
<220> FEATURE:
<223> OTHER INFORMATION: Amino acid sequence 1 of CDR 1 in the light
      chain of mouse anti-hTfR antibody No.14

<400> SEQUENCE: 71

Ser Asn Ile Asn Ser
1               5

<210> SEQ ID NO 72
<211> LENGTH: 10
<212> TYPE: PRT
<213> ORGANISM: Artificial Sequence
<220> FEATURE:
<223> OTHER INFORMATION: Amino acid sequence 2 of CDR 1 in the light
      chain of mouse anti-hTfR antibody No.14

<400> SEQUENCE: 72
```

Ser Ala Ser Ser Asn Ile Asn Ser Ile His
1               5                   10

<210> SEQ ID NO 73
<211> LENGTH: 6
<212> TYPE: PRT
<213> ORGANISM: Artificial Sequence
<220> FEATURE:
<223> OTHER INFORMATION: Amino acid sequence 1 of CDR 2 in the light
      chain of mouse anti-hTfR antibody No.14

<400> SEQUENCE: 73

Asp Thr Ser Asn Leu Ala
1               5

<210> SEQ ID NO 74
<211> LENGTH: 7
<212> TYPE: PRT
<213> ORGANISM: Artificial Sequence
<220> FEATURE:
<223> OTHER INFORMATION: Amino acid sequence 2 of CDR 2 in the light
      chain of mouse anti-hTfR antibody No.14

<400> SEQUENCE: 74

Asp Thr Ser Asn Leu Ala Ser
1               5

<210> SEQ ID NO 75
<211> LENGTH: 9
<212> TYPE: PRT
<213> ORGANISM: Artificial Sequence
<220> FEATURE:
<223> OTHER INFORMATION: Amino acid sequence of CDR 3 in the light chain
      of mouse anti-hTfR antibody No.14

<400> SEQUENCE: 75

His Gln Arg Ser Gly Tyr Pro Phe Thr
1               5

<210> SEQ ID NO 76
<211> LENGTH: 5
<212> TYPE: PRT
<213> ORGANISM: Artificial Sequence
<220> FEATURE:
<223> OTHER INFORMATION: Amino acid sequence 1 of CDR 1 in the heavy
      chain of mouse anti-hTfR antibody No.1

<400> SEQUENCE: 76

Asn Tyr Gly Met Ser
1               5

<210> SEQ ID NO 77
<211> LENGTH: 8
<212> TYPE: PRT
<213> ORGANISM: Artificial Sequence
<220> FEATURE:
<223> OTHER INFORMATION: Amino acid sequence 2 of CDR 1 in the heavy
      chain of mouse anti-hTfR antibody No.1

<400> SEQUENCE: 77

Gly Leu Thr Phe Ser Asn Tyr Gly
1               5

<210> SEQ ID NO 78
<211> LENGTH: 8
<212> TYPE: PRT
<213> ORGANISM: Artificial Sequence
<220> FEATURE:

<223> OTHER INFORMATION: Amino acid sequence 1 of CDR 2 in the heavy
      chain of mouse anti-hTfR antibody No.1

<400> SEQUENCE: 78

Ile Asn Thr Asn Gly Gly Ser Thr
1               5

<210> SEQ ID NO 79
<211> LENGTH: 17
<212> TYPE: PRT
<213> ORGANISM: Artificial Sequence
<220> FEATURE:
<223> OTHER INFORMATION: Amino acid sequence 2 of CDR 2 in the heavy
      chain of mouse anti-hTfR antibody No.1

<400> SEQUENCE: 79

Asn Ile Asn Thr Asn Gly Gly Ser Thr Tyr Tyr Pro Asp Ser Val Lys
1               5                   10                  15
Gly

<210> SEQ ID NO 80
<211> LENGTH: 7
<212> TYPE: PRT
<213> ORGANISM: Artificial Sequence
<220> FEATURE:
<223> OTHER INFORMATION: Amino acid sequence 1 of CDR 3 in the heavy
      chain of mouse anti-hTfR antibody No.1

<400> SEQUENCE: 80

Asn Arg Tyr Asp Glu Asp Tyr
1               5

<210> SEQ ID NO 81
<211> LENGTH: 9
<212> TYPE: PRT
<213> ORGANISM: Artificial Sequence
<220> FEATURE:
<223> OTHER INFORMATION: Amino acid sequence 2 of CDR 3 in the heavy
      chain of mouse anti-hTfR antibody No.1

<400> SEQUENCE: 81

Thr Asn Asn Arg Tyr Asp Glu Asp Tyr
1               5

<210> SEQ ID NO 82
<211> LENGTH: 5
<212> TYPE: PRT
<213> ORGANISM: Artificial Sequence
<220> FEATURE:
<223> OTHER INFORMATION: Amino acid sequence 1 of CDR 1in the heavy
      chain of mouse anti-hTfR antibody No.2

<400> SEQUENCE: 82

Asp Tyr Val Met His
1               5

<210> SEQ ID NO 83
<211> LENGTH: 8
<212> TYPE: PRT
<213> ORGANISM: Artificial Sequence
<220> FEATURE:
<223> OTHER INFORMATION: Amino acid sequence 2 of CDR 1 in the heavy
      chain of mouse anti-hTfR antibody No.2

<400> SEQUENCE: 83

Gly Tyr Thr Phe Thr Asp Tyr Val
1               5

<210> SEQ ID NO 84
<211> LENGTH: 8
<212> TYPE: PRT
<213> ORGANISM: Artificial Sequence
<220> FEATURE:
<223> OTHER INFORMATION: Amino acid sequence 1 of CDR 2 in the heavy
      chain of mouse anti-hTfR antibody No.2

<400> SEQUENCE: 84

Ile Ser Thr Tyr Tyr Gly His Gly
1               5

<210> SEQ ID NO 85
<211> LENGTH: 17
<212> TYPE: PRT
<213> ORGANISM: Artificial Sequence
<220> FEATURE:
<223> OTHER INFORMATION: Amino acid sequence 2 of CDR 2 in the heavy
      chain of mouse anti-hTfR antibody No.2

<400> SEQUENCE: 85

Val Ile Ser Thr Tyr Tyr Gly His Gly Ser Tyr Asn Gln Arg Phe Lys
1               5                   10                  15

Gly

<210> SEQ ID NO 86
<211> LENGTH: 14
<212> TYPE: PRT
<213> ORGANISM: Artificial Sequence
<220> FEATURE:
<223> OTHER INFORMATION: Amino acid sequence 1 of CDR 3 in the heavy
      chain of mouse anti-hTfR antibody No.2

<400> SEQUENCE: 86

Gly Gly Tyr Gly Ser Ser Ser Leu Ala Gly Asn Phe Asp Val
1               5                   10

<210> SEQ ID NO 87
<211> LENGTH: 16
<212> TYPE: PRT
<213> ORGANISM: Artificial Sequence
<220> FEATURE:
<223> OTHER INFORMATION: Amino acid sequence 2 of CDR 3 in the heavy
      chain of mouse anti-hTfR antibody No.2

<400> SEQUENCE: 87

Val Arg Gly Gly Tyr Gly Ser Ser Ser Leu Ala Gly Asn Phe Asp Val
1               5                   10                  15

<210> SEQ ID NO 88
<211> LENGTH: 5
<212> TYPE: PRT
<213> ORGANISM: Artificial Sequence
<220> FEATURE:
<223> OTHER INFORMATION: Amino acid sequence 1 of CDR 1 in the heavy
      chain of mouse anti-hTfR antibody No.3

<400> SEQUENCE: 88

Asn Tyr Trp Leu Gly
1               5

<210> SEQ ID NO 89
<211> LENGTH: 8
<212> TYPE: PRT
<213> ORGANISM: Artificial Sequence
<220> FEATURE:

<223> OTHER INFORMATION: Amino acid sequence 2 of CDR 1 in the heavy
      chain of mouse anti-hTfR antibody No.3

<400> SEQUENCE: 89

Gly Tyr Ser Phe Thr Asn Tyr Trp
1               5

<210> SEQ ID NO 90
<211> LENGTH: 8
<212> TYPE: PRT
<213> ORGANISM: Artificial Sequence
<220> FEATURE:
<223> OTHER INFORMATION: Amino acid sequence 1 of CDR 2 in the heavy
      chain of mouse anti-hTfR antibody No.3

<400> SEQUENCE: 90

Ile Tyr Pro Gly Gly Asp Tyr Pro
1               5

<210> SEQ ID NO 91
<211> LENGTH: 17
<212> TYPE: PRT
<213> ORGANISM: Artificial Sequence
<220> FEATURE:
<223> OTHER INFORMATION: Amino acid sequence 2 of CDR 2 in the heavy
      chain of mouse anti-hTfR antibody No.3

<400> SEQUENCE: 91

Asp Ile Tyr Pro Gly Gly Asp Tyr Pro Thr Tyr Ser Glu Lys Phe Lys
1               5                   10                  15

Val

<210> SEQ ID NO 92
<211> LENGTH: 9
<212> TYPE: PRT
<213> ORGANISM: Artificial Sequence
<220> FEATURE:
<223> OTHER INFORMATION: Amino acid sequence 1 of CDR 3 in the heavy
      chain of mouse anti-hTfR antibody No.3

<400> SEQUENCE: 92

Ser Gly Asn Tyr Asp Glu Val Ala Tyr
1               5

<210> SEQ ID NO 93
<211> LENGTH: 11
<212> TYPE: PRT
<213> ORGANISM: Artificial Sequence
<220> FEATURE:
<223> OTHER INFORMATION: Amino acid sequence 2 of CDR 3 in the heavy
      chain of mouse anti-hTfR antibody No.3

<400> SEQUENCE: 93

Ala Arg Ser Gly Asn Tyr Asp Glu Val Ala Tyr
1               5                   10

<210> SEQ ID NO 94
<211> LENGTH: 5
<212> TYPE: PRT
<213> ORGANISM: Artificial Sequence
<220> FEATURE:
<223> OTHER INFORMATION: Amino acid sequence 1 of CDR 1 in the heavy
      chain of mouse anti-hTfR antibody No.4

<400> SEQUENCE: 94

Asn Tyr Leu Ile Glu
1               5

<210> SEQ ID NO 95
<211> LENGTH: 8
<212> TYPE: PRT
<213> ORGANISM: Artificial Sequence
<220> FEATURE:
<223> OTHER INFORMATION: Amino acid sequence 2 of CDR 1 in the heavy
      chain of mouse anti-hTfR antibody No.4

<400> SEQUENCE: 95

Gly Tyr Ala Phe Thr Asn Tyr Leu
1               5

<210> SEQ ID NO 96
<211> LENGTH: 8
<212> TYPE: PRT
<213> ORGANISM: Artificial Sequence
<220> FEATURE:
<223> OTHER INFORMATION: Amino acid sequence 1 of CDR 2 in the heavy
      chain of mouse anti-hTfR antibody No.4

<400> SEQUENCE: 96

Ile Asn Pro Gly Ser Gly Gly Ile
1               5

<210> SEQ ID NO 97
<211> LENGTH: 16
<212> TYPE: PRT
<213> ORGANISM: Artificial Sequence
<220> FEATURE:
<223> OTHER INFORMATION: Amino acid sequence 2 of CDR 2 in the heavy
      chain of mouse anti-hTfR antibody No.4

<400> SEQUENCE: 97

Ile Asn Pro Gly Ser Gly Gly Ile Ile Tyr Asn Glu Lys Phe Thr Asp
1               5                   10                  15

<210> SEQ ID NO 98
<211> LENGTH: 13
<212> TYPE: PRT
<213> ORGANISM: Artificial Sequence
<220> FEATURE:
<223> OTHER INFORMATION: Amino acid sequence 1 of CDR 3 in the heavy
      chain of mouse anti-hTfR antibody No.4

<400> SEQUENCE: 98

Ser Asn Tyr Tyr Gly Thr Thr Tyr Trp His Phe Asp Val
1               5                   10

<210> SEQ ID NO 99
<211> LENGTH: 15
<212> TYPE: PRT
<213> ORGANISM: Artificial Sequence
<220> FEATURE:
<223> OTHER INFORMATION: Amino acid sequence 2 of CDR 3 in the heavy
      chain of mouse anti-hTfR antibody No.4

<400> SEQUENCE: 99

Ala Arg Ser Asn Tyr Tyr Gly Thr Thr Tyr Trp His Phe Asp Val
1               5                   10                  15

<210> SEQ ID NO 100
<211> LENGTH: 5
<212> TYPE: PRT
<213> ORGANISM: Artificial Sequence
<220> FEATURE:
<223> OTHER INFORMATION: Amino acid sequence 1 of CDR 1 in the heavy
      chain of mouse anti-hTfR antibody No.5

```
<400> SEQUENCE: 100

Asn Phe Val Ile His
1               5

<210> SEQ ID NO 101
<211> LENGTH: 8
<212> TYPE: PRT
<213> ORGANISM: Artificial Sequence
<220> FEATURE:
<223> OTHER INFORMATION: Amino acid sequence 2 of CDR 1 in the heavy
      chain of mouse anti-hTfR antibody No.5

<400> SEQUENCE: 101

Gly Tyr Thr Phe Thr Asn Phe Val
1               5

<210> SEQ ID NO 102
<211> LENGTH: 8
<212> TYPE: PRT
<213> ORGANISM: Artificial Sequence
<220> FEATURE:
<223> OTHER INFORMATION: Amino acid sequence 1 of CDR 2 in the heavy
      chain of mouse anti-hTfR antibody No.5

<400> SEQUENCE: 102

Phe Asn Pro His Lys Asn Gly Ala
1               5

<210> SEQ ID NO 103
<211> LENGTH: 16
<212> TYPE: PRT
<213> ORGANISM: Artificial Sequence
<220> FEATURE:
<223> OTHER INFORMATION: Amino acid sequence 2 of CDR 2 in the heavy
      chain of mouse anti-hTfR antibody No.5

<400> SEQUENCE: 103

Phe Asn Pro His Lys Asn Gly Ala Glu Tyr Asn Glu Lys Phe Gln Val
1               5                   10                  15

<210> SEQ ID NO 104
<211> LENGTH: 9
<212> TYPE: PRT
<213> ORGANISM: Artificial Sequence
<220> FEATURE:
<223> OTHER INFORMATION: Amino acid sequence 1 of CDR 3 in the heavy
      chain of mouse anti-hTfR antibody No.5

<400> SEQUENCE: 104

Ser Phe Tyr Tyr Tyr Ser Met Asp Tyr
1               5

<210> SEQ ID NO 105
<211> LENGTH: 11
<212> TYPE: PRT
<213> ORGANISM: Artificial Sequence
<220> FEATURE:
<223> OTHER INFORMATION: Amino acid sequence 2 of CDR 3 in the heavy
      chain of mouse anti-hTfR antibody No.5

<400> SEQUENCE: 105

Ala Arg Ser Phe Tyr Tyr Tyr Ser Met Asp Tyr
1               5                   10

<210> SEQ ID NO 106
<211> LENGTH: 5
```

```
<212> TYPE: PRT
<213> ORGANISM: Artificial Sequence
<220> FEATURE:
<223> OTHER INFORMATION: Amino acid sequence 1 of CDR 1 in the heavy
      chain of mouse anti-hTfR antibody No.6

<400> SEQUENCE: 106

Thr Tyr Gly Val Tyr
1               5

<210> SEQ ID NO 107
<211> LENGTH: 8
<212> TYPE: PRT
<213> ORGANISM: Artificial Sequence
<220> FEATURE:
<223> OTHER INFORMATION: Amino acid sequence 2 of CDR 1 in the heavy
      chain of mouse anti-hTfR antibody No.6

<400> SEQUENCE: 107

Gly Phe Ser Leu Ser Thr Tyr Gly
1               5

<210> SEQ ID NO 108
<211> LENGTH: 7
<212> TYPE: PRT
<213> ORGANISM: Artificial Sequence
<220> FEATURE:
<223> OTHER INFORMATION: Amino acid sequence of CDR 2 in the heavy chain
      of mouse anti-hTfR antibody No.6

<400> SEQUENCE: 108

Ile Trp Gly Asp Gly Ser Thr
1               5

<210> SEQ ID NO 109
<211> LENGTH: 4
<212> TYPE: PRT
<213> ORGANISM: Artificial Sequence
<220> FEATURE:
<223> OTHER INFORMATION: Amino acid sequence 1 of CDR 3 in the heavy
      chain of mouse anti-hTfR antibody No.6

<400> SEQUENCE: 109

Pro Asp Asp Val
1

<210> SEQ ID NO 110
<211> LENGTH: 6
<212> TYPE: PRT
<213> ORGANISM: Artificial Sequence
<220> FEATURE:
<223> OTHER INFORMATION: Amino acid sequence 2 of CDR 3 in the heavy
      chain of mouse anti-hTfR antibody No.6

<400> SEQUENCE: 110

Ala Lys Pro Asp Asp Val
1               5

<210> SEQ ID NO 111
<211> LENGTH: 5
<212> TYPE: PRT
<213> ORGANISM: Artificial Sequence
<220> FEATURE:
<223> OTHER INFORMATION: Amino acid sequence 1 of CDR 1 in the heavy
      chain of mouse anti-hTfR antibody No.7

<400> SEQUENCE: 111

Asn Tyr Phe Met Ser
```

<210> SEQ ID NO 112
<211> LENGTH: 8
<212> TYPE: PRT
<213> ORGANISM: Artificial Sequence
<220> FEATURE:
<223> OTHER INFORMATION: Amino acid sequence 2 of CDR 1 in the heavy
    chain of mouse
    anti-hTfR antibody No.7

<400> SEQUENCE: 112

Gly Ile Thr Phe Arg Asn Tyr Phe
1               5

<210> SEQ ID NO 113
<211> LENGTH: 8
<212> TYPE: PRT
<213> ORGANISM: Artificial Sequence
<220> FEATURE:
<223> OTHER INFORMATION: Amino acid sequence 1 of CDR 2 in the heavy
    chain of mouse anti-hTfR antibody No.7

<400> SEQUENCE: 113

Ile Ser Ser Ala Gly Gly Tyr Thr
1               5

<210> SEQ ID NO 114
<211> LENGTH: 16
<212> TYPE: PRT
<213> ORGANISM: Artificial Sequence
<220> FEATURE:
<223> OTHER INFORMATION: Amino acid sequence 2 of CDR 2 in the heavy
    chain of mouse anti-hTfR antibody No.7

<400> SEQUENCE: 114

Ile Ser Ser Ala Gly Gly Tyr Thr Tyr Tyr Ala Asp Ser Val Lys Gly
1               5                   10                  15

<210> SEQ ID NO 115
<211> LENGTH: 11
<212> TYPE: PRT
<213> ORGANISM: Artificial Sequence
<220> FEATURE:
<223> OTHER INFORMATION: Amino acid sequence 1 of CDR 3 in the heavy
    chain of mouse anti-hTfR antibody No.7

<400> SEQUENCE: 115

Gln Glu Val Pro Tyr Pro Tyr Ala Met Asp Tyr
1               5                   10

<210> SEQ ID NO 116
<211> LENGTH: 13
<212> TYPE: PRT
<213> ORGANISM: Artificial Sequence
<220> FEATURE:
<223> OTHER INFORMATION: Amino acid sequence 2 of CDR 3 in the heavy
    chain of mouse anti-hTfR antibody No.7

<400> SEQUENCE: 116

Ala Arg Gln Glu Val Pro Tyr Pro Tyr Ala Met Asp Tyr
1               5                   10

<210> SEQ ID NO 117
<211> LENGTH: 5
<212> TYPE: PRT
<213> ORGANISM: Artificial Sequence
<220> FEATURE:

```
<223> OTHER INFORMATION: Amino acid sequence 1 of CDR 1 in the heavy
      chain of mouse anti-hTfR antibody No.8

<400> SEQUENCE: 117

Thr Tyr Gly Val Ser
1               5

<210> SEQ ID NO 118
<211> LENGTH: 8
<212> TYPE: PRT
<213> ORGANISM: Artificial Sequence
<220> FEATURE:
<223> OTHER INFORMATION: Amino acid sequence 2 of CDR 1 in the heavy
      chain of mouse anti-hTfR antibody No.8

<400> SEQUENCE: 118

Gly Phe Ser Leu Thr Thr Tyr Gly
1               5

<210> SEQ ID NO 119
<211> LENGTH: 7
<212> TYPE: PRT
<213> ORGANISM: Artificial Sequence
<220> FEATURE:
<223> OTHER INFORMATION: Amino acid sequence of CDR 2 in the heavy chain
      of mouse anti-hTfR antibody No.8

<400> SEQUENCE: 119

Ile Trp Gly Asp Gly Ser Thr
1               5

<210> SEQ ID NO 120
<211> LENGTH: 4
<212> TYPE: PRT
<213> ORGANISM: Artificial Sequence
<220> FEATURE:
<223> OTHER INFORMATION: Amino acid sequence 1 of CDR 3 in the heavy
      chain of mouse anti-hTfR antibody No.8

<400> SEQUENCE: 120

Pro Asp Asp Tyr
1

<210> SEQ ID NO 121
<211> LENGTH: 6
<212> TYPE: PRT
<213> ORGANISM: Artificial Sequence
<220> FEATURE:
<223> OTHER INFORMATION: Amino acid sequence 2 of CDR 3 in the heavy
      chain of mouse anti-hTfR antibody No.8

<400> SEQUENCE: 121

Ala Lys Pro Asp Asp Tyr
1               5

<210> SEQ ID NO 122
<211> LENGTH: 5
<212> TYPE: PRT
<213> ORGANISM: Artificial Sequence
<220> FEATURE:
<223> OTHER INFORMATION: Amino acid sequence 1 of CDR 1 in the heavy
      chain of mouse anti-hTfR antibody No.9

<400> SEQUENCE: 122

Asn Tyr Gly Val Ser
1               5
```

```
<210> SEQ ID NO 123
<211> LENGTH: 8
<212> TYPE: PRT
<213> ORGANISM: Artificial Sequence
<220> FEATURE:
<223> OTHER INFORMATION: Amino acid sequence 2 of CDR 1 in the heavy
      chain of mouse anti-hTfR antibody No.9

<400> SEQUENCE: 123

Gly Tyr Thr Phe Thr Asn Tyr Gly
1               5

<210> SEQ ID NO 124
<211> LENGTH: 8
<212> TYPE: PRT
<213> ORGANISM: Artificial Sequence
<220> FEATURE:
<223> OTHER INFORMATION: Amino acid sequence 1 of CDR 2 in the heavy
      chain of mouse anti-hTfR antibody No.9

<400> SEQUENCE: 124

Ile Tyr Thr Phe Thr Gly Glu Ala
1               5

<210> SEQ ID NO 125
<211> LENGTH: 16
<212> TYPE: PRT
<213> ORGANISM: Artificial Sequence
<220> FEATURE:
<223> OTHER INFORMATION: Amino acid sequence 2 of CDR 2 in the heavy
      chain of mouse anti-hTfR antibody No.9

<400> SEQUENCE: 125

Ile Tyr Thr Phe Thr Gly Glu Ala Thr Tyr Ile Asp Asp Phe Arg Gly
1               5                   10                  15

<210> SEQ ID NO 126
<211> LENGTH: 8
<212> TYPE: PRT
<213> ORGANISM: Artificial Sequence
<220> FEATURE:
<223> OTHER INFORMATION: Amino acid sequence 1 of CDR 3 in the heavy
      chain of mouse anti-hTfR antibody No.9

<400> SEQUENCE: 126

Arg Asn Gly Ala Trp Phe Glu Asp
1               5

<210> SEQ ID NO 127
<211> LENGTH: 10
<212> TYPE: PRT
<213> ORGANISM: Artificial Sequence
<220> FEATURE:
<223> OTHER INFORMATION: Amino acid sequence 2 of CDR 3 in the heavy
      chain of mouse anti-hTfR antibody No.9

<400> SEQUENCE: 127

Ser Arg Arg Asn Gly Ala Trp Phe Glu Asp
1               5                   10

<210> SEQ ID NO 128
<211> LENGTH: 5
<212> TYPE: PRT
<213> ORGANISM: Artificial Sequence
<220> FEATURE:
<223> OTHER INFORMATION: Amino acid sequence 1 of CDR 1 in the heavy
      chain of mouse anti-hTfR antibody No.10

<400> SEQUENCE: 128
```

```
Asn Tyr Ala Met Ser
1               5

<210> SEQ ID NO 129
<211> LENGTH: 8
<212> TYPE: PRT
<213> ORGANISM: Artificial Sequence
<220> FEATURE:
<223> OTHER INFORMATION: Amino acid sequence 2 of CDR 1 in the heavy
      chain of mouse anti-hTfR antibody No.10

<400> SEQUENCE: 129

Gly Ile Thr Phe Arg Asn Tyr Ala
1               5

<210> SEQ ID NO 130
<211> LENGTH: 8
<212> TYPE: PRT
<213> ORGANISM: Artificial Sequence
<220> FEATURE:
<223> OTHER INFORMATION: Amino acid sequence 1 of CDR 2 in the heavy
      chain of mouse anti-hTfR antibody No.10

<400> SEQUENCE: 130

Ile Ser Ser Tyr Gly Gly Tyr Thr
1               5

<210> SEQ ID NO 131
<211> LENGTH: 16
<212> TYPE: PRT
<213> ORGANISM: Artificial Sequence
<220> FEATURE:
<223> OTHER INFORMATION: Amino acid sequence 2 of CDR 2 in the heavy
      chain of mouse anti-hTfR antibody No.10

<400> SEQUENCE: 131

Ile Ser Ser Tyr Gly Gly Tyr Thr Tyr Tyr Ala Asp Ser Val Lys Gly
1               5                   10                  15

<210> SEQ ID NO 132
<211> LENGTH: 11
<212> TYPE: PRT
<213> ORGANISM: Artificial Sequence
<220> FEATURE:
<223> OTHER INFORMATION: Amino acid sequence 1 of CDR 3 in the heavy
      chain of mouse anti-hTfR antibody No.10

<400> SEQUENCE: 132

Gln Glu Val Pro Tyr Pro Tyr Pro Met Asp Asn
1               5                   10

<210> SEQ ID NO 133
<211> LENGTH: 13
<212> TYPE: PRT
<213> ORGANISM: Artificial Sequence
<220> FEATURE:
<223> OTHER INFORMATION: Amino acid sequence 2 of CDR 3 in the heavy
      chain of mouse anti-hTfR antibody No.10

<400> SEQUENCE: 133

Ala Arg Gln Glu Val Pro Tyr Pro Tyr Pro Met Asp Asn
1               5                   10

<210> SEQ ID NO 134
<211> LENGTH: 5
<212> TYPE: PRT
<213> ORGANISM: Artificial Sequence
```

<220> FEATURE:
<223> OTHER INFORMATION: Amino acid sequence 1 of CDR 1 in the heavy
      chain of mouse anti-hTfR antibody No.11

<400> SEQUENCE: 134

Ile Tyr Trp Ile Asn
1               5

<210> SEQ ID NO 135
<211> LENGTH: 8
<212> TYPE: PRT
<213> ORGANISM: Artificial Sequence
<220> FEATURE:
<223> OTHER INFORMATION: Amino acid sequence 2 of CDR 1 in the heavy
      chain of mouse anti-hTfR antibody No.11

<400> SEQUENCE: 135

Gly Tyr Ala Phe Ser Ile Tyr Trp
1               5

<210> SEQ ID NO 136
<211> LENGTH: 8
<212> TYPE: PRT
<213> ORGANISM: Artificial Sequence
<220> FEATURE:
<223> OTHER INFORMATION: Amino acid sequence 1 of CDR 2 in the heavy
      chain of mouse anti-hTfR antibody No.11

<400> SEQUENCE: 136

Ile Tyr Pro Gly Asn Gly Asp Thr
1               5

<210> SEQ ID NO 137
<211> LENGTH: 16
<212> TYPE: PRT
<213> ORGANISM: Artificial Sequence
<220> FEATURE:
<223> OTHER INFORMATION: Amino acid sequence 2 of CDR 2 in the heavy
      chain of mouse anti-hTfR antibody No.11

<400> SEQUENCE: 137

Ile Tyr Pro Gly Asn Gly Asp Thr Asn Tyr Asn Gly Lys Phe Lys Gly
1               5                   10                  15

<210> SEQ ID NO 138
<211> LENGTH: 9
<212> TYPE: PRT
<213> ORGANISM: Artificial Sequence
<220> FEATURE:
<223> OTHER INFORMATION: Amino acid sequence 1 of CDR 3 in the heavy
      chain of mouse anti-hTfR antibody No.11

<400> SEQUENCE: 138

Trp Gly Asp Asp Tyr Ala Met Asp Phe
1               5

<210> SEQ ID NO 139
<211> LENGTH: 11
<212> TYPE: PRT
<213> ORGANISM: Artificial Sequence
<220> FEATURE:
<223> OTHER INFORMATION: Amino acid sequence 2 of CDR 3 in the heavy
      chain of mouse anti-hTfR antibody No.11

<400> SEQUENCE: 139

Gly Arg Trp Gly Asp Asp Tyr Ala Met Asp Phe
1               5                   10

<210> SEQ ID NO 140
<211> LENGTH: 5
<212> TYPE: PRT
<213> ORGANISM: Artificial Sequence
<220> FEATURE:
<223> OTHER INFORMATION: Amino acid sequence 1 of CDR 1 in the
      heavy chain of mouse anti-hTfR antibody No.12

<400> SEQUENCE: 140

Asn Tyr Leu Ile Glu
1               5

<210> SEQ ID NO 141
<211> LENGTH: 8
<212> TYPE: PRT
<213> ORGANISM: Artificial Sequence
<220> FEATURE:
<223> OTHER INFORMATION: Amino acid sequence 2 of CDR 1 in the heavy
      chain of mouse anti-hTfR antibody No.12

<400> SEQUENCE: 141

Gly Tyr Val Phe Ile Asn Tyr Leu
1               5

<210> SEQ ID NO 142
<211> LENGTH: 8
<212> TYPE: PRT
<213> ORGANISM: Artificial Sequence
<220> FEATURE:
<223> OTHER INFORMATION: Amino acid sequence 1 of CDR 2 in the heavy
      chain of mouse anti-hTfR antibody No.12

<400> SEQUENCE: 142

Ile His Ser Gly Ser Gly Gly Thr
1               5

<210> SEQ ID NO 143
<211> LENGTH: 16
<212> TYPE: PRT
<213> ORGANISM: Artificial Sequence
<220> FEATURE:
<223> OTHER INFORMATION: Amino acid sequence 2 of CDR 2 in the heavy
      chain of mouse anti-hTfR antibody No.12

<400> SEQUENCE: 143

Ile His Ser Gly Ser Gly Gly Thr Asn Tyr Asn Asp Asn Phe Lys Asp
1               5                   10                  15

<210> SEQ ID NO 144
<211> LENGTH: 10
<212> TYPE: PRT
<213> ORGANISM: Artificial Sequence
<220> FEATURE:
<223> OTHER INFORMATION: Amino acid sequence 1 of CDR 3 in the heavy
      chain of mouse anti-hTfR antibody No.12

<400> SEQUENCE: 144

Arg Asn Phe Gly Asn Tyr Tyr Phe Asp Tyr
1               5                   10

<210> SEQ ID NO 145
<211> LENGTH: 12
<212> TYPE: PRT
<213> ORGANISM: Artificial Sequence
<220> FEATURE:
<223> OTHER INFORMATION: Amino acid sequence 2 of CDR 3 in the heavy
      chain of mouse anti-hTfR antibody No.12

```
<400> SEQUENCE: 145

Ala Arg Arg Asn Phe Gly Asn Tyr Tyr Phe Asp Tyr
1               5                   10

<210> SEQ ID NO 146
<211> LENGTH: 5
<212> TYPE: PRT
<213> ORGANISM: Artificial Sequence
<220> FEATURE:
<223> OTHER INFORMATION: Amino acid sequence 1 of CDR 1 in the heavy
      chain of mouse anti-hTfR antibody No.13

<400> SEQUENCE: 146

Ile Tyr Trp Ile Asn
1               5

<210> SEQ ID NO 147
<211> LENGTH: 8
<212> TYPE: PRT
<213> ORGANISM: Artificial Sequence
<220> FEATURE:
<223> OTHER INFORMATION: Amino acid sequence 2 of CDR 1 in the heavy
      chain of mouse anti-hTfR antibody No.13

<400> SEQUENCE: 147

Gly Tyr Ala Phe Ser Ile Tyr Trp
1               5

<210> SEQ ID NO 148
<211> LENGTH: 8
<212> TYPE: PRT
<213> ORGANISM: Artificial Sequence
<220> FEATURE:
<223> OTHER INFORMATION: Amino acid sequence 1 of CDR 2 in the heavy
      chain of mouse anti-hTfR antibody No.13

<400> SEQUENCE: 148

Ile Tyr Pro Gly Asn Gly Asp Thr
1               5

<210> SEQ ID NO 149
<211> LENGTH: 16
<212> TYPE: PRT
<213> ORGANISM: Artificial Sequence
<220> FEATURE:
<223> OTHER INFORMATION: Amino acid sequence 2 of CDR 2 in the heavy
      chain of mouse anti-hTfR antibody No.13

<400> SEQUENCE: 149

Ile Tyr Pro Gly Asn Gly Asp Thr Asn Tyr Asn Gly Lys Phe Lys Gly
1               5                   10                  15

<210> SEQ ID NO 150
<211> LENGTH: 9
<212> TYPE: PRT
<213> ORGANISM: Artificial Sequence
<220> FEATURE:
<223> OTHER INFORMATION: Amino acid sequence 1 of CDR 3 in the heavy
      chain of mouse anti-hTfR antibody No.13

<400> SEQUENCE: 150

Trp Gly Asp Asp Tyr Ala Met Asp Phe
1               5

<210> SEQ ID NO 151
<211> LENGTH: 11
<212> TYPE: PRT
```

<210> SEQ ID NO 151 (continued)
<213> ORGANISM: Artificial Sequence
<220> FEATURE:
<223> OTHER INFORMATION: Amino acid sequence 2 of CDR 3 in the heavy
      chain of mouse anti-hTfR antibody No.13

<400> SEQUENCE: 151

Gly Arg Trp Gly Asp Asp Tyr Ala Met Asp Phe
1               5                   10

<210> SEQ ID NO 152
<211> LENGTH: 5
<212> TYPE: PRT
<213> ORGANISM: Artificial Sequence
<220> FEATURE:
<223> OTHER INFORMATION: Amino acid sequence 1 of CDR 1 in the heavy
      chain of mouse anti-hTfR antibody No.14

<400> SEQUENCE: 152

Gly Tyr Val Ile His
1               5

<210> SEQ ID NO 153
<211> LENGTH: 8
<212> TYPE: PRT
<213> ORGANISM: Artificial Sequence
<220> FEATURE:
<223> OTHER INFORMATION: Amino acid sequence 2 of CDR 1 in the heavy
      chain of mouse anti-hTfR antibody No.14

<400> SEQUENCE: 153

Gly Tyr Ala Phe Thr Gly Tyr Val
1               5

<210> SEQ ID NO 154
<211> LENGTH: 8
<212> TYPE: PRT
<213> ORGANISM: Artificial Sequence
<220> FEATURE:
<223> OTHER INFORMATION: Amino acid sequence 1 of CDR 2 in the heavy
      chain of mouse anti-hTfR antibody No.14

<400> SEQUENCE: 154

Leu Asn Pro His Lys Asp Asp Ser
1               5

<210> SEQ ID NO 155
<211> LENGTH: 16
<212> TYPE: PRT
<213> ORGANISM: Artificial Sequence
<220> FEATURE:
<223> OTHER INFORMATION: Amino acid sequence 2 of CDR 2 in the heavy
      chain of mouse anti-hTfR antibody No.14

<400> SEQUENCE: 155

Leu Asn Pro His Lys Asp Asp Ser Glu Tyr Asn Glu Lys Phe Arg Gly
1               5                   10                  15

<210> SEQ ID NO 156
<211> LENGTH: 9
<212> TYPE: PRT
<213> ORGANISM: Artificial Sequence
<220> FEATURE:
<223> OTHER INFORMATION: Amino acid sequence 1 of CDR 3 in the heavy
      chain of mouse anti-hTfR antibody No.14

<400> SEQUENCE: 156

Gly Tyr Tyr Tyr Tyr Ser Met Asp Tyr
1               5

<210> SEQ ID NO 157
<211> LENGTH: 11
<212> TYPE: PRT
<213> ORGANISM: Artificial Sequence
<220> FEATURE:
<223> OTHER INFORMATION: Amino acid sequence 2 of CDR 3 in the heavy
      chain of mouse anti-hTfR antibody No.14

<400> SEQUENCE: 157

Ala Arg Gly Tyr Tyr Tyr Ser Met Asp Tyr
1               5                   10

<210> SEQ ID NO 158
<211> LENGTH: 107
<212> TYPE: PRT
<213> ORGANISM: Artificial Sequence
<220> FEATURE:
<223> OTHER INFORMATION: Amino acid sequence 1 of the variable region of
      light chain of humanized anti-hTfR antibody No.1

<400> SEQUENCE: 158

Asp Ile Val Met Thr Gln Ser Pro Asp Ser Leu Ala Val Ser Leu Gly
1               5                   10                  15

Glu Arg Ala Thr Ile Asn Cys Lys Ala Ser Gln Asp Val Asn Ser Ala
            20                  25                  30

Val Ala Trp Tyr Gln Gln Lys Pro Gly Gln Pro Pro Lys Leu Leu Ile
        35                  40                  45

Tyr Trp Thr Ser Thr Arg His Thr Gly Val Pro Asp Arg Phe Ser Gly
    50                  55                  60

Ser Gly Ser Gly Thr Asp Phe Thr Leu Thr Ile Ser Ser Leu Gln Ala
65                  70                  75                  80

Glu Asp Val Ala Val Tyr Tyr Cys Gln Gln His Tyr Ser Thr Pro Arg
                85                  90                  95

Thr Phe Gly Gly Gly Thr Lys Leu Glu Ile Lys
            100                 105

<210> SEQ ID NO 159
<211> LENGTH: 107
<212> TYPE: PRT
<213> ORGANISM: Artificial Sequence
<220> FEATURE:
<223> OTHER INFORMATION: Amino acid sequence 2 of the variable region of
      light chain of humanized anti-hTfR antibody No.1

<400> SEQUENCE: 159

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Asn Ser Ala
            20                  25                  30

Val Ala Trp Tyr Gln Gln Lys Pro Gly Lys Ala Pro Lys Leu Leu Leu
        35                  40                  45

Tyr Trp Thr Ser Thr Arg His Thr Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln His Tyr Ser Thr Pro Arg
                85                  90                  95

Thr Phe Gly Gly Gly Thr Lys Val Glu Ile Lys
            100                 105

<210> SEQ ID NO 160
<211> LENGTH: 107
<212> TYPE: PRT
<213> ORGANISM: Artificial Sequence
<220> FEATURE:
<223> OTHER INFORMATION: Amino acid sequence 3 of the variable region of
    light chain of humanized anti-hTfR antibody No.1

<400> SEQUENCE: 160

Asp Ile Gln Val Thr Gln Ser Pro Ser Phe Leu Ser Ala Ser Val Gly
1               5                   10                  15

Asp Arg Val Thr Ile Thr Cys Lys Ala Ser Gln Asp Val Asn Ser Ala
            20                  25                  30

Val Ala Trp Tyr Gln Gln Lys Pro Gly Lys Ala Pro Lys Leu Leu Ile
        35                  40                  45

Tyr Trp Thr Ser Thr Arg His Thr Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln His Tyr Ser Thr Pro Arg
                85                  90                  95

Thr Phe Gly Gly Gly Thr Lys Val Glu Ile Lys
            100                 105

<210> SEQ ID NO 161
<211> LENGTH: 107
<212> TYPE: PRT
<213> ORGANISM: Artificial Sequence
<220> FEATURE:
<223> OTHER INFORMATION: Amino acid sequence 4 of the variable region of
    light chain of humanized anti-hTfR antibody No.1

<400> SEQUENCE: 161

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Asn Ser Ala
            20                  25                  30

Val Ala Trp Tyr Gln Gln Lys Pro Gly Lys Ala Pro Lys Leu Leu Ile
        35                  40                  45

Tyr Trp Thr Ser Thr Arg His Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Ser Thr Pro Arg
                85                  90                  95

Thr Phe Gly Gly Gly Thr Lys Val Glu Ile Lys
            100                 105

<210> SEQ ID NO 162
<211> LENGTH: 107
<212> TYPE: PRT
<213> ORGANISM: Artificial Sequence
<220> FEATURE:
<223> OTHER INFORMATION: Amino acid sequence 5 of the variable region of
    light chain of humanized anti-hTfR antibody No.1

<400> SEQUENCE: 162

Asp Ile Gln Met Thr Gln Ser Pro Ser Ser Val Ser Ala Ser Val Gly
1               5                   10                  15

Asp Arg Val Thr Ile Thr Cys Lys Ala Ser Gln Asp Val Asn Ser Ala

```
                20                  25                  30

Val Ala Trp Tyr Gln Gln Lys Pro Gly Lys Ala Pro Lys Leu Leu Ile
            35                  40                  45

Tyr Trp Thr Ser Thr Arg His Thr Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Ser Thr Pro Arg
                85                  90                  95

Thr Phe Gly Gln Gly Thr Lys Val Glu Ile Lys
                100                 105

<210> SEQ ID NO 163
<211> LENGTH: 107
<212> TYPE: PRT
<213> ORGANISM: Artificial Sequence
<220> FEATURE:
<223> OTHER INFORMATION: Amino acid sequence 6 of the variable region of
      light chain of humanized anti-hTfR antibody No.1

<400> SEQUENCE: 163

Asp Ile Gln Met Thr Gln Ser Pro Ser Ser Val Ser Ala Ser Val Gly
1               5                   10                  15

Asp Arg Val Thr Ile Thr Cys Lys Ala Ser Gln Asp Val Asn Ser Ala
            20                  25                  30

Val Ala Trp Tyr Gln Gln Lys Pro Gly Lys Ala Pro Lys Leu Leu Ile
        35                  40                  45

Tyr Trp Thr Ser Thr Arg His Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Ser Thr Pro Arg
                85                  90                  95

Thr Phe Gly Gln Gly Thr Lys Val Glu Ile Lys
                100                 105

<210> SEQ ID NO 164
<211> LENGTH: 214
<212> TYPE: PRT
<213> ORGANISM: Artificial Sequence
<220> FEATURE:
<223> OTHER INFORMATION: Amino acid sequence of the light chain of
      humanized anti-hTfR antibody No.1 containing amino acid sequence 6
      as the variable region

<400> SEQUENCE: 164

Asp Ile Gln Val Thr Gln Ser Pro Ser Phe Leu Ser Ala Ser Val Gly
1               5                   10                  15

Asp Arg Val Thr Ile Thr Cys Lys Ala Ser Gln Asp Val Asn Ser Ala
            20                  25                  30

Val Ala Trp Phe Gln Gln Lys Pro Gly Lys Ala Pro Lys Leu Leu Ile
        35                  40                  45

Tyr Trp Thr Ser Thr Arg His Thr Gly Val Pro Asp Arg Phe Ser Gly
    50                  55                  60

Ser Gly Ser Gly Thr Val Tyr Thr Leu Thr Ile Ser Ser Leu Gln Pro
65                  70                  75                  80

Glu Asp Phe Ala Thr Tyr Tyr Cys Gln Gln His Tyr Ser Thr Pro Arg
                85                  90                  95
```

```
Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 165
<211> LENGTH: 725
<212> TYPE: DNA
<213> ORGANISM: Artificial Sequence
<220> FEATURE:
<223> OTHER INFORMATION: Nucleotide sequence encoding the amino acid
      sequence of the light chain of humanized anti-hTfR antibody No.1
      containing amino acid sequence 6 as the variable region, synthetic
      sequence

<400> SEQUENCE: 165
acgcgtgccg ccaccatggg ctggagctgg attctgctgt tcctcctgag cgtgacagca      60
ggagtgcaca gcgacatcca ggtcacacag tcaccaagtt ttctgagcgc aagcgtgggc     120
gacagggtca ctatcacatg caaggcaagc caggacgtga actccgcagt ggcctggttc     180
cagcagaagc cagggaaagc acccaagctg ctgatctatt ggacctctac aaggcacacc     240
ggtgtcccag atcggttctc aggttccggc agcggaacag tgtatactct gaccatttcc     300
agcctgcagc ctgaagactt cgctacttac tattgccagc agcattactc cacccccaaga    360 acatttggcg gagggactaa agtggagatc aagaggaccg tggccgctcc ctccgtcttc     420
atttttcccc ctagcgacga acagctgaag agtggcacag cctcagtggt ctgtctgctg     480
aacaatttct accctaggga ggctaaagtg cagtggaagg tcgataacgc actgcagtct     540
ggaaatagtc aggagtcagt gacagaacag gactccaaag atagcactta ttctctgtct     600
agtacactga ctctgagcaa ggccgattac gaaaagcaca agtgtatgc ttgcgaagtc      660 acccatcagg ggctgtcatc accagtcacc aagtcattca atagaggcga gtgctaagcg     720
gccgc                                                                 725

<210> SEQ ID NO 166
<211> LENGTH: 116
<212> TYPE: PRT
<213> ORGANISM: Artificial Sequence
<220> FEATURE:
<223> OTHER INFORMATION: Amino acid sequence 1 of the variable region of
      the heavy chain of humanized anti-hTfR antibody No.1

<400> SEQUENCE: 166

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30
```

Gly Met Ser Trp Val Arg Gln Ala Pro Gly Lys Gly Leu Glu Trp Val
            35                  40                  45

Ser Asn Ile Asn Thr Asn Gly Gly Ser Thr Tyr Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asn Arg Tyr Asp Glu Asp Tyr Trp Gly Gln Gly Thr Leu Val
            100                 105                 110

Thr Val Ser Ser
        115

<210> SEQ ID NO 167
<211> LENGTH: 116
<212> TYPE: PRT
<213> ORGANISM: Artificial Sequence
<220> FEATURE:
<223> OTHER INFORMATION: Amino acid sequence 2 of the variable region of
      the heavy chain of humanized anti-hTfR antibody No.1

<400> SEQUENCE: 167

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met Ser Trp Val Arg Gln Ala Pro Gly Lys Gly Leu Glu Trp Val
            35                  40                  45

Ser Asn Ile Asn Thr Asn Gly Gly Ser Thr Tyr Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asn Arg Tyr Asp Glu Asp Tyr Trp Gly Gln Gly Thr Leu Val
            100                 105                 110

Thr Val Ser Ser
        115

<210> SEQ ID NO 168
<211> LENGTH: 116
<212> TYPE: PRT
<213> ORGANISM: Artificial Sequence
<220> FEATURE:
<223> OTHER INFORMATION: Amino acid sequence 3 of the variable region of
      the heavy chain of humanized anti-hTfR antibody No.1

<400> SEQUENCE: 168

Glu Val Gln Leu Val Glu Ser Gly Gly Gly Leu Val Gln Pro Gly Gly
1               5                   10                  15

Ser Leu Arg Leu Ser Cys Ser Ala Ser Gly Phe Thr Phe Ser Asn Tyr
            20                  25                  30

Gly Met Ser Trp Val Arg Gln Ala Pro Gly Lys Gly Leu Glu Tyr Val
            35                  40                  45

Ser Asn Ile Asn Thr Asn Gly Gly Ser Thr Tyr Tyr Pro Asp Ser Val
    50                  55                  60

Lys Gly Arg Phe Thr Ile Ser Arg Asp Asn Ser Lys Asn Thr Leu Tyr
65                  70                  75                  80

```
Leu Gln Met Ser Ser Leu Arg Ala Glu Asp Thr Ala Val Tyr Tyr Cys
                85                  90                  95

Val Lys Asn Arg Tyr Asp Glu Asp Tyr Trp Gly Gln Gly Thr Leu Val
            100                 105                 110

Thr Val Ser Ser
        115

<210> SEQ ID NO 169
<211> LENGTH: 116
<212> TYPE: PRT
<213> ORGANISM: Artificial Sequence
<220> FEATURE:
<223> OTHER INFORMATION: Amino acid sequence 4 of the variable region of
      the heavy chain of humanized anti-hTfR antibody No.1

<400> SEQUENCE: 169

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met Ser Trp Val Arg Gln Ala Pro Gly Lys Gly Leu Glu Trp Val
        35                  40                  45

Ala Asn Ile Asn Thr Asn Gly Gly Ser Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asn Arg Tyr Asp Glu Asp Tyr Trp Gly Gln Gly Thr Leu Val
            100                 105                 110

Thr Val Ser Ser
        115

<210> SEQ ID NO 170
<211> LENGTH: 116
<212> TYPE: PRT
<213> ORGANISM: Artificial Sequence
<220> FEATURE:
<223> OTHER INFORMATION: Amino acid sequence 5 of the variable region of
      the heavy chain of humanized anti-hTfR antibody No.1

<400> SEQUENCE: 170

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met Ser Trp Val Arg Gln Ala Pro Gly Lys Gly Leu Val Trp Val
        35                  40                  45

Ser Asn Ile Asn Thr Asn Gly Gly Ser Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Arg Tyr Asp Glu Asp Tyr Trp Gly Gln Gly Thr Leu Val
            100                 105                 110

Thr Val Ser Ser
        115
```

<210> SEQ ID NO 171
<211> LENGTH: 116
<212> TYPE: PRT
<213> ORGANISM: Artificial Sequence
<220> FEATURE:
<223> OTHER INFORMATION: Amino acid sequence 6 of the variable region of
      the heavy chain of humanized anti-hTfR antibody No.1

<400> SEQUENCE: 171

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Leu Thr Phe Ser Asn Tyr
            20                  25                  30

Gly Met Ser Trp Val Arg Gln Ala Pro Gly Lys Gly Leu Glu Leu Val
        35                  40                  45

Ala Asn Ile Asn Thr Asn Gly Gly Ser Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Thr Asn Asn Arg Tyr Asp Glu Asp Tyr Trp Gly Gln Gly Thr Leu Val
            100                 105                 110

Thr Val Ser Ser
            115
```

<210> SEQ ID NO 172
<211> LENGTH: 446
<212> TYPE: PRT
<213> ORGANISM: Artificial Sequence
<220> FEATURE:
<223> OTHER INFORMATION: Amino acid sequence of the heavy chain of
      humanized anti-hTfR antibody No.1 containing amino acid sequence 6
      as the variable region

<400> SEQUENCE: 172

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Leu Thr Phe Ser Asn Tyr
            20                  25                  30

Gly Met Ser Trp Val Arg Gln Ala Pro Gly Lys Gly Leu Glu Leu Val
        35                  40                  45

Ala Asn Ile Asn Thr Asn Gly Gly Ser Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Thr Asn Asn Arg Tyr Asp Glu Asp Tyr Trp Gly Gln Gly Thr Leu Val
            100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
        130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
```

```
                    165                 170                 175
Gly Leu Tyr Ser Leu Ser Ser Val Val Thr Val Pro Ser Ser Leu
                180                 185                 190
Gly Thr Gln Thr Tyr Ile Cys Asn Val Asn His Lys Pro Ser Asn Thr
            195                 200                 205
Lys Val Asp Lys Lys Val Glu Pro Lys Ser Cys Asp Lys Thr His Thr
    210                 215                 220
Cys Pro Pro Cys Pro Ala Pro Glu Leu Leu Gly Gly Pro Ser Val Phe
225                 230                 235                 240
Leu Phe Pro Pro Lys Pro Lys Asp Thr Leu Met Ile Ser Arg Thr Pro
                245                 250                 255
Glu Val Thr Cys Val Val Val Asp Val Ser His Glu Asp Pro Glu Val
            260                 265                 270
Lys Phe Asn Trp Tyr Val Asp Gly Val Glu Val His Asn Ala Lys Thr
        275                 280                 285
Lys Pro Arg Glu Glu Gln Tyr Asn Ser Thr Tyr Arg Val Val Ser Val
    290                 295                 300
Leu Thr Val Leu His Gln Asp Trp Leu Asn Gly Lys Glu Tyr Lys Cys
305                 310                 315                 320
Lys Val Ser Asn Lys Ala Leu Pro Ala Pro Ile Glu Lys Thr Ile Ser
                325                 330                 335
Lys Ala Lys Gly Gln Pro Arg Glu Pro Gln Val Tyr Thr Leu Pro Pro
            340                 345                 350
Ser Arg Asp Glu Leu Thr Lys Asn Gln Val Ser Leu Thr Cys Leu Val
        355                 360                 365
Lys Gly Phe Tyr Pro Ser Asp Ile Ala Val Glu Trp Glu Ser Asn Gly
    370                 375                 380
Gln Pro Glu Asn Asn Tyr Lys Thr Thr Pro Pro Val Leu Asp Ser Asp
385                 390                 395                 400
Gly Ser Phe Phe Leu Tyr Ser Lys Leu Thr Val Asp Lys Ser Arg Trp
                405                 410                 415
Gln Gln Gly Asn Val Phe Ser Cys Ser Val Met His Glu Ala Leu His
            420                 425                 430
Asn His Tyr Thr Gln Lys Ser Leu Ser Leu Ser Pro Gly Lys
        435                 440                 445

<210> SEQ ID NO 173
<211> LENGTH: 1421
<212> TYPE: DNA
<213> ORGANISM: Artificial Sequence
<220> FEATURE:
<223> OTHER INFORMATION: Nucleotide sequence encoding the amino acid
      sequence of the heavy chain of humanized anti-hTfR antibody No.1
      containing amino acid sequence 6 as the variable region, synthetic
      sequence

<400> SEQUENCE: 173
acgcgtgccg ccaccatggg ctggagctgg attctgctgt tcctcctgag cgtgacagca    60
ggagtgcaca gcgaagtgca gctggtcgaa tcagggggg ggctggtgca gcctggaggc   120
agcctgagac tgtcctgcgc cgcttctggc ttgaccttta gcaactacgg gatgtcctgg   180
gtgcggcagg ctcctggcaa gggactggag ttggtggcca acatcaatac caacggcgga   240
agtacatact atcccgattc agtgaagggc cggttcacca tcagcaggga caacgccaag   300
aacagcctgt atctgcagat gaactctctg agggccgagg atacagccgt gtactattgc   360
actaacaacc ggtacgacga ggactattgg ggccagggca ccctggtgac agtgtctagc   420
```

```
gcctctacca agggcccaag cgtgtttcct ctggctccat cctctaaatc cacctctggc      480
ggcacagccg ctctgggctg tctggtgaag gattacttcc cagagcccgt gacagtgtct      540
tggaacagcg gcgccctgac ctccggcgtg cacacatttc ctgctgtgct gcagagctcc      600
ggcctgtaca gcctgtctag cgtggtgacc gtgccatcct ctagcctggg cacccagaca      660
tatatctgca acgtgaatca caagcccagc aatacaaagg tggataagaa ggtggagcca      720
aagtcctgtg acaagaccca cacatgcccc ccttgtcctg ctccagagct gctgggagga      780
ccaagcgtgt tcctgtttcc acccaagccc aaggataccc tgatgatctc tcggaccccg      840
gaggtgacat gcgtggtggt ggatgtgagc cacgaggacc ccgaggtgaa gttcaactgg      900
tatgtggacg gcgtggaggt gcacaatgct aagaccaagc ccagggagga gcagtacaac      960
tccacctata gagtggtgtc tgtgctgaca gtgctgcacc aggattggct gaacggcaag     1020
gagtataagt gcaaggtgtc caataaggcc ctgccccgctc ctatcgagaa gaccatctct     1080
aaggccaagg gccagcccag agagcctcag gtgtacacac tgcctccatc ccgggatgag     1140
ctgaccaaga accaggtgtc tctgacatgt ctggtcaagg gcttctatcc ctctgacatc     1200
gccgtggagt gggagagcaa tggccagcct gagaacaatt acaagaccac accccctgtg     1260
ctggattccg acggctcttt ctttctgtat agcaagctga ccgtggacaa gtcccggtgg     1320
cagcagggca acgtgttcag ctgttccgtg atgcacgaag ctctgcataa tcactatact     1380
cagaaatccc tgtcactgtc acctggtaaa taagcggccg c                         1421
```

<210> SEQ ID NO 174
<211> LENGTH: 107
<212> TYPE: PRT
<213> ORGANISM: Artificial Sequence
<220> FEATURE:
<223> OTHER INFORMATION: Amino acid sequence 1 of the variable region of
      the light chain of humanized anti-hTfR antibody No.2

<400> SEQUENCE: 174

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Ile Ser Asn Asn
            20                  25                  30

Leu Gln Trp Tyr Gln Gln Lys Pro Gly Gln Ala Pro Arg Leu Leu Ile
        35                  40                  45

Tyr Tyr Ala Ser Gln Ser Ile Ser Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Ser Asn Ser Trp Pro Arg
                85                  90                  95

Thr Phe Gly Gln Gly Thr Lys Val Asp Ile Lys
            100                 105

<210> SEQ ID NO 175
<211> LENGTH: 107
<212> TYPE: PRT
<213> ORGANISM: Artificial Sequence
<220> FEATURE:
<223> OTHER INFORMATION: Amino acid sequence 2 of the variable region of
      the light chain of humanized anti-hTfR antibody No.2

<400> SEQUENCE: 175

Glu Ile Val Met Thr Gln Ser Pro Ala Thr Leu Ser Leu Ser Pro Gly

```
            1               5                  10                 15
Glu Arg Ala Thr Leu Ser Cys Arg Ala Ser Gln Ser Ile Ser Asn Asn
                    20                  25                  30

Leu Gln Trp Tyr Gln Gln Lys Pro Gly Gln Ala Pro Arg Leu Leu Ile
            35                  40                  45

Tyr Tyr Ala Ser Gln Ser Ile Ser Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Asn Ser Trp Pro Arg
                85                  90                  95

Thr Phe Gly Gly Gly Thr Lys Val Glu Ile Lys
            100                 105
```

<210> SEQ ID NO 176
<211> LENGTH: 107
<212> TYPE: PRT
<213> ORGANISM: Artificial Sequence
<220> FEATURE:
<223> OTHER INFORMATION: Amino acid sequence 3 of the variable region of the light chain of humanized anti-hTfR antibody No.2

<400> SEQUENCE: 176

```
Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Ser Asn Asn
                20                  25                  30

Leu Gln Trp Tyr Gln Gln Lys Pro Asp Gln Ser Pro Lys Leu Leu Ile
            35                  40                  45

Lys Tyr Ala Ser Gln Ser Ile Ser Gly Val Pro Ser Arg Phe Ser Gly
        50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Ser Asn Ser Trp Pro Arg
                85                  90                  95

Thr Phe Gly Gln Gly Thr Lys Val Glu Ile Lys
            100                 105
```

<210> SEQ ID NO 177
<211> LENGTH: 107
<212> TYPE: PRT
<213> ORGANISM: Artificial Sequence
<220> FEATURE:
<223> OTHER INFORMATION: Amino acid sequence 4 of the variable region of the light chain of humanized anti-hTfR antibody No.2

<400> SEQUENCE: 177

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Ser Asn Asn
                20                  25                  30

Leu Gln Trp Tyr Gln Gln Lys Pro Gly Gln Ala Pro Arg Leu Leu Ile
            35                  40                  45

Tyr Tyr Ala Ser Gln Ser Ile Ser Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Asn Ser Trp Pro Arg
```

85                  90                  95

Thr Phe Gly Gln Gly Thr Lys Val Glu Ile Lys
            100                 105

<210> SEQ ID NO 178
<211> LENGTH: 107
<212> TYPE: PRT
<213> ORGANISM: Artificial Sequence
<220> FEATURE:
<223> OTHER INFORMATION: Amino acid sequence 5 of the variable region of
      the light chain of humanized anti-hTfR antibody No.2

<400> SEQUENCE: 178

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Asn
            20                  25                  30

Leu Gln Trp Tyr Gln Gln Lys Pro Gly Lys Ala Pro Lys Leu Leu Ile
        35                  40                  45

Tyr Tyr Ala Ser Gln Ser Ile Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Asn Ser Trp Pro Arg
                85                  90                  95

Thr Phe Gly Gly Gly Thr Lys Val Glu Ile Lys
            100                 105

<210> SEQ ID NO 179
<211> LENGTH: 107
<212> TYPE: PRT
<213> ORGANISM: Artificial Sequence
<220> FEATURE:
<223> OTHER INFORMATION: Amino acid sequence 6 of the variable region of
      the light chain of humanized anti-hTfR antibody No.2

<400> SEQUENCE: 179

Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Ser Asn Asn
            20                  25                  30

Leu Gln Trp Tyr Gln Gln Lys Pro Asp Gln Ser Pro Lys Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Leu Cys Gln Gln Ser Asn Ser Trp Pro Arg
                85                  90                  95

Thr Phe Gly Gln Gly Thr Lys Val Glu Ile Lys
            100                 105

<210> SEQ ID NO 180
<211> LENGTH: 214
<212> TYPE: PRT
<213> ORGANISM: Artificial Sequence
<220> FEATURE:
<223> OTHER INFORMATION: Amino acid sequence of the light chain of
      humanized anti-hTfR antibody No.2 containing amino acid sequence 6
      as the variable region

<400> SEQUENCE: 180

| | | | | | | | | | | | | | | |
|---|---|---|---|---|---|---|---|---|---|---|---|---|---|---|
Glu Ile Val Leu Thr Gln Ser Pro Asp Phe Gln Ser Val Thr Pro Lys
1               5                  10                  15

Glu Lys Val Thr Ile Thr Cys Arg Ala Ser Gln Ser Ile Ser Asn Asn
                20                  25                  30

Leu Gln Trp Tyr Gln Gln Lys Pro Asp Gln Ser Pro Lys Leu Leu Ile
            35                  40                  45

Lys Tyr Ala Ser Gln Ser Ile Ser Gly Ile Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Leu Cys Gln Gln Ser Asn Ser Trp Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
    115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
    195                 200                 205

Phe Asn Arg Gly Glu Cys
    210

<210> SEQ ID NO 181
<211> LENGTH: 725
<212> TYPE: DNA
<213> ORGANISM: Artificial Sequence
<220> FEATURE:
<223> OTHER INFORMATION: Nucleotide sequence encoding the amino acid
      sequence of the light chain of humanized anti-hTfR antibody No.2
      containing amino acid sequence 6 as the variable region, synthetic
      sequence

<400> SEQUENCE: 181

```
acgcgtgccg ccaccatggg ctggagctgg attctgctgt tcctcctgag cgtgacagca      60
ggagtgcaca gcgaaattgt gctgacccag tctcccgatt tccagtccgt gacccccaag     120
gagaaagtca ccatcacatg cagagcatca cagtccatta gcaacaatct gcagtggtac     180
cagcagaagc cagaccagag ccccaagctg ctgatcaaat atgcctctca gagtatttca     240
ggcataccct ctaggttctc cggtagcggc tctggaaccg actttactct gaccatcaac     300
agtctggagg ctgaagatgc cgctacatac ttgtgccagc agagtaattc atggcctagg     360
acctttggcc aggggacaaa ggtggagatc aaaaggactg tggcagcccc aagtgtcttc     420
atttttcccc cttcagacga acagctgaag agcggcacag catctgtggt ctgtctgctg     480
aacaatttct acccacggga ggctaaggtg cagtggaaag tcgataacgc actgcagtcc     540
ggaaatagcc aggagtctgt gactgaacag gacagtaagg attcaaccta ttccctgtcc     600
agcacactga ctctgagcaa agccgattac gagaagcaca agtgtatgc ttgcgaagtc     660
```
acacatcagg ggctgtctag tcccgtgact aagtctttta ataggggtga atgttaagcg    720
gccgc    725

<210> SEQ ID NO 182
<211> LENGTH: 120
<212> TYPE: PRT
<213> ORGANISM: Artificial Sequence
<220> FEATURE:
<223> OTHER INFORMATION: Amino acid sequence 1 of the variable region of
      the heavy chain of humanized anti-hTfR antibody No.2

<400> SEQUENCE: 182

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Val Met His Trp Val Arg Gln Ala Pro Gly Gln Gly Leu Glu Trp Met
        35                  40                  45

Gly Val Ile Ser Thr Tyr Tyr Gly His Gly Ser Tyr Asn Gln Arg Phe
    50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Gly Tyr Gly Ser Ser Ser Leu Ala Gly Asn Phe Asp Val
            100                 105                 110

Trp Gly Gln Gly Thr Leu Val Thr
        115                 120

<210> SEQ ID NO 183
<211> LENGTH: 120
<212> TYPE: PRT
<213> ORGANISM: Artificial Sequence
<220> FEATURE:
<223> OTHER INFORMATION: Amino acid sequence 2 of the variable region of
      the heavy chain of humanized anti-hTfR antibody No.2

<400> SEQUENCE: 183

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Val Met His Trp Val Arg Gln Ala Pro Gly Gln Arg Leu Glu Trp Met
        35                  40                  45

Gly Val Ile Ser Thr Tyr Tyr Gly His Gly Ser Tyr Asn Gln Arg Phe
    50                  55                  60

Lys Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Tyr Gly Ser Ser Ser Leu Ala Gly Asn Phe Asp Val
            100                 105                 110

Trp Gly Gln Gly Thr Leu Val Thr
        115                 120

<210> SEQ ID NO 184
<211> LENGTH: 120
<212> TYPE: PRT
<213> ORGANISM: Artificial Sequence

```
<220> FEATURE:
<223> OTHER INFORMATION: Amino acid sequence 3 of the variable region of
      the heavy chain of humanized anti-hTfR antibody No.2

<400> SEQUENCE: 184

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Val Met His Trp Val Arg Gln Ala Pro Gly Gln Gly Leu Glu Trp Met
        35                  40                  45

Gly Val Ile Ser Thr Tyr Tyr Gly His Gly Ser Tyr Asn Gln Arg Phe
    50                  55                  60

Lys Gly Arg Val Thr Met Thr Thr Asp Thr Ser Thr Ser Ala Ala Tyr
65                  70                  75                  80

Met Glu Leu Arg Ser Leu Arg Ser Asp Asp Thr Ala Val Tyr Tyr Cys
                85                  90                  95

Ala Ser Gly Gly Tyr Gly Ser Ser Leu Ala Gly Asn Phe Asp Val
            100                 105                 110

Trp Gly Gln Gly Thr Leu Val Thr
        115                 120

<210> SEQ ID NO 185
<211> LENGTH: 120
<212> TYPE: PRT
<213> ORGANISM: Artificial Sequence
<220> FEATURE:
<223> OTHER INFORMATION: Amino acid sequence 4 of the variable region of
      the heavy chain of humanized anti-hTfR antibody No.2

<400> SEQUENCE: 185

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Val Met His Trp Val Arg Gln Ala Pro Gly Gln Gly Leu Glu Trp Met
        35                  40                  45

Gly Val Ile Ser Thr Tyr Tyr Gly His Gly Ser Tyr Asn Gln Arg Phe
    50                  55                  60

Lys Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Gly Tyr Gly Ser Ser Leu Ala Gly Asn Phe Asp Val
            100                 105                 110

Trp Gly Gln Gly Thr Thr Val Thr
        115                 120

<210> SEQ ID NO 186
<211> LENGTH: 120
<212> TYPE: PRT
<213> ORGANISM: Artificial Sequence
<220> FEATURE:
<223> OTHER INFORMATION: Amino acid sequence 5 of the variable region of
      the heavy chain of humanized anti-hTfR antibody No.2

<400> SEQUENCE: 186

Gln Val Gln Leu Val Gln Ser Gly Ala Glu Val Lys Lys Pro Gly Ser
1               5                   10                  15
```

```
Ser Val Lys Val Ser Cys Lys Ala Ser Gly Thr Phe Ser Asp Tyr
            20                  25                  30

Val Met His Trp Val Arg Gln Ala Pro Gly Gln Gly Leu Glu Trp Met
        35                  40                  45

Gly Val Ile Ser Thr Tyr Tyr Gly His Gly Ser Tyr Asn Gln Arg Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
            85                  90                  95

Ala Arg Gly Gly Tyr Gly Ser Ser Leu Ala Gly Asn Phe Asp Val
            100                 105                 110

Trp Gly Gln Gly Thr Val Val Thr
        115                 120

<210> SEQ ID NO 187
<211> LENGTH: 120
<212> TYPE: PRT
<213> ORGANISM: Artificial Sequence
<220> FEATURE:
<223> OTHER INFORMATION: Amino acid sequence 6 of the variable region of
      the heavy chain of humanized anti-hTfR antibody No.2

<400> SEQUENCE: 187

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Val Met His Trp Val Arg Gln Ala Pro Gly Gln Gly Leu Glu Trp Ile
        35                  40                  45

Gly Val Ile Ser Thr Tyr Tyr Gly His Gly Ser Tyr Asn Gln Arg Phe
    50                  55                  60

Lys Gly Arg Ala Thr Met Thr Val Asp Lys Ser Ile Ser Thr Ala Tyr
65                  70                  75                  80

Met Glu Leu Val Arg Leu Arg Ser Asp Thr Ala Val Tyr Tyr Cys
            85                  90                  95

Val Arg Gly Gly Tyr Gly Ser Ser Ser Leu Ala Gly Asn Phe Asp Val
            100                 105                 110

Trp Gly Gln Gly Thr Thr Val Thr
        115                 120

<210> SEQ ID NO 188
<211> LENGTH: 453
<212> TYPE: PRT
<213> ORGANISM: Artificial Sequence
<220> FEATURE:
<223> OTHER INFORMATION: Amino acid sequence of the heavy chain of
      humanized anti-hTfR antibody No.2 containing amino acid sequence 6
      as the variable region

<400> SEQUENCE: 188

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Val Met His Trp Val Arg Gln Ala Pro Gly Gln Gly Leu Glu Trp Ile
        35                  40                  45

Gly Val Ile Ser Thr Tyr Tyr Gly His Gly Ser Tyr Asn Gln Arg Phe
    50                  55                  60
```

```
Lys Gly Arg Ala Thr Met Thr Val Asp Lys Ser Ile Ser Thr Ala Tyr
 65                  70                  75                  80

Met Glu Leu Val Arg Leu Arg Ser Asp Asp Thr Ala Val Tyr Tyr Cys
                 85                  90                  95

Val Arg Gly Gly Tyr Gly Ser Ser Leu Ala Gly Asn Phe Asp Val
            100                 105                 110

Trp Gly Gln Gly Thr Thr Val Thr Val Ser Ser Ala Ser Thr Lys Gly
            115                 120                 125

Pro Ser Val Phe Pro Leu Ala Pro Ser Ser Lys Ser Thr Ser Gly Gly
            130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
            195                 200                 205

Asn His Lys Pro Ser Asn Thr Lys Val Asp Lys Lys Val Glu Pro Lys
            210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
                260                 265                 270

Ser His Glu Asp Pro Glu Val Lys Phe Asn Trp Tyr Val Asp Gly Val
            275                 280                 285

Glu Val His Asn Ala Lys Thr Lys Pro Arg Glu Glu Gln Tyr Asn Ser
290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
            355                 360                 365

Val Ser Leu Thr Cys Leu Val Lys Gly Phe Tyr Pro Ser Asp Ile Ala
            370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
                420                 425                 430

Val Met His Glu Ala Leu His Asn His Tyr Thr Gln Lys Ser Leu Ser
            435                 440                 445

Leu Ser Pro Gly Lys
            450

<210> SEQ ID NO 189
<211> LENGTH: 1442
```

<212> TYPE: DNA
<213> ORGANISM: Artificial Sequence
<220> FEATURE:
<223> OTHER INFORMATION: Nucleotide sequence encoding the amino acid
sequence of the heavy chain of humanized anti-hTfR antibody No.2
containing amino acid sequence 6 as the variable region, synthetic
sequence

<400> SEQUENCE: 189

```
acgcgtgccg ccaccatggg ctggagctgg attctgctgt tcctcctgag cgtgacagca    60
ggagtgcaca gccaggtgca gctggtccag tcaggagccg aagtgaaaaa gcccggagcc   120
tcagtcaaag tgtcttgtaa agcatcaggt tatacattta cagactacgt catgcactgg   180
gtgaggcagg cacctggaca gggtctggaa tggatcggcg tgatctccac ttactatggc   240
catggaagct acaaccagag attcaagggc agggcgacaa tgactgtaga caaatcaatt   300
tccactgctt atatggagct ggtaaggctg cggtccgacg ataccgctgt gtactattgc   360
gtacgaggag gatacggctc cagctctctg gctggtaatt tcgatgtgtg ggggcagggt   420
accacagtca ccgtgagttc agcaagcaca aagggcccat ctgtgtttcc actggccccc   480
tccagcaaaa gcacctctgg ggtacagcc gctctgggat gtctggtgaa ggattatttc   540
ccagagccag tcaccgtgtc ctggaacagc ggagccctga catctggagt ccacactttt   600
ccagctgtgc tgcagtctag tgggctgtac tccctgtcat ccgtggtcac tgtccccagc   660
tctagtctgg gtacccagac atatatctgc aacgtgaatc acaagccatc taataccaaa   720
gtcgacaaga agtggaacc caagtcctgt gataaaactc atacctgccc cccttgtcct   780
gcaccagagc tgctggggag gaccatccgtg ttcctgtttc acccaagcc taaagacacc   840
ctgatgatta gccgaactcc cgaagtcacc tgcgtggtcg tggacgtgtc tcacgaggac   900
cctgaagtca agtttaactg gtacgtggat ggcgtcgagg tgcataatgc taagacaaaa   960
ccccgagagg aacagtacaa cagtacatat cgtgtcgtgt cagtgctgac cgtcctgcat  1020
caggactggc tgaacgggaa ggaatataag tgcaaagtgt ccaataaggc actgcccgcc  1080
cctatcgaga aaaccattag caaggccaaa ggacagccta gggaaccaca ggtgtacaca  1140
ctgcctccat cccgggacga gctgactaag aaccaggtca gcctgacctg tctggtgaaa  1200
ggcttctatc cttcagatat cgctgtggag tgggaaagta tggacagcc agagaacaat  1260
tacaagacta ccccccctgt gctggactct gatgggagtt tctttctgta ttctaagctg  1320
accgtggata aaagtcggtg gcagcagggt aatgtcttta gttgttcagt gatgcacgaa  1380
gcactgcaca accactacac ccagaaatca ctgtcactgt caccagggaa ataagcggcc  1440
gc                                                                 1442
```

<210> SEQ ID NO 190
<211> LENGTH: 112
<212> TYPE: PRT
<213> ORGANISM: Artificial Sequence
<220> FEATURE:
<223> OTHER INFORMATION: Amino acid sequence 1 of the variable region of
the light chain of humanized anti-hTfR antibody No.3

<400> SEQUENCE: 190

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
            20                  25                  30

Asn Gly Asn Thr Tyr Leu His Trp Phe Gln Gln Arg Pro Gly Gln Ser
        35                  40                  45

Pro Arg Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Trp Thr Phe Gly Gly Gly Thr Lys Val Glu Ile Lys
                100                 105                 110

<210> SEQ ID NO 191
<211> LENGTH: 112
<212> TYPE: PRT
<213> ORGANISM: Artificial Sequence
<220> FEATURE:
<223> OTHER INFORMATION: Amino acid sequence 2 of the variable region of
      the light chain of humanized anti-hTfR antibody No.3

<400> SEQUENCE: 191

Asp Ile Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Val His Ser
                20                  25                  30

Asn Gly Asn Thr Tyr Leu His Trp Tyr Leu Gln Lys Pro Gly Gln Ser
            35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Trp Thr Phe Gly Gln Gly Thr Lys Val Glu Ile Lys
                100                 105                 110

<210> SEQ ID NO 192
<211> LENGTH: 112
<212> TYPE: PRT
<213> ORGANISM: Artificial Sequence
<220> FEATURE:
<223> OTHER INFORMATION: Amino acid sequence 3 of the variable region of
      the light chain of humanized anti-hTfR antibody No.3

<400> SEQUENCE: 192

Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Ser Leu Val His Ser
                20                  25                  30

Asn Gly Asn Thr Tyr Leu His Trp Leu Gln Gln Arg Pro Gly Gln Pro
            35                  40                  45

Pro Arg Leu Leu Ile Tyr Lys Val Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Trp Thr Phe Gly Gln Gly Thr Lys Leu Glu Ile Lys
                100                 105                 110

<210> SEQ ID NO 193

```
<211> LENGTH: 112
<212> TYPE: PRT
<213> ORGANISM: Artificial Sequence
<220> FEATURE:
<223> OTHER INFORMATION: Amino acid sequence 4 of the variable region of
      the light chain of humanized anti-hTfR antibody No.3

<400> SEQUENCE: 193

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Trp Thr Phe Gly Gln Gly Thr Lys Val Glu Ile Lys
            100                 105                 110

<210> SEQ ID NO 194
<211> LENGTH: 112
<212> TYPE: PRT
<213> ORGANISM: Artificial Sequence
<220> FEATURE:
<223> OTHER INFORMATION: Amino acid sequence 5 of the variable region of
      the light chain of humanized anti-hTfR antibody No.3

<400> SEQUENCE: 194

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Trp Thr Phe Gly Gln Gly Thr Arg Leu Glu Ile Lys
            100                 105                 110

<210> SEQ ID NO 195
<211> LENGTH: 112
<212> TYPE: PRT
<213> ORGANISM: Artificial Sequence
<220> FEATURE:
<223> OTHER INFORMATION: Amino acid sequence 6 of the variable region of
      the light chain of humanized anti-hTfR antibody No.3

<400> SEQUENCE: 195

Asp Ile Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Val His Ser
            20                  25                  30
```

Asn Gly Asn Thr Tyr Leu His Trp Tyr Leu Gln Lys Pro Gly Gln Ser
                35                  40                  45

Pro Gln Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Phe Phe Cys Ser Gln Ser
                 85                  90                  95

Thr His Val Pro Trp Thr Phe Gly Gln Gly Thr Lys Val Glu Ile Lys
                100                 105                 110

<210> SEQ ID NO 196
<211> LENGTH: 219
<212> TYPE: PRT
<213> ORGANISM: Artificial Sequence
<220> FEATURE:
<223> OTHER INFORMATION: Amino acid sequence of the light chain of
      humanized anti-hTfR antibody No.3 containing amino acid sequence 2
      as the variable region

<400> SEQUENCE: 196

Asp Ile Val Met Thr Gln Thr Pro Leu Ser Leu Ser Val Thr Pro Gly
 1               5                  10                  15

Gln Pro Ala Ser Ile Ser Cys Arg Ser Ser Gln Ser Leu Val His Ser
                20                  25                  30

Asn Gly Asn Thr Tyr Leu His Trp Tyr Leu Gln Lys Pro Gly Gln Ser
                35                  40                  45

Pro Gln Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Ser Gln Ser
                 85                  90                  95

Thr His Val Pro Trp Thr Phe Gly Gln Gly Thr Lys Val Glu Ile Lys
                100                 105                 110

Arg Thr Val Ala Ala Pro Ser Val Phe Ile Phe Pro Pro Ser Asp Glu
                115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
                180                 185                 190

Lys His Lys Val Tyr Ala Cys Glu Val Thr His Gln Gly Leu Ser Ser
                195                 200                 205

Pro Val Thr Lys Ser Phe Asn Arg Gly Glu Cys
                210                 215

<210> SEQ ID NO 197
<211> LENGTH: 740
<212> TYPE: DNA
<213> ORGANISM: Artificial Sequence
<220> FEATURE:
<223> OTHER INFORMATION: Nucleotide sequence encoding the amino acid
      sequence of the light chain of humanized anti-hTfR antibody No.3
      containing amino acid sequence 2 as the variable region, synthetic
      sequence

<400> SEQUENCE: 197

```
acgcgtgccg ccaccatggg ctggagctgg attctgctgt tcctcctgag cgtgacagca    60
ggagtgcaca gcgacatcgt gatgacccag actcccctga gcctgagcgt gacacctggc   120
cagcctgcca gcatcagctg cagaagctct cagagcctgg tgcacagcaa cggcaacacc   180
tacctgcact ggtatctgca gaagcccggc cagagccctc agctgctgat ctacaaggtg   240
tccaacagat tcagcggcgt gcccgacaga ttctccggca gcggctctgg caccgacttc   300
accctgaaga tttccagagt ggaagccgag gacgtgggcg tgtactactg cagccagagc   360
acccacgtgc cctggacatt cggccagggc accaaggtgg aaatcaagag aaccgtggcc   420
gctcccagcg tgttcatctt cccacctagc gacgagcagc tgaagtccgg cacagcctct   480
gtcgtgtgcc tgctgaacaa cttctacccc cgcgaggcca aggtgcagtg gaaggtggac   540
aacgccctgc agagcggcaa cagccaggaa agcgtgaccg agcaggactc caaggacagc   600
acctacagcc tgagcagcac cctgaccctg agcaaggccg actacgagaa gcacaaggtg   660
tacgcctgcg aagtgaccca ccagggcctg tctagccccg tgaccaagag cttcaacaga   720
ggcgagtgct aagcggccgc                                               740
```

<210> SEQ ID NO 198
<211> LENGTH: 219
<212> TYPE: PRT
<213> ORGANISM: Artificial Sequence
<220> FEATURE:
<223> OTHER INFORMATION: Amino acid sequence of the light chain of humanized anti-hTfR antibody No.3 containing amino acid sequence 4 as the variable region

<400> SEQUENCE: 198

```
Asp Ile Val Met Thr Gln Ser Pro Leu Ser Leu Pro Val Thr Pro Gly
  1               5                  10                  15

Glu Pro Ala Ser Ile Ser Cys Arg Ser Ser Gln Ser Leu Val His Ser
             20                  25                  30

Asn Gly Asn Thr Tyr Leu His Trp Tyr Leu Gln Lys Pro Gly Gln Ser
         35                  40                  45

Pro Gln Leu Leu Ile Tyr Lys Val Ser Asn Arg Phe Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Ser Gln Ser
                 85                  90                  95

Thr His Val Pro Trp Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205
```

Pro Val Thr Lys Ser Phe Asn Arg Gly Glu Cys
    210                 215

<210> SEQ ID NO 199
<211> LENGTH: 740
<212> TYPE: DNA
<213> ORGANISM: Artificial Sequence
<220> FEATURE:
<223> OTHER INFORMATION: Nucleotide sequence encoding the amino acid
      sequence of the light chain of humanized anti-hTfR antibody No.3
      containing amino acid sequence 4 as the variable region, synthetic
      sequence

<400> SEQUENCE: 199
acgcgtgccg ccaccatggg ctggagctgg attctgctgt tcctcctgag cgtgacagca      60
ggagtgcaca gcgacatcgt gatgacccag agcccctga gcctgcctgt gacacctggc     120
gagcctgcca gcatcagctg cagatctagc cagagcctgg tgcacagcaa cggcaacacc     180
tacctgcact ggtatctgca gaagcccggc cagagcccct cagctgctgat ctacaaggtg     240 tccaacagat tcagcggcgt gcccgacaga ttctccggca gcggctctgg caccgacttc     300
accctgaaga tctccagagt ggaagccgag gacgtgggcg tgtactactg cagccagagc     360
acccacgtgc cctggacatt cggccagggc accaaggtgg aaatcaagag aaccgtggcc     420
gctcccagcg tgttcatctt cccacctagc gacgagcagc tgaagtccgg cacagcctct     480
gtcgtgtgcc tgctgaacaa cttctacccc cgcgaggcca aggtgcagtg gaaggtggac     540
aacgccctgc agagcggcaa cagccaggaa agcgtgaccg agcaggactc caaggacagc     600
acctacagcc tgagcagcac cctgaccctg agcaaggccg actacgagaa gcacaaggtg     660
tacgcctgcg aagtgaccca ccagggcctg tctagccccg tgaccaagag cttcaacaga     720
ggcgagtgct aagcggccgc                                                 740

<210> SEQ ID NO 200
<211> LENGTH: 219
<212> TYPE: PRT
<213> ORGANISM: Artificial Sequence
<220> FEATURE:
<223> OTHER INFORMATION: Amino acid sequence of the light chain of
      humanized anti-hTfR antibody No.3 containing amino acid sequence 5
      as the variable region

<400> SEQUENCE: 200

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Trp Thr Phe Gly Gln Gly Thr Arg Leu Glu Ile Lys
            100                 105                 110

Arg Thr Val Ala Ala Pro Ser Val Phe Ile Phe Pro Pro Ser Asp Glu
        115                 120                 125

```
Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 201
<211> LENGTH: 740
<212> TYPE: DNA
<213> ORGANISM: Artificial Sequence
<220> FEATURE:
<223> OTHER INFORMATION: Nucleotide sequence encoding the amino acid
      sequence of the light chain of humanized anti-hTfR antibody No.3
      containing amino acid sequence 5 as the variable region, synthetic
      sequence

<400> SEQUENCE: 201
acgcgtgccg ccaccatggg ctggagctgg attctgctgt tcctcctgag cgtgacagca      60
ggagtgcaca gcgacatcgt gatgacccag acacccctga gcctgcctgt gacacctggc     120
gagcctgcca gcatcagctg cagatctagc cagagcctgg tgcacagcaa cggcaacacc     180
tacctgcact ggtatctgca gaagcccggc cagagccctc agctgctgat ctacaaggtg     240
tccaacagat tcagcggcgt gcccgacaga ttctccggca gcggctctgg caccgacttc     300
accctgaaga tctccagagt ggaagccgag gacgtgggcg tgtactactg cagccagagc     360
acccacgtgc cctggacatt cggccagggc accaggctgg aaatcaagag aaccgtggcc     420
gctcccagcg tgttcatctt cccacctagc gacgagcagc tgaagtccgg cacagcctct     480
gtcgtgtgcc tgctgaacaa cttctacccc cgcgaggcca aggtgcagtg gaaggtggac     540
aacgccctgc agagcggcaa cagccaggaa agcgtgaccg agcaggactc caaggacagc     600
acctacagcc tgagcagcac cctgaccctg agcaaggccg actacgagaa gcacaaggtg     660
tacgcctgcg aagtgaccca ccagggcctg tctagccccg tgaccaagag cttcaacaga     720
ggcgagtgct aagcggccgc                                                 740

<210> SEQ ID NO 202
<211> LENGTH: 219
<212> TYPE: PRT
<213> ORGANISM: Artificial Sequence
<220> FEATURE:
<223> OTHER INFORMATION: Amino acid sequence of the light chain of
      humanized anti-hTfR antibody No.3 containing amino acid sequence 6
      as the variable region

<400> SEQUENCE: 202

Asp Ile Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Val His Ser
                20                  25                  30

Asn Gly Asn Thr Tyr Leu His Trp Tyr Leu Gln Lys Pro Gly Gln Ser
            35                  40                  45

Pro Gln Leu Leu Ile Tyr Lys Val Ser Asn Arg Phe Ser Gly Val Pro
```

Asp Arg Phe Ser Gly Ser Gly Ser Gly Thr Asp Phe Thr Leu Lys Ile
65                  70                  75                  80

Ser Arg Val Glu Ala Glu Asp Val Gly Val Phe Phe Cys Ser Gln Ser
                85                  90                  95

Thr His Val Pro Trp Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 203
<211> LENGTH: 740
<212> TYPE: DNA
<213> ORGANISM: Artificial Sequence
<220> FEATURE:
<223> OTHER INFORMATION: Nucleotide sequence encoding the amino acid
      sequence of the light chain of humanized anti-hTfR antibody No.3
      containing amino acid sequence 6 as the variable region, synthetic
      sequence

<400> SEQUENCE: 203
acgcgtgccg ccaccatggg ctggagctgg attctgctgt tcctcctgag cgtgacagca    60
ggagtgcaca gcgacatcgt gatgacccag actcccctga gcctgagcgt gacacctggc   120
cagcctgcca gcatcagctg cagatccagc cagagcctgg tgcacagcaa cggcaacacc   180
tacctgcact ggtatctgca gaagcccggc cagagccctc agctgctgat ctacaaggtg   240
tccaacagat tcagcggcgt gcccgacaga ttctccggca gcggctctgg caccgacttc   300
accctgaaga tttccagagt ggaagccgag gacgtgggcg tgttcttctg cagccagagc   360
acccacgtgc cctggacatt cggccagggc accaaggtgg aaatcaagag aaccgtggcc   420
gctcccagcg tgttcatctt cccacctagc gacgagcagc tgaagtccgg cacagcctct   480
gtcgtgtgcc tgctgaacaa cttctacccc cgcgaggcca aggtgcagtg gaaggtggac   540
aacgccctgc agagcggcaa cagccaggaa agcgtgaccg agcaggactc caaggacagc   600
acctacagcc tgagcagcac cctgaccctg agcaaggccg actacgagaa gcacaaggtg   660
tacgcctgcg aagtgaccca ccagggcctg tctagccccg tgaccaagag cttcaacaga   720
ggcgagtgct aagcggccgc                                               740

<210> SEQ ID NO 204
<211> LENGTH: 118
<212> TYPE: PRT
<213> ORGANISM: Artificial Sequence
<220> FEATURE:
<223> OTHER INFORMATION: Amino acid sequence 1 of the variable region of
      the heavy chain of humanized anti-hTfR antibody No.3

<400> SEQUENCE: 204

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Leu Gly Trp Val Arg Gln Ala Pro Gly Gln Gly Leu Glu Trp Met
        35                  40                  45

Gly Asp Ile Tyr Pro Gly Gly Asp Tyr Pro Thr Tyr Ser Glu Lys Phe
    50                  55                  60

Lys Val Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Gly Asn Tyr Asp Glu Val Ala Tyr Trp Gly Gln Gly Thr
            100                 105                 110

Leu Val Thr Val Ser Ser
        115

<210> SEQ ID NO 205
<211> LENGTH: 118
<212> TYPE: PRT
<213> ORGANISM: Artificial Sequence
<220> FEATURE:
<223> OTHER INFORMATION: Amino acid sequence 2 of the variable region of
      the heavy chain of humanized anti-hTfR antibody No.3

<400> SEQUENCE: 205

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
            20                  25                  30

Trp Leu Gly Trp Val Arg Gln Met Pro Gly Lys Gly Leu Glu Trp Met
        35                  40                  45

Gly Asp Ile Tyr Pro Gly Gly Asp Tyr Pro Thr Tyr Ser Glu Lys Phe
    50                  55                  60

Lys Val Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Ser Gly Asn Tyr Asp Glu Val Ala Tyr Trp Gly Gln Gly Thr
            100                 105                 110

Leu Val Thr Val Ser Ser
        115

<210> SEQ ID NO 206
<211> LENGTH: 118
<212> TYPE: PRT
<213> ORGANISM: Artificial Sequence
<220> FEATURE:
<223> OTHER INFORMATION: Amino acid sequence 3 of the variable region of
      the heavy chain of humanized anti-hTfR antibody No.3

<400> SEQUENCE: 206

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Leu Gly Trp Val Arg Gln Ala Pro Gly Gln Gly Leu Glu Trp Met
            35                  40                  45

Gly Asp Ile Tyr Pro Gly Gly Asp Tyr Pro Thr Tyr Ser Glu Lys Phe
 50                      55                  60

Lys Val Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Gly Asn Tyr Asp Glu Val Ala Tyr Trp Gly Gln Gly Thr
                100                 105                 110

Thr Val Thr Val Ser Ser
            115

<210> SEQ ID NO 207
<211> LENGTH: 118
<212> TYPE: PRT
<213> ORGANISM: Artificial Sequence
<220> FEATURE:
<223> OTHER INFORMATION: Amino acid sequence 4 of the variable region of
      the heavy chain of humanized anti-hTfR antibody No.3

<400> SEQUENCE: 207

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Trp Leu Gly Trp Val Arg Gln Ala Pro Gly Gln Arg Leu Glu Trp Met
            35                  40                  45

Gly Asp Ile Tyr Pro Gly Gly Asp Tyr Pro Thr Tyr Ser Glu Lys Phe
 50                      55                  60

Lys Val Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Gly Asn Tyr Asp Glu Val Ala Tyr Trp Gly Gln Gly Thr
                100                 105                 110

Leu Val Thr Val Ser Ser
            115

<210> SEQ ID NO 208
<211> LENGTH: 118
<212> TYPE: PRT
<213> ORGANISM: Artificial Sequence
<220> FEATURE:
<223> OTHER INFORMATION: Amino acid sequence 5 of the variable region of
      the heavy chain of humanized anti-hTfR antibody No.3

<400> SEQUENCE: 208

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asn Tyr
                20                  25                  30

Trp Leu Gly Trp Val Arg Gln Ala Pro Gly Gln Gly Leu Glu Trp Met
            35                  40                  45

Gly Asp Ile Tyr Pro Gly Gly Asp Tyr Pro Thr Tyr Ser Glu Lys Phe
 50                      55                  60

Lys Val Arg Val Thr Ile Thr Ala Asp Lys Ser Thr Ser Thr Ala Tyr
65                  70                  75                  80

```
Met Glu Leu Ser Ser Leu Arg Ser Glu Asp Thr Ala Val Tyr Tyr Cys
             85                  90                  95

Ala Arg Ser Gly Asn Tyr Asp Glu Val Ala Tyr Trp Gly Gln Gly Thr
            100                 105                 110

Val Val Thr Val Ser Ser
        115

<210> SEQ ID NO 209
<211> LENGTH: 118
<212> TYPE: PRT
<213> ORGANISM: Artificial Sequence
<220> FEATURE:
<223> OTHER INFORMATION: Amino acid sequence 6 of the variable region of
      the heavy chain of humanized anti-hTfR antibody No.3

<400> SEQUENCE: 209

Glu Val Gln Leu Val Gln Ser Gly Ala Glu Val Lys Lys Pro Gly Glu
1               5                  10                  15

Ser Leu Lys Ile Ser Cys Lys Gly Ser Gly Tyr Ser Phe Met Asn Tyr
             20                  25                  30

Trp Leu Gly Trp Val Arg Gln Met Pro Gly Lys Gly Leu Glu Trp Ile
         35                  40                  45

Gly Asp Ile Tyr Pro Gly Gly Asp Tyr Pro Thr Tyr Ser Glu Lys Phe
     50                  55                  60

Lys Val Lys Ala Ile Ile Ser Ala Asp Thr Ser Ile Ser Thr Val Tyr
65                  70                  75                  80

Leu Gln Leu Ser Ser Leu Lys Ala Ser Asp Thr Ala Met Tyr Phe Cys
             85                  90                  95

Ala Arg Ser Gly Asn Tyr Asp Glu Val Ala Tyr Trp Gly Gln Gly Thr
            100                 105                 110

Leu Val Thr Val Ser Ser
        115

<210> SEQ ID NO 210
<211> LENGTH: 448
<212> TYPE: PRT
<213> ORGANISM: Artificial Sequence
<220> FEATURE:
<223> OTHER INFORMATION: Amino acid sequence of the heavy chain of
      humanized anti-hTfR antibody No.3 containing amino acid sequence 2
      as the variable region

<400> SEQUENCE: 210

Glu Val Gln Leu Val Gln Ser Gly Ala Glu Val Lys Lys Pro Gly Glu
1               5                  10                  15

Ser Leu Lys Ile Ser Cys Lys Gly Ser Gly Tyr Ser Phe Thr Asn Tyr
             20                  25                  30

Trp Leu Gly Trp Val Arg Gln Met Pro Gly Lys Gly Leu Glu Trp Met
         35                  40                  45

Gly Asp Ile Tyr Pro Gly Gly Asp Tyr Pro Thr Tyr Ser Glu Lys Phe
     50                  55                  60

Lys Val Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
             85                  90                  95

Ala Arg Ser Gly Asn Tyr Asp Glu Val Ala Tyr Trp Gly Gln Gly Thr
            100                 105                 110

Leu Val Thr Val Ser Ser Ala Ser Thr Lys Gly Pro Ser Val Phe Pro
        115                 120                 125
```

-continued

Leu Ala Pro Ser Ser Lys Ser Thr Ser Gly Gly Thr Ala Ala Leu Gly
            130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 211
<211> LENGTH: 1427
<212> TYPE: DNA
<213> ORGANISM: Artificial Sequence
<220> FEATURE:
<223> OTHER INFORMATION: Nucleotide sequence encoding the amino acid
      sequence of the heavy chain of humanized anti-hTfR antibody No.3
      containing amino acid sequence 2 as the variable region, synthetic
      sequence

<400> SEQUENCE: 211
acgcgtgccg ccaccatggg ctggagctgg attctgctgt tcctcctgag cgtgacagca      60
ggagtgcaca gcgaggtgca actagtgcag tctggagcag aggtgaaaaa gcccggggag     120
tctctgaaga tttcctgtaa gggttctgga tacagcttta ccaactactg gctgggatgg     180

```
gtgcgccaga tgcccgggaa aggcctggag tggatggggg acatctaccc cggcggagac    240
taccctacat acagcgagaa gttcaaggtc caggtcacca tctcagccga caagtccatc    300
agcaccgcct acctgcagtg gagcagcctg aaggcctcgg acaccgccat gtattactgt    360
gcgagatcag gcaattacga cgaagtggcc tactggggcc aaggaaccct ggtcaccgtc    420
tcctcagcta gcaccaaggg cccatcggtc ttccccctgg cacctcctc caagagcacc     480 tctgggggca cagcggccct gggctgcctg gtcaaggact acttccccga accggtgacg    540
gtgtcgtgga actcaggcgc cctgaccagc ggcgtgcaca ccttcccggc tgtcctacag    600
tcctcaggac tctactccct cagcagcgtg gtgaccgtgc cctccagcag cttgggcacc    660
cagacctaca tctgcaacgt gaatcacaag cccagcaaca ccaaggtgga caagaaagtt    720
gagcccaaat cttgtgacaa aactcacacg tgcccaccgt gcccagcacc tgaactcctg    780
ggaggtccgt cagtcttcct cttccccca aaacccaagg acaccctcat gatctcccgg     840
acccctgagg tcacatgcgt ggtggtggac gtgagccacg aagaccctga ggtcaagttc    900
aactggtacg tggacggcgt ggaggtgcat aatgccaaga caaagccgcg ggaggagcag    960
tacaacagca cgtaccgggt ggtcagcgtc ctcaccgtcc tgcaccagga ctggctgaat   1020
ggcaaggagt acaagtgcaa ggtctccaac aaagccctcc cagcccccat cgagaaaacc   1080
atctccaaag ccaaagggca gccccgagaa ccacaggtgt acaccctgcc cccatcccgg   1140
gatgagctga ccaagaacca ggtcagcctg acctgcctgg tcaaaggctt ctatcccagc   1200
gacatcgccg tggagtggga gagcaatggg cagccggaga caactacaa gaccacgcct    1260 cccgtgctgg actccgacgg ctccttcttc ctctacagca agctcaccgt ggacaagagc   1320
aggtggcagc aggggaacgt cttctcatgc tccgtgatgc atgaggctct gcacaaccac   1380
tacacgcaga agagcctctc cctgtctccg ggtaaataag cggccgc                 1427
```

<210> SEQ ID NO 212
<211> LENGTH: 445
<212> TYPE: PRT
<213> ORGANISM: Artificial Sequence
<220> FEATURE:
<223> OTHER INFORMATION: Amino acid sequence of the heavy chain (IgG4)
    of humanized anti-hTfR antibody No.3 containing amino acid
    sequence 2 as the variable region

<400> SEQUENCE: 212

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
            20                  25                  30

Trp Leu Gly Trp Val Arg Gln Met Pro Gly Lys Gly Leu Glu Trp Met
        35                  40                  45

Gly Asp Ile Tyr Pro Gly Gly Asp Tyr Pro Thr Tyr Ser Glu Lys Phe
    50                  55                  60

Lys Val Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Ser Gly Asn Tyr Asp Glu Val Ala Tyr Trp Gly Gln Gly Thr
            100                 105                 110

Leu Val Thr Val Ser Ser Ala Ser Thr Lys Gly Pro Ser Val Phe Pro
        115                 120                 125
```

Leu Ala Pro Cys Ser Arg Ser Thr Ser Glu Ser Thr Ala Ala Leu Gly
            130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
210                 215                 220

Pro Pro Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445

<210> SEQ ID NO 213
<211> LENGTH: 1418
<212> TYPE: DNA
<213> ORGANISM: Artificial Sequence
<220> FEATURE:
<223> OTHER INFORMATION: Nucleotide sequence encoding the amino acid
      sequence of the heavy chain (IgG4) of humanized anti-hTfR antibody
      No.3 containing amino acid sequence 2 as the variable region,
      synthetic sequence

<400> SEQUENCE: 213
acgcgtgccg ccaccatggg ctggagctgg attctgctgt tcctcctgag cgtgacagca      60
ggagtgcaca gcgaggtgca actagtgcag tctggagcag aggtgaaaaa gcccggggag     120
tctctgaaga tttcctgtaa gggttctgga tacagcttta ccaactactg gctgggatgg     180

```
gtgcgccaga tgcccgggaa aggcctggag tggatggggg acatctaccc cggcggagac    240
taccctacat acagcgagaa gttcaaggtc caggtcacca tctcagccga caagtccatc    300
agcaccgcct acctgcagtg gagcagcctg aaggcctcgg acaccgccat gtattactgt    360
gcgagatcag gcaattacga cgaagtggcc tactggggcc aaggaaccct ggtcaccgtc    420
tcctcagcta gcaccaaggg cccatcggtc ttccccctgg cgccctgctc caggagcacc    480
tccgagagca cagccgccct gggctgcctg gtcaaggact acttccccga accggtgacg    540
gtgtcgtgga actcaggcgc cctgaccagc ggcgtgcaca ccttcccggc tgtcctacag    600
tcctcaggac tctactccct cagcagcgtg gtgaccgtgc cctccagcag cttgggcacg    660
aagacctaca cctgcaacgt agatcacaag cccagcaaca ccaaggtgga caagagagtt    720
gagtccaaat atggtccccc atgcccacca tgcccagcac ctgagttcct ggggggtcca    780
tcagtcttcc tgttcccccc aaaacccaag gacactctca tgatctcccg gacccctgag    840
gtcacgtgcg tggtggtgga cgtgagccag gaagacccccg aggtccagtt caactggtac    900
gtggatggcg tggaggtgca taatgccaag acaaagccgc gggaggagca gttcaacagc    960
acgtaccgtg tggtcagcgt cctcaccgtc ctgcaccagg actggctgaa cggcaaggag   1020
tacaagtgca aggtctccaa caaaggcctc ccgtcctcca tcgagaaaac catctccaaa   1080
gccaaagggc agccccgaga gccacaggtg tacaccctgc ccccatccca ggaggagatg   1140
accaagaacc aggtcagcct gacctgcctg gtcaaaggct tctacccag cgacatcgcc   1200 gtggagtggg agagcaatgg gcagccggag aacaactaca agaccacgcc tcccgtgctg   1260
gactccgacg gctccttctt cctctacagc aggctcaccg tggacaagag caggtggcag   1320
gaggggaatg tcttctcatg ctccgtgatg catgaggctc tgcacaacca ctacacacag   1380
aagagcctct ccctgtctcc gggtaaataa gcggccgc                           1418

<210> SEQ ID NO 214
<211> LENGTH: 43
<212> TYPE: DNA
<213> ORGANISM: Artificial Sequence
<220> FEATURE:
<223> OTHER INFORMATION: Primer hTfR5', synthetic sequence

<400> SEQUENCE: 214
ccgacgcgtc gccaccatga tggatcaagc tagatcagca ttc                        43

<210> SEQ ID NO 215
<211> LENGTH: 59
<212> TYPE: DNA
<213> ORGANISM: Artificial Sequence
<220> FEATURE:
<223> OTHER INFORMATION: Primer hTfR3', synthetic sequence

<400> SEQUENCE: 215
ataatgcggc cgcttaatga tgatgatgat gatgaaactc attgtcaatg tcccaaacg       59

<210> SEQ ID NO 216
<211> LENGTH: 20
<212> TYPE: DNA
<213> ORGANISM: Artificial Sequence
<220> FEATURE:
<223> OTHER INFORMATION: Primer Hyg-Sfi5', synthetic sequence

<400> SEQUENCE: 216
gaggccgcct cggcctctga                                                  20
```

<210> SEQ ID NO 217
<211> LENGTH: 29
<212> TYPE: DNA
<213> ORGANISM: Artificial Sequence
<220> FEATURE:
<223> OTHER INFORMATION: Primer Hyg-BstX3', synthetic sequence

<400> SEQUENCE: 217
aaccatcgtg atgggtgcta ttcctttgc                                        29

<210> SEQ ID NO 218
<211> LENGTH: 108
<212> TYPE: PRT
<213> ORGANISM: Artificial Sequence
<220> FEATURE:
<223> OTHER INFORMATION: Amino acid sequence of the variable region of
      the light chain of anti-hTfR antibody No.1

<400> SEQUENCE: 218

Asp Ile Val Leu Thr Gln Ser Ser Lys Phe Met Ser Thr Ser Val Gly
1               5                   10                  15

Asp Arg Val Ser Ile Thr Cys Lys Ala Ser Gln Asp Val Asn Ser Ala
            20                  25                  30

Val Ala Trp Phe Gln Gln Lys Pro Gly Gln Ser Pro Lys Leu Leu Ile
        35                  40                  45

Tyr Trp Thr Ser Thr Arg His Thr Gly Val Pro Asp Arg Phe Thr Gly
50                  55                  60

Ser Gly Ser Gly Thr Val Tyr Thr Leu Thr Ile Ser Ser Val Gln Ala
65                  70                  75                  80

Glu Asp Leu Ala Leu Tyr Tyr Cys Gln Gln His Tyr Ser Thr Pro Arg
                85                  90                  95

Thr Phe Gly Gly Gly Thr Lys Leu Glu Ile Lys Arg
            100                 105

<210> SEQ ID NO 219
<211> LENGTH: 116
<212> TYPE: PRT
<213> ORGANISM: Artificial Sequence
<220> FEATURE:
<223> OTHER INFORMATION: Amino acid sequence of the variable region of
      the heavy chain of anti-hTfR antibody No.1

<400> SEQUENCE: 219

Glu Val Gln Leu Gln Glu Ser Gly Gly Gly Leu Val Gln Pro Gly Gly
1               5                   10                  15

Ser Leu Lys Leu Ser Cys Ala Ala Ser Gly Leu Thr Phe Ser Asn Tyr
            20                  25                  30

Gly Met Ser Trp Ile Arg Gln Thr Pro Asp Lys Arg Leu Glu Leu Val
        35                  40                  45

Ala Asn Ile Asn Thr Asn Gly Gly Ser Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Ser Glu Asp Thr Ala Ile Tyr Tyr Cys
                85                  90                  95

Thr Asn Asn Arg Tyr Asp Glu Asp Tyr Trp Gly Gln Gly Thr Ser Val
            100                 105                 110

Thr Val Ser Ser
        115

```
<210> SEQ ID NO 220
<211> LENGTH: 108
<212> TYPE: PRT
<213> ORGANISM: Artificial Sequence
<220> FEATURE:
<223> OTHER INFORMATION: Amino acid sequence of the variable region of
      the light chain of anti-hTfR antibody No.2

<400> SEQUENCE: 220

Asp Ile Val Leu Thr Gln Ser Pro Ala Thr Leu Ser Val Thr Pro Gly
1               5                   10                  15

Asp Ser Val Ser Leu Ser Cys Arg Ala Ser Gln Ser Ile Ser Asn Asn
            20                  25                  30

Leu Gln Trp Tyr Gln Gln Lys Ser His Glu Ser Pro Arg Leu Leu Ile
        35                  40                  45

Lys Tyr Ala Ser Gln Ser Ile Ser Gly Ile Pro Ser Arg Phe Ser Gly
50                  55                  60

Ser Gly Ser Gly Thr Asp Phe Thr Leu Ser Ile Asn Ser Val Glu Thr
65                  70                  75                  80

Glu Asp Phe Gly Met Tyr Phe Cys Gln Gln Ser Asn Ser Trp Pro Arg
                85                  90                  95

Thr Phe Gly Ala Gly Thr Lys Leu Glu Leu Lys Arg
            100                 105

<210> SEQ ID NO 221
<211> LENGTH: 123
<212> TYPE: PRT
<213> ORGANISM: Artificial Sequence
<220> FEATURE:
<223> OTHER INFORMATION: Amino acid sequence of the variable region of
      the heavy chain of anti-hTfR antibody No.2

<400> SEQUENCE: 221

Glu Val Gln Leu Gln Glu Ser Gly Ala Glu Leu Val Arg Pro Gly Val
1               5                   10                  15

Ser Val Lys Ile Ser Cys Lys Gly Ser Gly Tyr Thr Phe Thr Asp Tyr
            20                  25                  30

Val Met His Trp Val Arg Gln Ser His Ala Lys Ser Leu Glu Trp Ile
        35                  40                  45

Gly Val Ile Ser Thr Tyr Tyr Gly His Gly Ser Tyr Asn Gln Arg Phe
50                  55                  60

Lys Gly Lys Ala Thr Met Thr Val Asp Lys Ser Ser Ser Thr Ala Tyr
65                  70                  75                  80

Leu Glu Leu Val Arg Leu Thr Ser Glu Asp Ser Ala Ile Tyr Tyr Cys
                85                  90                  95

Val Arg Gly Gly Tyr Gly Ser Ser Ser Leu Ala Gly Asn Phe Asp Val
            100                 105                 110

Trp Gly Ala Gly Thr Thr Val Thr Val Ser Ser
        115                 120

<210> SEQ ID NO 222
<211> LENGTH: 113
<212> TYPE: PRT
<213> ORGANISM: Artificial Sequence
<220> FEATURE:
<223> OTHER INFORMATION: Amino acid sequence of the variable region of
      the light chain of anti-hTfR antibody No.3

<400> SEQUENCE: 222

Asp Ile Val Met Thr Gln Thr Thr Leu Ser Leu Pro Val Ser Leu Gly
1               5                   10                  15
```

```
Asp Gln Ala Ser Ile Ser Cys Arg Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Phe Phe Cys Ser Gln Ser
                85                  90                  95

Thr His Val Pro Trp Thr Phe Gly Gly Gly Thr Lys Leu Glu Ile Lys
                100                 105                 110

Arg
```

<210> SEQ ID NO 223
<211> LENGTH: 118
<212> TYPE: PRT
<213> ORGANISM: Artificial Sequence
<220> FEATURE:
<223> OTHER INFORMATION: Amino acid sequence of the variable region of
      the heavy chain of anti-hTfR antibody No.3

<400> SEQUENCE: 223

```
Glu Val Gln Leu Gln Glu Ser Gly Ala Glu Leu Val Arg Pro Gly Thr
1               5                   10                  15

Ser Val Lys Ile Ser Cys Lys Ala Ser Gly Tyr Thr Phe Met Asn Tyr
            20                  25                  30

Trp Leu Gly Trp Val Lys Gln Arg Pro Gly His Gly Leu Glu Trp Ile
        35                  40                  45

Gly Asp Ile Tyr Pro Gly Gly Asp Tyr Pro Thr Tyr Ser Glu Lys Phe
50                  55                  60

Lys Val Lys Ala Ile Leu Thr Ala Asp Thr Ser Ser Ser Ser Val Tyr
65                  70                  75                  80

Leu His Leu Ser Ser Leu Thr Ser Glu Asp Ser Ala Val Tyr Phe Cys
                85                  90                  95

Ala Arg Ser Gly Asn Tyr Asp Glu Val Ala Tyr Trp Gly Gln Gly Thr
                100                 105                 110

Leu Val Thr Val Ser Thr
        115
```

<210> SEQ ID NO 224
<211> LENGTH: 106
<212> TYPE: PRT
<213> ORGANISM: Artificial Sequence
<220> FEATURE:
<223> OTHER INFORMATION: Amino acid sequence of the variable region of
      the light chain of anti-hTfR antibody No.4

<400> SEQUENCE: 224

```
Asp Ile Val Leu Thr Gln Thr Pro Ala Ile Met Ser Ala Ser Pro Gly
1               5                   10                  15

Glu Lys Val Thr Met Thr Cys Ser Ala Ser Ser Asn Val Asn Tyr Met
            20                  25                  30

His Trp Tyr Gln Gln Lys Ser Ser Thr Ser Pro Lys Leu Trp Ile Tyr
        35                  40                  45

Asp Thr Ser Lys Leu Ala Ser Gly Val Pro Gly Arg Phe Ser Gly Ser
50                  55                  60
```

-continued

```
Gly Ser Gly Asn Ser Tyr Ser Leu Thr Ile Ser Ser Met Glu Ala Glu
 65                  70                  75                  80

Asp Val Ala Thr Tyr Tyr Cys Phe Gln Gly Asn Gly Asn Pro Tyr Thr
                 85                  90                  95

Phe Gly Gly Gly Thr Lys Leu Glu Ile Lys
            100                 105

<210> SEQ ID NO 225
<211> LENGTH: 122
<212> TYPE: PRT
<213> ORGANISM: Artificial Sequence
<220> FEATURE:
<223> OTHER INFORMATION: Amino acid sequence of the variable region of
      the heavy chain of anti-hTfR antibody No.4

<400> SEQUENCE: 225

Glu Val Gln Leu Gln Glu Ser Gly Ala Glu Leu Val Arg Pro Gly Thr
 1               5                  10                  15

Ser Val Arg Val Phe Cys Lys Ala Ser Gly Tyr Ala Phe Thr Asn Tyr
                20                  25                  30

Leu Ile Glu Trp Val Lys Gln Arg Pro Gly Gln Gly Leu Glu Trp Ile
         35                  40                  45

Gly Leu Ile Asn Pro Gly Ser Gly Gly Ile Ile Tyr Asn Glu Lys Phe
     50                  55                  60

Thr Asp Arg Ala Thr Leu Thr Ala Asp Lys Ser Ser Ser Thr Ala Tyr
 65                  70                  75                  80

Met Gln Leu Ser Ser Leu Thr Ser Asp Asp Ser Ala Val Tyr Phe Cys
                 85                  90                  95

Ala Arg Ser Asn Tyr Tyr Gly Thr Thr Tyr Trp His Phe Asp Val Trp
                100                 105                 110

Gly Ala Gly Thr Thr Val Thr Val Ser Ser
            115                 120

<210> SEQ ID NO 226
<211> LENGTH: 105
<212> TYPE: PRT
<213> ORGANISM: Artificial Sequence
<220> FEATURE:
<223> OTHER INFORMATION: Amino acid sequence of the variable region of
      the light chain of anti-hTfR antibody No.5

<400> SEQUENCE: 226

Asp Ile Val Met Thr Gln Thr Pro Ala Ile Met Ser Ala Ser Pro Gly
 1               5                  10                  15

Glu Lys Val Thr Met Thr Cys Ser Ala Ser Ser Ser Ile Ser Ser Ile
                20                  25                  30

His Trp Tyr Gln Gln Lys Pro Gly Thr Ser Pro Lys Arg Trp Ile Tyr
         35                  40                  45

Asp Thr Ser Thr Leu Ala Ser Gly Val Pro Val Arg Phe Ser Gly Ser
     50                  55                  60

Gly Ser Gly Thr Ser Tyr Ser Leu Thr Ile Ser Ser Met Glu Ala Glu
 65                  70                  75                  80

Asp Ala Ala Thr Tyr Tyr Cys His Gln Arg Ser Ser Tyr Pro Thr Phe
                 85                  90                  95

Gly Gly Gly Thr Lys Leu Glu Ile Lys
            100                 105

<210> SEQ ID NO 227
<211> LENGTH: 118
```

```
<212> TYPE: PRT
<213> ORGANISM: Artificial Sequence
<220> FEATURE:
<223> OTHER INFORMATION: Amino acid sequence of the variable region of
      the heavy chain of anti-hTfR antibody No.5

<400> SEQUENCE: 227
```

Glu Val Gln Leu Gln Glu Ser Gly Pro Glu Leu Val Lys Pro Gly Ala
1               5                   10                  15

Ser Val Lys Met Ser Cys Lys Ala Ser Gly Tyr Thr Phe Thr Asn Phe
            20                  25                  30

Val Ile His Trp Val Lys Gln Arg Pro Gly Gln Gly Leu Glu Trp Ile
        35                  40                  45

Gly Phe Phe Asn Pro His Lys Asn Gly Ala Glu Tyr Asn Glu Lys Phe
    50                  55                  60

Gln Val Lys Ala Thr Leu Thr Ser Asp Lys Ser Ser Thr Thr Ala Tyr
65                  70                  75                  80

Met Glu Leu Asn Ser Leu Thr Ser Glu Asp Ser Ala Val Tyr Tyr Cys
                85                  90                  95

Ala Arg Ser Phe Tyr Tyr Tyr Ser Met Asp Tyr Trp Gly Gln Gly Thr
            100                 105                 110

Ser Val Thr Val Ser Ser
        115

```
<210> SEQ ID NO 228
<211> LENGTH: 107
<212> TYPE: PRT
<213> ORGANISM: Artificial Sequence
<220> FEATURE:
<223> OTHER INFORMATION: Amino acid sequence of the variable region of
      the light chain of anti-hTfR antibody No.6

<400> SEQUENCE: 228
```

Asp Ile Val Leu Thr Gln Thr Pro Ser Ser Leu Ser Ala Ser Leu Gly
1               5                   10                  15

Glu Arg Val Ser Leu Thr Cys Arg Ala Ser Gln Glu Ile Ser Gly Tyr
            20                  25                  30

Leu Ser Trp Leu Gln Gln Lys Pro Asp Gly Thr Ile Lys Arg Leu Ile
        35                  40                  45

Tyr Ala Ala Ser Thr Leu Asp Ser Gly Val Pro Lys Arg Phe Ser Gly
    50                  55                  60

Ser Arg Ser Gly Ser Asp Tyr Ser Leu Thr Ile Ser Ser Leu Glu Ser
65                  70                  75                  80

Glu Asp Phe Ala Asp Tyr Tyr Cys Leu Gln Tyr Ser Ser Tyr Pro Arg
                85                  90                  95

Thr Phe Gly Gly Gly Thr Lys Leu Glu Ile Lys
            100                 105

```
<210> SEQ ID NO 229
<211> LENGTH: 112
<212> TYPE: PRT
<213> ORGANISM: Artificial Sequence
<220> FEATURE:
<223> OTHER INFORMATION: Amino acid sequence of the variable region of
      the heavy chain of anti-hTfR antibody No.6

<400> SEQUENCE: 229
```

Glu Val Gln Leu Gln Glu Ser Gly Pro Gly Leu Val Ala Pro Ser Gln
1               5                   10                  15

Ser Leu Ser Ile Thr Cys Ser Val Ser Gly Phe Ser Leu Ser Thr Tyr

```
                    20                  25                  30

Gly Val Tyr Trp Val Arg Gln Pro Pro Gly Lys Gly Leu Glu Trp Leu
                35                  40                  45

Gly Ile Ile Trp Gly Asp Gly Ser Thr Asn Tyr His Ser Ala Leu Ile
        50                  55                  60

Ser Arg Leu Thr Ile Ser Lys Asp Asn Ser Lys Ser Gln Val Phe Leu
65                  70                  75                  80

Lys Leu Asn Ser Leu Gln Thr Ala Asp Thr Ala Thr Tyr Tyr Cys Ala
                85                  90                  95

Lys Pro Asp Asp Val Trp Gly Ala Gly Thr Thr Val Thr Val Ser Ser
                100                 105                 110

<210> SEQ ID NO 230
<211> LENGTH: 106
<212> TYPE: PRT
<213> ORGANISM: Artificial Sequence
<220> FEATURE:
<223> OTHER INFORMATION: Amino acid sequence of the variable region of
      the light chain of anti-hTfR antibody No.7

<400> SEQUENCE: 230

Asp Ile Val Leu Thr Gln Ser Pro Val Ile Met Ser Ala Ser Leu Gly
1               5                   10                  15

Glu Glu Ile Thr Leu Thr Cys Ser Ala Ser Ser Ser Val Asn Tyr Ile
                20                  25                  30

His Trp Tyr Gln Gln Lys Ser Gly Thr Ser Pro Lys Val Leu Ile Tyr
            35                  40                  45

Gln Thr Ser Asn Leu Ala Ser Gly Val Pro Ser Arg Phe Ser Gly Ser
        50                  55                  60

Arg Ser Gly Thr Phe Tyr Ser Leu Lys Ile Ser Ser Val Glu Ala Glu
65                  70                  75                  80

Asp Ala Ala Asp Tyr Tyr Cys His Gln Trp Ser Ser Tyr Pro Trp Thr
                85                  90                  95

Phe Gly Gly Gly Thr Lys Leu Glu Ile Lys
            100                 105

<210> SEQ ID NO 231
<211> LENGTH: 120
<212> TYPE: PRT
<213> ORGANISM: Artificial Sequence
<220> FEATURE:
<223> OTHER INFORMATION: Amino acid sequence of the variable region of
      the heavy chain of anti-hTfR antibody No.7

<400> SEQUENCE: 231

Glu Val Gln Leu Gln Glu Ser Gly Gly Ala Leu Val Lys Pro Gly Gly
1               5                   10                  15

Ser Leu Lys Val Ser Cys Glu Ala Ser Gly Ile Thr Phe Arg Asn Tyr
                20                  25                  30

Phe Met Ser Trp Val Arg Gln Thr Pro Glu Lys Arg Leu Glu Trp Val
            35                  40                  45

Ala Thr Ile Ser Ser Ala Gly Gly Tyr Thr Tyr Tyr Ala Asp Ser Val
        50                  55                  60

Lys Gly Arg Phe Thr Ile Ser Arg Asp Asn Ala Gly Asn Thr Leu Tyr
65                  70                  75                  80

Leu Gln Met Ser Ser Leu Arg Ser Glu Asp Thr Ala Met Tyr Phe Cys
                85                  90                  95

Ala Arg Gln Glu Val Pro Tyr Pro Tyr Ala Met Asp Tyr Trp Gly Gln
```

```
                    100                 105                 110

Gly Thr Ser Val Ile Val Ser Ser
            115                 120

<210> SEQ ID NO 232
<211> LENGTH: 106
<212> TYPE: PRT
<213> ORGANISM: Artificial Sequence
<220> FEATURE:
<223> OTHER INFORMATION: Amino acid sequence of the variable region of
      the light chain of anti-hTfR antibody No.8

<400> SEQUENCE: 232

Asp Ile Val Leu Thr Gln Ser Pro Ala Ile Met Ser Ala Ser Leu Gly
1               5                   10                  15

Glu Glu Ile Thr Leu Thr Cys Ser Ala Ser Ser Ser Val Ser Tyr Met
            20                  25                  30

His Trp Tyr Gln Gln Lys Ser Gly Thr Ser Pro Lys Val Leu Ile Tyr
        35                  40                  45

Gly Thr Ser Asn Leu Ala Ser Glu Val Pro Ser Arg Phe Ser Gly Ser
    50                  55                  60

Gly Ser Gly Thr Phe Tyr Ser Leu Thr Ile Ser Ser Val Glu Ala Glu
65                  70                  75                  80

Asp Ala Ala Asp Tyr Tyr Cys His Gln Trp Ser Ser Tyr Pro Trp Thr
                85                  90                  95

Phe Gly Gly Gly Thr Lys Leu Glu Ile Lys
            100                 105

<210> SEQ ID NO 233
<211> LENGTH: 112
<212> TYPE: PRT
<213> ORGANISM: Artificial Sequence
<220> FEATURE:
<223> OTHER INFORMATION: Amino acid sequence of the variable region of
      the heavy chain of anti-hTfR antibody No.8

<400> SEQUENCE: 233

Glu Val Gln Leu Gln Glu Ser Gly Pro Gly Leu Val Ala Pro Ser Gln
1               5                   10                  15

Ser Leu Ser Ile Thr Cys Thr Val Ser Gly Phe Ser Leu Thr Thr Tyr
            20                  25                  30

Gly Val Ser Trp Ile Arg Gln Pro Pro Gly Lys Gly Leu Glu Trp Leu
        35                  40                  45

Gly Ile Ile Trp Gly Asp Gly Ser Thr Asn Tyr Arg Ser Ala Leu Ile
    50                  55                  60

Ser Arg Leu Ser Ile Ser Lys Asp Asn Ser Lys Asn Gln Val Phe Leu
65                  70                  75                  80

Lys Leu Asn Ser Leu Gln Thr Asp Asp Thr Ala Thr Tyr Tyr Cys Ala
                85                  90                  95

Lys Pro Asp Asp Tyr Trp Gly Gln Gly Thr Ser Val Thr Val Ser Ser
            100                 105                 110

<210> SEQ ID NO 234
<211> LENGTH: 106
<212> TYPE: PRT
<213> ORGANISM: Artificial Sequence
<220> FEATURE:
<223> OTHER INFORMATION: Amino acid sequence of the variable region of
      the light chain of anti-hTfR antibody No.9

<400> SEQUENCE: 234
```

-continued

```
Asp Ile Val Leu Thr Gln Ser Pro Ala Leu Met Ser Ala Ser Pro Gly
1               5                   10                  15

Glu Thr Val Thr Met Thr Cys Ser Ala Ser Ser Val Ser Leu Met
            20                  25                  30

Phe Trp Tyr Gln Gln Lys Pro Arg Ser Ser Pro Lys Pro Trp Ile Tyr
            35                  40                  45

Phe Thr Ser Tyr Arg Ala Ser Gly Val Pro Ile Arg Phe Ser Gly Ser
        50                  55                  60

Gly Ser Gly Thr Ser Phe Ser Leu Thr Ile Ser Asn Leu Glu Ala Glu
65              70                  75                  80

Asp Ala Ala Thr Tyr Tyr Cys Gln Gln Trp Thr Ser Asp Pro Pro Thr
                85                  90                  95

Phe Gly Ser Gly Thr Lys Leu Glu Ile Glu
            100                 105
```

<210> SEQ ID NO 235
<211> LENGTH: 117
<212> TYPE: PRT
<213> ORGANISM: Artificial Sequence
<220> FEATURE:
<223> OTHER INFORMATION: Amino acid sequence of the variable region of
      the heavy chain of anti-hTfR antibody No.9

<400> SEQUENCE: 235

```
Glu Val Gln Leu Gln Glu Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Val Ser Trp Val Lys Gln Ala Pro Gly Lys Asp Leu Lys Trp Met
        35                  40                  45

Gly Trp Ile Tyr Thr Phe Thr Gly Glu Ala Thr Tyr Ile Asp Asp Phe
    50                  55                  60

Arg Gly Arg Phe Ala Phe Ser Leu Glu Thr Ser Ala Asn Thr Ala Tyr
65              70                  75                  80

Leu Gln Ile Asn Asn Leu Lys Asn Glu Asp Thr Ala Thr Tyr Phe Cys
                85                  90                  95

Ser Arg Arg Asn Gly Ala Trp Phe Glu Asp Trp Gly Gln Gly Thr Leu
            100                 105                 110

Val Thr Val Ser Ala
        115
```

<210> SEQ ID NO 236
<211> LENGTH: 107
<212> TYPE: PRT
<213> ORGANISM: Artificial Sequence
<220> FEATURE:
<223> OTHER INFORMATION: Amino acid sequence of the variable region of
      the light chain of anti-hTfR antibody No.10

<400> SEQUENCE: 236

```
Asp Ile Val Met Thr Gln Thr Pro Ser Ser Leu Ser Ala Ser Leu Gly
1               5                   10                  15

Glu Arg Val Ser Leu Thr Cys Arg Pro Ser Gln Glu Ile Ser Gly Tyr
            20                  25                  30

Leu Ser Trp Leu Gln Gln Lys Pro Asp Gly Thr Ile Lys Arg Leu Ile
        35                  40                  45

Tyr Ala Ala Ser Thr Leu Asp Ser Gly Val Pro Lys Arg Phe Ser Gly
    50                  55                  60
```

```
Ser Arg Ser Gly Ser Asp Tyr Ser Leu Thr Ile Ser Ser Leu Glu Ser
 65                  70                  75                  80

Glu Asp Phe Ala Asp Tyr Tyr Cys Leu Gln Tyr Ala Ser Tyr Pro Arg
                 85                  90                  95

Thr Phe Gly Gly Gly Thr Lys Leu Glu Ile Lys
            100                 105

<210> SEQ ID NO 237
<211> LENGTH: 120
<212> TYPE: PRT
<213> ORGANISM: Artificial Sequence
<220> FEATURE:
<223> OTHER INFORMATION: Amino acid sequence of the variable region of
      the heavy chain of anti-hTfR antibody No.10

<400> SEQUENCE: 237

Glu Val Gln Leu Gln Glu Ser Gly Gly Gly Leu Val Lys Pro Gly Gly
 1               5                  10                  15

Ser Leu Lys Leu Ser Cys Glu Ala Ser Gly Ile Thr Phe Arg Asn Tyr
                20                  25                  30

Ala Met Ser Trp Val Arg Gln Thr Pro Glu Lys Arg Leu Glu Trp Val
             35                  40                  45

Ala Thr Ile Ser Ser Tyr Gly Gly Tyr Thr Tyr Tyr Ala Asp Ser Val
         50                  55                  60

Lys Gly Arg Phe Thr Val Ser Arg Asp Asn Ala Gly Asn Thr Leu Tyr
 65                  70                  75                  80

Leu Gln Met Ser Ser Leu Arg Ser Glu Asp Thr Ala Met Tyr His Cys
                 85                  90                  95

Ala Arg Gln Glu Val Pro Tyr Pro Tyr Pro Met Asp Asn Trp Gly Gln
                100                 105                 110

Gly Thr Ser Val Ile Val Ser Ser
            115                 120

<210> SEQ ID NO 238
<211> LENGTH: 107
<212> TYPE: PRT
<213> ORGANISM: Artificial Sequence
<220> FEATURE:
<223> OTHER INFORMATION: Amino acid sequence of the variable region of
      the light chain of anti-hTfR antibody No.11

<400> SEQUENCE: 238

Asp Ile Val Leu Thr Gln Ser Pro Ala Thr Leu Ser Val Thr Pro Gly
 1               5                  10                  15

Asp Arg Val Ser Leu Ser Cys Arg Ala Ser Gln Ser Ile Arg Asn Tyr
                20                  25                  30

Leu His Trp Tyr Gln Gln Lys Ser His Glu Ser Pro Arg Leu Leu Ile
             35                  40                  45

Lys Tyr Ala Ser Gln Ser Ile Ser Gly Ile Pro Ser Arg Phe Ser Gly
         50                  55                  60

Ser Gly Ser Gly Thr Asp Phe Thr Leu Ser Ile Asn Ser Val Glu Thr
 65                  70                  75                  80

Glu Asp Phe Gly Met Tyr Phe Cys Gln Gln Thr Asn Ser Trp Pro Tyr
                 85                  90                  95

Thr Phe Gly Gly Gly Thr Lys Leu Glu Ile Lys
            100                 105

<210> SEQ ID NO 239
```

```
<211> LENGTH: 118
<212> TYPE: PRT
<213> ORGANISM: Artificial Sequence
<220> FEATURE:
<223> OTHER INFORMATION: Amino acid sequence of the variable region of
      the heavy chain of anti-hTfR antibody No.11

<400> SEQUENCE: 239

Glu Val Gln Leu Gln Glu Ser Gly Ala Glu Leu Val Arg Pro Gly Ser
1               5                   10                  15

Ser Val Lys Ile Ser Cys Lys Ala Ser Gly Tyr Ala Phe Ser Ile Tyr
            20                  25                  30

Trp Ile Asn Trp Leu Lys Gln Arg Pro Gly Gln Gly Leu Glu Trp Ile
        35                  40                  45

Gly Gln Ile Tyr Pro Gly Asn Gly Asp Thr Asn Tyr Asn Gly Lys Phe
    50                  55                  60

Lys Gly Lys Ala Thr Leu Thr Ala Asp Lys Ser Ser Asn Thr Val Tyr
65                  70                  75                  80

Met Arg Leu Ser Ser Leu Thr Ser Glu Asp Ser Ala Val Tyr Phe Cys
                85                  90                  95

Gly Arg Trp Gly Asp Asp Tyr Ala Met Asp Phe Trp Gly Gln Gly Thr
            100                 105                 110

Ser Val Thr Val Ser Ser
        115

<210> SEQ ID NO 240
<211> LENGTH: 107
<212> TYPE: PRT
<213> ORGANISM: Artificial Sequence
<220> FEATURE:
<223> OTHER INFORMATION: Amino acid sequence of the variable region of
      the light chain of anti-hTfR antibody No.12

<400> SEQUENCE: 240

Asp Ile Val Leu Thr Gln Ser His Lys Phe Met Ser Thr Val Ile Gly
1               5                   10                  15

Asp Arg Val Ser Ile Thr Cys Lys Ala Ser His Asp Val Lys Thr Ala
            20                  25                  30

Val Ala Trp Tyr Gln Gln Thr Pro Gly Gln Ser Pro Lys Leu Leu Thr
        35                  40                  45

Tyr Trp Ser Ser Thr Arg His Thr Gly Val Pro Asp Arg Phe Thr Gly
    50                  55                  60

Ser Gly Ser Gly Thr Asp Tyr Thr Leu Thr Ile Ser Ser Val Gln Ala
65                  70                  75                  80

Glu Asp Leu Ala Leu Tyr Tyr Cys Gln Gln His Phe Ser Thr Pro Leu
                85                  90                  95

Thr Phe Gly Ala Gly Thr Lys Leu Glu Leu Lys
            100                 105

<210> SEQ ID NO 241
<211> LENGTH: 119
<212> TYPE: PRT
<213> ORGANISM: Artificial Sequence
<220> FEATURE:
<223> OTHER INFORMATION: Amino acid sequence of the variable region of
      the heavy chain of anti-hTfR antibody No.12

<400> SEQUENCE: 241

Glu Val Gln Leu Gln Glu Ser Gly Ala Glu Leu Ala Arg Pro Gly Thr
1               5                   10                  15
```

-continued

Ser Val Lys Val Ser Cys Lys Ala Ala Gly Tyr Val Phe Ile Asn Tyr
                20                  25                  30

Leu Ile Glu Trp Val Lys Gln Arg Pro Gly Gln Gly Leu Glu Trp Ile
            35                  40                  45

Gly Val Ile His Ser Gly Ser Gly Thr Asn Tyr Asn Asp Asn Phe
 50                  55                  60

Lys Asp Lys Ala Thr Leu Thr Arg Asp Val Ser Ser Thr Ala Tyr
 65                  70                  75                  80

Met Gln Leu Ser Ser Leu Thr Ser Asp Asp Ser Ala Val Tyr Phe Cys
                85                  90                  95

Ala Arg Arg Asn Phe Gly Asn Tyr Tyr Phe Asp Tyr Trp Gly Gln Gly
            100                 105                 110

Thr Thr Leu Thr Val Ser Ser
        115

<210> SEQ ID NO 242
<211> LENGTH: 107
<212> TYPE: PRT
<213> ORGANISM: Artificial Sequence
<220> FEATURE:
<223> OTHER INFORMATION: Amino acid sequence of the variable region of
      the light chain of anti-hTfR antibody No.13

<400> SEQUENCE: 242

Asp Ile Val Ile Thr Gln Thr Pro Ala Thr Leu Ser Val Thr Pro Gly
 1               5                  10                  15

Asp Arg Val Ser Leu Ser Cys Arg Ala Ser Gln Ser Ile Arg Asn Tyr
                20                  25                  30

Leu His Trp Tyr Gln Gln Lys Ser His Glu Ser Pro Arg Leu Leu Ile
            35                  40                  45

Lys Tyr Ala Ser Gln Ser Ile Ser Gly Ile Pro Ser Arg Phe Ser Gly
 50                  55                  60

Ser Gly Ser Gly Thr Asp Phe Thr Leu Thr Ile Asn Ser Val Glu Thr
 65                  70                  75                  80

Glu Asp Phe Gly Met Tyr Phe Cys Gln Gln Thr Asn Ser Trp Pro Tyr
                85                  90                  95

Thr Phe Gly Gly Gly Thr Lys Leu Glu Ile Lys
            100                 105

<210> SEQ ID NO 243
<211> LENGTH: 118
<212> TYPE: PRT
<213> ORGANISM: Artificial Sequence
<220> FEATURE:
<223> OTHER INFORMATION: Amino acid sequence of the variable region of
      the heavy chain of anti-hTfR antibody No.13

<400> SEQUENCE: 243

Glu Val Gln Leu Gln Glu Ser Gly Ala Glu Leu Val Arg Pro Gly Ser
 1               5                  10                  15

Ser Val Lys Ile Ser Cys Lys Ala Ser Gly Tyr Ala Phe Ser Ile Tyr
                20                  25                  30

Trp Ile Asn Trp Leu Lys Gln Arg Pro Gly Gln Gly Leu Glu Trp Ile
            35                  40                  45

Gly Gln Ile Tyr Pro Gly Asn Gly Asp Thr Asn Tyr Asn Gly Lys Phe
 50                  55                  60

Lys Gly Lys Ala Thr Leu Thr Ala Asp Lys Ser Ser Asn Thr Val Tyr
 65                  70                  75                  80

```
Met Arg Leu Ser Ser Leu Thr Ser Glu Asp Ser Ala Val Tyr Phe Cys
            85                  90                  95

Gly Arg Trp Gly Asp Asp Tyr Ala Met Asp Phe Trp Gly Gln Gly Thr
        100                 105                 110

Ser Val Thr Val Ser Ser
        115

<210> SEQ ID NO 244
<211> LENGTH: 106
<212> TYPE: PRT
<213> ORGANISM: Artificial Sequence
<220> FEATURE:
<223> OTHER INFORMATION: Amino acid sequence of the variable region of
      the light chain of anti-hTfR antibody No.14

<400> SEQUENCE: 244

Asp Ile Val Leu Thr Gln Thr Pro Val Ile Met Ser Ala Tyr Pro Gly
1               5                   10                  15

Glu Lys Val Thr Leu Thr Cys Ser Ala Ser Ser Asn Ile Asn Ser Ile
            20                  25                  30

His Trp Tyr Gln Gln Lys Pro Gly Thr Ser Pro Lys Arg Trp Ile Tyr
        35                  40                  45

Asp Thr Ser Asn Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Ser Tyr Tyr Cys His Gln Arg Ser Gly Tyr Pro Phe Thr
                85                  90                  95

Phe Gly Ser Gly Thr Lys Leu Glu Ile Lys
        100                 105

<210> SEQ ID NO 245
<211> LENGTH: 118
<212> TYPE: PRT
<213> ORGANISM: Artificial Sequence
<220> FEATURE:
<223> OTHER INFORMATION: Amino acid sequence of the variable region of
      the heavy chain of anti-hTfR antibody No.14

<400> SEQUENCE: 245

Glu Val Gln Leu Gln Glu Ser Gly Pro Glu Leu Leu Lys Pro Gly Ala
1               5                   10                  15

Ser Val Lys Met Ser Cys Lys Ala Ser Gly Tyr Ala Phe Thr Gly Tyr
            20                  25                  30

Val Ile His Trp Val Lys Gln Lys Pro Gly Gln Gly Leu Glu Trp Ile
        35                  40                  45

Gly Phe Leu Asn Pro His Lys Asp Asp Ser Gly Tyr Asn Glu Lys Phe
    50                  55                  60

Arg Gly Lys Ala Thr Leu Thr Ser Asp Lys Ser Ser Thr Ala Tyr
65                  70                  75                  80

Met Asp Leu Ser Ser Leu Thr Ser Glu Asp Ser Ala Val Tyr Tyr Cys
                85                  90                  95

Ala Arg Gly Tyr Tyr Tyr Tyr Ser Met Asp Tyr Trp Gly Gln Gly Thr
            100                 105                 110

Ser Val Thr Val Ser Ser
        115

<210> SEQ ID NO 246
<211> LENGTH: 357
```

<212> TYPE: DNA
<213> ORGANISM: Artificial Sequence
<220> FEATURE:
<223> OTHER INFORMATION: Nucleotide sequence encoding amino acid
      sequence of hBDNF

<400> SEQUENCE: 246
cactctgacc ctgcccgccg aggggagctg agcgtgtgtg acagtattag tgagtgggta    60
acggcggcag acaaaaagac tgcagtggac atgtcgggcg ggacggtcac agtccttgaa   120
aaggtccctg tatcaaaagg ccaactgaag caatacttct acgagaccaa gtgcaatccc   180
atgggttaca caaagaagg ctgcaggggc atagacaaaa ggcattggaa ctcccagtgc    240
cgaactaccc agtcgtacgt gcgggccctt accatggata gcaaaaagag aattggctgg   300
cgattcataa ggatagacac ttcttgtgta tgtacattga ccattaaaag gggaaga     357

<210> SEQ ID NO 247
<211> LENGTH: 119
<212> TYPE: PRT
<213> ORGANISM: Homo sapiens

<400> SEQUENCE: 247

His Ser Asp Pro Ala Arg Arg Gly Glu Leu Ser Val Cys Asp Ser Ile
1               5                   10                  15

Ser Glu Trp Val Thr Ala Ala Asp Lys Lys Thr Ala Val Asp Met Ser
            20                  25                  30

Gly Gly Thr Val Thr Val Leu Glu Lys Val Pro Val Ser Lys Gly Gln
        35                  40                  45

Leu Lys Gln Tyr Phe Tyr Glu Thr Lys Cys Asn Pro Met Gly Tyr Thr
    50                  55                  60

Lys Glu Gly Cys Arg Gly Ile Asp Lys Arg His Trp Asn Ser Gln Cys
65                  70                  75                  80

Arg Thr Thr Gln Ser Tyr Val Arg Ala Leu Thr Met Asp Ser Lys Lys
                85                  90                  95

Arg Ile Gly Trp Arg Phe Ile Arg Ile Asp Thr Ser Cys Val Cys Thr
            100                 105                 110

Leu Thr Ile Lys Arg Gly Arg
        115

<210> SEQ ID NO 248
<211> LENGTH: 567
<212> TYPE: PRT
<213> ORGANISM: Artificial Sequence
<220> FEATURE:
<223> OTHER INFORMATION: Amino acid sequence of fusion protein of the
      heavy chain of anti-hTfR antibody No.1 (humanized 6) and hBDNF

<400> SEQUENCE: 248

Glu Val Gln Leu Val Glu Ser Gly Gly Gly Leu Val Gln Pro Gly Gly
1               5                   10                  15

Ser Leu Arg Leu Ser Cys Ala Ala Ser Gly Leu Thr Phe Ser Asn Tyr
            20                  25                  30

Gly Met Ser Trp Val Arg Gln Ala Pro Gly Lys Gly Leu Glu Leu Val
        35                  40                  45

Ala Asn Ile Asn Thr Asn Gly Gly Ser Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys

-continued

```
                85                  90                  95
Thr Asn Asn Arg Tyr Asp Glu Asp Tyr Trp Gly Gln Gly Thr Leu Val
            100                 105                 110
Thr Val Ser Ser Ala Ser Thr Lys Gly Pro Ser Val Phe Pro Leu Ala
            115                 120                 125
Pro Ser Ser Lys Ser Thr Ser Gly Gly Thr Ala Ala Leu Gly Cys Leu
130                 135                 140
Val Lys Asp Tyr Phe Pro Glu Pro Val Thr Val Ser Trp Asn Ser Gly
145                 150                 155                 160
Ala Leu Thr Ser Gly Val His Thr Phe Pro Ala Val Leu Gln Ser Ser
                165                 170                 175
Gly Leu Tyr Ser Leu Ser Ser Val Val Thr Val Pro Ser Ser Ser Leu
                180                 185                 190
Gly Thr Gln Thr Tyr Ile Cys Asn Val Asn His Lys Pro Ser Asn Thr
                195                 200                 205
Lys Val Asp Lys Lys Val Glu Pro Lys Ser Cys Asp Lys Thr His Thr
            210                 215                 220
Cys Pro Pro Cys Pro Ala Pro Glu Leu Leu Gly Gly Pro Ser Val Phe
225                 230                 235                 240
Leu Phe Pro Pro Lys Pro Lys Asp Thr Leu Met Ile Ser Arg Thr Pro
                245                 250                 255
Glu Val Thr Cys Val Val Val Asp Val Ser His Glu Asp Pro Glu Val
                260                 265                 270
Lys Phe Asn Trp Tyr Val Asp Gly Val Glu Val His Asn Ala Lys Thr
            275                 280                 285
Lys Pro Arg Glu Glu Gln Tyr Asn Ser Thr Tyr Arg Val Val Ser Val
290                 295                 300
Leu Thr Val Leu His Gln Asp Trp Leu Asn Gly Lys Glu Tyr Lys Cys
305                 310                 315                 320
Lys Val Ser Asn Lys Ala Leu Pro Ala Pro Ile Glu Lys Thr Ile Ser
                325                 330                 335
Lys Ala Lys Gly Gln Pro Arg Glu Pro Gln Val Tyr Thr Leu Pro Pro
            340                 345                 350
Ser Arg Asp Glu Leu Thr Lys Asn Gln Val Ser Leu Thr Cys Leu Val
            355                 360                 365
Lys Gly Phe Tyr Pro Ser Asp Ile Ala Val Glu Trp Glu Ser Asn Gly
            370                 375                 380
Gln Pro Glu Asn Asn Tyr Lys Thr Thr Pro Pro Val Leu Asp Ser Asp
385                 390                 395                 400
Gly Ser Phe Phe Leu Tyr Ser Lys Leu Thr Val Asp Lys Ser Arg Trp
                405                 410                 415
Gln Gln Gly Asn Val Phe Ser Cys Ser Val Met His Glu Ala Leu His
                420                 425                 430
Asn His Tyr Thr Gln Lys Ser Leu Ser Leu Ser Pro Gly Lys Gly Ser
                435                 440                 445
His Ser Asp Pro Ala Arg Arg Gly Glu Leu Ser Val Cys Asp Ser Ile
            450                 455                 460
Ser Glu Trp Val Thr Ala Ala Asp Lys Lys Thr Ala Val Asp Met Ser
465                 470                 475                 480
Gly Gly Thr Val Thr Val Leu Glu Lys Val Pro Val Ser Lys Gly Gln
                485                 490                 495
Leu Lys Gln Tyr Phe Tyr Glu Thr Lys Cys Asn Pro Met Gly Tyr Thr
            500                 505                 510
```

Lys Glu Gly Cys Arg Gly Ile Asp Lys Arg His Trp Asn Ser Gln Cys
            515                 520                 525

Arg Thr Thr Gln Ser Tyr Val Arg Ala Leu Thr Met Asp Ser Lys Lys
        530                 535                 540

Arg Ile Gly Trp Arg Phe Ile Arg Ile Asp Thr Ser Cys Val Cys Thr
545                 550                 555                 560

Leu Thr Ile Lys Arg Gly Arg
                565

<210> SEQ ID NO 249
<211> LENGTH: 1784
<212> TYPE: DNA
<213> ORGANISM: Artificial Sequence
<220> FEATURE:
<223> OTHER INFORMATION: Nucleotide sequence encoding amino acid
      sequence of fusion protein of the heavy chain of anti-hTfR
      antibody No.1 (humanized 6) and hBDNF, synthetic sequence

<400> SEQUENCE: 249
acgcgtgccg ccaccatggg ctggagctgg attctgctgt tcctcctgag cgtgacagca      60
ggagtgcaca gcgaagtgca gctggtcgaa tcaggggggg gcctggtgca gcctggaggc     120
agcctgagac tgtcctgcgc cgcttctggc ttgaccttta gcaactacgg gatgtcctgg     180
gtgcggcagc ctcctggcaa gggactggag ttggtggcca acatcaatac caacggcgga     240
agtacatact atcccgattc agtgaagggc cggttcacca tcagcaggga caacgccaag     300
aacagcctgt atctgcagat gaactctctg agggccgagg atacagccgt gtactattgc     360
actaacaacc ggtacgacga ggactattgg ggccagggca ccctggtgac agtgtctagc     420
gcctctacca agggcccaag cgtgtttcct ctggctccat cctctaaatc cacctctggc     480
ggcacagccg ctctgggctg tctggtgaag gattacttcc cagagccgt gacagtgtct     540
tggaacagcg gcgccctgac ctccggcgtg cacacatttc ctgctgtgct gcagagctcc     600
ggcctgtaca gcctgtctag cgtggtgacc gtgccatcct ctagcctggg cacccagaca     660
tatatctgca acgtgaatca caagcccagc aatacaaagg tggataagaa ggtggagcca     720
aagtcctgtg acaagaccca cacatgcccc ccttgtcctg ctccagagct gctgggagga     780
ccaagcgtgt tcctgtttcc acccaagccc aaggataccc tgatgatctc tcggacccca     840
gaggtgacat gcgtggtggt ggatgtgagc acgaggaccc cgaggtgaa gttcaactgg     900
tatgtggacg gcgtggaggt gcacaatgct aagaccaagc caggggagga gcagtacaac     960
tccacctata gtggtgtc tgtgctgaca gtgctgcacc aggattggct gaacggcaag    1020
gagtataagt gcaaggtgtc caataaggcc ctgcccgctc ctatcgagaa gaccatctct    1080
aaggccaagg gccagcccag agagcctcag gtgtacacac tgcctccatc ccgggatgag    1140
ctgaccaaga accaggtgtc tctgacatgt ctggtcaagg gcttctatcc ctctgacatc    1200
gccgtggagt gggagagcaa tggccagcct gagaacaatt acaagaccac ccccctgtg    1260
ctggattccg acggctcttt cttctgtat agcaagctga ccgtggacaa gtcccggtgg    1320
cagcagggca acgtgttcag ctgttccgtg atgcacgaag ctctgcataa tcactatact    1380
cagaaatccc tgtcactgtc acctggtaaa ggatctcact gacccctgc cgccgaggg     1440
gagctgagcg tgtgtgacag tattagtgag tgggtaacgg cggcagacaa aaagactgca    1500
gtggacatgt cgggcgggac ggtcacagtc cttgaaaagg tccctgtatc aaaaggccaa    1560
ctgaagcaat acttctacga gaccaagtgc aatcccatgg gttacacaaa agaaggctgc    1620

-continued

```
agggcatag acaaaaggca ttggaactcc cagtgccgaa ctacccagtc gtacgtgcgg    1680
gcccttacca tggatagcaa aaagagaatt ggctggcgat tcataaggat agacacttct    1740
tgtgtatgta cattgaccat taaaagggga agataagcgg ccgc                    1784
```

<210> SEQ ID NO 250
<211> LENGTH: 574
<212> TYPE: PRT
<213> ORGANISM: Artificial Sequence
<220> FEATURE:
<223> OTHER INFORMATION: Amino acid sequence of fused protein of the
heavy chain of anti-hTfR antibody No.2 (humanized 6) and hBDNF

<400> SEQUENCE: 250

```
Gln Val Gln Leu Val Gln Ser Gly Ala Glu Val Lys Pro Gly Ala
1               5                   10                  15

Ser Val Lys Val Ser Cys Lys Ala Ser Gly Tyr Thr Phe Thr Asp Tyr
            20                  25                  30

Val Met His Trp Val Arg Gln Ala Pro Gly Gln Gly Leu Glu Trp Ile
        35                  40                  45

Gly Val Ile Ser Thr Tyr Tyr Gly His Gly Ser Tyr Asn Gln Arg Phe
    50                  55                  60

Lys Gly Arg Ala Thr Met Thr Val Asp Lys Ser Ile Ser Thr Ala Tyr
65                  70                  75                  80

Met Glu Leu Val Arg Leu Arg Ser Asp Asp Thr Ala Val Tyr Tyr Cys
                85                  90                  95

Val Arg Gly Gly Tyr Gly Ser Ser Ser Leu Ala Gly Asn Phe Asp Val
            100                 105                 110

Trp Gly Gln Gly Thr Thr Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335
```

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Thr Lys Asn Gln
        355                 360                 365

Val Ser Leu Thr Cys Leu Val Lys Gly Phe Tyr Pro Ser Asp Ile Ala
370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys Gly Ser His Ser Asp Pro Ala Arg Arg Gly Glu
    450                 455                 460

Leu Ser Val Cys Asp Ser Ile Ser Glu Trp Val Thr Ala Ala Asp Lys
465                 470                 475                 480

Lys Thr Ala Val Asp Met Ser Gly Gly Thr Val Thr Val Leu Glu Lys
                485                 490                 495

Val Pro Val Ser Lys Gly Gln Leu Lys Gln Tyr Phe Tyr Glu Thr Lys
            500                 505                 510

Cys Asn Pro Met Gly Tyr Thr Lys Glu Gly Cys Arg Gly Ile Asp Lys
        515                 520                 525

Arg His Trp Asn Ser Gln Cys Arg Thr Thr Gln Ser Tyr Val Arg Ala
    530                 535                 540

Leu Thr Met Asp Ser Lys Lys Arg Ile Gly Trp Arg Phe Ile Arg Ile
545                 550                 555                 560

Asp Thr Ser Cys Val Cys Thr Leu Thr Ile Lys Arg Gly Arg
                565                 570

<210> SEQ ID NO 251
<211> LENGTH: 1805
<212> TYPE: DNA
<213> ORGANISM: Artificial Sequence
<220> FEATURE:
<223> OTHER INFORMATION: Nucleotide sequence encoding the amino acid
      sequence of fusion protein of heavy chain of anti-hTfR antibody
      No.2 (humanized 6) and hBDNF, synthetic sequence

<400> SEQUENCE: 251
acgcgtgccg ccaccatggg ctggagctgg attctgctgt tcctcctgag cgtgacagca      60
ggagtgcaca gccaggtgca gctggtccag tcaggagccg aagtgaaaaa gcccggagcc     120
tcagtcaaag tgtcttgtaa agcatcaggt tatacattta cagactacgt catgcactgg     180
gtgaggcagg cacctggaca gggtctggaa tggatcggcg tgatctccac ttactatggc     240
catggaagct acaaccagag attcaagggc agggcgacaa tgactgtaga caaatcaatt     300
tccactgctt atatggagct ggtaaggctg cggtccgacg ataccgctgt gtactattgc     360
gtacgaggag atacggctc cagctctctg gctggtaatt tcgatgtgtg ggggcagggt     420
accacagtca ccgtgagttc agcaagcaca aagggcccat ctgtgtttcc actggccccc     480
tccagcaaaa gcacctctgg gggtacagcc gctctgggat gtctggtgaa ggattatttc     540
ccagagccag tcaccgtgtc ctggaacagc ggagccctga catctggagt ccacactttt     600
ccagctgtgc tgcagtctag tgggctgtac tccctgtcat ccgtggtcac tgtccccagc     660

```
tctagtctgg gtacccagac atatatctgc aacgtgaatc acaagccatc taataccaaa    720
gtcgacaaga aagtggaacc caagtcctgt gataaaactc atacctgccc ccttgtcct      780
gcaccagagc tgctgggagg accatccgtg ttcctgtttc acccaagcc taaagacacc      840
ctgatgatta gccgaactcc cgaagtcacc tgcgtggtcg tggacgtgtc tcacgaggac     900
cctgaagtca agtttaactg gtacgtggat ggcgtcgagg tgcataatgc taagacaaaa    960
ccccgagagg aacagtacaa cagtacatat cgtgtcgtgt cagtgctgac cgtcctgcat   1020
caggactggc tgaacgggaa ggaatataag tgcaaagtgt ccaataaggc actgcccgcc    1080
cctatcgaga aaaccattag caaggccaaa ggacagccta gggaaccaca ggtgtacaca    1140
ctgcctccat cccgggacga gctgactaag aaccaggtca gcctgacctg tctggtgaaa    1200
ggcttctatc cttcagatat cgctgtggag tgggaaagta atggacagcc agagaacaat    1260
tacaagacta ccccccctgt gctggactct gatgggagtt tctttctgta ttctaagctg    1320
accgtggata aaagtcggtg gcagcagggt aatgtcttta gttgttcagt gatgcacgaa    1380
gcactgcaca accactacac ccagaaatca ctgtcactgt caccagggaa aggatctcac    1440
tctgaccctg cccgccgagg ggagctgagc gtgtgtgaca gtattagtga gtgggtaacg    1500
gcggcagaca aaaagactgc agtggacatg tcgggcggga cggtcacagt ccttgaaaag    1560
gtccctgtat caaaaggcca actgaagcaa tacttctacg agaccaagtg caatcccatg    1620
ggttacacaa agaaggctg caggggcata gacaaaaggc attggaactc ccagtgccga    1680
actacccagt cgtacgtgcg ggcccttacc atggatagca aaagagaat tggctggcga    1740
ttcataagga tagacacttc ttgtgtatgt acattgacca ttaaaagggg aagataagcg    1800
gccgc                                                              1805
```

<210> SEQ ID NO 252
<211> LENGTH: 569
<212> TYPE: PRT
<213> ORGANISM: Artificial Sequence
<220> FEATURE:
<223> OTHER INFORMATION: Amino acid sequence of the fusion protein of
      heavy chain of anti-hTfR antibody No.3 (humanized 2) and hBDNF

<400> SEQUENCE: 252

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
            20                  25                  30

Trp Leu Gly Trp Val Arg Gln Met Pro Gly Lys Gly Leu Glu Trp Met
        35                  40                  45

Gly Asp Ile Tyr Pro Gly Gly Asp Tyr Pro Thr Tyr Ser Glu Lys Phe
    50                  55                  60

Lys Val Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Ser Gly Asn Tyr Asp Glu Val Ala Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140
```

-continued

```
Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
            165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
            210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Asp Val Ser His Glu Asp Pro
            260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
            325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
            355                 360                 365

Leu Val Lys Gly Phe Tyr Pro Ser Asp Ile Ala Val Glu Trp Glu Ser
            370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
            405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
            435                 440                 445

Gly Ser His Ser Asp Pro Ala Arg Arg Gly Glu Leu Ser Val Cys Asp
            450                 455                 460

Ser Ile Ser Glu Trp Val Thr Ala Ala Asp Lys Lys Thr Ala Val Asp
465                 470                 475                 480

Met Ser Gly Gly Thr Val Thr Val Leu Glu Lys Val Pro Val Ser Lys
            485                 490                 495

Gly Gln Leu Lys Gln Tyr Phe Tyr Glu Thr Lys Cys Asn Pro Met Gly
            500                 505                 510

Tyr Thr Lys Glu Gly Cys Arg Gly Ile Asp Lys Arg His Trp Asn Ser
            515                 520                 525

Gln Cys Arg Thr Thr Gln Ser Tyr Val Arg Ala Leu Thr Met Asp Ser
            530                 535                 540

Lys Lys Arg Ile Gly Trp Arg Phe Ile Arg Ile Asp Thr Ser Cys Val
545                 550                 555                 560

Cys Thr Leu Thr Ile Lys Arg Gly Arg
```

<210> SEQ ID NO 253
<211> LENGTH: 1790
<212> TYPE: DNA
<213> ORGANISM: Artificial Sequence
<220> FEATURE:
<223> OTHER INFORMATION: Nucleotide sequence encoding the amino acid
    sequence of fusion protein of heavy-chain of anti-hTfR antibody
    No.3 (humanized 2) and hBDNF, synthetic sequence

<400> SEQUENCE: 253

| | | | | | |
|---|---|---|---|---|---|
| acgcgtgccg | ccaccatggg | ctggagctgg | attctgctgt | tcctcctgag | cgtgacagca | 60 |
| ggagtgcaca | gcgaggtgca | actagtgcag | tctggagcag | aggtgaaaaa | gcccggggag | 120 |
| tctctgaaga | tttcctgtaa | gggttctgga | tacagcttta | ccaactactg | gctgggatgg | 180 |
| gtgcgccaga | tgcccgggaa | aggcctggag | tggatggggg | acatctaccc | cggcggagac | 240 |
| taccctacat | acagcgagaa | gttcaaggtc | caggtcacca | tctcagccga | caagtccatc | 300 |
| agcaccgcct | acctgcagtg | gagcagcctg | aaggcctcgg | acaccgccat | gtattactgt | 360 |
| gcgagatcag | gcaattacga | cgaagtggcc | tactggggcc | aaggaaccct | ggtcaccgtc | 420 |
| tcctcagcta | gcaccaaggg | cccatcggtc | ttccccctgg | caccctcctc | caagagcacc | 480 |
| tctgggggca | cagcggccct | gggctgcctg | gtcaaggact | acttccccga | accggtgacg | 540 |
| gtgtcgtgga | actcaggcgc | cctgaccagc | ggcgtgcaca | ccttcccggc | tgtcctacag | 600 |
| tcctcaggac | tctactccct | cagcagcgtg | gtgaccgtgc | cctccagcag | cttgggcacc | 660 |
| cagacctaca | tctgcaacgt | gaatcacaag | cccagcaaca | ccaaggtgga | caagaaagtt | 720 |
| gagcccaaat | cttgtgacaa | aactcacacg | tgcccaccgt | gcccagcacc | tgaactcctg | 780 |
| ggaggtccgt | cagtcttcct | cttcccccca | aaacccaagg | acaccctcat | gatctcccgg | 840 |
| acccctgagg | tcacatgcgt | ggtggtggac | gtgagccacg | aagaccctga | ggtcaagttc | 900 |
| aactggtacg | tggacggcgt | ggaggtgcat | aatgccaaga | caaagccgcg | ggaggagcag | 960 |
| tacaacagca | cgtaccgggt | ggtcagcgtc | ctcaccgtcc | tgcaccagga | ctggctgaat | 1020 |
| ggcaaggagt | acaagtgcaa | ggtctccaac | aaagccctcc | cagcccccat | cgagaaaacc | 1080 |
| atctccaaag | ccaaagggca | gccccgagaa | ccacaggtgt | acaccctgcc | cccatcccgg | 1140 |
| gatgagctga | ccaagaacca | ggtcagcctg | acctgcctgg | tcaaaggctt | ctatcccagc | 1200 |
| gacatcgccg | tggagtggga | gagcaatggg | cagccggaga | caactacaa | gaccacgcct | 1260 |
| cccgtgctgg | actccgacgg | ctccttcttc | ctctacagca | agctcaccgt | ggacaagagc | 1320 |
| aggtggcagc | aggggaacgt | cttctcatgc | tccgtgatgc | atgaggctct | gcacaaccac | 1380 |
| tacacgcaga | agagcctctc | cctgtctccg | ggtaaaggat | ctcactctga | ccctgccgc | 1440 |
| cgaggggagc | tgagcgtgtg | tgacagtatt | agtgagtggg | taacggcggc | agacaaaaag | 1500 |
| actgcagtgg | acatgtcggg | cggacggtc | acagtccttg | aaaaggtccc | tgtatcaaaa | 1560 |
| ggccaactga | agcaatactt | ctacgagacc | aagtgcaatc | catgggtta | cacaaaagaa | 1620 |
| ggctgcaggg | gcatagacaa | aaggcattgg | aactcccagt | gccgaactac | ccagtcgtac | 1680 |
| gtgcgggccc | ttaccatgga | tagcaaaaag | agaattggct | ggcgattcat | aaggatagac | 1740 |
| acttcttgtg | tatgtacatt | gaccattaaa | aggggaagat | aagcggccgc | | 1790 |

<210> SEQ ID NO 254
<211> LENGTH: 594
<212> TYPE: PRT
<213> ORGANISM: Artificial Sequence
<220> FEATURE:
<223> OTHER INFORMATION: Amino acid sequence of the fusion protein of heavy-chain of anti-hTfR antibody No.3 (humanized 2) and hBDNF

<400> SEQUENCE: 254

| | | | | | | | | | | | | | | |
|---|---|---|---|---|---|---|---|---|---|---|---|---|---|---|
| Glu | Val | Gln | Leu | Val | Gln | Ser | Gly | Ala | Glu | Val | Lys | Lys | Pro | Gly | Glu |
| 1 | | | | 5 | | | | | 10 | | | | | 15 | |
| Ser | Leu | Lys | Ile | Ser | Cys | Lys | Gly | Ser | Gly | Tyr | Ser | Phe | Thr | Asn | Tyr |
| | | | 20 | | | | | 25 | | | | | 30 | | |
| Trp | Leu | Gly | Trp | Val | Arg | Gln | Met | Pro | Gly | Lys | Gly | Leu | Glu | Trp | Met |
| | | 35 | | | | | 40 | | | | | 45 | | | |
| Gly | Asp | Ile | Tyr | Pro | Gly | Gly | Asp | Tyr | Pro | Thr | Tyr | Ser | Glu | Lys | Phe |
| 50 | | | | | 55 | | | | | 60 | | | | | |
| Lys | Val | Gln | Val | Thr | Ile | Ser | Ala | Asp | Lys | Ser | Ile | Ser | Thr | Ala | Tyr |
| 65 | | | | 70 | | | | | 75 | | | | | 80 | |
| Leu | Gln | Trp | Ser | Ser | Leu | Lys | Ala | Ser | Asp | Thr | Ala | Met | Tyr | Tyr | Cys |
| | | | | 85 | | | | | 90 | | | | | 95 | |
| Ala | Arg | Ser | Gly | Asn | Tyr | Asp | Glu | Val | Ala | Tyr | Trp | Gly | Gln | Gly | Thr |
| | | | 100 | | | | | 105 | | | | | 110 | | |
| Leu | Val | Thr | Val | Ser | Ser | Ala | Ser | Thr | Lys | Gly | Pro | Ser | Val | Phe | Pro |
| | | 115 | | | | | 120 | | | | | 125 | | | |
| Leu | Ala | Pro | Ser | Ser | Lys | Ser | Thr | Ser | Gly | Gly | Thr | Ala | Ala | Leu | Gly |
| 130 | | | | | 135 | | | | | 140 | | | | | |
| Cys | Leu | Val | Lys | Asp | Tyr | Phe | Pro | Glu | Pro | Val | Thr | Val | Ser | Trp | Asn |
| 145 | | | | | 150 | | | | | 155 | | | | | 160 |
| Ser | Gly | Ala | Leu | Thr | Ser | Gly | Val | His | Thr | Phe | Pro | Ala | Val | Leu | Gln |
| | | | | 165 | | | | | 170 | | | | | 175 | |
| Ser | Ser | Gly | Leu | Tyr | Ser | Leu | Ser | Ser | Val | Val | Thr | Val | Pro | Ser | Ser |
| | | | 180 | | | | | 185 | | | | | 190 | | |
| Ser | Leu | Gly | Thr | Gln | Thr | Tyr | Ile | Cys | Asn | Val | Asn | His | Lys | Pro | Ser |
| | | | 195 | | | | | 200 | | | | | 205 | | |
| Asn | Thr | Lys | Val | Asp | Lys | Lys | Val | Glu | Pro | Lys | Ser | Cys | Asp | Lys | Thr |
| | 210 | | | | | 215 | | | | | 220 | | | | |
| His | Thr | Cys | Pro | Pro | Cys | Pro | Ala | Pro | Glu | Leu | Leu | Gly | Gly | Pro | Ser |
| 225 | | | | | 230 | | | | | 235 | | | | | 240 |
| Val | Phe | Leu | Phe | Pro | Pro | Lys | Pro | Lys | Asp | Thr | Leu | Met | Ile | Ser | Arg |
| | | | | 245 | | | | | 250 | | | | | 255 | |
| Thr | Pro | Glu | Val | Thr | Cys | Val | Val | Val | Asp | Val | Ser | His | Glu | Asp | Pro |
| | | | | 260 | | | | | 265 | | | | | 270 | |
| Glu | Val | Lys | Phe | Asn | Trp | Tyr | Val | Asp | Gly | Val | Glu | Val | His | Asn | Ala |
| | | | 275 | | | | | 280 | | | | | 285 | | |
| Lys | Thr | Lys | Pro | Arg | Glu | Glu | Gln | Tyr | Asn | Ser | Thr | Tyr | Arg | Val | Val |
| | 290 | | | | | 295 | | | | | 300 | | | | |
| Ser | Val | Leu | Thr | Val | Leu | His | Gln | Asp | Trp | Leu | Asn | Gly | Lys | Glu | Tyr |
| 305 | | | | | 310 | | | | | 315 | | | | | 320 |
| Lys | Cys | Lys | Val | Ser | Asn | Lys | Ala | Leu | Pro | Ala | Pro | Ile | Glu | Lys | Thr |
| | | | | 325 | | | | | 330 | | | | | 335 | |
| Ile | Ser | Lys | Ala | Lys | Gly | Gln | Pro | Arg | Glu | Pro | Gln | Val | Tyr | Thr | Leu |
| | | | 340 | | | | | 345 | | | | | 350 | | |
| Pro | Pro | Ser | Arg | Asp | Glu | Leu | Thr | Lys | Asn | Gln | Val | Ser | Leu | Thr | Cys |
| | | 355 | | | | | 360 | | | | | 365 | | | |
| Leu | Val | Lys | Gly | Phe | Tyr | Pro | Ser | Asp | Ile | Ala | Val | Glu | Trp | Glu | Ser |
| | 370 | | | | | 375 | | | | | 380 | | | | |
| Asn | Gly | Gln | Pro | Glu | Asn | Asn | Tyr | Lys | Thr | Thr | Pro | Pro | Val | Leu | Asp |

Ser Asp Gly Ser Phe Phe Leu Tyr Ser Lys Leu Thr Val Asp Lys Ser
385                 390                 395                 400
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly Lys
            435                 440                 445

Gly Ser Gly Gly Gly Gly Ser Gly Gly Gly Ser Gly Gly Gly Gly
    450                 455                 460

Ser Gly Gly Gly Ser Gly Gly Gly Ser His Ser Asp Pro Ala
465                 470                 475                 480

Arg Arg Gly Glu Leu Ser Val Cys Asp Ser Ile Ser Glu Trp Val Thr
                485                 490                 495

Ala Ala Asp Lys Lys Thr Ala Val Asp Met Ser Gly Gly Thr Val Thr
                500                 505                 510

Val Leu Glu Lys Val Pro Val Ser Lys Gly Gln Leu Lys Gln Tyr Phe
                515                 520                 525

Tyr Glu Thr Lys Cys Asn Pro Met Gly Tyr Thr Lys Glu Gly Cys Arg
                530                 535                 540

Gly Ile Asp Lys Arg His Trp Asn Ser Gln Cys Arg Thr Thr Gln Ser
545                 550                 555                 560

Tyr Val Arg Ala Leu Thr Met Asp Ser Lys Lys Arg Ile Gly Trp Arg
                565                 570                 575

Phe Ile Arg Ile Asp Thr Ser Cys Val Cys Thr Leu Thr Ile Lys Arg
                580                 585                 590

Gly Arg

<210> SEQ ID NO 255
<211> LENGTH: 1865
<212> TYPE: DNA
<213> ORGANISM: Artificial Sequence
<220> FEATURE:
<223> OTHER INFORMATION: Nucleotide sequence encoding the amino acid
      sequence of fusion protein of heavy-chain of anti-hTfR antibody
      No.3 (humanized 2) and hBDNF, synthetic sequence

<400> SEQUENCE: 255
acgcgtgccg ccaccatggg ctggagctgg attctgctgt tcctcctgag cgtgacagca      60
ggagtgcaca gcgaggtgca actagtgcag tctggagcag aggtgaaaaa gcccggggag     120
tctctgaaga tttcctgtaa gggttctgga tacagcttta ccaactactg gctgggatgg     180
gtgcgccaga tgcccgggaa aggcctggag tggatggggg acatctaccc cggcggagac     240
tacccctaca tacagcgagaa gttcaaggtc caggtcacca tctcagccga caagtccatc     300
agcaccgcct acctgcagtg gagcagcctg aaggcctcgg acaccgccat gtattactgt     360
gcgagatcag gcaattacga cgaagtggcc tactggggcc aaggaaccct ggtcaccgtc     420
tcctcagcta gcaccaaggg cccatcggtc ttcccctgg cacctcctc caagagcacc     480 tctgggggca gcgggccct gggctgcctg gtcaaggact acttccccga accggtgacg     540
gtgtcgtgga actcaggcgc cctgaccagc ggcgtgcaca ccttcccggc tgtcctacag     600
tcctcaggac tctactccct cagcagcgtg gtgaccgtgc cctccagcag cttgggcacc     660
cagacctaca tctgcaacgt gaatcacaag cccagcaaca ccaaggtgga caagaaagtt     720
gagcccaaat cttgtgacaa aactcacacg tgcccaccgt gcccagcacc tgaactcctg     780
ggaggtccgt cagtcttcct cttccccca aaacccaagg acaccctcat gatctcccgg     840

```
acccctgagg tcacatgcgt ggtggtggac gtgagccacg aagaccctga ggtcaagttc    900
aactggtacg tggacggcgt ggaggtgcat aatgccaaga caaagccgcg ggaggagcag    960
tacaacagca cgtaccgggt ggtcagcgtc ctcaccgtcc tgcaccagga ctggctgaat   1020
ggcaaggagt acaagtgcaa ggtctccaac aaagccctcc cagcccccat cgagaaaacc   1080
atctccaaag ccaaagggca gccccgagaa ccacaggtgt acaccctgcc cccatcccgg   1140
gatgagctga ccaagaacca ggtcagcctg acctgcctgg tcaaaggctt ctatcccagc   1200
gacatcgccg tggagtggga gagcaatggg cagccggaga caactacaa gaccacgcct   1260 cccgtgctgg actccgacgg ctccttcttc ctctacagca agctcaccgt ggacaagagc   1320
aggtggcagc aggggaacgt cttctcatgc tccgtgatgc atgaggctct gcacaaccac   1380
tacacgcaga gagcctctc cctgtctccg ggtaaaggat ctggtggcgg agggtctgga   1440
ggtggcggat caggcggagg aggttccggg ggcggtggaa gcggaggcgg tggaagccac   1500
tctgaccctg cccgccgagg ggagctgagc gtgtgtgaca gtattagtga gtgggtaacg   1560
gcggcagaca aaagactgc agtggacatg tcggcggga cggtcacagt ccttgaaaag   1620
gtccctgtat caaaaggcca actgaagcaa tacttctacg agaccaagtg caatcccatg   1680
ggttacacaa agaaggctg cagggggcata gacaaaaggc attggaactc ccagtgccga   1740
actacccagt cgtacgtgcg ggcccttacc atggatagca aaagagaat ggctggcga   1800 ttcataagga tagacacttc ttgtgtatgt acattgacca ttaaaagggg aagataagcg   1860
gccgc                                                                1865
```

<210> SEQ ID NO 256
<211> LENGTH: 229
<212> TYPE: PRT
<213> ORGANISM: Homo sapiens

<400> SEQUENCE: 256

```
Ala Pro Met Lys Glu Ala Asn Ile Arg Gly Gln Gly Gly Leu Ala Tyr
1               5                   10                  15

Pro Gly Val Arg Thr His Gly Thr Leu Glu Ser Val Asn Gly Pro Lys
            20                  25                  30

Ala Gly Ser Arg Gly Leu Thr Ser Leu Ala Asp Thr Phe Glu His Val
        35                  40                  45

Ile Glu Glu Leu Leu Asp Glu Asp Gln Lys Val Arg Pro Asn Glu Glu
    50                  55                  60

Asn Asn Lys Asp Ala Asp Leu Tyr Thr Ser Arg Val Met Leu Ser Ser
65                  70                  75                  80

Gln Val Pro Leu Glu Pro Pro Leu Leu Phe Leu Leu Glu Glu Tyr Lys
                85                  90                  95

Asn Tyr Leu Asp Ala Ala Asn Met Ser Met Arg Val Arg Arg His Ser
            100                 105                 110

Asp Pro Ala Arg Arg Gly Glu Leu Ser Val Cys Asp Ser Ile Ser Glu
        115                 120                 125

Trp Val Thr Ala Ala Asp Lys Lys Thr Ala Val Asp Met Ser Gly Gly
    130                 135                 140

Thr Val Thr Val Leu Glu Lys Val Pro Val Ser Lys Gly Gln Leu Lys
145                 150                 155                 160

Gln Tyr Phe Tyr Glu Thr Lys Cys Asn Pro Met Gly Tyr Thr Lys Glu
                165                 170                 175

Gly Cys Arg Gly Ile Asp Lys Arg His Trp Asn Ser Gln Cys Arg Thr
```

```
            180             185             190
Thr Gln Ser Tyr Val Arg Ala Leu Thr Met Asp Ser Lys Lys Arg Ile
            195             200             205

Gly Trp Arg Phe Ile Arg Ile Asp Thr Ser Cys Val Cys Thr Leu Thr
            210             215             220

Ile Lys Arg Gly Arg
225

<210> SEQ ID NO 257
<211> LENGTH: 245
<212> TYPE: PRT
<213> ORGANISM: Artificial Sequence
<220> FEATURE:
<223> OTHER INFORMATION: Amino acid sequence of anti-hTfR single-chain
      antibody

<400> SEQUENCE: 257

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
            20                  25                  30

Trp Leu Gly Trp Val Arg Gln Met Pro Gly Lys Gly Leu Glu Trp Met
        35                  40                  45

Gly Asp Ile Tyr Pro Gly Gly Asp Tyr Pro Thr Tyr Ser Glu Lys Phe
    50                  55                  60

Lys Val Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Ser Gly Asn Tyr Asp Glu Val Ala Tyr Trp Gly Gln Gly Thr
            100                 105                 110

Leu Val Thr Val Ser Ser Gly Gly Gly Gly Ser Gly Gly Gly Gly Ser
        115                 120                 125

Gly Gly Gly Gly Ser Asp Ile Val Met Thr Gln Thr Pro Leu Ser Leu
    130                 135                 140

Ser Val Thr Pro Gly Gln Pro Ala Ser Ile Ser Cys Arg Ser Ser Gln
145                 150                 155                 160

Ser Leu Val His Ser Asn Gly Asn Thr Tyr Leu His Trp Tyr Leu Gln
                165                 170                 175

Lys Pro Gly Gln Ser Pro Gln Leu Leu Ile Tyr Lys Val Ser Asn Arg
            180                 185                 190

Phe Ser Gly Val Pro Asp Arg Phe Ser Gly Ser Gly Ser Gly Thr Asp
        195                 200                 205

Phe Thr Leu Lys Ile Ser Arg Val Glu Ala Glu Asp Val Gly Val Tyr
    210                 215                 220

Tyr Cys Ser Gln Ser Thr His Val Pro Trp Thr Phe Gly Gln Gly Thr
225                 230                 235                 240

Lys Val Glu Ile Lys
                245

<210> SEQ ID NO 258
<211> LENGTH: 1583
<212> TYPE: DNA
<213> ORGANISM: Artificial Sequence
<220> FEATURE:
<223> OTHER INFORMATION: Nucleotide sequence encoding a fusion protein
      of pro-hBDNF and anti-hTfR single-chain antibody
```

-continued

<400> SEQUENCE: 258

```
acgcgtgccg ccaccatgac catccttttc cttactatgg ttatttcata ctttggttgc    60
atgaaggctg cccccatgaa agaagcaaac atccgaggac aaggtggctt ggcctaccca   120
ggtgtgcgga cccatgggac tctggagagc gtgaatgggc ccaaggcagg ttcaagaggc   180
ttgacatcat tggctgacac tttcgaacac gtgatagaag agctgttgga tgaggaccag   240
aaagttcggc ccaatgaaga aacaataag gacgcagact tgtacacgtc cagggtgatg   300
ctcagtagtc aagtgccttt ggagcctcct cttctctttc tgctggagga atacaaaaat   360
tacctagatg ctgcaaacat gtccatgagg tccggcgcc actctgaccc tgcccgccga   420
ggggagctga gcgtgtgtga cagtattagt gagtgggtaa cggcggcaga caaaaagact   480
gcagtggaca tgtcgggcgg gacggtcaca gtccttgaaa aggtccctgt atcaaaaggc   540
caactgaagc aatacttcta cgagaccaag tgcaatccca tgggttacac aaaagaaggc   600
tgcaggggca tagacaaaag gcattggaac tcccagtgcc gaactaccca gtcgtacgtg   660
cgggccctta ccatggatag caagaagaga attggctggc gattcataag gatagacact   720
tcttgtgtat gtacattgac cattaaaagg ggaagaggat ctggtggcgg agggtctgga   780
ggtggcggat caggcggagg aggttccggg gcggtggaa gcggaggcgg tggaagtgag   840
gtgcaactag tgcagtctgg agcagaggtg aaaaagcccg gggagtctct gaagatttcc   900
tgtaagggtt ctggatacag ctttaccaac tactggctgg gatgggtgcg ccagatgccc   960
gggaaaggcc tggagtggat gggggacatc taccccggcg agactaccc tacatacagc  1020
gagaagttca aggtccaggt caccatctca gccgacaagt ccatcagcac cgcctacctg  1080
cagtggagca gcctgaaggc ctcggacacc gccatgtatt actgtgcgag atcaggcaat  1140
tacgacgaag tggcctactg gggccaagga accctggtca ccgtctcctc aggcggtggt  1200
ggaagtggag gcggtgggtc gggaggaggt ggcagcgaca tcgtgatgac ccagactccc  1260
ctgagcctga gcgtgacacc tggccagcct gccagcatca gctgcagaag ctctcagagc  1320
ctggtgcaca gcaacggcaa cacctacctg cactggtatc tgcagaagcc cggccagagc  1380
cctcagctgc tgatctacaa ggtgtccaac agattcagcg gcgtgcccga cagattctcc  1440
ggcagcggct ctggcaccga cttcaccctg aagatttcca gagtggaagc cgaggacgtg  1500
ggcgtgtact actgcagcca gagcacccac gtgccctgga cattcggcca gggcaccaag  1560
gtggaaatca agtaagcggc cgc                                          1583
```

<210> SEQ ID NO 259
<211> LENGTH: 501
<212> TYPE: PRT
<213> ORGANISM: Artificial Sequence
<220> FEATURE:
<223> OTHER INFORMATION: Amino acid sequence of a fusion protein of
      pro-hBDNF and anti-hTfR single-chain antibody

<400> SEQUENCE: 259

```
Ala Pro Met Lys Glu Ala Asn Ile Arg Gly Gln Gly Gly Leu Ala Tyr
 1               5                  10                  15

Pro Gly Val Arg Thr His Gly Thr Leu Glu Ser Val Asn Gly Pro Lys
            20                  25                  30

Ala Gly Ser Arg Gly Leu Thr Ser Leu Ala Asp Thr Phe Glu His Val
        35                  40                  45

Ile Glu Glu Leu Leu Asp Glu Asp Gln Lys Val Arg Pro Asn Glu Glu
    50                  55                  60
```

-continued

```
Asn Asn Lys Asp Ala Asp Leu Tyr Thr Ser Arg Val Met Leu Ser Ser
 65                  70                  75                  80

Gln Val Pro Leu Glu Pro Pro Leu Leu Phe Leu Leu Glu Glu Tyr Lys
                 85                  90                  95

Asn Tyr Leu Asp Ala Ala Asn Met Ser Met Arg Val Arg Arg His Ser
            100                 105                 110

Asp Pro Ala Arg Arg Gly Glu Leu Ser Val Cys Asp Ser Ile Ser Glu
        115                 120                 125

Trp Val Thr Ala Ala Asp Lys Lys Thr Ala Val Asp Met Ser Gly Gly
    130                 135                 140

Thr Val Thr Val Leu Glu Lys Val Pro Val Ser Lys Gly Gln Leu Lys
145                 150                 155                 160

Gln Tyr Phe Tyr Glu Thr Lys Cys Asn Pro Met Gly Tyr Thr Lys Glu
                165                 170                 175

Gly Cys Arg Gly Ile Asp Lys Arg His Trp Asn Ser Gln Cys Arg Thr
            180                 185                 190

Thr Gln Ser Tyr Val Arg Ala Leu Thr Met Asp Ser Lys Lys Arg Ile
        195                 200                 205

Gly Trp Arg Phe Ile Arg Ile Asp Thr Ser Cys Val Cys Thr Leu Thr
    210                 215                 220

Ile Lys Arg Gly Arg Gly Ser Gly Gly Gly Ser Gly Gly Gly Gly
225                 230                 235                 240

Ser Gly Gly Gly Gly Ser Gly Gly Gly Gly Ser Gly Gly Gly Gly Ser
                245                 250                 255

Glu Val Gln Leu Val Gln Ser Gly Ala Glu Val Lys Lys Pro Gly Glu
            260                 265                 270

Ser Leu Lys Ile Ser Cys Lys Gly Ser Gly Tyr Ser Phe Thr Asn Tyr
        275                 280                 285

Trp Leu Gly Trp Val Arg Gln Met Pro Gly Lys Gly Leu Glu Trp Met
    290                 295                 300

Gly Asp Ile Tyr Pro Gly Gly Asp Tyr Pro Thr Tyr Ser Glu Lys Phe
305                 310                 315                 320

Lys Val Gln Val Thr Ile Ser Ala Asp Lys Ser Ile Ser Thr Ala Tyr
                325                 330                 335

Leu Gln Trp Ser Ser Leu Lys Ala Ser Asp Thr Ala Met Tyr Tyr Cys
            340                 345                 350

Ala Arg Ser Gly Asn Tyr Asp Glu Val Ala Tyr Trp Gly Gln Gly Thr
        355                 360                 365

Leu Val Thr Val Ser Ser Gly Gly Gly Ser Gly Gly Gly Gly Ser
    370                 375                 380

Gly Gly Gly Gly Ser Asp Ile Val Met Thr Gln Thr Pro Leu Ser Leu
385                 390                 395                 400

Ser Val Thr Pro Gly Gln Pro Ala Ser Ile Ser Cys Arg Ser Ser Gln
                405                 410                 415

Ser Leu Val His Ser Asn Gly Asn Thr Tyr Leu His Trp Tyr Leu Gln
            420                 425                 430

Lys Pro Gly Gln Ser Pro Gln Leu Leu Ile Tyr Lys Val Ser Asn Arg
        435                 440                 445

Phe Ser Gly Val Pro Asp Arg Phe Ser Gly Ser Gly Ser Gly Thr Asp
    450                 455                 460

Phe Thr Leu Lys Ile Ser Arg Val Glu Ala Glu Asp Val Gly Val Tyr
465                 470                 475                 480

Tyr Cys Ser Gln Ser Thr His Val Pro Trp Thr Phe Gly Gln Gly Thr
```

```
                    485              490             495
Lys Val Glu Ile Lys
            500

<210> SEQ ID NO 260
<211> LENGTH: 391
<212> TYPE: PRT
<213> ORGANISM: Artificial Sequence
<220> FEATURE:
<223> OTHER INFORMATION: Amino acid sequence of a fusion protein of
      hBDNF and anti-hTfR single-chain antibody

<400> SEQUENCE: 260

His Ser Asp Pro Ala Arg Arg Gly Glu Leu Ser Val Cys Asp Ser Ile
1               5                   10                  15

Ser Glu Trp Val Thr Ala Ala Asp Lys Lys Thr Ala Val Asp Met Ser
            20                  25                  30

Gly Gly Thr Val Thr Val Leu Glu Lys Val Pro Val Ser Lys Gly Gln
        35                  40                  45

Leu Lys Gln Tyr Phe Tyr Glu Thr Lys Cys Asn Pro Met Gly Tyr Thr
    50                  55                  60

Lys Glu Gly Cys Arg Gly Ile Asp Lys Arg His Trp Asn Ser Gln Cys
65                  70                  75                  80

Arg Thr Thr Gln Ser Tyr Val Arg Ala Leu Thr Met Asp Ser Lys Lys
                85                  90                  95

Arg Ile Gly Trp Arg Phe Ile Arg Ile Asp Thr Ser Cys Val Cys Thr
            100                 105                 110

Leu Thr Ile Lys Arg Gly Arg Gly Ser Gly Gly Gly Ser Gly Gly
        115                 120                 125

Gly Gly Ser Gly Gly Gly Gly Ser Gly Gly Gly Gly Ser Gly Gly Gly
    130                 135                 140

Gly Ser Glu Val Gln Leu Val Gln Ser Gly Ala Glu Val Lys Lys Pro
145                 150                 155                 160

Gly Glu Ser Leu Lys Ile Ser Cys Lys Gly Ser Gly Tyr Ser Phe Thr
                165                 170                 175

Asn Tyr Trp Leu Gly Trp Val Arg Gln Met Pro Gly Lys Gly Leu Glu
            180                 185                 190

Trp Met Gly Asp Ile Tyr Pro Gly Gly Asp Tyr Pro Thr Tyr Ser Glu
        195                 200                 205

Lys Phe Lys Val Gln Val Thr Ile Ser Ala Asp Lys Ser Ile Ser Thr
    210                 215                 220

Ala Tyr Leu Gln Trp Ser Ser Leu Lys Ala Ser Asp Thr Ala Met Tyr
225                 230                 235                 240

Tyr Cys Ala Arg Ser Gly Asn Tyr Asp Glu Val Ala Tyr Trp Gly Gln
                245                 250                 255

Gly Thr Leu Val Thr Val Ser Ser Gly Gly Gly Gly Ser Gly Gly Gly
            260                 265                 270

Gly Ser Gly Gly Gly Gly Ser Asp Ile Val Met Thr Gln Thr Pro Leu
        275                 280                 285

Ser Leu Ser Val Thr Pro Gly Gln Pro Ala Ser Ile Ser Cys Arg Ser
    290                 295                 300

Ser Gln Ser Leu Val His Ser Asn Gly Asn Thr Tyr Leu His Trp Tyr
305                 310                 315                 320

Leu Gln Lys Pro Gly Gln Ser Pro Gln Leu Leu Ile Tyr Lys Val Ser
                325                 330                 335
```

```
Asn Arg Phe Ser Gly Val Pro Asp Arg Phe Ser Gly Ser Gly
            340                 345                 350

Thr Asp Phe Thr Leu Lys Ile Ser Arg Val Glu Ala Glu Asp Val Gly
        355                 360                 365

Val Tyr Tyr Cys Ser Gln Ser Thr His Val Pro Trp Thr Phe Gly Gln
    370                 375                 380

Gly Thr Lys Val Glu Ile Lys
385                 390

<210> SEQ ID NO 261
<211> LENGTH: 226
<212> TYPE: PRT
<213> ORGANISM: Artificial Sequence
<220> FEATURE:
<223> OTHER INFORMATION: Amino acid sequence of an Fab of H-chain of
      humanized anti-hTfR antibody

<400> SEQUENCE: 261

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
            20                  25                  30

Trp Leu Gly Trp Val Arg Gln Met Pro Gly Lys Gly Leu Glu Trp Met
        35                  40                  45

Gly Asp Ile Tyr Pro Gly Gly Asp Tyr Pro Thr Tyr Ser Glu Lys Phe
    50                  55                  60

Lys Val Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Ser Gly Asn Tyr Asp Glu Val Ala Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr
225

<210> SEQ ID NO 262
<211> LENGTH: 1526
<212> TYPE: DNA
<213> ORGANISM: Artificial Sequence
<220> FEATURE:
<223> OTHER INFORMATION: Nucleotide sequence encoding the amino acid
      sequence of a fusion protein of pro-hBDNF and Fab of heavy chain
      of humanized anti-hTfR antibody, synthetic sequence

<400> SEQUENCE: 262
```

```
acgcgtgccg ccaccatgac catccttttc cttactatgg ttatttcata ctttggttgc    60
atgaaggctg ccccatgaa agaagcaaac atccgaggac aaggtggctt ggcctaccca    120
ggtgtgcgga cccatgggac tctggagagc gtgaatgggc caaggcagg ttcaagaggc    180
ttgacatcat tggctgacac tttcgaacac gtgatagaag agctgttgga tgaggaccag    240
aaagttcggc ccaatgaaga aaacaataag gacgcagact tgtacacgtc agggtgatg    300
ctcagtagtc aagtgccttt ggagcctcct cttctctttc tgctggagga atacaaaaat    360
tacctagatg ctgcaaacat gtccatgagg gtccggcgcc actctgaccc tgcccgccga    420
ggggagctga gcgtgtgtga cagtattagt gagtgggtaa cggcggcaga caaaaagact    480
gcagtggaca tgtcgggcgg gacggtcaca gtccttgaaa aggtccctgt atcaaaaggc    540
caactgaagc aatacttcta cgagaccaag tgcaatccca tgggttacac aaaagaaggc    600
tgcagggca tagacaaaag gcattggaac tcccagtgcc gaactaccca gtcgtacgtg    660
cgggccctta ccatggatag caagaagaga attggctggc gattcataag gatagacact    720
tcttgtgtat gtacattgac cattaaaagg ggaagaggat ctggtggcgg agggtctgga    780
ggtggcggat caggcggagg aggttccggg ggcggtggaa gcggaggcgg tggaagtgag    840
gtgcaactag tgcagtctgg agcagaggtg aaaaagcccg gggagtctct gaagatttcc    900
tgtaagggtt ctggatacag ctttaccaac tactggctgg gatgggtgcg ccagatgccc    960
gggaaaggcc tggagtggat gggggacatc taccccggcg gagactaccc tacatacagc    1020
gagaagttca aggtccaggt caccatctca gccgacaagt ccatcagcac cgcctacctg    1080
cagtggagca gcctgaaggc ctcggacacc gccatgtatt actgtgcgag atcaggcaat    1140
tacgacgaag tggcctactg gggccaagga accctggtca ccgtctcctc agctagcacc    1200
aagggcccat cggtcttccc cctggcaccc tcctccaaga gcacctctgg gggcacagcg    1260
gccctgggct gcctggtcaa ggactacttc cccgaaccgg tgacggtgtc gtggaactca    1320
ggcgccctga ccagcggcgt gcacaccttc ccggctgtcc tacagtcctc aggactctac    1380
tccctcagca gcgtggtgac cgtgccctcc agcagcttgg gcacccagac ctacatctgc    1440
aacgtgaatc acaagcccag caacaccaag gtggacaaga agttgagcc caaatcttgt    1500
gacaaaactc acacgtaagc ggccgc                                        1526
```

<210> SEQ ID NO 263
<211> LENGTH: 482
<212> TYPE: PRT
<213> ORGANISM: Artificial Sequence
<220> FEATURE:
<223> OTHER INFORMATION: Amino acid sequence of a fusion protein of
      pro-hBDNF and Fab of heavy chain of humanized anti-hTfR antibody,
      synthetic sequence

<400> SEQUENCE: 263

Ala Pro Met Lys Glu Ala Asn Ile Arg Gly Gln Gly Gly Leu Ala Tyr
1               5                   10                  15

Pro Gly Val Arg Thr His Gly Thr Leu Glu Ser Val Asn Gly Pro Lys
            20                  25                  30

Ala Gly Ser Arg Gly Leu Thr Ser Leu Ala Asp Thr Phe Glu His Val
        35                  40                  45

Ile Glu Glu Leu Leu Asp Glu Asp Gln Lys Val Arg Pro Asn Glu Glu
    50                  55                  60

Asn Asn Lys Asp Ala Asp Leu Tyr Thr Ser Arg Val Met Leu Ser Ser
65                  70                  75                  80

-continued

```
Gln Val Pro Leu Glu Pro Pro Leu Leu Phe Leu Leu Glu Glu Tyr Lys
                 85                  90                  95

Asn Tyr Leu Asp Ala Ala Asn Met Ser Met Arg Val Arg Arg His Ser
                100                 105                 110

Asp Pro Ala Arg Arg Gly Glu Leu Ser Val Cys Asp Ser Ile Ser Glu
                115                 120                 125

Trp Val Thr Ala Ala Asp Lys Lys Thr Ala Val Asp Met Ser Gly Gly
            130                 135                 140

Thr Val Thr Val Leu Glu Lys Val Pro Val Ser Lys Gly Gln Leu Lys
145                 150                 155                 160

Gln Tyr Phe Tyr Glu Thr Lys Cys Asn Pro Met Gly Tyr Thr Lys Glu
                165                 170                 175

Gly Cys Arg Gly Ile Asp Lys Arg His Trp Asn Ser Gln Cys Arg Thr
                180                 185                 190

Thr Gln Ser Tyr Val Arg Ala Leu Thr Met Asp Ser Lys Lys Arg Ile
                195                 200                 205

Gly Trp Arg Phe Ile Arg Ile Asp Thr Ser Cys Val Cys Thr Leu Thr
            210                 215                 220

Ile Lys Arg Gly Arg Gly Ser Gly Gly Gly Ser Gly Gly Gly Gly
225                 230                 235                 240

Ser Gly Gly Gly Ser Gly Gly Gly Gly Ser Gly Gly Gly Gly Ser
                245                 250                 255

Glu Val Gln Leu Val Gln Ser Gly Ala Glu Val Lys Lys Pro Gly Glu
                260                 265                 270

Ser Leu Lys Ile Ser Cys Lys Gly Ser Gly Tyr Ser Phe Thr Asn Tyr
                275                 280                 285

Trp Leu Gly Trp Val Arg Gln Met Pro Gly Lys Gly Leu Glu Trp Met
            290                 295                 300

Gly Asp Ile Tyr Pro Gly Gly Asp Tyr Pro Thr Tyr Ser Glu Lys Phe
305                 310                 315                 320

Lys Val Gln Val Thr Ile Ser Ala Asp Lys Ser Ile Ser Thr Ala Tyr
                325                 330                 335

Leu Gln Trp Ser Ser Leu Lys Ala Ser Asp Thr Ala Met Tyr Tyr Cys
                340                 345                 350

Ala Arg Ser Gly Asn Tyr Asp Glu Val Ala Tyr Trp Gly Gln Gly Thr
                355                 360                 365

Leu Val Thr Val Ser Ser Ala Ser Thr Lys Gly Pro Ser Val Phe Pro
            370                 375                 380

Leu Ala Pro Ser Ser Lys Ser Thr Ser Gly Gly Thr Ala Ala Leu Gly
385                 390                 395                 400

Cys Leu Val Lys Asp Tyr Phe Pro Glu Pro Val Thr Val Ser Trp Asn
                405                 410                 415

Ser Gly Ala Leu Thr Ser Gly Val His Thr Phe Pro Ala Val Leu Gln
                420                 425                 430

Ser Ser Gly Leu Tyr Ser Leu Ser Ser Val Val Thr Val Pro Ser Ser
            435                 440                 445

Ser Leu Gly Thr Gln Thr Tyr Ile Cys Asn Val Asn His Lys Pro Ser
450                 455                 460

Asn Thr Lys Val Asp Lys Lys Val Glu Pro Lys Ser Cys Asp Lys Thr
465                 470                 475                 480

His Thr
```

<210> SEQ ID NO 264
<211> LENGTH: 372
<212> TYPE: PRT
<213> ORGANISM: Artificial Sequence
<220> FEATURE:
<223> OTHER INFORMATION: Amino acid sequence of a fusion protein of hBDNF and Fab of heavy chain of humanized anti-hTfR antibody, synthetic sequence

<400> SEQUENCE: 264

| | | | | | | | | | | | | | | |
|---|---|---|---|---|---|---|---|---|---|---|---|---|---|---|
| His | Ser | Asp | Pro | Ala | Arg | Arg | Gly | Glu | Leu | Ser | Val | Cys | Asp | Ser | Ile |
| 1 | | | | 5 | | | | | 10 | | | | | 15 | |
| Ser | Glu | Trp | Val | Thr | Ala | Ala | Asp | Lys | Lys | Thr | Ala | Val | Asp | Met | Ser |
| | | | 20 | | | | | 25 | | | | | 30 | | |
| Gly | Gly | Thr | Val | Thr | Val | Leu | Glu | Lys | Val | Pro | Val | Ser | Lys | Gly | Gln |
| | | | 35 | | | | | 40 | | | | | 45 | | |
| Leu | Lys | Gln | Tyr | Phe | Tyr | Glu | Thr | Lys | Cys | Asn | Pro | Met | Gly | Tyr | Thr |
| | 50 | | | | | 55 | | | | | 60 | | | | |
| Lys | Glu | Gly | Cys | Arg | Gly | Ile | Asp | Lys | Arg | His | Trp | Asn | Ser | Gln | Cys |
| 65 | | | | | 70 | | | | | 75 | | | | | 80 |
| Arg | Thr | Thr | Gln | Ser | Tyr | Val | Arg | Ala | Leu | Thr | Met | Asp | Ser | Lys | Lys |
| | | | | 85 | | | | | 90 | | | | | 95 | |
| Arg | Ile | Gly | Trp | Arg | Phe | Ile | Arg | Ile | Asp | Thr | Ser | Cys | Val | Cys | Thr |
| | | | | 100 | | | | | 105 | | | | | 110 | |
| Leu | Thr | Ile | Lys | Arg | Gly | Arg | Gly | Ser | Gly | Gly | Gly | Ser | Gly | Gly | |
| | | | 115 | | | | | 120 | | | | | 125 | | |
| Gly | Gly | Ser | Gly | Gly | Gly | Gly | Ser | Gly | Gly | Gly | Gly | Ser | Gly | Gly | Gly |
| | | 130 | | | | | 135 | | | | | 140 | | | |
| Gly | Ser | Glu | Val | Gln | Leu | Val | Gln | Ser | Gly | Ala | Glu | Val | Lys | Lys | Pro |
| 145 | | | | | 150 | | | | | 155 | | | | | 160 |
| Gly | Glu | Ser | Leu | Lys | Ile | Ser | Cys | Lys | Gly | Ser | Gly | Tyr | Ser | Phe | Thr |
| | | | | 165 | | | | | 170 | | | | | 175 | |
| Asn | Tyr | Trp | Leu | Gly | Trp | Val | Arg | Gln | Met | Pro | Gly | Lys | Gly | Leu | Glu |
| | | | 180 | | | | | 185 | | | | | 190 | | |
| Trp | Met | Gly | Asp | Ile | Tyr | Pro | Gly | Gly | Asp | Tyr | Pro | Thr | Tyr | Ser | Glu |
| | | | 195 | | | | | 200 | | | | | 205 | | |
| Lys | Phe | Lys | Val | Gln | Val | Thr | Ile | Ser | Ala | Asp | Lys | Ser | Ile | Ser | Thr |
| | 210 | | | | | 215 | | | | | 220 | | | | |
| Ala | Tyr | Leu | Gln | Trp | Ser | Ser | Leu | Lys | Ala | Ser | Asp | Thr | Ala | Met | Tyr |
| 225 | | | | | 230 | | | | | 235 | | | | | 240 |
| Tyr | Cys | Ala | Arg | Ser | Gly | Asn | Tyr | Asp | Glu | Val | Ala | Tyr | Trp | Gly | Gln |
| | | | | 245 | | | | | 250 | | | | | 255 | |
| Gly | Thr | Leu | Val | Thr | Val | Ser | Ser | Ala | Ser | Thr | Lys | Gly | Pro | Ser | Val |
| | | | 260 | | | | | 265 | | | | | 270 | | |
| Phe | Pro | Leu | Ala | Pro | Ser | Ser | Lys | Ser | Thr | Ser | Gly | Gly | Thr | Ala | Ala |
| | | | 275 | | | | | 280 | | | | | 285 | | |
| Leu | Gly | Cys | Leu | Val | Lys | Asp | Tyr | Phe | Pro | Glu | Pro | Val | Thr | Val | Ser |
| | | 290 | | | | | 295 | | | | | 300 | | | |
| Trp | Asn | Ser | Gly | Ala | Leu | Thr | Ser | Gly | Val | His | Thr | Phe | Pro | Ala | Val |
| 305 | | | | | 310 | | | | | 315 | | | | | 320 |
| Leu | Gln | Ser | Ser | Gly | Leu | Tyr | Ser | Leu | Ser | Val | Val | Thr | Val | Pro | |
| | | | | 325 | | | | | 330 | | | | | 335 | |
| Ser | Ser | Ser | Leu | Gly | Thr | Gln | Thr | Tyr | Ile | Cys | Asn | Val | Asn | His | Lys |
| | | | 340 | | | | | 345 | | | | | 350 | | |
| Pro | Ser | Asn | Thr | Lys | Val | Asp | Lys | Lys | Val | Glu | Pro | Lys | Ser | Cys | Asp |
| | | | | 355 | | | | | 360 | | | | | 365 | |

Lys Thr His Thr
    370

<210> SEQ ID NO 265
<211> LENGTH: 1196
<212> TYPE: DNA
<213> ORGANISM: Artificial Sequence
<220> FEATURE:
<223> OTHER INFORMATION: Nucleotide sequence encoding the amino acid
      sequence of a fusion protein of hBDNF and Fab of heavy chain of
      humanized anti-hTfR antibody, synthetic sequence

<400> SEQUENCE: 265

```
acgcgtgccg ccaccatgac catccttttc cttactatgg ttatttcata ctttggttgc    60
atgaaggctc actctgaccc tgcccgccga ggggagctga gcgtgtgtga cagtattagt   120
gagtgggtaa cggcggcaga caaaaagact gcagtggaca tgtcgggcgg gacggtcaca   180
gtccttgaaa aggtccctgt atcaaaaggc caactgaagc aatacttcta cgagaccaag   240
tgcaatccca tgggttacac aaaagaaggc tgcaggggca tagacaaaag gcattggaac   300
tcccagtgcc gaactaccca gtcgtacgtg cgggccctta ccatggatag caaaaagaga   360
attggctggc gattcataag gatagacact tcttgtgtat gtacattgac cattaaaagg   420
ggaagaggat ctggtggcgg agggtctgga ggtggcggat caggcggagg aggttccggg   480
ggcggtggaa gcggaggcgg tggaagtgag gtgcaactag tgcagtctgg agcagaggtg   540
aaaaagcccg gggagtctct gaagatttcc tgtaagggtt ctggatacag ctttaccaac   600
tactggctgg atgggtgcg ccagatgccc gggaaaggcc tggagtggat ggggacatc   660
taccccggcg agactaccc tacatacagc gagaagttca aggtccaggt caccatctca   720
gccgacaagt ccatcagcac cgcctacctg cagtggagca gcctgaaggc ctcggacacc   780
gccatgtatt actgtgcgag atcaggcaat tacgacgaag tggcctactg ggccaagga   840
accctggtca ccgtctcctc agctagcacc aagggcccat cggtcttccc cctggcaccc   900
tcctccaaga gcacctctgg gggcacagcg gccctgggct gcctggtcaa ggactacttc   960
cccgaaccgg tgacggtgtc gtggaactca ggcgccctga ccagcggcgt gcacaccttc  1020
ccggctgtcc tacagtcctc aggactctac tccctcagca gcgtggtgac cgtgccctcc  1080
agcagcttgg gcacccagac ctacatctgc aacgtgaatc acaagcccag caacaccaag  1140
gtggacaaga agttgagcc caaatcttgt gacaaaactc acacgtaagc ggccgc       1196
```

<210> SEQ ID NO 266
<211> LENGTH: 16
<212> TYPE: PRT
<213> ORGANISM: Artificial Sequence
<220> FEATURE:
<223> OTHER INFORMATION: mino acid sequence 2 of CDR 2 in the heavy
      chain of mouse anti-hTfR antibody No. 6

<400> SEQUENCE: 266

Ile Ile Trp Gly Asp Gly Ser Thr Asn Tyr His Ser Ala Leu Ile Ser
1               5                   10                  15

<210> SEQ ID NO 267
<211> LENGTH: 16
<212> TYPE: PRT
<213> ORGANISM: Artificial Sequence
<220> FEATURE:
<223> OTHER INFORMATION: Amino acid sequence 2 of CDR 2 in the heavy
      chain of mouse anti-hTfR antibody No. 8

```
<400> SEQUENCE: 267

Ile Ile Trp Gly Asp Gly Ser Thr Asn Tyr Arg Ser Ala Leu Ile Ser
1               5                   10                  15
```

The invention claimed is:

1. A fusion protein of brain-derived neurotrophic factor (BDNF) and an anti-human transferrin receptor (anti-hTfR) antibody, wherein the fusion protein comprises a BDNF linked to an anti-hTfR antibody or antigen-binding fragment thereof; wherein the anti-hTfR antibody or antigen-binding fragment thereof comprises a light chain (LC) having a light chain variable region (LCVR) comprising three complementarity-determining regions (LCDR1-3) and a heavy chain (HC) having a heavy chain variable region (HCVR) comprising three complementarity-determining regions (HCDR1-3), wherein the LCDR1 comprises the amino acid sequence of SEQ ID NO:16, the LCDR2 comprises the amino acid sequence of SEQ ID NO:18, the LCDR3 comprises the amino acid sequence of SEQ ID NO:20, the HCDR1 comprises the amino acid sequence of SEQ ID NO:88, the HCDR2 comprises the amino acid sequence of SEQ ID NO:90, and the HCDR3 comprises the amino acid sequence of SEQ ID NO:92, and wherein the BDNF is linked directly or via a linker to the HC of the anti-hTfR antibody or antigen-binding fragment thereof and the C-terminus of the BDNF is linked to the N-terminus of the HC.

2. The fusion protein according to claim 1, wherein the LCVR comprises the amino acid sequence of SEQ ID NO:191, and the HCVR comprises the amino acid sequence of SEQ ID NO:205.

3. The fusion protein according to claim 1, wherein the LCVR comprises the amino acid sequence having at least 95% sequence identity to SEQ ID NO:191 and having the LCDR1-3 of SEQ ID NOs:16, 18 and 20 respectively, and the HCVR comprises the amino acid sequence having at least 95% sequence identity to SEQ ID NO:205 and having the HCDR1-3 of SEQ ID NOs: 88, 90 and 92 respectively.

4. The fusion protein according to claim 3, wherein the LCVR comprises the amino acid sequence having at least 98% sequence identity to SEQ ID NO:191 and having the LCDR1-3 of SEQ ID NOs:16, 18 and 20 respectively, and the HCVR comprises the amino acid sequence having at least 98% sequence identity to SEQ ID NO:205 and having the HCDR1-3 of SEQ ID NOs: 88, 90 and 92 respectively.

5. The fusion protein according to claim 1, wherein the LCVR comprises the amino acid sequence of SEQ ID NO:191 with a substitution, deletion or addition of 1 to 3 amino acids and has the LCDR1-3 of SEQ ID NOs:16, 18 and 20 respectively, or wherein the HCVR comprises the amino acid sequence of SEQ ID NO:205 with a substitution, deletion or addition of 1 to 3 amino acids and has the HCDR1-3 of SEQ ID NOs: 88, 90 and 92 respectively.

6. The fusion protein according to claim 1, wherein the antigen-binding fragment is a Fab, F(ab')$_2$, or F(ab') of the anti-hTfR antibody and the BDNF is human BDNF; wherein the human BDNF is linked, directly or via a linker, to the heavy chain of the Fab, F(ab')$_2$, or F(ab').

7. The fusion protein according to claim 6, wherein the light chain of the antigen-binding fragment consists of the amino acid sequence of SEQ ID NO:196, and the heavy chain of the antigen-binding fragment consists of the amino acid sequence of SEQ ID NO:261.

8. The fusion protein according to claim 6, wherein the light chain consists of the amino acid sequence of SEQ ID NO:196, and the BDNF linked to the heavy chain of the antigen-binding fragment consists of the amino acid sequence of SEQ ID NO:263.

9. The fusion protein according to claim 6, wherein the light chain consists of the amino acid sequence of SEQ ID NO:196, and the BDNF linked to the heavy chain of the antigen-binding fragment consists of the amino acid sequence of SEQ ID NO:264.

10. The fusion protein according to claim 1, wherein the linker is a peptide consisting of 1 to 50 amino acid residues.

11. The fusion protein according to claim 1, wherein the linker is a peptide comprising the amino acid sequence selected from the group consisting of the amino acid sequence (Gly-Ser), the amino acid sequence (Gly-Gly-Ser), SEQ ID NO:3, SEQ ID NO:4, and SEQ ID NO:5.

12. The fusion protein according to claim 1, wherein the BDNF is human BDNF.

13. The fusion protein according to claim 12, wherein the human BDNF comprises the amino acid sequence having an identity not lower than 97% to the amino acid sequence set forth as SEQ ID NO:247, or the human BDNF comprises the amino acid sequence having an identity not lower than 97% to the amino acid sequence set forth as SEQ ID NO:256.

14. The fusion protein according to claim 1, having an affinity to both the extracellular region of human transferrin receptor and the extracellular region of monkey transferrin receptor.

15. The fusion protein according to claim 14, wherein the dissociation constant of the anti-transferrin receptor antibody with the extracellular region of human transferrin receptor is not greater than $1 \times 10^{-8}$ M, and the dissociation constant of the anti-transferrin receptor antibody with the extracellular region of monkey transferrin receptor is not greater than $5 \times 10^{-8}$ M.

16. A fusion protein of brain-derived neurotrophic factor (BDNF) and an anti-human transferrin receptor (anti-hTfR) antibody, wherein the fusion protein comprises a BDNF linked to an anti-hTfR scFv antibody, wherein the anti-hTfR scFv antibody comprises a light chain variable region (LCVR) comprising three complementarity-determining regions (LCDR1-3) and a heavy chain variable region (HCVR) comprising three complementarity-determining regions (HCDR1-3), wherein the LCDR1 comprises the amino acid sequence of SEQ ID NO:16, the LCDR2 comprises the amino acid sequence of SEQ ID NO:18, the LCDR3 comprises the amino acid sequence of SEQ ID NO:20, the HCDR1 comprises the amino acid sequence of SEQ ID NO:88, the HCDR2 comprises the amino acid sequence of SEQ ID NO:90, and the HCDR3 comprises the amino acid sequence of SEQ ID NO:92, wherein the BDNF is human BDNF, and wherein the C-terminus of the BDNF is linked to the N-terminus of the HCVR via a first linker and the C-terminus of the HCVR is linked to the N-terminus of the LCVR via a second linker.

17. The fusion protein according to claim 16, wherein the HCVR comprises the amino acid sequence of SEQ ID NO:205.

18. The fusion protein according to claim 16, wherein the linker consists of 2 to 50 amino acid residues.

19. The fusion protein according to claim 18, wherein the linker comprises the amino acid sequence selected from the group consisting of the amino acid sequence (Gly-Ser), the amino acid sequence (Gly-Gly-Ser), the amino acid sequence (Gly-Gly-Gly), SEQ ID NO:3, SEQ ID NO:4, SEQ ID NO:5, and the amino acid sequence consisting of 2 to 10 thereof that are consecutively linked.

20. The fusion protein according to claim 16, wherein the anti-hTfR scFv antibody consists of the amino acid sequence of SEQ ID NO:257.

21. The fusion protein according to claim 20, wherein the anti-hTfR scFv antibody consists of the amino acid sequence of SEQ ID NO:257, the human BDNF is human pro-BDNF, and the fusion protein comprises the amino acid sequence of SEQ ID NO:259.

22. The fusion protein according to claim 20, wherein the anti-hTfR scFv antibody consists of the amino acid sequence of SEQ ID NO:257, and the fusion protein comprises the amino acid sequence of SEQ ID NO:260.

* * * * *